United States Patent
Denecker et al.

(10) Patent No.: US 10,017,778 B2
(45) Date of Patent: Jul. 10, 2018

(54) MEANS AND METHODS FOR THE REDUCTION OF PHOTORESPIRATION IN CROPS

(71) Applicants: VIB VZW, Ghent (BE); Universiteit Gent, Ghent (BE)

(72) Inventors: Jordi Denecker, Cambridgeshire (GB); Frank Hoeberichts, KW Wageningen (NL); Per Muhlenbock, Lidingö (CH); Frank Van Breusegem, Ledeberg (BE); Katrien Van Der Kelen, Ledeberg (BE)

(73) Assignees: VIB VZW, Ghent (BE); UNIVERSITEIT GENT, Ghent (BE)

( * ) Notice: Subject to any disclaimer, the term of this patent is extended or adjusted under 35 U.S.C. 154(b) by 0 days.

(21) Appl. No.: 14/777,963

(22) PCT Filed: Mar. 21, 2014

(86) PCT No.: PCT/EP2014/055760
§ 371 (c)(1),
(2) Date: Sep. 17, 2015

(87) PCT Pub. No.: WO2014/147249
PCT Pub. Date: Sep. 25, 2014

(65) Prior Publication Data
US 2016/0272991 A1 Sep. 22, 2016

(30) Foreign Application Priority Data
Mar. 21, 2013 (EP) .................................... 13160452

(51) Int. Cl.
C12N 15/82 (2006.01)
C12N 9/04 (2006.01)
C12N 15/01 (2006.01)

(52) U.S. Cl.
CPC ....... *C12N 15/8269* (2013.01); *C12N 9/0006* (2013.01); *C12N 15/01* (2013.01); *C12N 15/8218* (2013.01); *C12N 15/8271* (2013.01); Y02P 60/247 (2015.11)

(58) Field of Classification Search
CPC ................................................ C12N 15/8269
See application file for complete search history.

(56) References Cited

U.S. PATENT DOCUMENTS

| | | |
|---|---|---|
| 4,987,071 A | 1/1991 | Cech et al. |
| 5,034,323 A | 7/1991 | Jorgensen et al. |
| 5,283,184 A | 2/1994 | Jorgensen et al. |
| 5,565,350 A | 10/1996 | Kmiec |
| 5,731,181 A | 3/1998 | Kmiec |
| 5,756,325 A | 5/1998 | Kmiec |
| 5,759,829 A | 6/1998 | Shewmaker et al. |
| 5,760,012 A | 6/1998 | Kmiec |
| 5,795,972 A | 8/1998 | Kmiec |
| 5,871,984 A | 2/1999 | Kmiec |
| 5,942,657 A | 8/1999 | Bird et al. |
| 5,962,764 A | 10/1999 | Briggs et al. |
| 6,453,242 B1 | 9/2002 | Eisenberg et al. |
| 6,635,805 B1 | 10/2003 | Baulcombe et al. |
| 2003/0037355 A1 | 2/2003 | Barbas, III et al. |
| 2003/0180945 A1 | 9/2003 | Wang et al. |
| 2012/0005773 A1* | 1/2012 | Aasen ................ C12N 15/8261 800/275 |

FOREIGN PATENT DOCUMENTS

| | | |
|---|---|---|
| EP | 1198-985 A1 | 2/2001 |
| WO | WO-99/49029 A1 | 9/1999 |
| WO | WO-99/53050 A1 | 10/1999 |
| WO | WO-99/61631 A1 | 12/1999 |
| WO | WO-00/49035 A1 | 8/2000 |
| WO | WO-02/00904 A2 | 1/2002 |
| WO | WO-03/100066 A1 | 12/2003 |
| WO | WO-2009/103782 A1 | 8/2009 |
| WO | WO-2011/112570 A1 | 9/2011 |
| WO | WO-2014/147249 A1 | 9/2014 |

OTHER PUBLICATIONS

Breitkreuz, K. et al. (2003) The Journal of Biological Chemistry; vol. 278, No. 42, pp. 41552-41556.*
Zarei, A. et al., Fronteirs in Plant Science; Aug. 2017, vol. 8 pp. 1-13.*
Rhodora R. Aldemita et al., "Agrobacterium tumefaciens-mediated transformation of japonica and indica rice varieties," Planta, 1996, vol. 199, pp. 612-617.
Wendy L. Allan et al., "Hydroxybutyrate accumulation in *Arabidopsis* and tobacco plants in a general response to abiotic stress: putative regulation by redox balance and glyoxylate reductase isoforms," Journal of Experimental Botany, 2008, vol. 59, pp. 2555-2564.
Wendy L. Allan et al., "Role of plant glyoxylate reductases during stress: a hypothesis," Biochem J., 2009, vol. 423, pp. 15-22.
Wendy L. Allan et al., "Detoxification of succinate semialdehyde in *Arabidopsis* glyoxylate reductase and NAD Kinase mutants subjected to submergence stress," Botany, 2011, vol. 90, pp. 51-61.
Michael Bevan et al., "Binary Agrobacterium vectors for plant transformation," Nucleic Acids Research, 1984, vol. 12, pp. 8711-8721.
Ralph Bock, "Transgenic Plastids in Basic Research and Plant Biotechnology," J. Mol. Biol., 2001, vol. 312, pp. 425-438.
Mélanie Broin et al., "The Plastidic 2-Cysteine Peroxiredoxin is a Target for a Thioredoxin Involved in the Protection of the Photosynthetic Apparatus against Oxidative Damage," The Plant Cell, Jun. 2002, vol. 14, pp. 1417-1432.

(Continued)

*Primary Examiner* — Russell Kallis
(74) *Attorney, Agent, or Firm* — Arent Fox LLP

(57) ABSTRACT

The present invention relates to the field of plant molecular biology and concerns methods for enhancing the abiotic stress tolerance in plants by modulating the expression of the glyoxylate reductase gene. The present invention also provides chimeric constructs useful in the methods in the invention. In addition, the invention provides transgenic plants having an enhanced abiotic stress resistance, in particular an enhanced tolerance to high light conditions and an improved $CO_2$ fixation.

12 Claims, 8 Drawing Sheets

(56) References Cited

OTHER PUBLICATIONS

Figure 1:
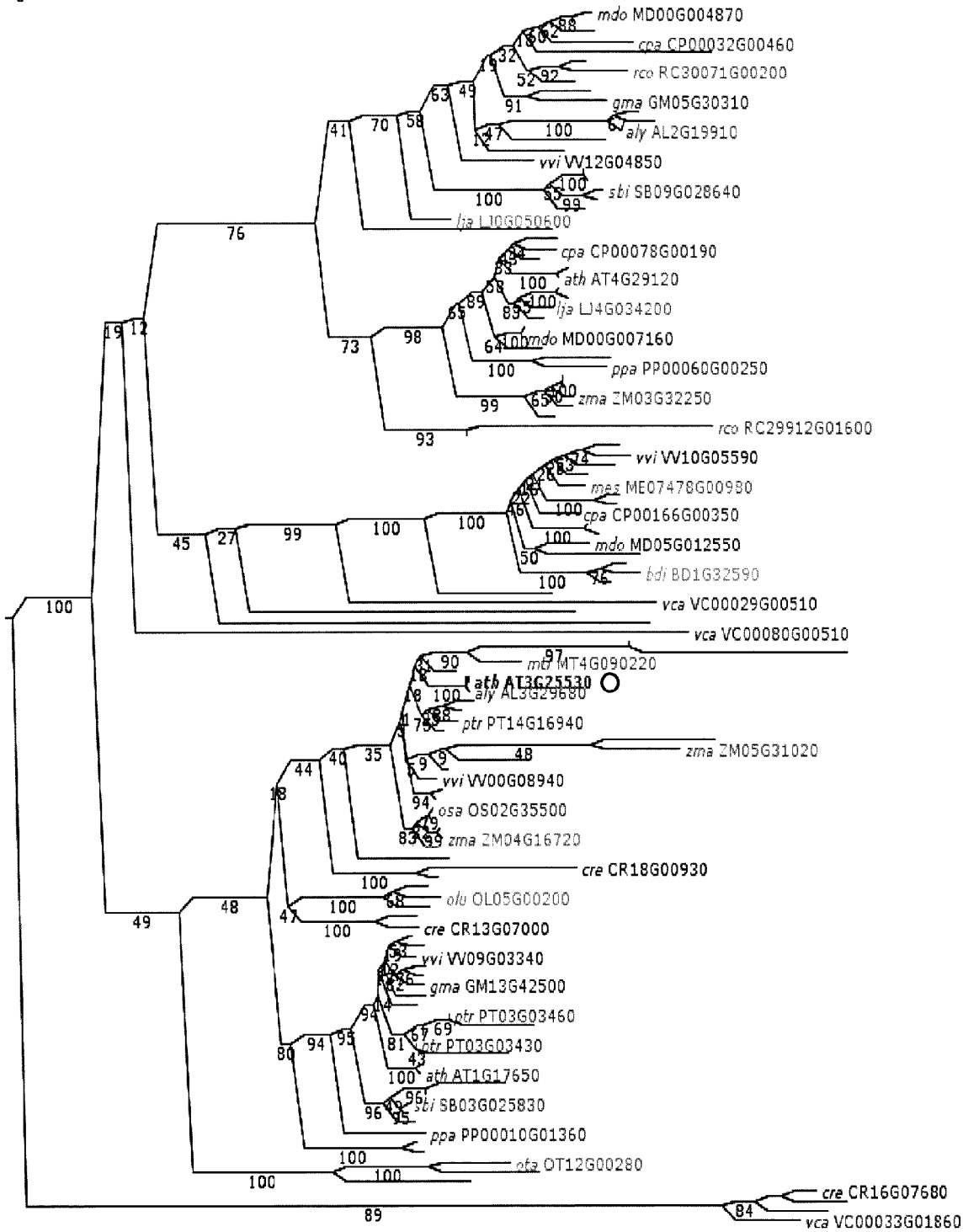

Andrew R. Buchman et al., "Comparison of Intron-Dependent and Intron-Independent Gene Expression," Molecular and Cellular biology, 1988, vol. 8, pp. 4395-4405.
Judy Callis et al., "Introns increase gene expression in cultured maize cells," Genes Dev., 1987, vol. 1, pp. 1183-1200.
Ming-Tsair Chan et al., "Agrobacterium-mediated production of transgenic rice plants expressing a chimeric α-amylase promoter / β-glucuronidase gene," Plant Molecular Biology, 1993, vol. 22, pp. 491-506.
Seok So Chang et al., "Stable genetic transformation of *Arabidopsis thaliana* by Agrobacterium inoculation in planta," The Plant Journal, 1994, vol. 5, pp. 551-558.
Steven J. Clough et al., "Floral dip: a simplified method of Agrobacterium-mediated transformation of *Arabidopsis thaliana*," The Plant Journal, 1998, vol. 16, pp. 735-743.
Udo Conrad et al., "Potatoes expressing single-domain antibodies in their plastids inhibit a starch-branching enzyme and produce high-amylose starch," Nature Biotech., 2003, vol. 21, pp. 35-36.
Anne Crossway et al., "Integration of foreign DNA following microinjection of tobacco mesophyll protoplasts," Mol. Gen Genet, 1986, vol. 202, pp. 179-185.
Kenneth A. Feldman et al., "Agrobacterium-mediated transformation of germinating seeds of *Arabidopsis thaliana*: A non-tissue culture approach," Mol. Gen. Genet., 1987, vol. 208, pp. 1-9.
Da-Fei Feng et al., "Progressive Sequence Alignment as a Prerequisite to Correct Phylogenetic Trees," J. Mol. Evol., 1987, vol. 25, pp. 351-360.
Bronwyn R. Frame et al., "Agrobacterium tumefaciens-Mediated Transformation of Maize Embryos Using a Standard Binary Vector System," Plant Physiol. 2002, vol. 129, pp. 13-22.
C. Gatz, "Chemical Control of Gene Expression," Ann. Rev. Plant Physiol. Plant Mol. Biol., 1997, vol. 48, pp. 89-108.
Darren (Fred) Gruis et al., "Redundant Proteolytic Mechanisms Process Seed Storage Proteins in the Absence of Seed-Type Members of the Vacuolar Processing Enzyme Family of Cystein Proteases," The Plant Cell, Nov. 2002, vol. 14, pp. 2863-2882.
Christian A. Heid et al., "Real Time Quantitative PCR," Genome Research,1996, vol. 6, pp. 986-994.
Chris Helliwell et al., "Constructs and methods for high-throughput gene silencing in plants," Methods, 2003, vol. 30, pp. 289-295.
Yukoh Hiei et al., "Efficient transformation of rice (*Oryza sative* L.) mediated by Agrobacterium and sequence analysis of the boundaries of the T-DNA," The Plant Journal, 1994, vol. 6, pp. 271-282.
Rainer Höfgen et al., "Storage of competent cells for Agrobacterium transformation," Nucleic Acids Research, 1988, vol. 16, p. 9877.
Gordon J. Hoover et al., "Characteristics of an *Arabidopsis* glyoxylate reductase: general biochemical properties and substrate specificity for the recombinant protein, and developmental expression and implications of glyoxylate and succinic semialdehyde metabolism in planta," Can. J. Bot.,2007, vol. 85, pp. 883-895.
Gordon J. Hoover et al., "Identification of catalytically important amino acid residues for enzymatic reduction of glyoxylate in plants," Biochimica et Biophysica Acta, 2013, vol. 1834, pp. 2663-2671.
Yuji Ishida et al., "High efficiency transformation of maize (*Zea mays* L.) mediated by Agrobacterium tumefaciens," 1996, Nat. Biotech. vol. 14, pp. 745-750.
Vesna Katavic et al., "In planta transformation of *Arabidopsis thaliana*," 1994, Mol Gen Genet., vol. 245, pp. 363-370.
Sebastian M J Klaus et al., "Generation of marker-free plastid transformants using a transiently cointegrated selection gene," Nature Biotechnology, 2004, vol. 22, pp. 225-229.
T.M. Klein et al., "High-velocity microprojectiles for delivering nucleic acids into living cells," Nature, 1987, vol. 327, pp. 70-73.
Makoto Kusaba et al., "Low glutelin content1: A Dominate Mutation that Suppresses the Glutelin Multigene Family via RNA Silencing in Rice," The Plant Cell, Jun. 2003, vol. 15, pp. 1455-1467.
Arthur L. Lawyer et al., "Inhibition of Glutamate: Glyoxylate Aminotransferase Activity in Tobacco Leaves and Callus by Glycidate, an Inhibitor of Protorespiration," Plant Physiology, 1978, vol. 61, pp. 242-247.
Yuandan Lee et al., "Cross-Referencing Eukaryotic Genomes: TIGR Orthologous Gene Alignments (TOGA)," Genome Res., 2002, vol. 12, pp. 493-502.
Pal Maliga, "Progress towards commercialization of plastid information technology," Trends Biotechnology, Jan. 2003, vol. 21, pp. 20-28.
Claire M. McCallum et al., "Targeted screening for induced mutations," Nature Biotechnology, 2000, vol. 18, pp. 455-457.
Judy Meinkoth et al., "Hybridization of Nucleic Acids Immobilized on Solid Supports," Analytical Biochemistry, 1984, vol. 138, pp. 267-284.
Rafael Meissner et al., "A high throughput system for transposon tagging and promoter trapping in tomato," The Plant Journal, 2000, vol. 22, pp. 265-274.
Robert Morbitzer et al., "Regulation of selected genome loci using de novo-engineered transcription activator-like effector (TALE)-type transcription factors," Proc. Natl. Acad. Sci. USA, 2010, vol. 107, pp. 21617-21622.
Matthew J. Moscou et al., "A simple Cipher Governs DNA Recognition by TAL Effectors," Science, 2009, vol. 326, p. 1501.
I. Negrutiu et al., "Hybrid genes in the analysis of transformation conditions," Plant Molecular Biology, 1987, vol. 8, pp. 363-373.
Kiyoshi Ohshima et al., "Isolation of a Mutant of *Arabidopsis thaliana* Carrying Two Simultaneous Mutations Affecting Tobacco Mosaic Virus Multiplication within a Single Cell," Virology, 1998, vol. 243, pp. 472-481.
Patricia A. Okubara et al., "Mutants of Downy Mildew Resistance in Lactuca sativa (Lettuce)," Genetics, 1994, vol. 137, pp. 867-874.
Stephan Ossowski et al., "Sequencing of natural strains of *Arabidopsis thaliana* with short reads," Genome Res., 2008, vol. 18, pp. 2024-2033.
Javier F. Palatnik et al., "Control of leaf morphogenesis by microRNAs," Nature, 2003, vol. 425, pp. 257-263.
Ralph Panstruga et al., "Testing the efficiency of dsRNAi constructs in vivo: A transient expression assay based on two fluorescent proteins," Molecular Biology Reports, 2003, vol. 30, pp. 135-140.
Christoph Peterhansel et al., "Photorespiratory bypasses: how can they work?" Journal of Experimental Botany, 2013, vol. 64, pp. 709-715.
I. Potrykus, "Gene Transfer to Plants: Assessment of Published Approaches and Results," Annu. Rev. Plant Physiol. Plant Mol. Biol., 1991, vol. 42, pp. 205-225.
Le Qing Qu et al., "Evaluation of tissue specificity and expression strength of rice and seed component gene promoters in transgenic rice," Plant Biotechnology Journal, 2004, vol. 2, pp. 113-125.
Victor Quesada et al., "Genetic Analysis of Salt-Tolerant Mutants in *Arabidopsis thaliana*," Genetics, 2000, vol. 154, pp. 421-436.
M. Ashiq Rabbani et al., "Monitoring Expression Profiles of Rice Genes under Cold, Drought, and High-Salinity Stresses and Abscisic Acid Application Using cDNA Microarray and RNA Gel-Blot Analyses," Plant Physiol., 2003, pp. 1755-1767.
Maido Remm et al., "Automatic Clustering of Orthologs and In-paralogs from Pairwise Species Comparisons," J. Mol. Biol, 2001, vol. 314, pp. 1041-1052.
Joost Schymkowitz et al., "The FoldX web server: an online force field," Nucleic Acids Research, 2005, vol. 33, pp. W382-W388.
R.D. Shillito et al., "High Efficiency Direct Gene Transfer to Plants," Bio/Technol., 1985, vol. 3, pp. 1099-1102.
Jeffrey P. Simpson et al., "Identification and characterization of a plastid-localized *Arabidopsis* glyoxylate reductase isoform: comparison with a cytosolic isoform and implications for cellular redox homeostasis and aldehyde detoxification," Journal of Experimental Botany, 2008, vol. 59, pp. 2545-2554.
Neil A. Smith et al., "Total Silencing by intronspliced hairpin RNAs," Nature, 2000, vol. 407, pp. 319-320.
Julie D. Thompson et al., "CLUSTAL W: improving the sensitivity of progressive multiple sequence alignment through sequence weighting, position-specific gap penalties and weight matrix choice," Nucleic Acid Res., 1994, vol. 22, pp. 4673-4680.

(56) References Cited

OTHER PUBLICATIONS

Gena Tribble et al., "DNA Recognition, Strand Selectivity, and Cleavage Mode during Integrase Family Site-specific Recombination," The Journal of Biological Chemistry, 2000, vol. 275, pp. 22255-22267.

Steven Vandenabeele et al., "Catalase deficiency drastically affects gene expression induced by high light in *Arabidopsis thaliana*," The Plant Journal, 2004, vol. 39, pp. 45-58.

Soundarapandian Velmurugan et al., "Partitioning of the 2-μm Circle Plasmid of *Saccharomyces cerevisiae*. Functional Coordination with Chromosome Segregation and Plasmid-encoded Rep Protein Distribution," J. Cell Biol., 2000, vol. 149, pp. 553-566.

Wangxia Wang et al., "Plant responses to drought, salinity and extreme temperatures: towards genetic engineering for stress tolerance," Planta, 2003, vol. 218, pp. 1-14.

Peter M. Waterhouse et al., "Exploring Plant Genomes by RNA-Induced Gene Silencing," Nat. Rev. Genet, 2003, vol. 4, pp. 29-38.

Gen Bank Accession No. AT3G25530.1, "Locus: AT3G25530," https://www.arabidopsis.org/servlets/TairObject?type=locus &name=AT3G25530, last updated date Jul. 24, 2015.

Gen Bank Accession No. AT3G60830.1, "Locus: AT3G60830," https://www.arabidopsis.org/servlets/TairObject?id=40397 &type=locus, last updated date Feb. 11, 2013.

\* cited by examiner

Fig. 2

Overview of gene family content

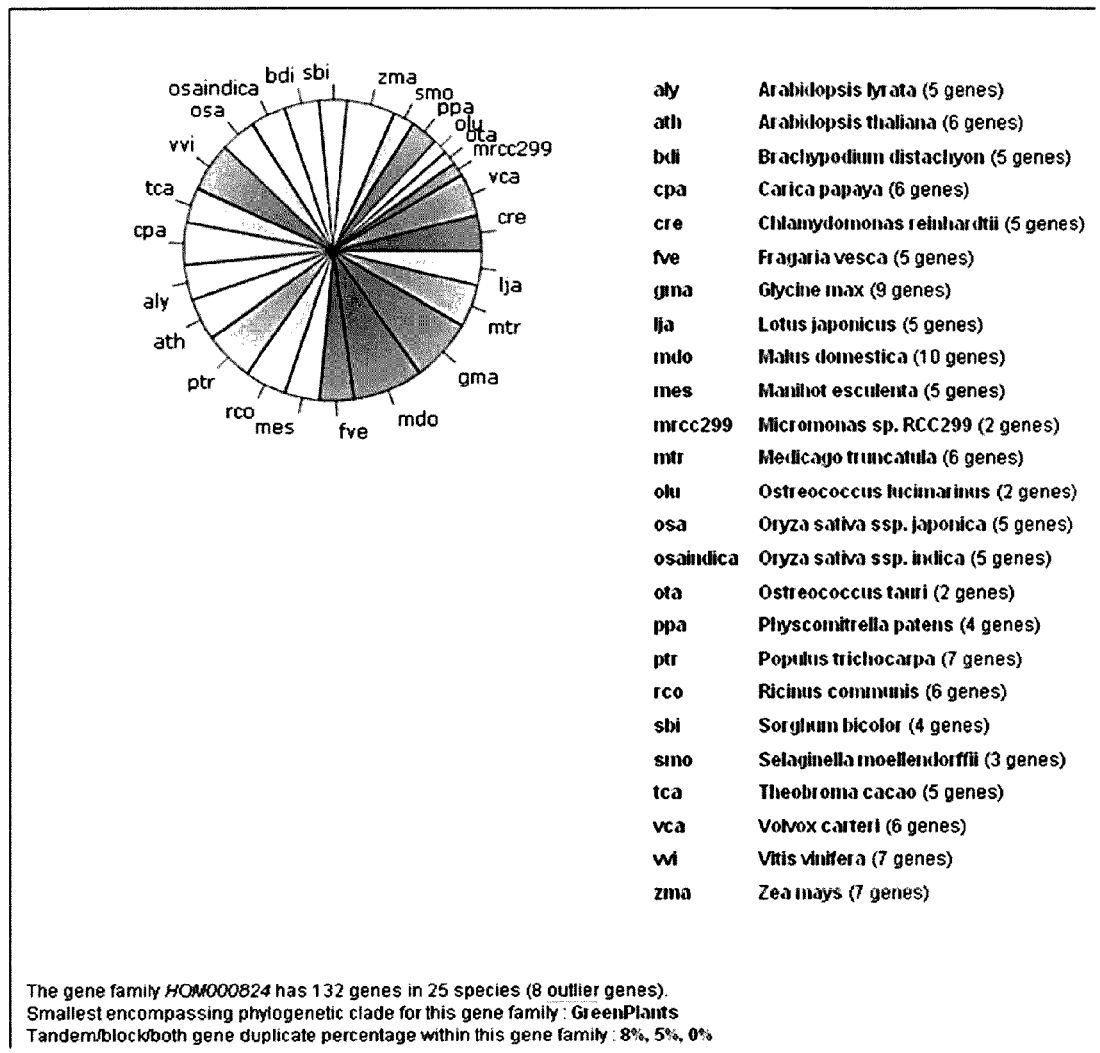

| | |
|---|---|
| aly | Arabidopsis lyrata (5 genes) |
| ath | Arabidopsis thaliana (6 genes) |
| bdi | Brachypodium distachyon (5 genes) |
| cpa | Carica papaya (6 genes) |
| cre | Chlamydomonas reinhardtii (5 genes) |
| fve | Fragaria vesca (5 genes) |
| gma | Glycine max (9 genes) |
| lja | Lotus japonicus (5 genes) |
| mdo | Malus domestica (10 genes) |
| mes | Manihot esculenta (5 genes) |
| mrcc299 | Micromonas sp. RCC299 (2 genes) |
| mtr | Medicago truncatula (6 genes) |
| olu | Ostreococcus lucimarinus (2 genes) |
| osa | Oryza sativa ssp. japonica (5 genes) |
| osaindica | Oryza sativa ssp. indica (5 genes) |
| ota | Ostreococcus tauri (2 genes) |
| ppa | Physcomitrella patens (4 genes) |
| ptr | Populus trichocarpa (7 genes) |
| rco | Ricinus communis (6 genes) |
| sbi | Sorghum bicolor (4 genes) |
| smo | Selaginella moellendorffii (3 genes) |
| tca | Theobroma cacao (5 genes) |
| vca | Volvox carteri (6 genes) |
| vvi | Vitis vinifera (7 genes) |
| zma | Zea mays (7 genes) |

The gene family HOM000824 has 132 genes in 25 species (8 outlier genes).
Smallest encompassing phylogenetic clade for this gene family : GreenPlants
Tandem/block/both gene duplicate percentage within this gene family : 8%, 5%, 0%

MEANS AND METHODS FOR THE REDUCTION OF PHOTORESPIRATION IN CROPS

CROSS REFERENCE TO RELATED APPLICATION

This application is a 35 U.S.C. 371 National Phase of PCT Application No. PCT/EP2014/055760 filed Mar. 21, 2014, which claims priority to European Patent Application No. 13160452.2 filed Mar. 21, 2013, the disclosure of these prior applications are hereby incorporated in their entirety by reference.

FIELD OF THE INVENTION

The invention generally relates to the field of molecular biology, specifically the field of agricultural biology. In particular, the invention relates to the yield preservation of plants growing under abiotic stress conditions, such as high light conditions, through a modulation of the activity of a plant glyoxylate reductase gene.

INTRODUCTION TO THE INVENTION

Photorespiration is a high-flux pathway that operates alongside carbon assimilation in $C_3$ plants. Some important crops such as rice, wheat, barley, cotton and potato belong to the $C_3$ plants. Photorespiration has a major impact on cellular metabolism, particularly under high light, high temperatures and $CO_2$ or water deficits. Although the functions of photorespiration remain controversial, it is widely accepted that this pathway influences a wide range of processes from bioenergetics, photosystem II function, and carbon metabolism to nitrogen assimilation and respiration. Crucially, the photorespiratory pathway is a major source of $H_2O_2$ production and pyridine nucleotide interactions, photorespiration makes a key contribution to cellular redox homeostasis. $CO_2$ fixation in $C_3$ plants is primarily catalyzed by the enzyme ribulose-1,5-bisphosphate carboxylase (RUBISCO) which is located inside the chloroplasts. The enzyme RUBISCO catalyzes two reactions: carboxylation and oxygenation of ribulose-1,5-bisphosphate. The product of the first reaction are two molecules of 3-phosphoglycerate which enter the Calvin cycle to form starch and ribulose-1, 5-bisphosphate. The products of the oxygenase reaction are each one molecule of 3-phosphoglycerate and phosphoglycolate. The latter is converted to 3-phosphoglycerate in a biosynthetic pathway named photorespiration. In the course of this complex sequence of reactions one molecule of $CO_2$ is released and lost for the plant. This loss of $CO_2$ reduces the formation of sugars and polysaccharides in the plant and thus reduces their productivity. Furthermore, $NH_3$ is released which has to be refixed. These effects are exacerbated further when plants are grown under abiotic stress conditions, such as for example suboptimal water supply. Here, leaf stomata are closed and the intercellular oxygen concentration rises because of molecular oxygen released from the light reactions of photosynthesis. High amounts of phosphoglycolate are produced that enter the photorespiratory cycle. It has been estimated that plants loose approximately 25% of the already fixed carbon due to photorespiration. However, this cycle is absolutely intrinsic to all $C_3$ plants because of the oxygenase activity of RUBISCO. $C_4$ plants have evolved a mechanism to largely avoid these losses, although photorespiration is also not completely eliminated in $C_4$ plants. The latter plants have employed enzymes already present in their $C_3$ ancestors, but changed the degree of expression as well as the localization on a subcellular and cell-type specific level. By separating primary and secondary carbon fixation in two different tissues, they drastically increase the local $CO_2$ concentration at the site of RUBISCO activity. Shortly, the first $CO_2$ fixation takes place in the cytoplasm of mesophyll cells and is catalyzed by PEPC, an enzyme without intrinsic oxygenase activity and significantly higher affinity to its substrate compared to RUBISCO. The resulting $C_4$ acid diffuses into the gas tight bundle sheath and is here decarboxylated to liberate $CO_2$. The remaining monocarbonic acid serves to regenerate the primary $CO_2$ acceptor in the mesophyll. This $CO_2$ concentration mechanism results in a drastic suppression of photorespiration. A similar mechanism with a temporal instead of spatial separation of enzymatic activities is applied by the crassulacean acid metabolism (CAM) plants. A number of transgenic approaches are described in the art which aim at mimicking the elevated $CO_2$-dependent repression of photorespiratory carbon and ammonia recycling pathways by introducing $C_4$ characteristics into $C_3$ plants or by circumventing photorespiratory glycolate metabolism by introducing novel pathways. In addition, it was suggested that the overexpression of glyoxylate reductase 1 (GLYR1) in transgenic plants would be beneficial for engineering stress tolerance, and in particular a reduced photorespiration, in plants, due to its detoxifying activity (Allan et al (2008) Journal of Experimental Botany 59 (9); Allan W L et al (2009) *Biochem. J.* 423, 12-22, Allan et al., Botany 90 (2012) 51-61, and Hoover et al, Biochimica et Biophysica Acta 1834 (2013) 2663-2671).

SUMMARY OF THE INVENTION

The present invention surprisingly shows that a downregulation (or a loss of function) of the glyoxylate reductase 1 (also designated herein further as the cytosolic glyoxylate reductase) is beneficial to overcome yield losses when plants are subjected to abiotic stress conditions, in particular high light conditions. It is shown that plants having a downregulation of the cytosolic glyoxylate reductase gene have improved $CO_2$ fixation even under normal growth conditions and in addition, also do not suffer from yield losses when subjected to abiotic stress conditions, such as high light conditions. Methods and compositions for improving plant yield are provided. In some embodiments, plant yield is improved under stress, particularly abiotic stress, such as high light conditions. In still other aspects the plant yield is improved under normal growth conditions. Methods of improving plant yield include inhibiting the endogenous glyoxylate reductase gene activity. The activity of a glyoxylate reductase gene can be inhibited using any method known in the art, including but not limited to the disruption of a glyoxylate reductase gene, or a decrease in the expression of the gene through the use of cosuppression, antisense, or RNA silencing.

Inhibiting the activity of at least one glyoxylate reductase in a plant can improve the growing of the plant under abiotic stress conditions, such as high light conditions, and such plants can maintain their productive rates, or in other words, such plants can maintain their yield stability under abiotic stress conditions, such as high light conditions, because of improved $CO_2$ fixation. In addition to an overall increase in yield, the improvement of growth under abiotic stress conditions through the inhibition of the glyoxylate reductase can also result in increased root mass and/or length, increased ear, leaf, seed, and/or endosperm size. Accordingly, in some aspects of the invention, the methods further comprise growing mutated plants under high light conditions and optionally selecting those plants exhibiting greater tolerance to these high light conditions, followed by selecting those mutated plants having loss-of-function mutations in the glyoxylated reductase gene, in particular a loss function in the cytosolic glyoxylate reductase gene.

Further, methods and compositions are provided for improving yield under abiotic stress, which include evaluating the environmental conditions of an area of cultivation for abiotic stressors (e.g. high light conditions or high salt levels in the soil or other types of abiotic stress conditions as explained herein further) and planting seeds or plants having improved $CO_2$ fixation, which is due to reduced activity of at least one glyoxylate reductase, in particular in abiotic stress environments.

Constructs and expression cassettes comprising nucleotide sequences that can efficiently reduce the expression of a glyoxylate reductase are also provided herein.

FIGURES

FIG. 1: phylogenetic tree of ortologous gene families for AT3G25530 (indicated with circle).

FIG. 2: pie chart of orthologous gene families for AT3G25530 (GLYR1).

Figure 3:
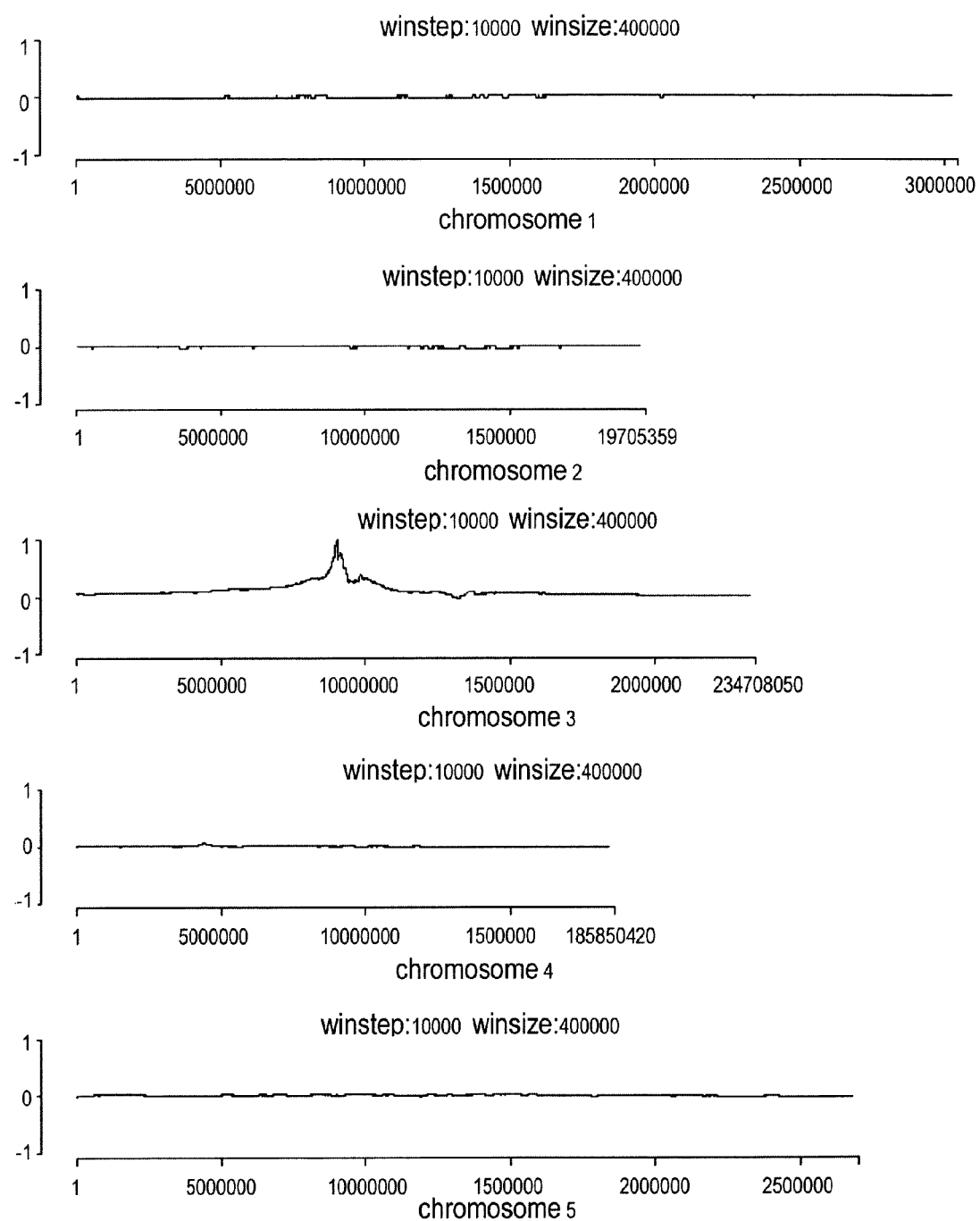

FIG. 3: Interval plot generated by SHOREmap. The identified candidate region containing the causative mutation is located on chromosome 3.

Figure 4:
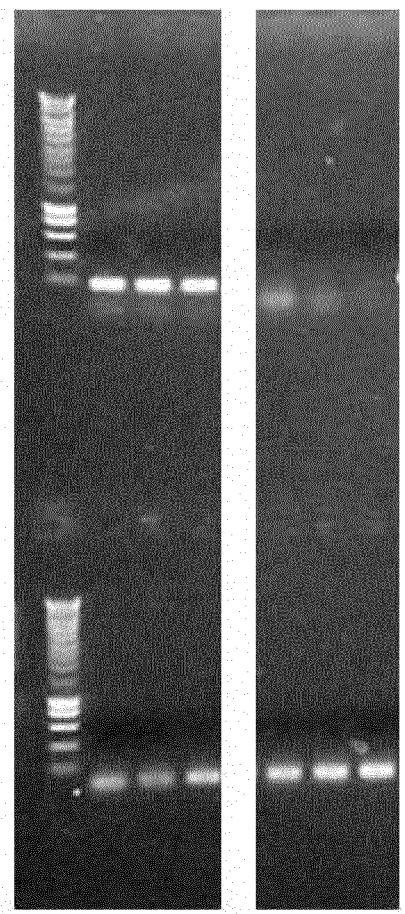

FIG. 4: RT-PCR analysis of GLYR transcripts in the wild type and in glyr1ko (GK-316D041). ARP7 (AT3G60830) was used as control.

Figure 5:
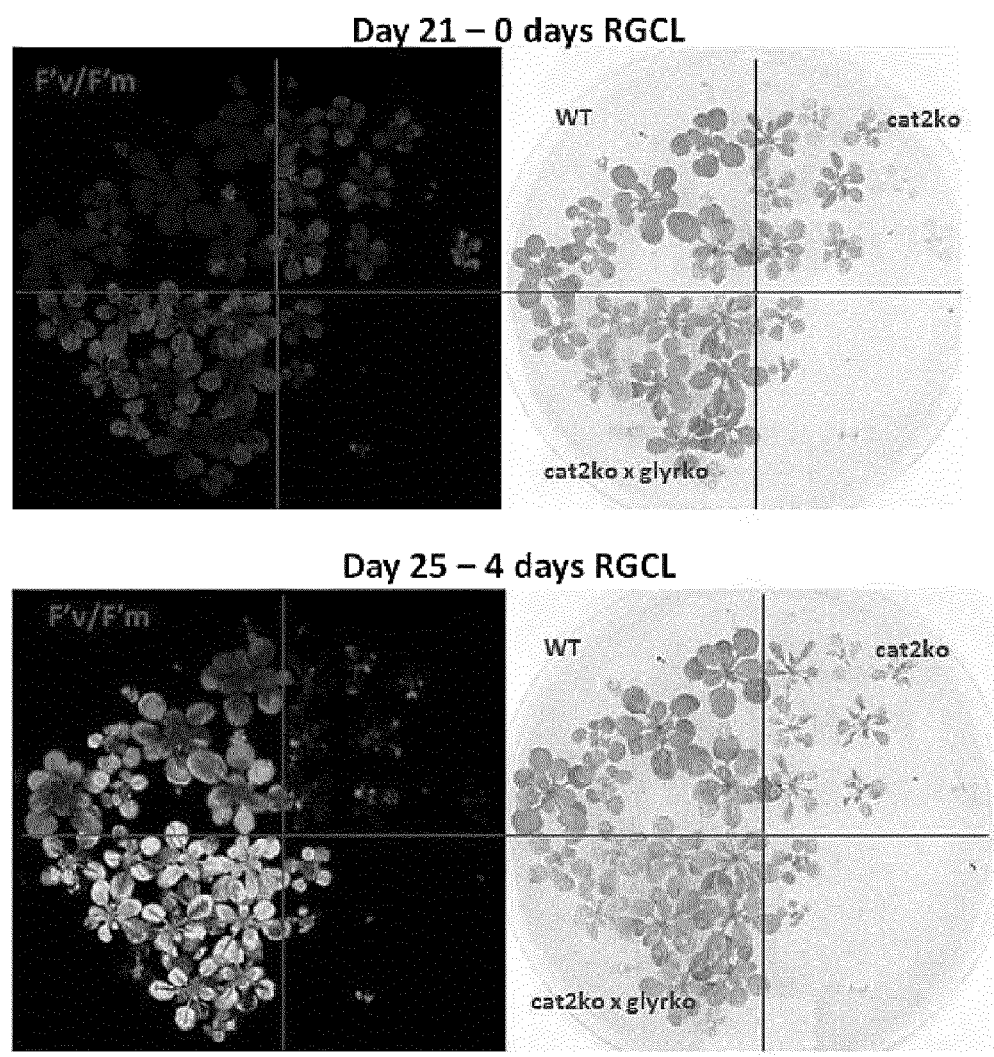

FIG. 5: RGCL treatment of glyr1×cat2_2 double homozygous KO plants as compared to cat2ko plants.

Figure 6:
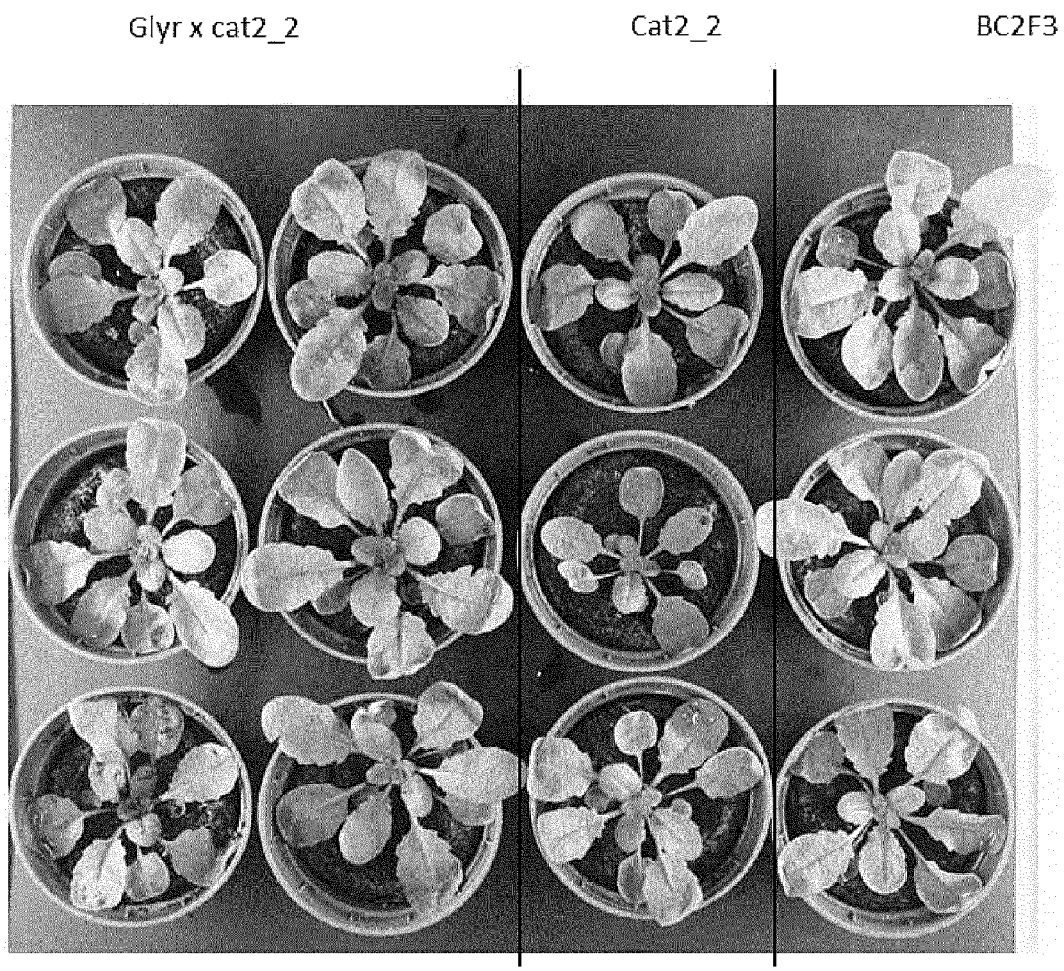

FIG. 6: Growth performance in the soil of cat2ko/glyr1ko double mutants as compared to cat2ko plants.

Figure 7:
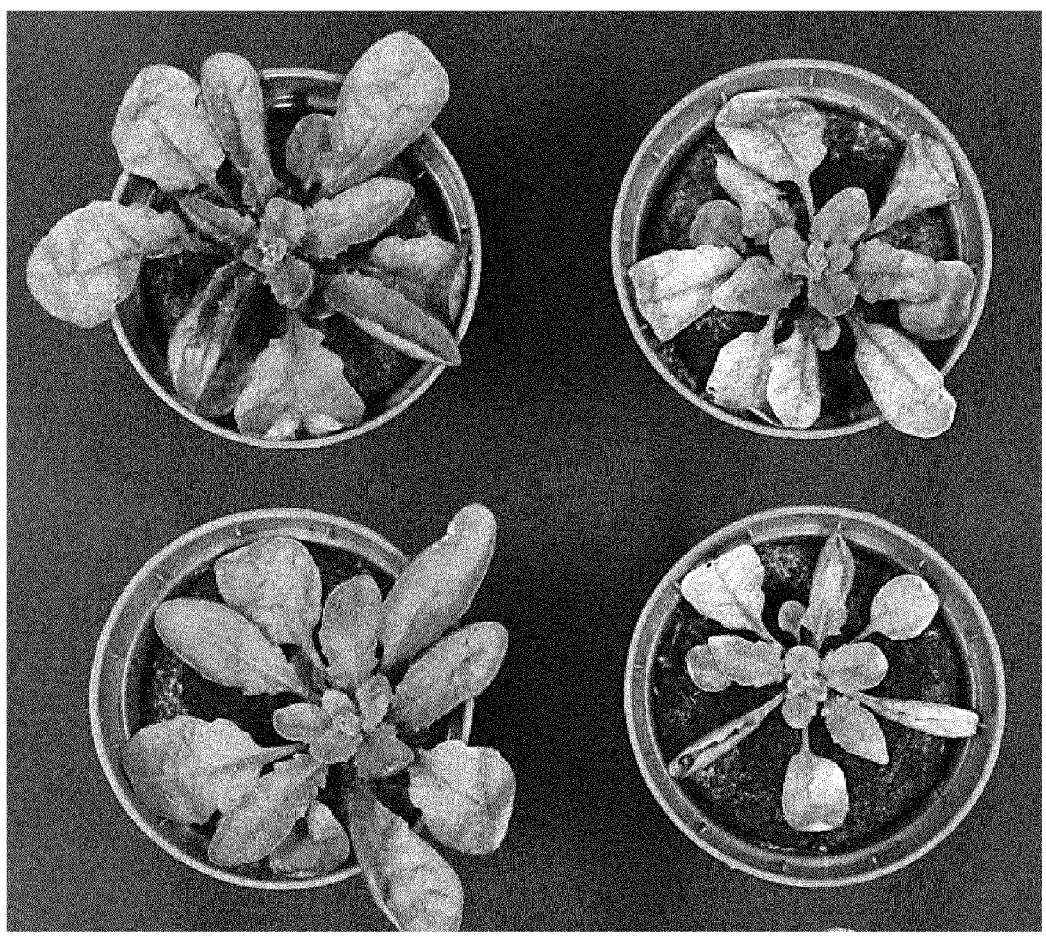

FIG. 7: Resistance to High Light stress of cat2ko/glyr1ko double mutants as compared to cat2ko plants.

Figure 8:
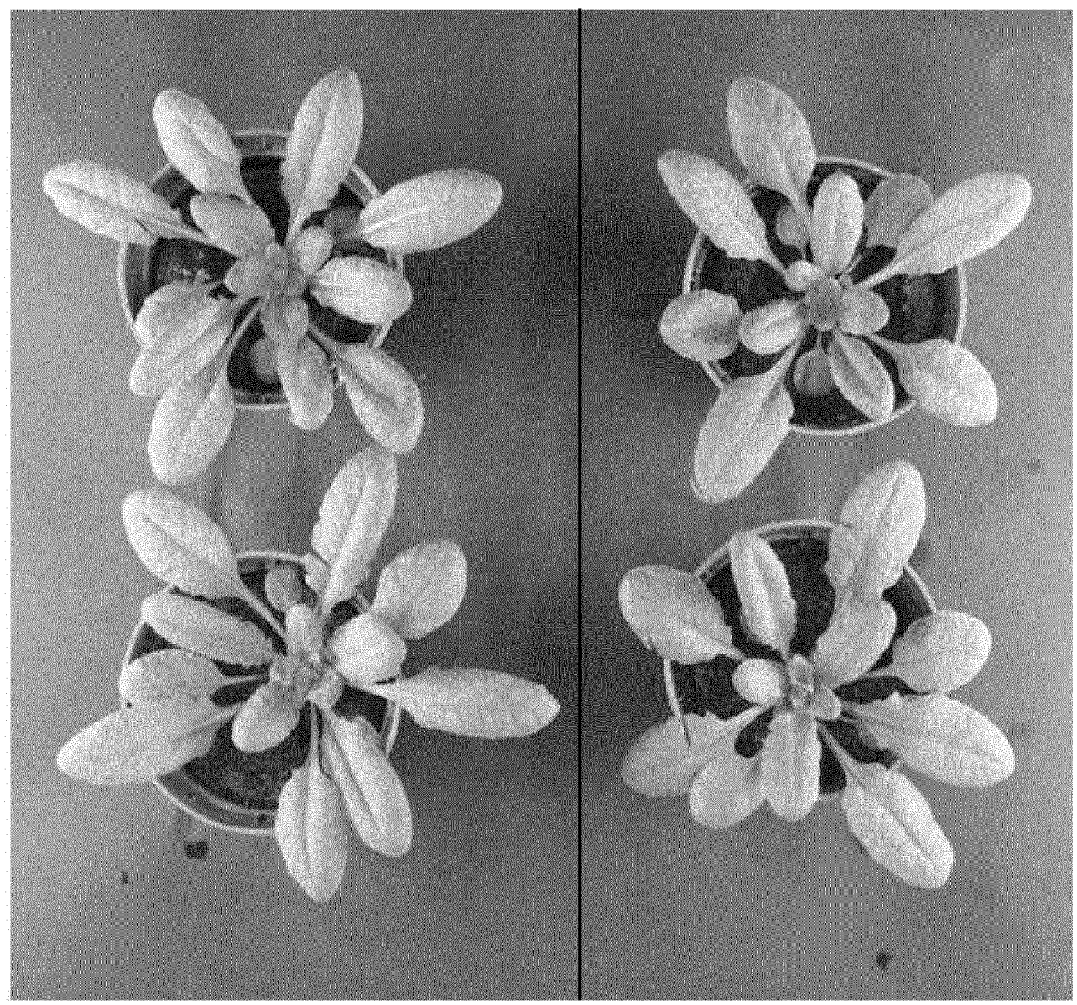

FIG. 8: Growth of glyr1ko plants as compared to wt Col-0 plants.

DETAILED DESCRIPTION OF THE INVENTION

To facilitate the understanding of this invention a number of terms are defined below. Terms defined herein (unless otherwise specified) have meanings as commonly understood by a person of ordinary skill in the areas relevant to the present invention. As used in this specification and its appended claims, terms such as "a", an and the are not intended to refer to only a singular entity, but include the general class of which a specific example may be used for illustration, unless the context dictates otherwise. The terminology herein is used to describe specific embodiments of the invention, but their usage does not delimit the invention, except as outlined in the claims.

Despite its importance for agriculture, environmental stress-induced growth inhibition, in particular when plants are subject to conditions of abiotic stress, such as high light, is responsible for significant yield reductions, is only poorly understood. In the present invention we have identified a key gene (i.e. glyoxylate reducatase) which when its activity is downregulated leads to a reduction in photorespiration, an enhanced CO2 production (even under normal growth conditions, i.e. growth conditions with a minimum of abiotic stress, and an enhanced tolerance to abiotic stress conditions, such as high light conditions.

Plant glyoxylate reductases are enzymes from the oxidoreductase family and participate in glyoxylate and dicarboxylate metabolism. An alternative name for glyoxylate reductase is 3-hydroxybutyrate dehydrogenase/phosphogluconate dehydrogenase. A preferred representative of the plant glyoxylate reductase in *Arabidopsis* is AT3G25530 (TAIR accession, www.arabidopsis.org), which is the cytosolic glyoxylate reductase (abbreviated as GLYR1) for which its genomic sequence is depicted in SEQ ID NO: 25, its coding sequence is depicted in SEQ ID NO: 1 and its protein sequence is depicted in SEQ ID NO: 2. Further GLYR1 sequences coding sequences are represented by SEQ ID NO. 3, 5, 7, 9, 11, 13, 15, 17, 19, 21, 23, 26, 28, 30, 32, 34, 36, 38, 40, 42, 44, 46, 48, 50, 52, 54, 56 and 58, while the corresponding protein sequences are represented by SEQ ID NO. 4, 6, 8, 10, 12, 14, 16, 18, 20, 22, 24, 27, 29, 31, 33, 35, 37, 39, 41, 43, 45, 47, 49, 51, 53, 55, 57 and 59. The enzymatic activity of the glyoxylate reductase, such as the GLYR1 protein, can be measured in cellular extracts since the enzyme has a documented 3-hydroxybutyrate dehydrogenase activity and also a phosphogluconate dehydrogenase (decarboxylating) activity.

Glyoxylate reductases, such as GLYR1, catalyze the following chemical reaction:

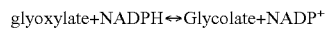

The activity of glyoxylate reductase, such as GLYR1, can also be measured in vitro (e.g. plant cell extracts) by measuring the oxidation of NADPH spectrophotometrically.

For the sake of completeness, next to the cytosolic glyoxylate reductase, there exists also a plant encoded plastidial glyoxylate reductase (in *Arabidopsis thaliana* this gene is abbreviated as GLYR2) which is different from the glyoxylate reductase (GLYR1). The present invention envisages that preferably the down-regulation of GLYR1 leads to an enhanced abiotic stress tolerance, in particular an enhanced tolerance to growth under abiotic stress conditions, such as high light conditions; which is reflected in an improved $CO_2$ incorporation and in an increased yield. But the present invention does not rule out that the activity of all glyoxylate reductases (both cytosolic and plastidial) present in a plant cell should be downregulated to obtain the desired effect as described before. Thus in a particular embodiment the invention provides plants with a downregulation of the plastidial reductase gene (GLR2) or plants with a downregulation of both the cytosolic and the plastidial reductase genes (GLYR1 and GLYR2). The *A. thaliana* GLYR2 coding sequence is represented by SEQ ID NO 60, while the corresponding protein sequence is represented by SEQ ID NO: 61. Further GLYR2 coding sequences are represented by SEQ ID NO's 62, 64, 66, 68, 70, 72, 74, 76, 78, 80, 82, 84, 86, 88, 90, 92, 94, 96, 98, 100 and 102, while the corresponding GLYR2 protein sequences are represented by SEQ ID NO: 63, 65, 67, 69, 71, 73, 75, 77, 79, 81, 83, 85, 87, 89, 91, 93, 95, 97, 99, 101 and 103.

Thus, a plant having reduced glyoxylate reductase activity can have at least one of the following phenotypes, especially under abiotic stress conditions but also under normal conditions, such as high light conditions, including but not limited to: increased overall plant yield, increased root mass, increased root length, increased leaf size, increased ear size, increased seed size, increased endosperm size, improved standability, alterations in the relative size of embryos and endosperms leading to changes in the relative levels of protein, oil and/or starch in the seeds, altered floral development, changes in leaf number, altered leaf surface, altered vasculature, altered internodes, alterations in leaf senescence, absence of tassels, absence of functional pollen bearing tassels, or increased plant size when compared to a non-modified plant under normal growth conditions or under conditions of abiotic stress conditions, such as high light conditions.

Any method known in the art to reduce or eliminate the activity of a plant glyoxylate reductase polypeptide can be used to improve plant phenotype as described above or to improve abiotic stress tolerance, in particular tolerance to high light conditions, of a plant. In some embodiments, a polynucleotide is introduced into a plant that may inhibit the expression of a glyoxylate reductase polypeptide directly, by preventing transcription or translation of a glyoxylate reductase messenger RNA, or indirectly, by encoding a polypeptide that inhibits the transcription or translation of a glyoxylate reductase gene encoding a glyoxylate reductase polypeptide. Methods for inhibiting or eliminating the expression of a gene in a plant are well known in the art, and any such method may be used in the present invention to inhibit the expression of the glyoxylate reductase polypeptide. In other embodiments, a polynucleotide that encodes a polypeptide that inhibits the activity of a glyoxylate reductase polypeptide is introduced into a plant. In yet other embodiments, the activity of a glyoxylate reductase is inhibited through disruption of a glyoxylate reductase gene. Many methods may be used to reduce or eliminate the activity of a glyoxylate reductase polypeptide. In addition, more than one method may be used to reduce the activity of a single glyoxylate reductase polypeptide. In some embodiments, the glyoxylate reductase activity is reduced through the disruption of at least one glyoxylate reductase gene or a reduction in the expression of at least one glyoxylate reductase gene. As used herein, a "glyoxylate reductase gene" refers to a gene that encodes a glyoxylate reductase polypeptide, such as for example a cytosolic or a plastidial glyoxylate reductase polypeptide. A glyoxylate reductase gene can comprise, e.g. at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5% or more sequence identity to SEQ ID NO: 1 or SEQ ID NO: 25. Many glyoxylate reductase genes are known to those of skill in the art and are readily available through sources such as GENBANK and the like. The expression of any glyoxylate reductase gene may be reduced according to the invention.

In accordance with the present invention, the expression of a glyoxylate reductase is inhibited if the transcript or protein level of the glyoxylate reductase is statistically lower than the transcript or protein level of the same glyoxylate reductase in a plant that has not been genetically modified or mutagenized to inhibit the expression of that glyoxylate reductase. In particular embodiments of the invention, the transcript or protein level of the glyoxylate reductase in a modified plant according to the invention is less than 95%, less than 90%, less than 85%, less than 80%, less than 75%, less than 70%, less than 60%, less than 50%, less than 40%, less than 30%, less than 20%, less than 10%, or less than 5% of the protein level of the same glyoxylate reductase in a plant that is not a mutant or that has not been genetically modified to inhibit the expression of that glyoxylate reductase. The expression level of the glyoxylate reductase may be measured directly, for example, by assaying for the level of glyoxylate reductase expressed in the cell or plant, or indirectly, for example, by measuring the glyoxylate reductase activity in the cell or plant. The activity of a glyoxylate reductase protein is "eliminated" according to the invention when it is not detectable by at least one assay method. Methods for assessing glyoxylate reductase activity are known in the art and include measuring levels of glyoxylate reductase, which can be recovered and assayed from cell extracts.

In other embodiments of the invention, the activity of one or more glyoxylate reductases is reduced or eliminated by transforming a plant cell with an expression cassette comprising a polynucleotide encoding a polypeptide that inhibits the activity of one or more glyoxylate reductases. The activity of a glyoxylate reductase is inhibited according to the present invention if the activity of that glyoxylate reductase in the transformed plant or cell is statistically lower than the activity of that glyoxylate reductase in a plant that has not been genetically modified to inhibit the activity of at least one glyoxylate reductase. In particular embodiments of the invention, a glyoxylate reductase activity of a modified plant according to the invention is less than 95%, less than 90%, less than 85%, less than 80%, less than 75%, less than 70%, less than 60%, less than 50%, less than 40%, less than 30%, less than 20%, less than 10%, or less than 5% of that glyoxylate reductase activity in an appropriate control plant that has not been genetically modified to inhibit the expression or activity of the glyoxylate reductase.

In other embodiments, the activity of a glyoxylate reductase may be reduced or eliminated by disrupting at least one gene encoding the glyoxylate reductase. The disruption inhibits expression or activity of at least one glyoxylate reductase protein compared to a corresponding control plant cell lacking the disruption. In one embodiment, the at least one endogenous glyoxylate reductase gene comprises two or more endogenous glyoxylate reductase genes, such as in the case of *Arabidopsis* the cytosolic GLYR1 and the plastidial GLYR2. Similarly, in another embodiment, the at least one endogenous glyoxylate reductase gene comprises three or more endogenous glyoxylate reductase synthase genes. The disruption results in the plant's improved performance under abiotic stress conditions, such as for example high light conditions, and/or the plant's increased yield under non-stress conditions as compared to a control plant in similar conditions.

In another embodiment, the disruption step comprises insertion of one or more transposons, where the one or more transposons are inserted into the at least one endogenous glyoxylate reductase gene. In yet another embodiment, the disruption comprises one or more point mutations in the at least one endogenous glyoxylate reductase gene. The disruption can be a homozygous disruption in the at least one glyoxylate reductase gene. Alternatively, the disruption is a heterozygous disruption in the at least one glyoxylate reductase gene. In certain embodiments, when more than one glyoxylate reductase gene is involved, there is more than one disruption, which can include homozygous disruptions, heterozygous disruptions or a combination of homozygous disruptions and heterozygous disruptions.

Detection of expression products is performed either qualitatively (by detecting presence or absence of one or more product of interest) or quantitatively (by monitoring the level of expression of one or more product of interest). In one embodiment, the expression product is an RNA expression product. Aspects of the invention optionally include monitoring an expression level of a nucleic acid, polypeptide as noted herein for detection of glyoxylate reductase or tolerance to abiotic stress conditions, such as high light conditions, in a plant or in a population of plants.

Thus, many methods may be used to reduce or eliminate the activity of a glyoxylate reductase. More than one method may be used to reduce the activity of a single plant glyoxylate reductase. In addition, combinations of methods may be employed to reduce or eliminate the activity of two or more different glyoxylate reductases. Non-limiting examples of methods of reducing or eliminating the expression of a plant glyoxylate reductase are given below.

In some embodiments of the present invention, a polynucleotide is introduced into a plant that upon introduction or expression, inhibits the expression of a glyoxylate reductase of the invention, i.e. a glyoxylate reductase inhibitory RNA molecule. The term "expression" as used herein refers to the biosynthesis of a gene product, including the transcription and/or translation of said gene product. For example, for the purposes of the present invention, an expression cassette capable of expressing a polynucleotide that inhibits the expression of at least one glyoxylate reductase polypeptide is an expression cassette capable of producing an RNA molecule that inhibits the transcription and/or translation of at least one glyoxylate reductase polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Further, "expression" of a gene can refer to the transcription of the gene into a non-protein coding transcript.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g. peptide nucleic acids).

By "encoding" or "encoded," with respect to a specified nucleic acid, is meant comprising the information for transcription into an RNA and in some embodiments, translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

Examples of polynucleotides that inhibit the expression of a glyoxylate reductase polypeptide, i.e. DNA regions which when transcribed yield a glyoxylate reductase inhibitory RNA molecule, are given below, and include RNA molecules containing all or part of the sequence of the GLYR gene present in a plant in which it is desired to reduce the GLYR1 activity. Such RNA molecules specifically target the endogenous GLYR gene/mRNA. In some embodiments of the invention, inhibition of the expression of a glyoxylate reductase polypeptide may be obtained by sense suppression or cosuppression. For cosuppression, an expression cassette is designed to express an RNA molecule corresponding to all or part of a messenger RNA encoding a glyoxylate reductase polypeptide in the "sense" orientation. Overexpression of the RNA molecule can result in reduced expression of the native gene. Accordingly, multiple plant lines transformed with the cosuppression expression cassette are screened to identify those that show the greatest inhibition of glyoxylate reductase polypeptide expression.

The polynucleotide used for cosuppression may correspond to all or part of the sequence encoding the glyoxylate reductase polypeptide, all or part of the 5' and/or 3' untranslated region of a glyoxylate reductase polypeptide transcript or all or part of both the coding sequence and the untranslated regions of a transcript encoding a glyoxylate reductase polypeptide. A polynucleotide used for cosuppression or other gene silencing methods may share 99%, 98%, 97%, 96%, 95%, 94%, 93%, 92%, 91%, 90%, 89%, 88%, 87%, 85%, 80%, or less sequence identity with the target sequence. When portions of the polynucleotides (e.g., of SEQ ID NO: 1, 3, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102) are used to disrupt the expression of the target gene, generally, sequences of at least 15, 19, 20, 21, 22, 23, 24, 25, 26, 27, 28, 29, 30, 35, 40, 45, 50, 60, 70, 80, 90, 100, 200, 300, 400, 450, 500, 550, 600, 650, 700, 750, 800, 900, or 1000 contiguous nucleotides or greater may be used. In some embodiments where the polynucleotide comprises all or part of the coding region for the glyoxylate reductase polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in U.S. Pat. No. 5,034,323, U.S. Pat. No. 5,283, 184 and U.S. Pat. No. 5,942,657, each of which is herein incorporated by reference. The efficiency of cosuppression may be increased by including a poly-dT region in the expression cassette at a position 3' to the sense sequence and 5' of the polyadenylation signal. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. No. 5,283,184 and U.S. Pat. No. 5,034,323, herein incorporated by reference.

In some embodiments of the invention, inhibition of the expression of the glyoxylate reductase polypeptide may be obtained by antisense suppression. For antisense suppression, the expression cassette is designed to express an RNA molecule complementary to all or part of a messenger RNA encoding the glyoxylate reductase polypeptide. Overexpression of the antisense RNA molecule can result in reduced expression of the native gene. Accordingly, multiple plant lines transformed with the antisense suppression expression cassette are screened to identify those that show the greatest inhibition glyoxylate reductase polypeptide expression.

The polynucleotide for use in antisense suppression may correspond to all or part of the complement of the sequence encoding the glyoxylate reductase polypeptide, all or part of the complement of the 5' and/or 3' untranslated region of the glyoxylate reductase transcript or all or part of the complement of both the coding sequence and the untranslated regions of a transcript encoding the glyoxylate reductase polypeptide.

In addition, the antisense polynucleotide may be fully complementary (i.e. 100% identical to the complement of the target sequence) or partially complementary (i.e. less than 100%, including but not limited to, 99%, 98%, 97%, 96%, 95%, 94%, 93%, 92%, 91%, 90%, 89%, 88%, 87%, 85%, 80%, identical to the complement of the target sequence, which in some embodiments is SEQ ID NO: 1, 3, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used.

Methods for using antisense suppression to inhibit the expression of endogenous genes in plants are described, for example, in U.S. Pat. No. 5,759,829, which is herein incorporated by reference. Efficiency of antisense suppression may be increased by including a poly-dT region in the expression cassette at a position 3' to the antisense sequence and 5 of the polyadenylation signal.

In some embodiments of the invention, inhibition of the expression of a glyoxylate reductase polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA. Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of glyoxylate reductase polypeptide expression. Methods for using dsRNA interference to inhibit the expression of endogenous plant genes are described in WO9949029, WO9953050, WO9961631 and WO0049035, each of which is herein incorporated by reference.

In some embodiments of the invention, inhibition of the expression of a glyoxylate reductase polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) Nat. Rev. Genet. 4:29-38 and the references cited therein. For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. The antisense sequence may be located "upstream" of the sense sequence (i.e. the antisense sequence may be closer to the promoter driving expression of the hairpin RNA than the sense sequence). The base-paired stem region may correspond to a portion of a promoter sequence controlling expression of the gene to be inhibited. A polynucleotide designed to express an RNA molecule having a hairpin structure comprises a first nucleotide sequence and a second nucleotide sequence that is the complement of the first nucleotide sequence, and wherein the second nucleotide sequence is in an inverted orientation relative to the first nucleotide sequence. Thus, the base-paired stem region of the molecule generally determines the specificity of the RNA interference. The sense sequence and the antisense sequence are generally of similar lengths but may differ in length. Thus, these sequences may be portions or fragments of at least 10, 19, 20, 21, 22, 23, 24, 25, 26, 27, 28, 29, 30, 50, 70, 90, 100, 120, 140, 160, 180, 200, 220, 240, 260, 280, 300, 320, 340, 360, 380, 400, 500, 600, 700, 800, 900 nucleotides in length, or at least 1, 2, 3, 4, 5, 6, 7, 8, 9, or 10 kb in length. The loop region of the expression cassette may vary in length. Thus, the loop region may be at least 10, 20, 30, 40, 50, 75, 100, 200, 300, 400, 500, 600, 700, 800, 900 nucleotides in length, or at least 1, 2, 3, 4, 5, 6, 7, 8, 9, or 10 kb in length. hpRNA molecules are highly efficient at inhibiting the expression of endogenous genes and the RNA interference they induce is inherited by subsequent generations of plants. See, for example, Waterhouse and Helliwell, (2003) Nat. Rev. Genet. 4:29-38. A transient assay for the efficiency of hpRNA constructs to silence gene expression in vivo has been described by Panstruga, et al. (2003) Mol. Biol. Rep. 30: 135-140, herein incorporated by reference. For ihpRNA, the interfering molecules have the same general structure as for hpRNA, but the RNA molecule additionally comprises an intron in the loop of the hairpin that is capable of being spliced in the cell in which the ihpRNA is expressed. The use of an intron minimizes the size of the loop in the hairpin RNA molecule following splicing, and this increases the efficiency of interference. See, for example, Smith et al (2000) Nature 407:319-320. In fact, Smith et al, show 100% suppression of endogenous gene expression using ihpRNA-mediated interference. In some embodiments, the intron is the ADHI intron 1. Methods for using ihpRNA interference to inhibit the expression of endogenous plant genes are described, for example, in Smith et al, (2000) Nature 407:319-320; Waterhouse and Helliwell, (2003) Nat. Rev. Genet. 4:29-38; Helliwell and Waterhouse, (2003) Methods 30:289-295 and US2003180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO0200904 herein incorporated by reference.

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the glyoxylate reductase polypeptide). Methods of using amplicons to inhibit the expression of endogenous plant genes are described, for example, in U.S. Pat. No. 6,635,805, which is herein incorporated by reference.

In some embodiments, the polynucleotide expressed by the expression cassette of the invention is catalytic RNA or has ribozyme activity specific for the messenger RNA of the glyoxylate reductase polypeptide. Thus, the polynucleotide causes the degradation of the endogenous messenger RNA, resulting in reduced expression of the glyoxylate reductase polypeptide. This method is described, for example, in U.S. Pat. No. 4,987,071, herein incorporated by reference. In some embodiments of the invention, inhibition of the expression of a glyoxylate reductase polypeptide may be obtained by RNA interference by expression of a polynucleotide encoding a micro RNA (miRNA). miRNAs are regulatory agents consisting of about 22 ribonucleotides. miRNA are highly efficient at inhibiting the expression of endogenous genes. See, for example Javier et al (2003) *Nature* 425:257-263, herein incorporated by reference.

For miRNA interference, the expression cassette is designed to express an RNA molecule that is modeled on an endogenous pre-miRNA gene wherein the endogenous miRNA and miRNA* sequence are replaced by sequences targeting the glyoxylate reductase mRNA. The miRNA gene encodes an RNA that forms a hairpin structure containing a 21 or 22-nucleotide sequence that is complementary to another endogenous gene (target sequence). For suppression of the glyoxylate reductase, the 21 or 22-nucleotide sequence is selected from a glyoxylate reductase transcript sequence, e.g. from SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102, and contains 22 nucleotides of said glyoxylate reductase in sense orientation (the miRNA* sequence) and 21 or 22 nucleotides of a corresponding antisense sequence that is complementary to the sense sequence and complementary to the target mRNA (the miRNA sequence). No perfect complementarity between the miRNA and its target is required, but some mismatches are allowed. Up to 4 mismatches between the miRNA and miRNA* sequence are also allowed, such as at position 1 and/or 18. miRNA molecules are highly efficient at inhibiting the expression of endogenous genes, and the RNA interference they induce is inherited by subsequent generations of plants.

In some embodiments, polypeptides or polynucleotide encoding polypeptides can be introduced into a plant, wherein the polypeptide is capable of inhibiting the activity of a glyoxylate reductase polypeptide. The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

In one embodiment, the polynucleotide encodes a zinc finger protein that binds to a gene encoding a glyoxylate reductase polypeptide, resulting in reduced expression of the gene. In particular embodiments, the zinc finger protein binds to a regulatory region of a glyoxylate reductase. In other embodiments, the zinc finger protein binds to a messenger RNA encoding a glyoxylate reductase polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US2003/0037355, each of which is herein incorporated by reference.

In another embodiment, the polynucleotide encodes a TALE protein that binds to a gene encoding a glyoxylate reductase polypeptide, resulting in reduced expression of the gene. In particular embodiments, the TALE protein binds to a regulatory region of a glyoxylate reductase. In other embodiments, the TALE protein binds to a messenger RNA encoding a glyoxylate reductase polypeptide and prevents its translation. Methods of selecting sites for targeting by zinc finger proteins have been described in e.g. Moscou M J, Bogdanove A J (2009) (A simple cipher governs DNA recognition by TAL effectors. Science 326:1501) and Morbitzer R, Romer P, Boch J, Lahaye T (2010) (Regulation of selected genome loci using de novo-engineered transcription activator-like effector (TALE)-type transcription factors. Proc Natl Acad Sci USA 107:21617-21622.)

In some embodiments, the polynucleotide encodes a nuclease, e.g. a meganuclease, zinc finger nuclease, TALEN, or CRISPR/CAS nuclease that specifically inactivates the endogenous GLYR gene by recognizing and cleaving a sequence specific for said endogenous GLYR gene. Using a template DNA, also specific mutations can be introduced into the GLYR gene. Chimeric genes encoding such nuclease can be removed afterwards by segregation.

In some embodiments of the invention, the polynucleotide encodes an antibody that binds to at least one glyoxylate reductase polypeptide and reduces the activity of the glyoxylate reductase polypeptide. In another embodiment, the binding of the antibody results in increased turnover of the antibody-glyoxylate reductase complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

In some embodiments of the present invention, the activity of a glyoxylate reductase is reduced or eliminated by disrupting the gene encoding the glyoxylate reductase polypeptide. The gene encoding the glyoxylate reductase polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have enhanced abiotic stress tolerance, such as enhanced tolerance to high light conditions.

In one embodiment of the invention, transposon tagging is used to reduce or eliminate the glyoxylate reductase activity of one or more glyoxylate reductase polypeptides. Transposon tagging comprises inserting a transposon within an endogenous glyoxylate reductase gene to reduce or eliminate expression of the glyoxylate reductase polypeptide. In this embodiment, the expression of one or more glyoxylate reductase polypeptides is reduced or eliminated by inserting a transposon within a regulatory region or coding region of the gene encoding the glyoxylate reductase polypeptide. A transposon that is within an exon, intron, 5 ' or 3' untranslated sequence, a promoter or any other regulatory sequence of a glyoxylate reductase gene may be used to reduce or eliminate the expression and/or activity of the encoded glyoxylate reductase polypeptide.

Methods for the transposon tagging of specific genes in plants are well known in the art. See, for example, Meissner, et al (2000) Plant J. 22:265-21. In addition, the TUSC process for selecting Mu insertions in selected genes has been described in U.S. Pat. No. 5,962,764, which is herein incorporated by reference.

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see, Ohshima, et al, (1998) Virology 243:472-481; Okubara, et al, (1994) Genetics 137:867-874 and Quesada, et al, (2000) Genetics 154:421-436, each of which is herein incorporated by reference. In addition, a fast and automatable method for screening for chemically induced mutations, TILLING (Targeting Induced Local Lesions in Genomes), using denaturing HPLC or selective endonuclease digestion of selected PCR products is also applicable to the instant invention. See, McCallum, et al, (2000) Nat. Biotechnol 18:455-457, herein incorporated by reference. Mutations that impact gene expression or that interfere with the function of the encoded protein are well known in the art. Insertional mutations in gene exons usually result in null-mutants. Mutations in conserved residues are particularly effective in inhibiting the activity of the encoded protein. Conserved residues of plant glyoxylate reductase polypeptides suitable for mutagenesis with the goal to eliminate glyoxylate reductase activity have been described. Such mutants can be isolated according to well-known procedures, and mutations in different glyoxylate reductase loci can be stacked by genetic crossing. See, for example, Gruis, et al (2002) Plant Cell 14:2863-2882. In another embodiment of this invention, dominant mutants can be used to trigger RNA silencing due to gene inversion and recombination of a duplicated gene locus. See, for example, Kusaba, et al, (2003) Plant Cell 15:1455-1467.

In alternative embodiments, glyoxylate reductase down-regulation can be induced at the desired moment using a spray (systemic application) with inhibitory nucleic acids, such as RNA or DNA molecules that function in RNA-mediated gene silencing (similar to the above described molecules) which target endogenous glyoxylate reductase, as e.g. described in WO2011/112570 (incorporated herein by reference).

In yet another embodiment the invention encompasses additional methods for reducing or eliminating the activity of one or more glyoxylate reductase polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleotide bases. Such vectors and methods of use are known in the art. See, for example, U.S. Pat. No. 5,565,350; U.S. Pat. No. 5,731,181; U.S. Pat. No. 5,756,325; U.S. Pat. No. 5,760,012; U.S. Pat. No. 5,795,972 and U.S. Pat. No. 5,871,984, each of which are herein incorporated by reference. Where polynucleotides are used to decrease or inhibit glyoxylate reductase activity, it is recognized that modifications of the exemplary sequences disclosed herein may be made as long as the sequences act to decrease or inhibit expression of the corresponding mRNA. Thus, for example, polynucleotides having at least 70%, 80%, 85%, 86%, 87%, 88%, 89%, 90%, 91%, 92%, 93%, 94%, 95%, 96%, 97%, 98%, 99%, or 100% sequence identity to the exemplary sequences disclosed herein (e.g. SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 and 102) may be used. Furthermore, portions or fragments of the exemplary sequences or portions or fragments of polynucleotides sharing a particular percent sequence identity to the exemplary sequences may be used to disrupt the expression of the target gene. Generally, fragments or sequences of at least 10, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 250, 260, 280, 300, 350, 400, 450, 500, 600, 700, 800, 900, 1000, or more contiguous nucleotides, or greater of, for example, SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102 may be used. It is recognized that in particular embodiments, the complementary sequence of such sequences may be used. For example, hairpin constructs comprise both a sense sequence fragment and a complementary, or antisense, sequence fragment corresponding to the gene of interest. Antisense constructs may share less than 100% sequence identity with the gene of interest, and may comprise portions or fragments of the gene of interest, so long as the object of the embodiment is achieved, i.e., as long as expression of the gene of interest is decreased.

The glyoxylate reductase nucleic acids that may be used for the present invention comprise at least one glyoxylate reductase polynucleotide selected from the group consisting of:

(a) a polynucleotide encoding a glyoxylate reductase polypeptide and conservatively modified and polymorphic variants thereof; such as SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102, or a polynucleotide encoding a glyoxylate reductase polypeptide having the amino acid sequence of SEQ ID NO: 2, 4, 6, 8, 10, 12, 14, 16, 18, 20, 22, 24, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or 103;

(b) a polynucleotide having at least 70% sequence identity with polynucleotides of (a);

(c) a fragment of a polynucleotide encoding an glyoxylate reductase polypeptide; and (d) complementary sequences of polynucleotides of (a), (b), or (c).

Thus, in some embodiments, the method comprises introducing at least one polynucleotide sequence comprising a glyoxylate reductase nucleic acid sequence, or subsequence thereof, into a plant cell, such that the at least one polynucleotide sequence is linked to a plant-expressible promoter in a sense or antisense orientation, and where the at least one polynucleotide sequence comprises, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, about 99.5% or more sequence identity to SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102 or a subsequence thereof or a complement thereof. In another embodiment, the disruption is effected by introducing into the plant cell at least one polynucleotide sequence comprising one or more subsequences of a glyoxylate reductase nucleic acid sequence configured for RNA silencing or interference. In other embodiments, the methods of the invention are practiced with a polynucleotide comprising a member selected from the group consisting of: (a) a polynucleotide or a complement thereof, comprising, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, about 99.5% or more sequence identity to SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102 or a subsequence thereof, or a conservative variation thereof; (b) a polynucleotide, or a complement thereof, encoding a polypeptide sequence of SEQ ID NO: 2, 4, 6, 8, 10, 12, 14, 16, 18, 20, 22, 24, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or 103 or a subsequence thereof, or a conservative variation thereof; (c) a polynucleotide, or a complement thereof, that hybridizes under stringent conditions over substantially the entire length of a polynucleotide subsequence comprising at least 100 contiguous nucleotides of SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102 or that hybridizes to a polynucleotide sequence of (a) or (b); and (d) a polynucleotide that is at least about 85% identical to a polynucleotide sequence of (a), (b) or (c). In particular embodiments, a heterologous polynucleotide is introduced into a plant, wherein the heterologous polynucleotide is selected from the group consisting of: a) a nucleic acid comprising a glyoxylate reductase nucleic acid; b) a nucleic acid comprising at least 15 contiguous nucleotides of the complement of a glyoxylate reductase nucleic acid; and c) a nucleic acid encoding a transcript that is capable of forming a double-stranded RNA (e.g., a hairpin) and mediated RNA interference of a glyoxylate reductase nucleic acid, wherein said nucleic acid comprises a first nucleotide sequence comprising at least 20 contiguous nucleotides of a glyoxylate reductase nucleic acid, and a second nucleotide sequence comprising the complement of said first nucleotide sequence. In other particular embodiments, the methods comprise introducing into a plant a heterologous polynucleotide selected from the group consisting of: a) the nucleotide sequence set forth in SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102, or a complete complement thereof; b) a nucleotide sequence having at least 70%, at least 75%, at least 80%, at least 85%, at least 90%, at least 91%, at least 92%, at least 93%, at least 94%, at least 95%, at least 96%, at least 97%, at least 98%, at least 99% or greater sequence identity to SEQ ID NO: 1, 3, 5, 7, 9, 11, 13, 15, 17, 19, 21, and 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102, or a complete complement thereof; c) a nucleotide sequence encoding the polypeptide sequence of SEQ ID NO: 2, 4, 6, 8, 10, 12, 14, 16, 18, 20, 22, 24, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or 103; d) a nucleotide sequence encoding a polypeptide sequence having at least 70%, at least 75%, at least 80%, at least 85%, at least 90%, at least 91%, at least 92%, at least 93%, at least 94%, at least 95%, at least 96%, at least 97%, at least 98%, at least 99% or greater sequence identity to SEQ ID NO: 2, 4, 6, 8, 10, 12, 14, 16, 18, 20, 22, 24, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or 103; e) a nucleotide sequence comprising at least 15 contiguous nucleotides of 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102; f) a nucleotide sequence comprising at least 15 contiguous nucleotides of the complement of SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102; and g) a nucleotide sequence encoding a transcript that is capable of forming a double-stranded RNA (e.g., hairpin) and mediating RNA interference of a glyoxylate reductase nucleic acid, wherein said nucleotide sequence comprises at least 20 contiguous nucleotides of SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102, and the complement thereof. In other embodiments, the heterologous polynucleotide comprises at least 500 contiguous nucleotides of SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102 and the complement thereof. In some of these embodiments, the heterologous polynucleotide encodes a transcript that is capable of forming a double-stranded RNA (e.g., hairpin) and mediating RNA interference of a glyoxylate reductase nucleic acid. In some of these embodiments, the plant comprises a mRNA encoded by a polynucleotide having the target sequence set forth in SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102.

Methods are provided for improving yield under abiotic stress conditions, such as high light conditions, comprising planting seeds or plants having a reduced activity of at least one glyoxylate reductase in an area of cultivation having conditions of abiotic stress, in particular conditions of high light.

Prior to the planting of the seeds or plants in the area of cultivation having abiotic stress conditions, such as high light conditions, the environment can be evaluated to determine if abiotic stress conditions, such as high light conditions are present. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc.), a greenhouse, a growth chamber, etc.

The present invention provides methods utilizing, inter alia, isolated nucleic acids of RNA, DNA, homologs, paralogous genes and orthologous genes and/or chimeras thereof, comprising a glyoxylate reductase polynucleotide. This includes naturally occurring as well as synthetic variants and homologs of the sequences.

The terms "isolated" or "isolated nucleic acid" or "isolated protein" refer to material, such as a nucleic acid or a protein, which is substantially or essentially free from components which normally accompany or interact with it as found in its naturally occurring environment. The isolated material optionally comprises material not found with the material in its natural environment. Preferably, an "isolated" nucleic acid is free of sequences (preferably protein encoding sequences) that naturally flank the nucleic acid (i.e., sequences located at the 5 and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Sequences homologous, i.e., that share significant sequence identity or similarity, to those provided herein derived from maize, *Arabidopsis thaliana* or from other plants of choice, can also be used in the methods of the invention. Homologous sequences can be derived from any plant including monocots and dicots and in particular agriculturally important plant species, including but not limited to, crops such as soybean, wheat, corn (maize), potato, cotton, rice, rape, oilseed rape (including canola), sunflower, alfalfa, clover, sugarcane and turf, or fruits and vegetables, such as banana, blackberry, blueberry, strawberry and raspberry, cantaloupe, carrot, cauliflower, coffee, cucumber, eggplant, grapes, honeydew, lettuce, mango, melon, onion, *papaya*, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts and kohlrabi). Other crops, including fruits and vegetables, whose phenotype can be changed and which comprise homologous sequences include barley; rye; millet; *sorghum*; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam and sweet potato and beans. The homologous sequences may also be derived from woody species, such pine, poplar and *eucalyptus* or mint or other labiates. Homologous sequences as described above can comprise orthologous or paralogous sequences. Several different methods are known by those of skill in the art for identifying and defining these functionally homologous sequences. Three general methods for defining orthologous and paralogous genes are described; an ortholog, paralog or homolog may be identified by one or more of the methods described below. Orthologs and paralogs are evolutionarily related genes that have similar sequence and similar functions. Orthologs are structurally related genes in different species that are derived by a speciation event. Paralogs are structurally related genes within a single species that are derived by a duplication event. Within a single plant species, gene duplication may result in two copies of a particular gene, giving rise to two or more genes with similar sequence and often similar function known as paralogs. A paralog is therefore a similar gene formed by duplication within the same species. Paralogs typically cluster together or in the same Glade (a group of similar genes) when a gene family phylogeny is analyzed using programs such as CLUSTAL (Thompson, et ah, (1994) Nucleic Acids Res. 22:4673-4680; Higgins, et al, (1996) Methods Enzymol. 266:383-402).

Groups of similar genes can also be identified with pair-wise BLAST analysis (Feng and Doolittle, (1987) J. Mol. Evol. 25:351-360). Orthologous sequences can also be identified by a reciprocal BLAST strategy. Once an orthologous sequence has been identified, the function of the ortholog can be deduced from the identified function of the reference sequence. Orthologous genes from different organisms have highly conserved functions, and very often essentially identical functions (Lee, et al, (2002) Genome Res. 12:493-502; Remm, et al, (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

Glyoxylate reductase polynucleotides, such as those disclosed herein, can be used to isolate homologs, paralogs and orthologs. In this manner, methods such as PCR, hybridization, and the like can be used to identify such sequences based on their sequence homology to the glyoxylate reductase polynucleotide. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like. By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS) and strand displacement amplification (SDA). See, e.g., Diagnostic Molecular Microbiology: Principles and Applications, Persing, et al., eds., American Society for Microbiology, Washington, D.C. (1993). The product of amplification is termed an amplicon.

In hybridization techniques, all or part of a known polynucleotide is used as a probe that selectively hybridizes to other nucleic acids comprising corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as P, or any other detectable marker. Thus, for example, probes for hybridization can be made by labeling synthetic oligonucleotides based on the glyoxylate reductase sequences disclosed herein. Methods for preparation of probes for hybridization and for construction of cDNA and genomic libraries are generally known in the art and are disclosed in Sambrook et al. (1989) Molecular Cloning: A Laboratory Manual (2d ed., Cold Spring Harbor Laboratory Press, Plainview, N.Y.).

For example, the entire glyoxylate reductase sequences disclosed herein, or one or more portions thereof, may be used as probes capable of specifically hybridizing to corresponding glyoxylate reductase sequences and messenger RNAs. To achieve specific hybridization under a variety of conditions, such probes include sequences that are unique among glyoxylate reductase sequences and are at least about 10, 12, 15, 16, 17, 18, 19, 20, 21, 22, 23, 24, 25, 30, 35, 40, 50, 60, 70, 80, 90, or more nucleotides in length. Such probes may be used to amplify corresponding glyoxylate reductase sequences from a chosen plant by PCR. This technique may be used to isolate additional coding sequences from a desired plant or as a diagnostic assay to determine the presence of coding sequences in a plant. Hybridization techniques include hybridization screening of plated nucleic acid (e.g., DNA) libraries (either plaques or colonies; see, for example, Sambrook et al. (1989) Molecular Cloning: A Laboratory Manual (2d ed., Cold Spring Harbor Laboratory Press, Plainview, N.Y.). By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) Guide To Molecular Cloning Techniques, from the series Methods in Enzymology, vol. 152, Academic Press, Inc., San Diego, Calif.; Sambrook, et al., (1989) Molecular Cloning: A Laboratory Manual, 2nd ed., vols. 1-3; and Current Protocols in Molecular Biology, Ausubel, et al., eds, Current Protocols, a joint venture between Greene Publishing Associates, Inc. and John Wiley & Sons, Inc. (1994 Supplement).

Hybridization of such sequences may be carried out under stringent conditions. The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS at 37° C., and a wash in 1× to 2×SSC at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) Anal. Biochem., 138:267-84: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, part I, chapter 2, "Overview of principles of hybridization and the strategy of nucleic acid probe assays," Elsevier, New York (1993); and Current Protocols in Molecular Biology, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA and 25 mM Na phosphate at 65° C. and a wash in 0.1×SSC, 0.1% SDS at 65° C.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other. The term "hybridization complex" includes reference to a duplex nucleic acid structure formed by two single-stranded nucleic acid sequences selectively hybridized with each other.

In yet another embodiment the invention provides for a chimeric gene comprising the following operably linked DNA elements: a) a plant expressible promoter, b) a DNA region which when transcribed yields a glyoxylate reductase inhibitory RNA molecule as described above and optionally c) a 3' end region comprising transcription termination and polyadenylation signals functioning in cells of a plant.

In the present invention a "plant expressible promoter" comprises regulatory elements, which mediate the expression of a coding sequence segment in plant cells. For expression in plants, the nucleic acid molecule must be linked operably to or comprise a suitable promoter which expresses the gene at the right point in time and with the required spatial expression pattern. For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about $1/10,000$ transcripts to about $1/100,000$ transcripts, to about $1/500,0000$ transcripts per cell. Conversely, a "strong promoter" drives expression of a coding sequence at high level, or at about $1/10$ transcripts to about $1/100$ transcripts to about $1/1000$ transcripts per cell. Generally, by "medium strength promoter" is intended a promoter that drives expression of a coding sequence at a lower level than a strong promoter, in particular at a level that is in all instances below that obtained when under the control of a 35S CaMV promoter.

The term "operably linked" as used herein refers to a functional linkage between the promoter sequence and the gene of interest, such that the promoter sequence is able to initiate transcription of the gene of interest.

A "constitutive promoter" refers to a promoter that is transcriptionally active during most, but not necessarily all, phases of growth and development and under most environmental conditions, in at least one cell, tissue or organ. An "ubiquitous" promoter is active in substantially all tissues or cells of an organism. A developmentally-regulated promoter is active during certain developmental stages or in parts of the plant that undergo developmental changes. An inducible promoter has induced or increased transcription initiation in response to a chemical (for a review see Gatz 1997, *Ann. Rev. Plant Physiol. Plant Mol. Biol.*, 48:89-108), environmental or physical stimulus, or may be "stress-inducible", i.e. activated when a plant is exposed to various stress conditions, or a "pathogen-inducible" i.e. activated when a plant is exposed to exposure to various pathogens. An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific". A seed-specific promoter is transcriptionally active predominantly in seed tissue, but not necessarily exclusively in seed tissue (in cases of leaky expression). The seed-specific promoter may be active during seed development and/or during germination. The seed specific promoter may be endosperm/aleurone/embryo specific. Examples of seed-specific promoters are given in Qing Qu and Takaiwa (*Plant Biotechnol. J.* 2, 1 13-125, 2004), which disclosure is incorporated by reference herein as if fully set forth. A green tissue-specific promoter as defined herein is a promoter that is transcriptionally active predominantly in green tissue, substantially to the exclusion of any other parts of a plant, whilst still allowing for any leaky expression in these other plant parts.

Examples of constitutive promoters capable of driving such expression are the 35S, rice actin, maize ubiquitin, and eIF-4A promoters.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

"Selectable or screenable marker", "selectable or screenable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose. Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., *J. Biol. Chem.*, 275, 2000: 22255-22267; Velmurugan et al., *J. Cell Biol.*, 149, 2000: 553-566). A site-specific integration into the plant genome of the nucleic acid sequences according to the invention is possible. Similarly, marker genes can be excised using one or more rare-cleaving double strand break inducing enzyme such as megenucleases (naturally occurring or engineered to recognize a specific DNA sequence), zinc finger nucleases, TALE nucleases and the like, if recognition sites for such enzymes are present in the vicinity of the marker gene. Excision can occur via homologous recombination if homology regions flank the marker gene, or via non-homologous end-joining with two recognition sites flanking the marker gene.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention. The term "nucleic acid molecule" as used interchangeably with the term "polynucleotide" in accordance with the present invention, includes DNA, such as cDNA or genomic DNA, and RNA.

The invention further provides transgenic plants comprising a chimeric genes according to the invention, i.e. a chimeric gene comprising a DNA region which when transcribed yields a glyoxylate reductase inhibitory RNA molecule as described above. A transgenic plant for the purposes of the invention is thus understood as meaning, as above, that the nucleic acids used in the method of the invention (e.g. the chimeric genes) are not present in, or originating from, the genome of said plant, or are present in the genome of said plant but not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, heterologous expression of the nucleic acids takes place. Preferred transgenic plants are mentioned herein.

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

The term "increased expression" or "overexpression" as used herein means any form of expression that is additional to the original wild-type expression level. For the purposes of this invention, the original wild-type expression level might also be zero, i.e. absence of expression or immeasurable expression.

Methods for increasing expression of genes or gene products are well documented in the art and include, for example, overexpression driven by appropriate promoters (as described herein before), the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1 183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 1 16, Freeling and Walbot, Eds., Springer, N.Y. (1994).

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1 102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP1198985, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (*Nat. Biotech.* 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Mol. Biol. 42 (1991) 205-225). The nucleic acids or the construct to be expressed is preferably cloned into a vector, which is suitable for transforming *Agrobacterium tumefaciens*, for example pBin19 (Bevan et al (1984) *Nucl. Acids Res.* 12-8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:1-9; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). CR Acad Sci Paris Life Sci, 316: 1 194-1 199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

The genetically modified plant cells can be regenerated via all methods with which the skilled worker is familiar. Suitable methods can be found in the abovementioned publications by S. D. Kung and R. Wu, Potrykus or Hofgen and Willmitzer. Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The invention also provides mutant GLYR alleles that result in a decrease in GLYR expression/activity, and plants, plant parts and plant cells comprising such a mutant allele. For example, provided is a mutant GLYR1 allele comprising a mutation resulting in an amino acid substitution, preferably a non-synonymous amino acid substitution, such as leucine (L) to phenylalanine (F), on a position corresponding to position 244 of SEQ ID NO: 2, or a plant, plant cell or plant part comprising said mutant allele. The position corresponding to position 244 of SEQ ID NO: 2 can be established in any GLYR sequence by determining the optimal alignment between said sequence and SEQ ID NO. 2. This can for example be a mutation.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/ nucleic acid of interest.

In particular embodiments the plant cell described herein is a non-propagating plant cell, or a plant cell that cannot be regenerated into a plant, or a plant cell that cannot maintain its life by synthesizing carbohydrate and protein from the inorganics, such as water, carbon dioxide, and inorganic salt, through photosynthesis.

Plants that are particularly useful in the methods of the invention include in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena* hybrida), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera), Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja* max), *Gossypium hirsutum, Helianthus* spp. (e.g. *Helianthus annuus), Hemerocallis fulva, Hibiscus* spp., *Hordeum* spp. (e.g.

Hordeum vulgare), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

Usually an increase in yield and/or growth rate occurs whether the plant is under non-stress conditions. Plants typically respond to exposure to stress by growing more slowly. In conditions of severe stress, the plant may even stop growing altogether. Mild stress on the other hand is defined herein as being any stress to which a plant is exposed which does result in the plant ceasing to grow slower (or temporarily) but still has the capacity to resume growth when the (mild) stress disappears. Mild stress in the sense of the invention leads to a reduction in the growth of the stressed plants of less than 40%, 35%, 30% or 25%, more preferably less than 20% or 15% in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. "Mild stresses" are the everyday biotic and/or abiotic (environmental) stresses to which a plant is exposed. Abiotic stresses may be due to drought or excess water, anaerobic stress, high light stresses, salt stress, chemical toxicity, oxidative stress and hot, cold or freezing temperatures.

"Biotic stresses" are typically those stresses caused by pathogens, such as bacteria, viruses, fungi, nematodes and insects.

The "abiotic stress" may be an osmotic stress caused by a water stress, e.g. due to drought, salt stress, or freezing stress. Abiotic stress may also be an oxidative stress or a cold stress. "Freezing stress" is intended to refer to stress due to freezing temperatures, i.e. temperatures at which available water molecules freeze and turn into ice. "Cold stress", also called "chilling stress", is intended to refer to cold temperatures, e.g. temperatures below 10°, or preferably below 5° C., but at which water molecules do not freeze. As reported in Wang et al. (Planta (2003) 218: 1-14), abiotic stress leads to a series of morphological, physiological, biochemical and molecular changes that adversely affect plant growth and productivity. Drought, salinity, extreme temperatures, high light stress and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signalling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location. Plants with optimal growth conditions, (grown under non-stress conditions) typically yield in increasing order of preference at least 101%, 102%, 103%, 104%, 105%, 110%, 115%, 120%, 130%, 140% or 150% of the average production of such plant in a given environment. Average production may be calculated on harvest and/or season basis. Persons skilled in the art are aware of average yield productions of a crop.

In particular, the methods of the present invention may be performed under non-stress conditions. In an example, the methods of the present invention may be performed under non-stress conditions such as mild drought to give plants having increased yield relative to control plants.

In another embodiment, the methods of the present invention may be performed under stress conditions.

In an example, the methods of the present invention may be performed under stress conditions such as drought or high light to give plants having increased yield relative to control plants. In another example, the methods of the present invention may be performed under stress conditions such as nutrient deficiency to give plants having increased yield relative to control plants.

Nutrient deficiency may result from a lack of nutrients such as nitrogen, phosphates and other phosphorous-containing compounds, potassium, calcium, magnesium, manganese, iron and boron, amongst others.

In yet another example, the methods of the present invention may be performed under stress conditions such as salt stress to give plants having increased yield relative to control plants. The term salt stress is not restricted to common salt (NaCl), but may be any one or more of: NaCl, KCl, LiCl, $MgCl_2$, $CaCl_2$, amongst others.

In yet another example, the methods of the present invention may be performed under stress conditions such as cold stress or freezing stress to give plants having increased yield relative to control plants.

The terms "increase", "improve" or "enhance" are interchangeable and shall mean in the sense of the application at least a 3%, 4%, 5%, 6%, 7%, 8%, 9% or 10%, preferably at least 15% or 20%, more preferably 25%, 30%, 35% or 40% more yield and/or growth in comparison to control plants as defined herein.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The sequence listing contained in the file named "BCS13_2004_WO1_ST25", which is 318 kilobytes (size as measured in Microsoft Windows®), contains 105 sequences SEQ ID NO: 1 through SEQ ID NO: 105, is filed herewith by electronic submission and is incorporated by reference herein.

Examples

1. Sequences of the *Arabidopsis thaliana* Cytosolic Glyoxylate Reductase (GLYR1)

The genomic sequence of the *Arabidopsis thaliana* GLYR1 is depicted in SEQ ID NO: 25.

The coding sequence of the *Arabidopsis thaliana* GLYR1 (AT3G25530_full length CDS) is depicted in SEQ ID NO: 1.

```
                                                          SEQ ID NO: 1
   1    ATGGAAGTAG GGTTTCTGGG TTTGGGAATC ATGGGAAAAG CCATGTCAAT
  51    GAATCTATTG AAGAATGGAT TCAAAGTCAC TGTATGGAAC AGAACACTCT
 101    CCAAGTGTGA TGAGCTTGTG GAGCATGGTG CATCAGTATG TGAGAGTCCA
 151    GCTGAAGTAA TCAAGAAATG CAAATACACT ATTGCTATGC TCTCTGATCC
 201    TTGTGCTGCT CTTTCGGTTG TTTTCGATAA AGGCGGTGTT TTGGAGCAGA
 251    TATGTGAAGG AAAAGGTTAT ATCGATATGT CGACTGTTGA TGCAGAGACT
 301    TCTTTGAAGA TCAATGAGGC AATCACCGGG AAGGGTGGTC GGTTCGTAGA
 351    AGGTCCGGTT TCAGGTAGCA AAAAGCCAGC TGAAGATGGC CAACTCATTA
 401    TCCTTGCTGC TGGTGACAAG GCACTCTTTG AGGAATCAAT CCCAGCTTTT
 451    GATGTCTTGG GAAGAGATC GTTTTACTTG GGACAAGTTG GAAACGGAGC
 501    TAAAATGAAG CTAATAGTGA ACATGATAAT GGGAAGCATG ATGAATGCAT
 551    TCTCTGAGGG GCTTGTATTG GCTGACAAGA GTGGACTTAG CTCTGACACT
 601    CTTTTGGATA TTCTGGATCT GGGAGCAATG ACTAACCCGA TGTTCAAGGG
 651    GAAAGGACCT TCAATGAACA AGAGTAGTTA CCCACCAGCA TTTCCATTGA
 701    AACATCAGCA GAAAGACATG AGGCTAGCTC TTGCTCTTGG CGATGAAAAC
 751    GCGGTTTCCA TGCCTGTAGC CGCGGCTGCA AACGAGGCTT TTAAGAAGGC
 801    GAGAAGCTTG GGACTAGGAG ATCTCGACTT CTCTGCTGTG ATTGAAGCTG
 851    TGAAATTCTC CCGCGAATAG
```

The amino acid sequence of the *Arabidopsis* is depicted in SEQ ID NO: 2.

```
AT3G25530_protein sequence,
                                                          SEQ ID NO: 2
   1    MEVGFLGLGI MGKAMSMNLL KNGFKVTVWN RTLSKCDELV EHGASVCESP
  51    AEVIKKCKYT IAMLSDPCAA LSVVFDKGGV LEQICEGKGY IDMSTVDAET
 101    SLKINEAITG KGGRFVEGPV SGSKKPAEDG QLIILAAGDK ALFEESIPAF
 151    DVLGKRSFYL GQVGNGAKMK LIVNMIMGSM MNAFSEGLVL ADKSGLSSDT
 201    LLDILDLGAM TNPMFKGKGP SMNKSSYPPA FPLKHQQKDM RLALALGDEN
 251    AVSMPVAAAA NEAFKKARSL GLGDLDFSAV IEAVKFSRE
```

2. Orthologous Genes of the *Arabidopsis Thaliana* GLYR1 Gene Present in Crops

Using PLAZA 2.5 (http://bioinformatics.psb.ugent./be/plaza/) orthologous gene families have been identified in different plant species. A phylogenetic tree of the orthologous gene families is depicted in FIG. 1.

FIG. 2 shows the pie chart of the number of orthologous genes found in different species. Table 1 contains the identifiers of the orthologous genes of AT3G25530 in relevant crop species.

TABLE 1

| Species | gene_id | evidence_count | evidences |
|---|---|---|---|
| *Glycine max* | GM16G03160 | 3 | ORTHO BHIF TROG |
| *Glycine max* | GM07G06570 | 3 | ORTHO BHIF TROG |
| *Medicago truncatula* | MT4G090220 | 3 | ORTHO BHIF TROG |
| *Oryza sativa* ssp. *japonica* | OS02G35500 | 3 | ORTHO BHIF TROG |
| *Oryza sativa* ssp. *indica* | OSINDICA_02G34170 | 3 | ORTHO BHIF TROG |
| *Populus trichocarpa* | PT14G16940 | 4 | ORTHO anchor_point BHIF TROG |
| *Sorghum bicolor* | SB04G023180 | 3 | ORTHO BHIF TROG |
| *Vitis vinifera* | VV00G08940 | 2 | ORTHO BHIF |
| *Vitis vinifera* | VV00G15140 | 1 | TROG |
| *Zea mays* | ZM04G16720 | 2 | ORTHO BHIF |
| *Zea mays* | ZM05G31020 | 1 | TROG |
| *Lotus japonicus* | LJ0G027490 | 1 | BHIF |
| *Lotus japonicus* | LJ0G240980 | 1 | TROG |

Orthologous genes of AT3G25530 in *Glycine max*, *Medicago truncatula*, *Oryza sativa* ssp. *japonica*, *Oryza sativa* ssp. *indica*, *Populus trichocarpa*, *Sorghum bicolor*, *Vitis venifera*, *Zea mays*, *Lotus japonicus*. ORTHO: part of same orthoMCL cluster; BHIF: Best Hit Family definition; anchor point: is anchorpoint within colinear region; TROG: part of same tree orthologous group.

Sequence of the identified orthologous genes (coding sequences) and their corresponding proteins of both GLYR1 and GLYR2 are depicted in the sequence listing:

GLYR1:
 *Glycine max* (GM16G03160)—SEQ ID NO: 3, Protein sequence: SEQ ID NO: 4
 *Glycine max* (GM07G06570); SEQ ID NO: 5, Protein sequence, SEQ ID NO: 6
 *Medicago truncatula* (MT4G090220); SEQ ID NO: 7, Protein sequence: SEQ ID NO: 8
 *Oryza sativa* ssp. *japonica* (0502G35500); SEQ ID NO: 9, Protein sequence: SEQ ID NO: 10
 *Oryza sativa* ssp. *indica* (OSINDICA_02 G34170, SEQ ID NO: 11, Protein sequence: SEQ ID NO: 12
 *Populus trichocarpa* (PT14G16940), SEQ ID NO: 13, Protein sequence: SEQ ID NO: 14
 *Sorghum bicolor* (SB04G023180), SEQ ID NO: 15, Protein sequence: SEQ ID NO: 16
 *Vitis vinifera* (VV00G08940), SEQ ID NO: 17, Protein sequence: SEQ ID NO: 18
 *Vitis vinifera* (VV00G15140), SEQ ID NO: 19, Protein sequence: SEQ ID NO: 20
 *Zea mays* (ZM04G16720), SEQ ID NO: 21, Protein sequence: SEQ ID NO: 22
 *Zea mays* (ZM05G31020), SEQ ID NO: 23, Protein sequence: SEQ ID NO: 24
 *Hordeum vulgare vulgare*, SEQ ID NO: 26, Protein sequence: SEQ ID NO: 27
 *Solanum lycopersicum*, SEQ ID NO: 28, Protein sequence: SEQ ID NO: 29
 *Brachypodium distachyon*, SEQ ID NO: 30, Protein sequence: SEQ ID NO: 31
 *Brassica napus*, SEQ ID NO: 32, Protein sequence: SEQ ID NO: 33
 *Brassica napus*, SEQ ID NO: 34 Protein sequence: SEQ ID NO: 35
 *Brassica napus*, SEQ ID NO: 36, Protein sequence: SEQ ID NO: 37
 *Brassica rapa*, SEQ ID NO: 38, Protein sequence: SEQ ID NO: 39
 *Brassica rapa*, SEQ ID NO: 40, Protein sequence: SEQ ID NO: 41
 *Brassica oleracea*, SEQ ID NO: 42, Protein sequence: SEQ ID NO: 43
 *Brassica juncea*, SEQ ID NO: 44, Protein sequence: SEQ ID NO: 45
 *Brassica juncea*, SEQ ID NO: 46, Protein sequence: SEQ ID NO: 47
 *Gossypium hirsitum*, SEQ ID NO: 48, Protein sequence: SEQ ID NO: 49
 *Gossypium hirsitum*, SEQ ID NO: 50, Protein sequence: SEQ ID NO: 51
 *Gossypium arboreum*, SEQ ID NO: 52, Protein sequence: SEQ ID NO: 53
 *Triticum aestivum*, SEQ ID NO: 54, Protein sequence: SEQ ID NO: 55
 *Triticum aestivum*, SEQ ID NO: 56, Protein sequence: SEQ ID NO: 57
 *Triticum aestivum*, SEQ ID NO: 58, Protein sequence: SEQ ID NO: 59

GLYR2:
 *Arabidopsis thaliana* SEQ ID NO 60, Protein sequence: SEQ ID NO: 61
 *Glycine max* SEQ ID NO: 62, Protein sequence: SEQ ID NO: 63
 *Glycine max* SEQ ID NO: 64, Protein sequence, SEQ ID NO: 65
 *Medicago truncatula*, SEQ ID NO: 66, Protein sequence: SEQ ID NO: 67
 *Oryza sativa* ssp. *japonica*; SEQ ID NO: 68, Protein sequence: SEQ ID NO: 69
 *Oryza sativa* ssp. *indica* SEQ ID NO: 70, Protein sequence: SEQ ID NO: 71
 *Populus trichocarpa*, SEQ ID NO: 72, Protein sequence: SEQ ID NO: 73
 *Sorghum bicolor*, SEQ ID NO: 74, Protein sequence: SEQ ID NO: 75
 *Vitis vinifera* SEQ ID NO: 76, Protein sequence: SEQ ID NO: 77
 *Zea mays* SEQ ID NO: 78, Protein sequence: SEQ ID NO: 79
 *Hordeum vulgare vulgare*, SEQ ID NO: 80, Protein sequence: SEQ ID NO: 81
 *Solanum lycopersicum*, SEQ ID NO: 82, Protein sequence: SEQ ID NO: 83
 *Brachypodium distachyon*, SEQ ID NO: 84, Protein sequence: SEQ ID NO: 85
 *Brassica napus*, SEQ ID NO: 86, Protein sequence: SEQ ID NO: 87
 *Brassica napus*, SEQ ID NO: 88, Protein sequence: SEQ ID NO: 89
 *Brassica rapa*, SEQ ID NO: 90, Protein sequence: SEQ ID NO: 91
 *Brassica rapa*, SEQ ID NO: 92, Protein sequence: SEQ ID NO: 93
 *Brassica oleracea*, SEQ ID NO: 94 Protein sequence: SEQ ID NO: 95
 *Brassica oleracea*, SEQ ID NO: 96 Protein sequence: SEQ ID NO: 97
 *Gossypium hirsitum*, SEQ ID NO: 98, Protein sequence: SEQ ID NO: 99

Triticum aestivum, SEQ ID NO: 100, Protein sequence: SEQ ID NO: 101
Triticum aestivum, SEQ ID NO: 102, Protein sequence: SEQ ID NO: 103

3. Identification of a Loss-Of-Function Mutation in GLYR1

Exposure of catalase deficient Arabidopsis (Cat2-KO) plants to photorespiration promoting growth conditions leads to the onset of peroxisomal hydrogen peroxide proeduction, photoinhibition and finally leading to the induction of cell death (Vandenabeele et al., (2004) Plant J. 2004 July; 39(1):45-58.

We screened an EMS-mutagenised population of Arabidopsis thaliana catalase-deficient T-DNA insertion line cat2-2 (SALK_076998) for causative second site mutations that impaired the cell death phenotype and, to identify more subtle phenotypes, mutants that showed a less strong decrease in the F'v/F'm chlorophyll fluorescence parameter as an additional selection criterion. This reflects a reduced sensitivity of PSII function due to decreased production of photorespiratory hydrogen peroxide and/or presence of protective mechanisms directly against increased hydrogen peroxide levels or the subsequent effects. To induce photorespiration, the plants were grown in plates taped with parafilm in order to restrict gas exchange with the environment. This growing condition was combined with a constant light regime. (RGCL assay: Kerchev et al. 2014 Plant, Cell and Environment).

Mutants, showing a reversion in the catalase deficient phenotype, were retested. Confirmed mutants were further validated by verifying the presence of the cat2-2 T-DNA insert with genomic PCR and by measuring catalase enzyme activity. To estimate the level of photorespiration, the Gly/Ser ratio was determined.

library. Sequencing was performed on an Illumina HiSeq 2000 resulting in 2×100 bp paired end reads.

Analysis of deep sequencing data was performed using SHORE software (Ossowski et al., 2008) Genome Res. December; 18(12):2024-33; freely available from http://1001genomes.org) followed by SHOREmap (Schneeberger et al., (2009) Nature Methods 6(8):550-1; freely available from http://1001genomes.org). The SHORE tool is used to align small sequence reads to the reference genome. Subsequently, SHOREmap can be used to identify point mutations and/or small deletions causing the phenotype of the identified mutant. The SHOREmap interval plot provides a narrow candidate region containing the mutation. The 'annotate' tool implemented in SHOREmap is used to compare mutations in the identified candidate region with the reference sequence. Candidate mutations are ranked based on distance to the peak, effect of the base change resulting in either a synonymous or non-synonymous amino acid substitution and location, i.e. intronic, intergenic or exonic.

Raw data was quality filtered and trimmed, resulting in an average coverage of 26×. The interval plot gives a peak on chromosome 3 for our mutant (FIG. 3). Priority list of possible candidate mutations are given in table 2.

Top candidate mutation identified by deep sequencing followed by SHOREmap is a G to A change on position 730 of the CDS of AT3G25530 (SEQ ID NO: 1). This results in a non-synonymous amino acid substitution from leucine (L) to phenylalanine (F) on position 244 of SEQ ID NO: 2.

It is expected that the amino acid change in the cytosolic glyoxylate reductase protein (SEQ ID NO: 2) L244F: provokes an increased instability (based on Gibbs Free Energy calculations with the program FoldX; Schymkowitz J. et al (2005) Nucleic Acids Res. July 1, 33).

TABLE 2

Priority list of identified mutations in the candidate region. The list is pre-filtered: no SNPs in intergenic regions and no synonymous amino acid substitutions were considered.

| chrom | position | ref base | mut base | distance to peak | reads supporting base change | concordance | quality | type (either newsnp or referr) | type DNA affected | ID | isoform of gene | codon sequence position of change | codon position of change | type of AA change | ref AA | mut AA |
|---|---|---|---|---|---|---|---|---|---|---|---|---|---|---|---|---|
| 3 | 9273432 | G | A | 7226 | 15 | 1 | 10 | NEWSNP | CDS | AT3G25530 | 1 | 730 | 1 | Nonsyn | L | F |
| 3 | 8802800 | G | A | 463406 | 12 | 0.92 | 10 | NEWSNP | CDS | AT3G24290 | 1 | 98 | 2 | Nonsyn | S | F |
| 3 | 8553471 | G | A | 712735 | 21 | 1 | 10 | NEWSNP | intronic | AT3G23740 | 1 | | | | | |
| 3 | 10028222 | G | A | 762016 | 16 | 1 | 10 | NEWSNP | 3'UTR | AT3G27180 | 1 | | | | | |
| 3 | 10229222 | G | A | 963016 | 17 | 1 | 10 | NEWSNP | CDS | AT3G27610 | 1 | 92 | 2 | Nonsyn | S | F |
| 3 | 10469871 | G | A | 1203665 | 21 | 0.91 | 10 | NEWSNP | CDS | AT3G28130 | 1 | 740 | 2 | Nonsyn | G | E |
| 3 | 8004438 | G | A | 1261768 | 25 | 0.93 | 10 | NEWSNP | CDS | AT3G22590 | 1 | 433 | 1 | Nonsyn | D | N |
| 3 | 7917114 | G | A | 1349092 | 17 | 0.94 | 10 | NEWSNP | CDS | AT3G22380 | 1 | 2881 | 1 | Nonsyn | D | N |
| 3 | 7689943 | G | A | 1576263 | 20 | 0.87 | 10 | NEWSNP | intronic | AT3G21820 | 1 | | | | | |
| 3 | 7641970 | G | A | 1624236 | 14 | 1 | 10 | NEWSNP | 3'UTR | AT3G21690 | 1 | | | | | |
| 3 | 6874078 | G | A | 2392128 | 22 | 0.96 | 10 | NEWSNP | CDS | AT3G19780 | 1 | 2440 | 1 | Nonsyn | V | M |
| 3 | 11748779 | A | G | 2482573 | 4 | 0.8 | 10 | NEWSNP | intronic | AT3G29970 | 1 | | | | | |
| 3 | 6588688 | C | A | 2677518 | 20 | 0.8 | 10 | NEWSNP | intronic | AT3G19050 | 1 | | | | | |
| 3 | 6570917 | G | A | 2695289 | 24 | 0.89 | 10 | NEWSNP | CDS | AT3G19040 | 1 | 2738 | 2 | Nonsyn | T | I |

Confirmed cat2-2 cell death revertants were crossed with wild-type Landsberg erecta. More than 800 F2 individuals were scored for the reversion of the cat2-2 dependent decrease in Fv/Fm and cell death phenotype. 200 cat2-2 revertants were identified and pooled.

One single genomic DNA sample from this pool of 200 homozygous F2 revertants was used for the preparation of a 4. Characterization of GLYR1 T-DNA Insertion Mutants Transcript Analysis T-DNA insertion line GK-316D041 was identified having an insertion in the 5th exon of the GLYR1 gene. Homozygous plants were obtained and the absence of the GLYR1 transcript was confirmed by RT-PCT (FIG. 4), thereby establishing that the T-DNA insertion indeed results in a loss of function of the GLYR1 gene.

Photorespiratory Bioassay

The GK-316D041 insertion line (glyrko) was crossed into catalase deficient background (cat2ko) and subjected to the photorespiratory bioassay (RGCL) as described above in Example 3. In contrast to the single knockout (cat2ko), the double mutant cat2ko×glyr2ko is better protected (FIG. 5, table 3 and 4), thereby confirming the GLYR1 EMS mutant phenotype.

TABLE 3 cell death in photorespiratory bioassay after 4 days of RGCL

|  | glyr1 × cat2_2 | | cat2_2 KO | | wt | |
| --- | --- | --- | --- | --- | --- | --- |
|  | double KO | | no cell | cell | no cell | cell |
|  | no cell death | cell death | death | death | death | death |
| # plants | 41 | 0 | 2 | 23 | 39 | 0 |
| % plants | 100 | 0 | 8 | 92 | 100 | 0 |

TABLE 4

F'v/F'm values of Col-0, glyr1 × cat2_2 double KO and cat2_2 plants at the start of RGCL treatment and after 2 and 4 days of RGCL

|  | 0 days RGCL | 2 days RGCL | 4 days RGCL |
| --- | --- | --- | --- |
| Col-0 | 0.736 ± 0.006 | 0.671 ± 0.009 | 0.608 ± 0.013 |
| glyr1 × cat2_2 | 0.661 ± 0.006 | 0.436 ± 0.005 | 0.230 ± 0.007 |
| cat2_2 | 0.647 ± 0.009 | 0.291 ± 0.008 | 0.079 ± 0.004 |

Plant Phenotype in Soil

When comparing the growth performance of cat2ko/glyr1ko with cat2ko, double mutant was clearly growing better. BC2F3 is the backcross of the original EMS mutant (FIG. 6). Quantification of the leaf area (green) using ImageJ™ is depicted in table 5.

TABLE 5

Quantification of green leaf area (pixels) of FIG. 6

| Plant (top to bottom) | Glyr × cat2_2 (left) | Glyr × cat2_2 (right) | Cat2_2 | BCF3 |
| --- | --- | --- | --- | --- |
| Plant 1 | 11004 | 15225 | 10925 | 15820 |
| Plant 2 | 13477 | 15462 | 6343 | 14074 |
| Plant 3 | 11241 | 13534 | 12103 | 11728 |

When grown under high light stress conditions, this provoked clear cell death in cat2ko, while no cell death was observed after 48 hrs in double mutant (FIG. 7). Quantification of the leaf area (green) using ImageJ™ is depicted in table 6. Thus, the GLYR1 mutation improves the high light stress resistance of the cat2ko.

TABLE 6

Quantification of green leaf area (pixels) of FIG. 7

| Plant (Top to bottom) | Glyr1ko/cat2ko | cat2ko |
| --- | --- | --- |
| Plant 1 | 46206 | 31058 |
| Plant 2 | 46750 | 17792 |
| Plant 3 | 42680 | 35067 |

When comparing the growth performance of glyrKO line GK-316D041 with WT plants in soil, glyrKO plants appeared grow at least as good as wt plants (FIG. 8 shows representative plants). Quantification of the leaf area (green) using ImageJ™ is depicted in table 7.

TABLE 7

Quantification of green leaf area (pixels) of FIG. 8

| Plant (top to bottom) | glyrKO | Col-0 |
| --- | --- | --- |
| Plant 1 | 24910 | 21938 |
| Plant 2 | 28706 | 25455 |

5. Generation of Transgenic *Arabidopsis* Plants

Overexpression lines expressing both wild type glyr1 and mutant glyr1 (containing the originally identified a G to A change on position 730 of the CDS) were generated. The genomic sequence was amplified by PCR from respectively *Arabidopsis* Col-0 and mutant 12_4 (the original mutant) genomic DNA and cloned into a pK7WG2D vector.

Lines expressing both wild type glyr1 and mutant glyr1 under the control of the endogenous promoter were generated. The promoter region was identified using the AGRIS database (http://arabidopsis.med.ohio-state.edu/). The 1.135 kb upstream region of the transcription initiation site, together with the genomic sequence was amplified by PCR and cloned into pB7WG.

To generate artificial microRNA plants, GLYR1-specific sequences were identified with the Web MicroRNA Designer3 (http://wmd3.weigelworld.org/cgi-bin/webapp-.cgi). The microRNA precursors were designed according to Schwab et al. (2006) and consisted of a GLYR1 miRNA and miRNA* sequence in the miR319a backbone (SEQ ID NO. 104 and 105). The precursors were cloned into pK7WG2D, operably linked to the 35S promoter and 35S terminator.

Constructs containing the genomic sequence of wild type and mutant glyr1 and the amiRNA constructs were transformed into *Arabidopsis* Col-0, cat2_2 KO by Agrobacteriumtumefaciens-mediated floral dipping (Clough and Bent, 1998). Constructs containing the wild type glyr1 were also transformed into *Arabidopsis* glyr1ko (GK-316D041) and mutant 12_4 (the original mutant).

T1 seeds obtained from self-fertilization of the primary transformants were surface-sterilized and sown on full strength Murashige and Skoog's medium supplemented with kanamycin (30 mg/mL). Kanamycin-resistant plants were transferred to soil, and the T2 seeds resulting from self-fertilization were collected. The T2 seeds were surface-sterilized, plated on the same selection medium and scored for resistance to kanamycin. Transgenic lines that displayed a 3:1 segregation ratio for kanamycin resistance to sensitivity in the T2 generation and that were 100% kanamycin-resistant in the T3 generation were selected for further analysis.

GLYR1 expression/activity in the transformants is measured by e.g. RT-PCT, western blotting, or by measuring GLYR activity as described in Hoover et al, Can. J. Bot. 85: 883-895 (2007).

6. Abiotic Stress Assays of Plants Having Down-Regulated or Upregulated Activity of the Glyoxylate Reductase Growth of the transformed plants as described in Example 5, as well as the GLYR1 EMS mutant and T-DNA mutant lines (GK-316D04, SALK_057410, SAIL_894_G08) is compared to wt plants by measuring e.g. leaf area, fresh weight or dry weight at various time points. Plants having reduced GLYR1 expression/activity show increased growth compared to control plants.

Growth of the transformed and mutant plants under high light conditions in vitro: seeds of recombinants and non-recombinant plants are plated on full strength MS medium with 1% sucrose (w/v) and 0.8% agar (w/v). The plants are grown at 21° C. with a photoperiod of 16 h light and a photon flux of 100 μmol m$^{-2}$ s$^{-1}$. 14-days-old seedlings are transferred to a continuous photon flux of 400 μmol m$^{-2}$ s$^{-1}$ (high light conditions) and the effect on yield (or CO$_2$ incorporation) is monitored.

Growth of the transformed and mutant plants under high light conditions in soil: seeds of recombinants and non-recombinant plants are grown under following growing conditions: 21° C., 60% RH, 100 μmol photons m$^{-2}$ s$^{-1}$ with a 16 h light/8 h dark cycle. 3 week old plants are then transferred to continuous HL (1000 mol μmol photons m$^{-2}$ s$^{-1}$) for 4 days. Other growing conditions remain the same.

Plants having reduced GLYR1 expression/activity show increased high light tolerance compared to control plants.

Growth of the transformed and mutant plants under high salt conditions: for the salt and osmotic tolerance assay, 4-day-old seedlings (both recombinants and non-transformed controls) are transferred to full strength MS medium supplemented with 75 or 200 mM NaCl and 150 or 300 mM mannitol, respectively. Plants having reduced GLYR1 expression/activity show increased tolerance to salt/osmotic stress compared to control plants.

To determine the effect of excess heat in vitro, 6-days-old seedlings (recombinants, mutants and controls) are incubated at 40° C. for 9 h. The effect of heat is also assessed in soil: seeds of recombinants and non-recombinant plants are grown under following growing conditions: 21° C., 60% RH, 100 μmol photons m$^{-2}$ s$^{-1}$ with a 16 h light/8 h dark cycle. 3 week old plants are then transferred to 37° C. for 4 days. Plants having reduced GLYR1 expression/activity show increased tolerance to heat stress compared to control plants.

To assess the oxidative stress tolerance, 14-day-old plants (recombinants, mutants and controls) are transferred to full strength MS medium supplemented with 8 or 16 mM H$_2$O$_2$ and with 4 or 8 μM methyl viologen. Plants having reduced GLYR1 expression/activity show increased tolerance to oxidative stress compared to control plants.

Tolerance to mild cold stress is monitored in soil. Plants (recombinants, mutants and controls) are grown under following growing conditions: 21° C., 60% RH, 100 μmol photons m$^{-2}$ s$^{-1}$ with a 16 h light/8 h dark cycle. 3 week old plants are then transferred to 4° C. for 7 days. Plants having reduced GLYR1 expression/activity show increased tolerance to cold stress compared to control plants.

To asses drought stress, recombinants, mutants and controls are maintained under normal watering and reduced watering conditions. Plants having reduced GLYR1 expression/activity show increased tolerance to drought stress compared to control plants.

The invention claimed is:

1. A plant comprising plant cells comprising a chimeric gene, said chimeric gene comprising the following elements:
   i) a plant-expressible promoter,
   ii) a DNA region which when transcribed yields a glyoxylate reductase inhibitory RNA molecule; and optionally
   iii) a 3' end region involved in transcription termination and polyadenylation, wherein said plant has suppressed photorespiration and improved CO2 fixation or wherein said plant has improved tolerance to high light stress conditions, when compared to a control plant.

2. The plant according to claim 1, which is oilseed rape, cotton, corn, rice, wheat, vegetable plants, sugarcane, sugar beets, or soybean.

3. Seeds or propagating material of a plant according to claim 1, comprising a chimeric gene a plant expressible promoter, a DNA region which when transcribed yields a glyoxylate reductase inhibitory RNA molecule, and optionally a 3' end region involved in transcription termination and polyadenylation.

4. A method to produce a plant with suppressed photorespiration and improved CO2 fixation or to produce a plant with increased tolerance to high light stress conditions comprising the following steps
   a) providing transgenic plant cells with a chimeric gene to create transgenic plant cells, said chimeric gene comprising the following operably linked DNA fragments
      1) a plant-expressible promoter;
      2) a DNA region, which when transcribed yields a glyoxylate reductase inhibitory RNA molecule; and optionally
      3) a 3' end region involved in transcription termination and polyadenylation.

5. The method of claim 4, further comprising the further steps of:
b) regenerating a population of transgenic plant lines from said transgenic plant cell; and optionally
c) identifying a plant with suppressed photorespiration and improved CO2 fixation, optionally wherein said selection occurs by growing the population of transgenic plant lines under high light stress conditions.

6. The method of claim 4, wherein said inhibitory glyoxylate reductase RNA molecule comprises at least 19 nucleotides having at least 90% identity to the nucleotide sequence of a glyoxylate reductase gene present in said plant cells.

7. The method of claim 4, wherein said inhibitory glyoxylate reductase RNA molecule comprises at least 19 nucleotides having at least 90% identity to the complement of the nucleotide sequence of a glyoxylate reductase gene present in said plant cells.

8. The method of claim 4, wherein said inhibitory glyoxylate reductase RNA molecule comprises a sense region comprising a nucleotide sequence of at least 19 nucleotides having at least 90% identity to the nucleotide sequence of the glyoxylate reductase gene present in said plant cells and an antisense region comprising a nucleotide sequence of at least 19 nucleotides having at least 90% identity to the complement of the nucleotide sequence of the glyoxylate reductase gene present in said plant cells, wherein said sense and antisense region are capable of forming a double stranded RNA region comprising said at least 19 nucleotides.

9. A method to produce a plant with suppressed photorespiration and improved CO2 fixation or with improved tolerance to stress conditions, comprising the following steps
a) subjecting a plant cell line or a plant to mutagenesis;
b) identifying those plant cells or plants that have a mutation in an endogenous glyoxylate reductase gene resulting in a reduction of the glyoxylate reductase activity;
c) optionally subjecting the identified plant cells or plants to abiotic stress conditions;
d) identifying plant cells or plants with suppressed photorespiration and improved CO2 fixation or with increased tolerance to high light stress conditions.

10. A method according to claim 4, wherein the plant is oilseed rape, cotton, corn, rice, wheat, vegetable plants, sugarcane, sugar beets, or soybean.

11. The plant according to claim 1, wherein said DNA region which when transcribed yields a glyoxylate reductase inhibitory RNA molecule comprises:
a. a nucleotide sequence of at least 19 nucleotides having at least 90% identity to a nucleotide sequence encoding a protein comprising the amino acid sequence of SEQ ID NO: 2, 4, 6, 8, 10, 12, 14, 16, 18, 20, 22, 24, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or 103;
b. a nucleotide sequence of at least 19 nucleotides having at least 90% identity to the complement of a nucleotide sequence encoding a protein comprising the amino acid sequence of SEQ ID NO: 2, 4, 6, 8, 10, 12, 14, 16, 18, 20, 22, 24, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or 103;
c. a nucleotide sequence of at least 19 nucleotides having at least 90% identity to the nucleotide sequence of SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102; or
d. a nucleotide sequence of at least 19 nucleotides having at least 90% identity to the complement of a nucleotide sequence of SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102.

12. The method according to claim 4, wherein said DNA region which when transcribed yields a glyoxylate reductase inhibitory RNA molecule comprises:
a. a nucleotide sequence of at least 19 nucleotides having at least 90% identity to a nucleotide sequence encoding a protein comprising the amino acid sequence of SEQ ID NO: 2, 4, 6, 8, 10, 12, 14, 16, 18, 20, 22, 24, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or 103;
b. a nucleotide sequence of at least 19 nucleotides having at least 90% identity to the complement of a nucleotide sequence encoding a protein comprising the amino acid sequence of SEQ ID NO: 2, 4, 6, 8, 10, 12, 14, 16, 18, 20, 22, 24, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101 or 103;
c. a nucleotide sequence of at least 19 nucleotides having at least 90% identity to the nucleotide sequence of SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102; or
d. a nucleotide sequence of at least 19 nucleotides having at least 90% identity to the complement of a nucleotide sequence of SEQ ID NO: 1, 3, 5, 7, 9, 11, 13, 15, 17, 19, 21, 23, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 or 102.

* * * * *

SEQUENCE LISTING

```
<160> NUMBER OF SEQ ID NOS: 105

<210> SEQ ID NO 1
<211> LENGTH: 870
<212> TYPE: DNA
<213> ORGANISM: Arabidopsis thaliana
<220> FEATURE:
<221> NAME/KEY: CDS
<222> LOCATION: (1)..(870)

<400> SEQUENCE: 1 atg gaa gta ggg ttt ctg ggt ttg gga atc atg gga aaa gcc atg tca      48
Met Glu Val Gly Phe Leu Gly Leu Gly Ile Met Gly Lys Ala Met Ser
1               5                   10                  15 atg aat cta ttg aag aat gga ttc aaa gtc act gta tgg aac aga aca      96
Met Asn Leu Leu Lys Asn Gly Phe Lys Val Thr Val Trp Asn Arg Thr
            20                  25                  30 ctc tcc aag tgt gat gag ctt gtg gag cat ggt gca tca gta tgt gag     144
Leu Ser Lys Cys Asp Glu Leu Val Glu His Gly Ala Ser Val Cys Glu
        35                  40                  45 agt cca gct gaa gta atc aag aaa tgc aaa tac act att gct atg ctc     192
Ser Pro Ala Glu Val Ile Lys Lys Cys Lys Tyr Thr Ile Ala Met Leu
    50                  55                  60 tct gat cct tgt gct gct ctt tcg gtt gtt ttc gat aaa ggc ggt gtt     240
Ser Asp Pro Cys Ala Ala Leu Ser Val Val Phe Asp Lys Gly Gly Val
65                  70                  75                  80 ttg gag cag ata tgt gaa gga aaa ggt tat atc gat atg tcg act gtt     288
Leu Glu Gln Ile Cys Glu Gly Lys Gly Tyr Ile Asp Met Ser Thr Val
                85                  90                  95 gat gca gag act tct ttg aag atc aat gag gca atc acc ggg aag ggt     336
Asp Ala Glu Thr Ser Leu Lys Ile Asn Glu Ala Ile Thr Gly Lys Gly
            100                 105                 110 ggt cgg ttc gta gaa ggt ccg gtt tca ggt agc aaa aag cca gct gaa     384
Gly Arg Phe Val Glu Gly Pro Val Ser Gly Ser Lys Lys Pro Ala Glu
        115                 120                 125 gat ggc caa ctc att atc ctt gct gct ggt gac aag gca ctc ttt gag     432
```

```
Asp Gly Gln Leu Ile Ile Leu Ala Ala Gly Asp Lys Ala Leu Phe Glu
        130                 135                 140 gaa tca atc cca gct ttt gat gtc ttg ggg aag aga tcg ttt tac ttg      480
Glu Ser Ile Pro Ala Phe Asp Val Leu Gly Lys Arg Ser Phe Tyr Leu
145                 150                 155                 160 gga caa gtt gga aac gga gct aaa atg aag cta ata gtg aac atg ata      528
Gly Gln Val Gly Asn Gly Ala Lys Met Lys Leu Ile Val Asn Met Ile
                165                 170                 175 atg gga agc atg atg aat gca ttc tct gag ggg ctt gta ttg gct gac      576
Met Gly Ser Met Met Asn Ala Phe Ser Glu Gly Leu Val Leu Ala Asp
            180                 185                 190 aag agt gga ctt agc tct gac act ctt ttg gat att ctg gat ctg gga      624
Lys Ser Gly Leu Ser Ser Asp Thr Leu Leu Asp Ile Leu Asp Leu Gly
        195                 200                 205 gca atg act aac ccg atg ttc aag ggg aaa gga cct tca atg aac aag      672
Ala Met Thr Asn Pro Met Phe Lys Gly Lys Gly Pro Ser Met Asn Lys
    210                 215                 220 agt agt tac cca cca gca ttt cca ttg aaa cat cag cag aaa gac atg      720
Ser Ser Tyr Pro Pro Ala Phe Pro Leu Lys His Gln Gln Lys Asp Met
225                 230                 235                 240 agg cta gct ctt gct ctt ggc gat gaa aac gcg gtt tcc atg cct gta      768
Arg Leu Ala Leu Ala Leu Gly Asp Glu Asn Ala Val Ser Met Pro Val
                245                 250                 255 gcc gcg gct gca aac gag gct ttt aag aag gcg aga agc ttg gga cta      816
Ala Ala Ala Ala Asn Glu Ala Phe Lys Lys Ala Arg Ser Leu Gly Leu
            260                 265                 270 gga gat ctc gac ttc tct gct gtg att gaa gct gtg aaa ttc tcc cgc      864
Gly Asp Leu Asp Phe Ser Ala Val Ile Glu Ala Val Lys Phe Ser Arg
        275                 280                 285 gaa tag                                                              870
Glu

<210> SEQ ID NO 2
<211> LENGTH: 289
<212> TYPE: PRT
<213> ORGANISM: Arabidopsis thaliana

<400> SEQUENCE: 2

Met Glu Val Gly Phe Leu Gly Leu Gly Ile Met Gly Lys Ala Met Ser
1               5                   10                  15

Met Asn Leu Leu Lys Asn Gly Phe Lys Val Thr Val Trp Asn Arg Thr
                20                  25                  30

Leu Ser Lys Cys Asp Glu Leu Val Glu His Gly Ala Ser Val Cys Glu
            35                  40                  45

Ser Pro Ala Glu Val Ile Lys Lys Cys Lys Tyr Thr Ile Ala Met Leu
        50                  55                  60

Ser Asp Pro Cys Ala Ala Leu Ser Val Val Phe Asp Lys Gly Gly Val
65                  70                  75                  80

Leu Glu Gln Ile Cys Glu Gly Lys Gly Tyr Ile Asp Met Ser Thr Val
                85                  90                  95

Asp Ala Glu Thr Ser Leu Lys Ile Asn Glu Ala Ile Thr Gly Lys Gly
                100                 105                 110

Gly Arg Phe Val Glu Gly Pro Val Ser Gly Ser Lys Lys Pro Ala Glu
        115                 120                 125

Asp Gly Gln Leu Ile Ile Leu Ala Ala Gly Asp Lys Ala Leu Phe Glu
    130                 135                 140

Glu Ser Ile Pro Ala Phe Asp Val Leu Gly Lys Arg Ser Phe Tyr Leu
145                 150                 155                 160
```

```
Gly Gln Val Gly Asn Gly Ala Lys Met Lys Leu Ile Val Asn Met Ile
            165                 170                 175

Met Gly Ser Met Met Asn Ala Phe Ser Glu Gly Leu Val Leu Ala Asp
        180                 185                 190

Lys Ser Gly Leu Ser Ser Asp Thr Leu Leu Asp Ile Leu Asp Leu Gly
    195                 200                 205

Ala Met Thr Asn Pro Met Phe Lys Gly Lys Gly Pro Ser Met Asn Lys
210                 215                 220

Ser Ser Tyr Pro Pro Ala Phe Pro Leu Lys His Gln Gln Lys Asp Met
225                 230                 235                 240

Arg Leu Ala Leu Ala Leu Gly Asp Glu Asn Ala Val Ser Met Pro Val
                245                 250                 255

Ala Ala Ala Ala Asn Glu Ala Phe Lys Lys Ala Arg Ser Leu Gly Leu
            260                 265                 270

Gly Asp Leu Asp Phe Ser Ala Val Ile Glu Ala Val Lys Phe Ser Arg
        275                 280                 285

Glu

<210> SEQ ID NO 3
<211> LENGTH: 873
<212> TYPE: DNA
<213> ORGANISM: Glycine max
<220> FEATURE:
<221> NAME/KEY: CDS
<222> LOCATION: (1)..(873)

<400> SEQUENCE: 3 atg gag gtt gga ttt ttg ggt ttg ggg ata atg ggc aag gct atg gca        48
Met Glu Val Gly Phe Leu Gly Leu Gly Ile Met Gly Lys Ala Met Ala
1               5                   10                  15 atc aat ctt cta cgc cat ggc ttc aaa gtc act gtt tgg aac aga acc        96
Ile Asn Leu Leu Arg His Gly Phe Lys Val Thr Val Trp Asn Arg Thr
                20                  25                  30 ctc tcc aag tgt gac gaa ctc gtg caa cat ggt gct tca gtt gga gaa       144
Leu Ser Lys Cys Asp Glu Leu Val Gln His Gly Ala Ser Val Gly Glu
            35                  40                  45 acc cca gca act gta gtc aag aaa tgc aag tat aca att gca atg tta       192
Thr Pro Ala Thr Val Val Lys Lys Cys Lys Tyr Thr Ile Ala Met Leu
        50                  55                  60 tct gat cct tcg gct gct tta tcg gtt gtg ttt gat aat gat ggt gtt       240
Ser Asp Pro Ser Ala Ala Leu Ser Val Val Phe Asp Asn Asp Gly Val
65                  70                  75                  80 ctt gag cat att aat gga aaa ggt tat att gac atg tca aca gtt aat       288
Leu Glu His Ile Asn Gly Lys Gly Tyr Ile Asp Met Ser Thr Val Asn
                85                  90                  95 gct gat aca tct tcc aaa ata tct gag gct atc aaa gca aaa ggt ggt       336
Ala Asp Thr Ser Ser Lys Ile Ser Glu Ala Ile Lys Ala Lys Gly Gly
            100                 105                 110 tac ttc ctt gaa ggt cct gtt tcg ggt agc aag aag cct gca gaa gat       384
Tyr Phe Leu Glu Gly Pro Val Ser Gly Ser Lys Lys Pro Ala Glu Asp
        115                 120                 125 ggc caa ctc ata ata ctt gct gct gga cat aag gca ttg tat gat gaa       432
Gly Gln Leu Ile Ile Leu Ala Ala Gly His Lys Ala Leu Tyr Asp Glu
    130                 135                 140 gtg ctt cca gca ttt gat ata ctg ggg aag aag tct ttc ttt ctg ggt       480
Val Leu Pro Ala Phe Asp Ile Leu Gly Lys Lys Ser Phe Phe Leu Gly
145                 150                 155                 160 gag gtt gga aat ggt gca aaa atg aaa cta gtt gtt aac atg ata atg       528
```

```
                   Glu Val Gly Asn Gly Ala Lys Met Lys Leu Val Val Asn Met Ile Met
                                   165                 170                 175 ggc agt atg atg aat gct ttc tct gag gga atc aca cta gct gaa aga                576
Gly Ser Met Met Asn Ala Phe Ser Glu Gly Ile Thr Leu Ala Glu Arg
            180                 185                 190 agt ggt ttg aac cct ggt act ctt ctt gat gtg ctg gat ctt ggt gcc                624
Ser Gly Leu Asn Pro Gly Thr Leu Leu Asp Val Leu Asp Leu Gly Ala
        195                 200                 205 ata agt aac ggc atg ttt aaa ttg aaa gga cct aca atg ctc caa aac                672
Ile Ser Asn Gly Met Phe Lys Leu Lys Gly Pro Thr Met Leu Gln Asn
    210                 215                 220 agt tat tcc cca gct ttt ccg ctg aaa cac cag cag aag gac atg aga                720
Ser Tyr Ser Pro Ala Phe Pro Leu Lys His Gln Gln Lys Asp Met Arg
225                 230                 235                 240 tta gct ctt gcc ctt gga gat gaa aat gct gta tca atg cca gta gca                768
Leu Ala Leu Ala Leu Gly Asp Glu Asn Ala Val Ser Met Pro Val Ala
                245                 250                 255 gct gca gca aac gag gct ttc aag aaa gcc aga agc atg ggg ttg gga                816
Ala Ala Ala Asn Glu Ala Phe Lys Lys Ala Arg Ser Met Gly Leu Gly
            260                 265                 270 gac ctt gat ttt tca gca gtt cat gag act ttg aaa gct cct gat cat                864
Asp Leu Asp Phe Ser Ala Val His Glu Thr Leu Lys Ala Pro Asp His
        275                 280                 285 tca tct tga                                                                    873
Ser Ser
    290

<210> SEQ ID NO 4
<211> LENGTH: 290
<212> TYPE: PRT
<213> ORGANISM: Glycine max

<400> SEQUENCE: 4

Met Glu Val Gly Phe Leu Gly Leu Gly Ile Met Gly Lys Ala Met Ala
1               5                   10                  15

Ile Asn Leu Leu Arg His Gly Phe Lys Val Thr Val Trp Asn Arg Thr
            20                  25                  30

Leu Ser Lys Cys Asp Glu Leu Val Gln His Gly Ala Ser Val Gly Glu
        35                  40                  45

Thr Pro Ala Thr Val Val Lys Lys Cys Lys Tyr Thr Ile Ala Met Leu
    50                  55                  60

Ser Asp Pro Ser Ala Ala Leu Ser Val Val Phe Asp Asn Asp Gly Val
65                  70                  75                  80

Leu Glu His Ile Asn Gly Lys Gly Tyr Ile Asp Met Ser Thr Val Asn
                85                  90                  95

Ala Asp Thr Ser Ser Lys Ile Ser Glu Ala Ile Lys Ala Lys Gly Gly
            100                 105                 110

Tyr Phe Leu Glu Gly Pro Val Ser Gly Ser Lys Lys Pro Ala Glu Asp
        115                 120                 125

Gly Gln Leu Ile Ile Leu Ala Ala Gly His Lys Ala Leu Tyr Asp Glu
    130                 135                 140

Val Leu Pro Ala Phe Asp Ile Leu Gly Lys Lys Ser Phe Phe Leu Gly
145                 150                 155                 160

Glu Val Gly Asn Gly Ala Lys Met Lys Leu Val Val Asn Met Ile Met
                165                 170                 175

Gly Ser Met Met Asn Ala Phe Ser Glu Gly Ile Thr Leu Ala Glu Arg
            180                 185                 190
```

```
Ser Gly Leu Asn Pro Gly Thr Leu Asp Val Leu Asp Leu Gly Ala
            195                 200                 205

Ile Ser Asn Gly Met Phe Lys Leu Lys Gly Pro Thr Met Leu Gln Asn
    210                 215                 220

Ser Tyr Ser Pro Ala Phe Pro Leu Lys His Gln Gln Lys Asp Met Arg
225                 230                 235                 240

Leu Ala Leu Ala Leu Gly Asp Glu Asn Ala Val Ser Met Pro Val Ala
                245                 250                 255

Ala Ala Ala Asn Glu Ala Phe Lys Lys Ala Arg Ser Met Gly Leu Gly
            260                 265                 270

Asp Leu Asp Phe Ser Ala Val His Glu Thr Leu Lys Ala Pro Asp His
        275                 280                 285

Ser Ser
    290

<210> SEQ ID NO 5
<211> LENGTH: 873
<212> TYPE: DNA
<213> ORGANISM: Glycine max
<220> FEATURE:
<221> NAME/KEY: CDS
<222> LOCATION: (1)..(873)

<400> SEQUENCE: 5
```

| | | | | | | | | | | | | | | | | |
|---|---|---|---|---|---|---|---|---|---|---|---|---|---|---|---|---|
| atg | gag | ttt | gga | ttt | ttg | ggt | ttg | ggg | ata | atg | ggt | aag | gct | atg | gca | 48 |
| Met | Glu | Phe | Gly | Phe | Leu | Gly | Leu | Gly | Ile | Met | Gly | Lys | Ala | Met | Ala | |
| 1 | | | | 5 | | | | | 10 | | | | | 15 | | |
| atc | aat | ctg | cta | cgc | cat | ggc | ttc | aag | gtc | act | att | tgg | aac | aga | acc | 96 |
| Ile | Asn | Leu | Leu | Arg | His | Gly | Phe | Lys | Val | Thr | Ile | Trp | Asn | Arg | Thr | |
| | | | 20 | | | | | 25 | | | | | 30 | | | |
| ctc | tcc | aag | tgt | gat | gaa | ctc | gtg | caa | cat | ggt | gct | tca | gtt | gga | gaa | 144 |
| Leu | Ser | Lys | Cys | Asp | Glu | Leu | Val | Gln | His | Gly | Ala | Ser | Val | Gly | Glu | |
| | 35 | | | | | 40 | | | | | 45 | | | | | |
| acc | cca | gca | act | gta | gtc | aag | aaa | tgc | aag | tat | acc | att | gca | atg | tta | 192 |
| Thr | Pro | Ala | Thr | Val | Val | Lys | Lys | Cys | Lys | Tyr | Thr | Ile | Ala | Met | Leu | |
| 50 | | | | | 55 | | | | | 60 | | | | | | |
| tct | gat | cct | tcg | gct | gct | tta | tcg | gtt | gtg | ttt | gat | aaa | gat | ggt | gtt | 240 |
| Ser | Asp | Pro | Ser | Ala | Ala | Leu | Ser | Val | Val | Phe | Asp | Lys | Asp | Gly | Val | |
| 65 | | | | 70 | | | | | 75 | | | | | 80 | | |
| ctt | gag | cat | att | aat | gga | aaa | tgt | tat | att | gac | atg | tca | aca | gtt | gat | 288 |
| Leu | Glu | His | Ile | Asn | Gly | Lys | Cys | Tyr | Ile | Asp | Met | Ser | Thr | Val | Asp | |
| | | | | 85 | | | | | 90 | | | | | 95 | | |
| gct | gat | aca | tct | tcc | aaa | ata | tct | gag | act | atc | aaa | gca | aaa | ggt | ggt | 336 |
| Ala | Asp | Thr | Ser | Ser | Lys | Ile | Ser | Glu | Thr | Ile | Lys | Ala | Lys | Gly | Gly | |
| | | | 100 | | | | | 105 | | | | | 110 | | | |
| tac | ttc | ctt | gaa | gct | cct | gtt | tcg | ggt | agc | aag | aag | cca | gca | gaa | gat | 384 |
| Tyr | Phe | Leu | Glu | Ala | Pro | Val | Ser | Gly | Ser | Lys | Lys | Pro | Ala | Glu | Asp | |
| | | 115 | | | | | 120 | | | | | 125 | | | | |
| ggc | caa | ctc | ata | ata | ctt | gct | gct | gga | gat | aag | gca | ttg | tat | gat | gaa | 432 |
| Gly | Gln | Leu | Ile | Ile | Leu | Ala | Ala | Gly | Asp | Lys | Ala | Leu | Tyr | Asp | Glu | |
| | 130 | | | | | 135 | | | | | 140 | | | | | |
| gtg | ctt | cca | gca | ttt | gat | gta | ctg | ggg | aag | aag | tct | ttc | ttt | ctg | ggt | 480 |
| Val | Leu | Pro | Ala | Phe | Asp | Val | Leu | Gly | Lys | Lys | Ser | Phe | Phe | Leu | Gly | |
| 145 | | | | 150 | | | | | 155 | | | | | 160 | | |
| gag | gtt | gga | aat | ggt | gca | aaa | atg | aaa | ctt | gtt | gtt | aac | atg | ata | atg | 528 |
| Glu | Val | Gly | Asn | Gly | Ala | Lys | Met | Lys | Leu | Val | Val | Asn | Met | Ile | Met | |
| | | | | 165 | | | | | 170 | | | | | 175 | | |
| ggc | agt | atg | atg | aat | gct | ttc | tct | gag | gga | ctc | aca | cta | gct | gaa | aga | 576 |
| Gly | Ser | Met | Met | Asn | Ala | Phe | Ser | Glu | Gly | Leu | Thr | Leu | Ala | Glu | Arg | |
| | | | 180 | | | | | 185 | | | | | 190 | | | |

```
agt ggt ttg aac cct gga act ctt ctc gat gtg ctg gat ctt ggt gcc    624
Ser Gly Leu Asn Pro Gly Thr Leu Leu Asp Val Leu Asp Leu Gly Ala
            195                 200                 205 ata agt aac ggc atg ttt aaa ttg aaa gga cct aca atg ctc caa aac    672
Ile Ser Asn Gly Met Phe Lys Leu Lys Gly Pro Thr Met Leu Gln Asn
    210                 215                 220 agt tat tcc cca gct ttt ccg ctg aaa cac cag cag aag gac atg aga    720
Ser Tyr Ser Pro Ala Phe Pro Leu Lys His Gln Gln Lys Asp Met Arg
225                 230                 235                 240 tta gct ctt gcc ctt gga gat gaa aat gct gta tca atg cca gta gca    768
Leu Ala Leu Ala Leu Gly Asp Glu Asn Ala Val Ser Met Pro Val Ala
                245                 250                 255 gct gct gca aat gag gct ttc aag aaa gcc aga agc atg ggg ttg gga    816
Ala Ala Ala Asn Glu Ala Phe Lys Lys Ala Arg Ser Met Gly Leu Gly
            260                 265                 270 gac ctt gat ttt tca gca gtt cat gag act ttg aaa gct cct gat cat    864
Asp Leu Asp Phe Ser Ala Val His Glu Thr Leu Lys Ala Pro Asp His
            275                 280                 285 tca tct tga                                                         873
Ser Ser
    290

<210> SEQ ID NO 6
<211> LENGTH: 290
<212> TYPE: PRT
<213> ORGANISM: Glycine max

<400> SEQUENCE: 6

Met Glu Phe Gly Phe Leu Gly Leu Gly Ile Met Gly Lys Ala Met Ala
1               5                   10                  15

Ile Asn Leu Leu Arg His Gly Phe Lys Val Thr Ile Trp Asn Arg Thr
            20                  25                  30

Leu Ser Lys Cys Asp Glu Leu Val Gln His Gly Ala Ser Val Gly Glu
        35                  40                  45

Thr Pro Ala Thr Val Val Lys Lys Cys Lys Tyr Thr Ile Ala Met Leu
    50                  55                  60

Ser Asp Pro Ser Ala Ala Leu Ser Val Val Phe Asp Lys Asp Gly Val
65                  70                  75                  80

Leu Glu His Ile Asn Gly Lys Cys Tyr Ile Asp Met Ser Thr Val Asp
                85                  90                  95

Ala Asp Thr Ser Ser Lys Ile Ser Glu Thr Ile Lys Ala Lys Gly Gly
            100                 105                 110

Tyr Phe Leu Glu Ala Pro Val Ser Gly Ser Lys Lys Pro Ala Glu Asp
        115                 120                 125

Gly Gln Leu Ile Ile Leu Ala Ala Gly Asp Lys Ala Leu Tyr Asp Glu
    130                 135                 140

Val Leu Pro Ala Phe Asp Val Leu Gly Lys Ser Phe Phe Leu Gly
145                 150                 155                 160

Glu Val Gly Asn Gly Ala Lys Met Lys Leu Val Val Asn Met Ile Met
                165                 170                 175

Gly Ser Met Met Asn Ala Phe Ser Glu Gly Leu Thr Leu Ala Glu Arg
            180                 185                 190

Ser Gly Leu Asn Pro Gly Thr Leu Leu Asp Val Leu Asp Leu Gly Ala
        195                 200                 205

Ile Ser Asn Gly Met Phe Lys Leu Lys Gly Pro Thr Met Leu Gln Asn
    210                 215                 220
```

```
Ser Tyr Ser Pro Ala Phe Pro Leu Lys His Gln Gln Lys Asp Met Arg
225                 230                 235                 240

Leu Ala Leu Ala Leu Gly Asp Glu Asn Ala Val Ser Met Pro Val Ala
                245                 250                 255

Ala Ala Ala Asn Glu Ala Phe Lys Lys Ala Arg Ser Met Gly Leu Gly
            260                 265                 270

Asp Leu Asp Phe Ser Ala Val His Glu Thr Leu Lys Ala Pro Asp His
        275                 280                 285

Ser Ser
    290

<210> SEQ ID NO 7
<211> LENGTH: 579
<212> TYPE: DNA
<213> ORGANISM: Medicago truncatula
<220> FEATURE:
<221> NAME/KEY: CDS
<222> LOCATION: (1)..(579)

<400> SEQUENCE: 7 atg gag att gga ttt ctg ggt ttg gga ata atg ggc aaa gcc atg tca    48
Met Glu Ile Gly Phe Leu Gly Leu Gly Ile Met Gly Lys Ala Met Ser
1               5                   10                  15 att aac ctt cta cgc cat ggc ttc aaa gtc act gtt tgg aac aga acc    96
Ile Asn Leu Leu Arg His Gly Phe Lys Val Thr Val Trp Asn Arg Thr
            20                  25                  30 ctc tcc aag tgt gat gaa ctc gtg gaa cat ggt gct tca gtt gga gaa   144
Leu Ser Lys Cys Asp Glu Leu Val Glu His Gly Ala Ser Val Gly Glu
        35                  40                  45 aca cct gca gct gta gtc aag aaa tgc aaa tat aca att gca atg tta   192
Thr Pro Ala Ala Val Val Lys Lys Cys Lys Tyr Thr Ile Ala Met Leu
    50                  55                  60 tct gat cct gca gct gct ttg gcg gtt gtg ttt gat aag gat ggt gtt   240
Ser Asp Pro Ala Ala Ala Leu Ala Val Val Phe Asp Lys Asp Gly Val
65                  70                  75                  80 ctc gag caa att aat gga aaa ggt tat att gac atg tca aca gtt gat   288
Leu Glu Gln Ile Asn Gly Lys Gly Tyr Ile Asp Met Ser Thr Val Asp
                85                  90                  95 gct gag aca tct atc aag ata tcc gag gca atc aaa gca aaa ggt ggt   336
Ala Glu Thr Ser Ile Lys Ile Ser Glu Ala Ile Lys Ala Lys Gly Gly
            100                 105                 110 gac ttc ctt gaa gct cct gtt tcg ggt agc aag aag cct gca gaa gat   384
Asp Phe Leu Glu Ala Pro Val Ser Gly Ser Lys Lys Pro Ala Glu Asp
        115                 120                 125 ggt caa cta gtt ata ctt gct gcc gga gac aag gca ttc tat gat gaa   432
Gly Gln Leu Val Ile Leu Ala Ala Gly Asp Lys Ala Phe Tyr Asp Glu
    130                 135                 140 gca ctt cca gca ttt gat gta ctt gga aag aaa tct ttc ttt ttg ggt   480
Ala Leu Pro Ala Phe Asp Val Leu Gly Lys Lys Ser Phe Phe Leu Gly
145                 150                 155                 160 gag gtt gga aat gga gca aaa atg aaa ctt gtt gtc aac atg gta atg   528
Glu Val Gly Asn Gly Ala Lys Met Lys Leu Val Val Asn Met Val Met
                165                 170                 175 gga agg tac ttt tca tcc ctt ttt ttc ttc ctt cta ttt tta att tgg   576
Gly Arg Tyr Phe Ser Ser Leu Phe Phe Phe Leu Leu Phe Leu Ile Trp
            180                 185                 190 tag                                                                579

<210> SEQ ID NO 8
<211> LENGTH: 192
```

```
<212> TYPE: PRT
<213> ORGANISM: Medicago truncatula

<400> SEQUENCE: 8

Met Glu Ile Gly Phe Leu Gly Leu Gly Ile Met Gly Lys Ala Met Ser
1               5                   10                  15

Ile Asn Leu Leu Arg His Gly Phe Lys Val Thr Val Trp Asn Arg Thr
            20                  25                  30

Leu Ser Lys Cys Asp Glu Leu Val Glu His Gly Ala Ser Val Gly Glu
        35                  40                  45

Thr Pro Ala Ala Val Val Lys Lys Cys Lys Tyr Thr Ile Ala Met Leu
    50                  55                  60

Ser Asp Pro Ala Ala Ala Leu Ala Val Val Phe Asp Lys Asp Gly Val
65                  70                  75                  80

Leu Glu Gln Ile Asn Gly Lys Gly Tyr Ile Asp Met Ser Thr Val Asp
                85                  90                  95

Ala Glu Thr Ser Ile Lys Ile Ser Glu Ala Ile Lys Ala Lys Gly Gly
            100                 105                 110

Asp Phe Leu Glu Ala Pro Val Ser Gly Ser Lys Lys Pro Ala Glu Asp
        115                 120                 125

Gly Gln Leu Val Ile Leu Ala Ala Gly Asp Lys Ala Phe Tyr Asp Glu
    130                 135                 140

Ala Leu Pro Ala Phe Asp Val Leu Gly Lys Lys Ser Phe Phe Leu Gly
145                 150                 155                 160

Glu Val Gly Asn Gly Ala Lys Met Lys Leu Val Val Asn Met Val Met
                165                 170                 175

Gly Arg Tyr Phe Ser Ser Leu Phe Phe Phe Leu Leu Phe Leu Ile Trp
            180                 185                 190

<210> SEQ ID NO 9
<211> LENGTH: 882
<212> TYPE: DNA
<213> ORGANISM: Oryza sativa
<220> FEATURE:
<221> NAME/KEY: CDS
<222> LOCATION: (1)..(882)

<400> SEQUENCE: 9 atg gag gtg ggg ttc ctg ggg ctg ggc atc atg ggg aag gca atg gcg    48
Met Glu Val Gly Phe Leu Gly Leu Gly Ile Met Gly Lys Ala Met Ala
1               5                   10                  15 gcc aac ctc ctc cgc cac ggc ttc cgc gtc acc gtc tgg aac cgg act    96
Ala Asn Leu Leu Arg His Gly Phe Arg Val Thr Val Trp Asn Arg Thr
            20                  25                  30 ctc tcc aag tgc cag gag ctc gtc gcg ctg ggc gcc gcc gtg ggg gag   144
Leu Ser Lys Cys Gln Glu Leu Val Ala Leu Gly Ala Ala Val Gly Glu
        35                  40                  45 acg ccg gcg gcc gtc gtc gcc aag tgc aga tac acc atc gcc atg ctc   192
Thr Pro Ala Ala Val Val Ala Lys Cys Arg Tyr Thr Ile Ala Met Leu
    50                  55                  60 tcc gac ccc agc gcc gcg cta tct gtt gta ttc gac aag gac ggc gtg   240
Ser Asp Pro Ser Ala Ala Leu Ser Val Val Phe Asp Lys Asp Gly Val
65                  70                  75                  80 ctc gag cag att ggg gaa ggg aag ggt tat gtg gac atg tcc act gtt   288
Leu Glu Gln Ile Gly Glu Gly Lys Gly Tyr Val Asp Met Ser Thr Val
                85                  90                  95 gat gcc gcc act tct tgc aag ata agc gag gct ata aaa caa aaa ggt   336
Asp Ala Ala Thr Ser Cys Lys Ile Ser Glu Ala Ile Lys Gln Lys Gly
            100                 105                 110
```

```
ggg gct ttt gtt gaa gct cca gtt tca gga agc aaa aag cca gct gaa    384
Gly Ala Phe Val Glu Ala Pro Val Ser Gly Ser Lys Lys Pro Ala Glu
        115                 120                 125 gat ggc caa ttg gtc att ctt gct gca ggg gac aag gta ttg tat gat    432
Asp Gly Gln Leu Val Ile Leu Ala Ala Gly Asp Lys Val Leu Tyr Asp
    130                 135                 140 gat atg gtc cct gca ttt gat gta ctt ggg aaa aag tcg ttc ttt ttg    480
Asp Met Val Pro Ala Phe Asp Val Leu Gly Lys Lys Ser Phe Phe Leu
145                 150                 155                 160 gga gag att gga aat gga gca aag atg aaa ctg gtg gtc aac atg atc    528
Gly Glu Ile Gly Asn Gly Ala Lys Met Lys Leu Val Val Asn Met Ile
                165                 170                 175 atg gga agt atg atg aat gct ttg tct gag gga ctc tct ctg gct gat    576
Met Gly Ser Met Met Asn Ala Leu Ser Glu Gly Leu Ser Leu Ala Asp
            180                 185                 190 aac agt ggt ttg agc ccc cag aca ctt ctt gat gtc ctg gac ctt ggc    624
Asn Ser Gly Leu Ser Pro Gln Thr Leu Leu Asp Val Leu Asp Leu Gly
        195                 200                 205 gcc atc gcg aat cca atg ttc aag ctg aaa ggg ccc tcg atg ctg caa    672
Ala Ile Ala Asn Pro Met Phe Lys Leu Lys Gly Pro Ser Met Leu Gln
    210                 215                 220 ggc agc tac aac cct gca ttt ccc ctg aaa cac cag cag aag gat atg    720
Gly Ser Tyr Asn Pro Ala Phe Pro Leu Lys His Gln Gln Lys Asp Met
225                 230                 235                 240 agg ttg gca ctt gcc cta gga gac gag aac gct gtc tcc atg cca gtg    768
Arg Leu Ala Leu Ala Leu Gly Asp Glu Asn Ala Val Ser Met Pro Val
                245                 250                 255 gca gct gct tcc aac gag gcg ttc aag aaa gca aga agc ttg gga cta    816
Ala Ala Ala Ser Asn Glu Ala Phe Lys Lys Ala Arg Ser Leu Gly Leu
            260                 265                 270 ggg gac ctg gat ttc tca gcg gtt tac gag gta ctg aag ggc gca ggt    864
Gly Asp Leu Asp Phe Ser Ala Val Tyr Glu Val Leu Lys Gly Ala Gly
        275                 280                 285 ggc tca ggc aag gcg tga                                             882
Gly Ser Gly Lys Ala
    290
```

<210> SEQ ID NO 10
<211> LENGTH: 293
<212> TYPE: PRT
<213> ORGANISM: Oryza sativa

<400> SEQUENCE: 10

```
Met Glu Val Gly Phe Leu Gly Leu Gly Ile Met Gly Lys Ala Met Ala
1               5                   10                  15

Ala Asn Leu Leu Arg His Gly Phe Arg Val Thr Val Trp Asn Arg Thr
            20                  25                  30

Leu Ser Lys Cys Gln Glu Leu Val Ala Leu Gly Ala Ala Val Gly Glu
        35                  40                  45

Thr Pro Ala Ala Val Val Ala Lys Cys Arg Tyr Thr Ile Ala Met Leu
    50                  55                  60

Ser Asp Pro Ser Ala Ala Leu Ser Val Val Phe Asp Lys Asp Gly Val
65                  70                  75                  80

Leu Glu Gln Ile Gly Glu Gly Lys Gly Tyr Val Asp Met Ser Thr Val
                85                  90                  95

Asp Ala Ala Thr Ser Cys Lys Ile Ser Glu Ala Ile Lys Gln Lys Gly
            100                 105                 110

Gly Ala Phe Val Glu Ala Pro Val Ser Gly Ser Lys Lys Pro Ala Glu
```

```
                115                 120                 125
Asp Gly Gln Leu Val Ile Leu Ala Ala Gly Asp Lys Val Leu Tyr Asp
    130                 135                 140

Asp Met Val Pro Ala Phe Asp Val Leu Gly Lys Lys Ser Phe Phe Leu
145                 150                 155                 160

Gly Glu Ile Gly Asn Gly Ala Lys Met Lys Leu Val Val Asn Met Ile
                165                 170                 175

Met Gly Ser Met Met Asn Ala Leu Ser Glu Gly Leu Ser Leu Ala Asp
            180                 185                 190

Asn Ser Gly Leu Ser Pro Gln Thr Leu Leu Asp Val Leu Asp Leu Gly
        195                 200                 205

Ala Ile Ala Asn Pro Met Phe Lys Leu Lys Gly Pro Ser Met Leu Gln
    210                 215                 220

Gly Ser Tyr Asn Pro Ala Phe Pro Leu Lys His Gln Gln Lys Asp Met
225                 230                 235                 240

Arg Leu Ala Leu Ala Leu Gly Asp Glu Asn Ala Val Ser Met Pro Val
                245                 250                 255

Ala Ala Ala Ser Asn Glu Ala Phe Lys Lys Ala Arg Ser Leu Gly Leu
            260                 265                 270

Gly Asp Leu Asp Phe Ser Ala Val Tyr Glu Val Leu Lys Gly Ala Gly
        275                 280                 285

Gly Ser Gly Lys Ala
        290

<210> SEQ ID NO 11
<211> LENGTH: 771
<212> TYPE: DNA
<213> ORGANISM: Oryza sativa
<220> FEATURE:
<221> NAME/KEY: CDS
<222> LOCATION: (1)..(771)

<400> SEQUENCE: 11 atg gag gtg ggg ttc ctg ggg ctg ggc atc atg ggg aag gca atg gcg      48
Met Glu Val Gly Phe Leu Gly Leu Gly Ile Met Gly Lys Ala Met Ala
1               5                  10                  15 gcc aac ctc ctc cgc cac ggc ttc cgc gtc acc gtc tgg aac cgg act      96
Ala Asn Leu Leu Arg His Gly Phe Arg Val Thr Val Trp Asn Arg Thr
            20                  25                  30 ctc tcc aag gtt gta ttc gac aag gac ggc gtg ctc gag cag att ggg     144
Leu Ser Lys Val Val Phe Asp Lys Asp Gly Val Leu Glu Gln Ile Gly
        35                  40                  45 gaa ggg aag ggt tat gtg gac atg tcc act gtt gat gcc gcc act tct     192
Glu Gly Lys Gly Tyr Val Asp Met Ser Thr Val Asp Ala Ala Thr Ser
    50                  55                  60 tgc aag ata agc gag gct ata aaa caa aaa ggt ggg gct ttt gtt gaa     240
Cys Lys Ile Ser Glu Ala Ile Lys Gln Lys Gly Gly Ala Phe Val Glu
65                  70                  75                  80 gct cca gtt tca gga agc aaa aag cca gct gaa gat ggc caa ttg gtc     288
Ala Pro Val Ser Gly Ser Lys Lys Pro Ala Glu Asp Gly Gln Leu Val
                85                  90                  95 att ctt gct gca ggg gac aag gta ttg tat gat gat atg gtc cct gca     336
Ile Leu Ala Ala Gly Asp Lys Val Leu Tyr Asp Asp Met Val Pro Ala
            100                 105                 110 ttt gat gta ctt ggg aaa aag tcg ttc ttt ttg gga gag att gga aat     384
Phe Asp Val Leu Gly Lys Lys Ser Phe Phe Leu Gly Glu Ile Gly Asn
        115                 120                 125 gga gca aag atg aaa ctg gta gtc aac atg atc atg gga agt atg atg     432
```

```
Gly Ala Lys Met Lys Leu Val Val Asn Met Ile Met Gly Ser Met Met
            130                 135                 140 aat gct ttg tct gag gga ctc tct ctg gct gat aac agt ggt ttg agc      480
Asn Ala Leu Ser Glu Gly Leu Ser Leu Ala Asp Asn Ser Gly Leu Ser
145                 150                 155                 160 ccc cag aca ctt ctt gat gtc ctg gac ctt ggc gcc atc gcg aat ccg      528
Pro Gln Thr Leu Leu Asp Val Leu Asp Leu Gly Ala Ile Ala Asn Pro
                165                 170                 175 atg ttc aag ctg aaa ggg ccc tcg atg ctg caa ggc agc tac aac cct      576
Met Phe Lys Leu Lys Gly Pro Ser Met Leu Gln Gly Ser Tyr Asn Pro
            180                 185                 190 gca ttt ccc ctg aaa cac cag cag aag gat atg agg ttg gca ctt gcc      624
Ala Phe Pro Leu Lys His Gln Gln Lys Asp Met Arg Leu Ala Leu Ala
        195                 200                 205 cta gga gac gag aac gct gtc tcc atg cca gtg gca gct gct tcc aac      672
Leu Gly Asp Glu Asn Ala Val Ser Met Pro Val Ala Ala Ala Ser Asn
210                 215                 220 gag gcg ttc aag aaa gca aga agc ttg gga cta ggg gac ctg gat ttc      720
Glu Ala Phe Lys Lys Ala Arg Ser Leu Gly Leu Gly Asp Leu Asp Phe
225                 230                 235                 240 tca gcg gtt tac gag gta ctg aag ggc gca ggt ggc tca ggc aag gcg      768
Ser Ala Val Tyr Glu Val Leu Lys Gly Ala Gly Gly Ser Gly Lys Ala
                245                 250                 255 tga                                                                   771
```

<210> SEQ ID NO 12
<211> LENGTH: 256
<212> TYPE: PRT
<213> ORGANISM: Oryza sativa

<400> SEQUENCE: 12

```
Met Glu Val Gly Phe Leu Gly Leu Gly Ile Met Gly Lys Ala Met Ala
1               5                   10                  15

Ala Asn Leu Leu Arg His Gly Phe Arg Val Thr Val Trp Asn Arg Thr
            20                  25                  30

Leu Ser Lys Val Val Phe Asp Lys Asp Gly Val Leu Glu Gln Ile Gly
        35                  40                  45

Glu Gly Lys Gly Tyr Val Asp Met Ser Thr Val Asp Ala Ala Thr Ser
    50                  55                  60

Cys Lys Ile Ser Glu Ala Ile Lys Gln Lys Gly Gly Ala Phe Val Glu
65                  70                  75                  80

Ala Pro Val Ser Gly Ser Lys Lys Pro Ala Glu Asp Gly Gln Leu Val
                85                  90                  95

Ile Leu Ala Ala Gly Asp Lys Val Leu Tyr Asp Asp Met Val Pro Ala
            100                 105                 110

Phe Asp Val Leu Gly Lys Lys Ser Phe Phe Leu Gly Glu Ile Gly Asn
        115                 120                 125

Gly Ala Lys Met Lys Leu Val Val Asn Met Ile Met Gly Ser Met Met
    130                 135                 140

Asn Ala Leu Ser Glu Gly Leu Ser Leu Ala Asp Asn Ser Gly Leu Ser
145                 150                 155                 160

Pro Gln Thr Leu Leu Asp Val Leu Asp Leu Gly Ala Ile Ala Asn Pro
                165                 170                 175

Met Phe Lys Leu Lys Gly Pro Ser Met Leu Gln Gly Ser Tyr Asn Pro
            180                 185                 190

Ala Phe Pro Leu Lys His Gln Gln Lys Asp Met Arg Leu Ala Leu Ala
        195                 200                 205
```

| | | | | | | | | | | | | |
|---|---|---|---|---|---|---|---|---|---|---|---|---|
| Leu | Gly | Asp | Glu | Asn | Ala | Val | Ser | Met | Pro | Val | Ala | Ala | Ser | Asn |
| | 210 | | | | 215 | | | | 220 | | | | | |
| Glu | Ala | Phe | Lys | Lys | Ala | Arg | Ser | Leu | Gly | Leu | Gly | Asp | Leu | Asp | Phe |
| 225 | | | | | 230 | | | | | 235 | | | | | 240 |
| Ser | Ala | Val | Tyr | Glu | Val | Leu | Lys | Gly | Ala | Gly | Ser | Gly | Lys | Ala |
| | | | | 245 | | | | | 250 | | | | | 255 |

<210> SEQ ID NO 13
<211> LENGTH: 870
<212> TYPE: DNA
<213> ORGANISM: Populus balsamifera subsp. trichocarpa
<220> FEATURE:
<221> NAME/KEY: CDS
<222> LOCATION: (1)..(870)

<400> SEQUENCE: 13

```
atg gag gta ggg ttc ttg ggg tta ggg ata atg gga aag gcc atg tcc      48
Met Glu Val Gly Phe Leu Gly Leu Gly Ile Met Gly Lys Ala Met Ser
1               5                   10                  15 atg aat tta ctt aaa aat ggc ttc aag gtc act gtc tgg aac agg acg      96
Met Asn Leu Leu Lys Asn Gly Phe Lys Val Thr Val Trp Asn Arg Thr
            20                  25                  30 ctc tcc aag tgt aat gaa ctg gtg gag ttt ggt gca tca att gga gaa     144
Leu Ser Lys Cys Asn Glu Leu Val Glu Phe Gly Ala Ser Ile Gly Glu
        35                  40                  45 acc cct gca caa gta gtc aag aaa tgc agg ctt act att gct atg ttg     192
Thr Pro Ala Gln Val Val Lys Lys Cys Arg Leu Thr Ile Ala Met Leu
    50                  55                  60 tcg gat cct gcc gcg gct ctt tcg gtg gtt ttt gat aaa gat ggt gta     240
Ser Asp Pro Ala Ala Ala Leu Ser Val Val Phe Asp Lys Asp Gly Val
65                  70                  75                  80 ctt gag caa att gac agc gga aaa ggt tat att gac atg tcc acg gtt     288
Leu Glu Gln Ile Asp Ser Gly Lys Gly Tyr Ile Asp Met Ser Thr Val
                85                  90                  95 gat cca gaa aca tct tcc aag atc agc cag gca att aca tca aag ggc     336
Asp Pro Glu Thr Ser Ser Lys Ile Ser Gln Ala Ile Thr Ser Lys Gly
            100                 105                 110 ggt gcc ttc ctt gag gct cct gtg tca ggt agc aag cag cct gca gaa     384
Gly Ala Phe Leu Glu Ala Pro Val Ser Gly Ser Lys Gln Pro Ala Glu
        115                 120                 125 act ggt caa ctt gta atc ctt gct gct ggg gat aag ggg ttg tat gag     432
Thr Gly Gln Leu Val Ile Leu Ala Ala Gly Asp Lys Gly Leu Tyr Glu
    130                 135                 140 gaa tca att cca gct ttt gat gtt ttg ggg aag aag tct ttc ttc ttg     480
Glu Ser Ile Pro Ala Phe Asp Val Leu Gly Lys Lys Ser Phe Phe Leu
145                 150                 155                 160 ggg caa gtc gga aat gga gca aaa atg aaa ctt gtg gtc aac atg ata     528
Gly Gln Val Gly Asn Gly Ala Lys Met Lys Leu Val Val Asn Met Ile
                165                 170                 175 atg ggc agt atg atg aat gca ttt tca gag gga ctg gtg ctg tca gaa     576
Met Gly Ser Met Met Asn Ala Phe Ser Glu Gly Leu Val Leu Ser Glu
            180                 185                 190 agg agt gga ctc aac cca cat gat ctt ctt gat atc ttg gat ctt ggt     624
Arg Ser Gly Leu Asn Pro His Asp Leu Leu Asp Ile Leu Asp Leu Gly
        195                 200                 205 gga ata gct aat cca atg ttc agg gga aaa gga cca gct atg ctc aag     672
Gly Ile Ala Asn Pro Met Phe Arg Gly Lys Gly Pro Ala Met Leu Lys
    210                 215                 220 agt aat cac tcc cct gca ttt cct ctg aaa cat cag caa aag gac atg     720
Ser Asn His Ser Pro Ala Phe Pro Leu Lys His Gln Gln Lys Asp Met
```

```
                  225                 230                 235                 240
cgg ttg gct cta gct ctt ggg gat gaa aat gct gtg tca atg cca gta           768
Arg Leu Ala Leu Ala Leu Gly Asp Glu Asn Ala Val Ser Met Pro Val
                245                 250                 255 gca gcg gca gca aat gag tct ttc aag aag gcc aga agc atg gga ttg           816
Ala Ala Ala Ala Asn Glu Ser Phe Lys Lys Ala Arg Ser Met Gly Leu
            260                 265                 270 ggg gac cta gac ttt tca gct gtg cat gag att ctg aag atg acc aag           864
Gly Asp Leu Asp Phe Ser Ala Val His Glu Ile Leu Lys Met Thr Lys
        275                 280                 285 gat taa                                                                    870
Asp
```

<210> SEQ ID NO 14
<211> LENGTH: 289
<212> TYPE: PRT
<213> ORGANISM: Populus balsamifera subsp. trichocarpa

<400> SEQUENCE: 14

```
Met Glu Val Gly Phe Leu Gly Leu Gly Ile Met Gly Lys Ala Met Ser
1               5                   10                  15

Met Asn Leu Leu Lys Asn Gly Phe Lys Val Thr Val Trp Asn Arg Thr
            20                  25                  30

Leu Ser Lys Cys Asn Glu Leu Val Glu Phe Gly Ala Ser Ile Gly Glu
        35                  40                  45

Thr Pro Ala Gln Val Val Lys Lys Cys Arg Leu Thr Ile Ala Met Leu
    50                  55                  60

Ser Asp Pro Ala Ala Ala Leu Ser Val Val Phe Asp Lys Asp Gly Val
65                  70                  75                  80

Leu Glu Gln Ile Asp Ser Gly Lys Gly Tyr Ile Asp Met Ser Thr Val
                85                  90                  95

Asp Pro Glu Thr Ser Ser Lys Ile Ser Gln Ala Ile Thr Ser Lys Gly
            100                 105                 110

Gly Ala Phe Leu Glu Ala Pro Val Ser Gly Ser Lys Gln Pro Ala Glu
        115                 120                 125

Thr Gly Gln Leu Val Ile Leu Ala Ala Gly Asp Lys Gly Leu Tyr Glu
    130                 135                 140

Glu Ser Ile Pro Ala Phe Asp Val Leu Gly Lys Lys Ser Phe Phe Leu
145                 150                 155                 160

Gly Gln Val Gly Asn Gly Ala Lys Met Lys Leu Val Asn Met Ile
                165                 170                 175

Met Gly Ser Met Met Asn Ala Phe Ser Glu Gly Leu Val Leu Ser Glu
            180                 185                 190

Arg Ser Gly Leu Asn Pro His Asp Leu Leu Asp Ile Leu Asp Leu Gly
        195                 200                 205

Gly Ile Ala Asn Pro Met Phe Arg Gly Lys Gly Pro Ala Met Leu Lys
    210                 215                 220

Ser Asn His Ser Pro Ala Phe Pro Leu Lys His Gln Gln Lys Asp Met
225                 230                 235                 240

Arg Leu Ala Leu Ala Leu Gly Asp Glu Asn Ala Val Ser Met Pro Val
                245                 250                 255

Ala Ala Ala Ala Asn Glu Ser Phe Lys Lys Ala Arg Ser Met Gly Leu
            260                 265                 270

Gly Asp Leu Asp Phe Ser Ala Val His Glu Ile Leu Lys Met Thr Lys
        275                 280                 285
```

Asp

<210> SEQ ID NO 15
<211> LENGTH: 888
<212> TYPE: DNA
<213> ORGANISM: Sorghum bicolor
<220> FEATURE:
<221> NAME/KEY: CDS
<222> LOCATION: (1)..(888)

<400> SEQUENCE: 15

```
atg gag gtg ggg ttc ctg ggt cta ggc atc atg ggc aag gca atg gcg        48
Met Glu Val Gly Phe Leu Gly Leu Gly Ile Met Gly Lys Ala Met Ala
1               5                   10                  15 gcc aac ctc ctc cgc cac ggc ttc cgc gtc acc gtc tgg aac cgg acc        96
Ala Asn Leu Leu Arg His Gly Phe Arg Val Thr Val Trp Asn Arg Thr
                20                  25                  30 ctc gcc aag tgc caa gag ctc gcc gcg ctc ggc gcc acc gtc ggg gag       144
Leu Ala Lys Cys Gln Glu Leu Ala Ala Leu Gly Ala Thr Val Gly Glu
            35                  40                  45 acg ccc gcc tcc gtc gtc tcc aag tgc aga tac acc atc gcc atg ctc       192
Thr Pro Ala Ser Val Val Ser Lys Cys Arg Tyr Thr Ile Ala Met Leu
        50                  55                  60 tcc gac cct agc gcc gca cta tca gtt gtc ttc gac aag gat ggc gtg       240
Ser Asp Pro Ser Ala Ala Leu Ser Val Val Phe Asp Lys Asp Gly Val
65                  70                  75                  80 ctc gag cag atc ggt agc ggg aag ggc tat gtg gac atg tcc act gtt       288
Leu Glu Gln Ile Gly Ser Gly Lys Gly Tyr Val Asp Met Ser Thr Val
                85                  90                  95 gac gct gca act tcg acc aag att agc gag gca gtt aaa caa aaa ggg       336
Asp Ala Ala Thr Ser Thr Lys Ile Ser Glu Ala Val Lys Gln Lys Gly
                100                 105                 110 gga gct ttc ctt gaa gct cca gtt tca ggg agc aag aag cca gct gaa       384
Gly Ala Phe Leu Glu Ala Pro Val Ser Gly Ser Lys Lys Pro Ala Glu
            115                 120                 125 gat ggt caa ttg gtc att ctt gct gca ggg gac aag cca ttg tat gac       432
Asp Gly Gln Leu Val Ile Leu Ala Ala Gly Asp Lys Pro Leu Tyr Asp
        130                 135                 140 ggt atg gtt cct gca ttt gat gta ctg ggg aag aag tca ttc ttt ctg       480
Gly Met Val Pro Ala Phe Asp Val Leu Gly Lys Lys Ser Phe Phe Leu
145                 150                 155                 160 gga gag att gga aat ggg gca aag atg aag ctt gtg gtc aac atg atc       528
Gly Glu Ile Gly Asn Gly Ala Lys Met Lys Leu Val Val Asn Met Ile
                165                 170                 175 atg gga agt atg atg aat gct ttg tcc gag gga ctt tgt ttg gcc gac       576
Met Gly Ser Met Met Asn Ala Leu Ser Glu Gly Leu Cys Leu Ala Asp
            180                 185                 190 aaa agt ggg ttg agc ccc caa aca ctt ctc gat gta ctg gac ctt ggt       624
Lys Ser Gly Leu Ser Pro Gln Thr Leu Leu Asp Val Leu Asp Leu Gly
        195                 200                 205 gcc atc gca aac cca atg ttc aag ttg aag ggg cct aca atg ctg caa       672
Ala Ile Ala Asn Pro Met Phe Lys Leu Lys Gly Pro Thr Met Leu Gln
    210                 215                 220 ggc agc tac aac cct gcg ttt ccc ctg aaa cat cag cag aag gac atg       720
Gly Ser Tyr Asn Pro Ala Phe Pro Leu Lys His Gln Gln Lys Asp Met
225                 230                 235                 240 agg tta gct ctt gct ctg gga gat gag aac gcc gtc gct atg ccc gtc       768
Arg Leu Ala Leu Ala Leu Gly Asp Glu Asn Ala Val Ala Met Pro Val
                245                 250                 255 tca gca gct gcc aat gag gcg ttc aag aag gcg aga agc ctg ggg ctg       816
Ser Ala Ala Ala Asn Glu Ala Phe Lys Lys Ala Arg Ser Leu Gly Leu
```

```
                       260                 265                 270
ggg gac cag gat ttt tcg gcg gtc tat gag gta gtg aag ggc gcg ggt        864
Gly Asp Gln Asp Phe Ser Ala Val Tyr Glu Val Val Lys Gly Ala Gly
        275                 280                 285 ggt tct ggg tct ggc cag gcg tga                                        888
Gly Ser Gly Ser Gly Gln Ala
        290                 295

<210> SEQ ID NO 16
<211> LENGTH: 295
<212> TYPE: PRT
<213> ORGANISM: Sorghum bicolor

<400> SEQUENCE: 16

Met Glu Val Gly Phe Leu Gly Leu Gly Ile Met Gly Lys Ala Met Ala
1               5                   10                  15

Ala Asn Leu Leu Arg His Gly Phe Arg Val Thr Val Trp Asn Arg Thr
            20                  25                  30

Leu Ala Lys Cys Gln Glu Leu Ala Ala Leu Gly Ala Thr Val Gly Glu
        35                  40                  45

Thr Pro Ala Ser Val Val Ser Lys Cys Arg Tyr Thr Ile Ala Met Leu
    50                  55                  60

Ser Asp Pro Ser Ala Ala Leu Ser Val Val Phe Asp Lys Asp Gly Val
65                  70                  75                  80

Leu Glu Gln Ile Gly Ser Lys Gly Tyr Val Asp Met Ser Thr Val
            85                  90                  95

Asp Ala Ala Thr Ser Thr Lys Ile Ser Glu Ala Val Lys Gln Lys Gly
            100                 105                 110

Gly Ala Phe Leu Glu Ala Pro Val Ser Gly Ser Lys Lys Pro Ala Glu
        115                 120                 125

Asp Gly Gln Leu Val Ile Leu Ala Ala Gly Asp Lys Pro Leu Tyr Asp
130                 135                 140

Gly Met Val Pro Ala Phe Asp Val Leu Gly Lys Lys Ser Phe Phe Leu
145                 150                 155                 160

Gly Glu Ile Gly Asn Gly Ala Lys Met Lys Leu Val Val Asn Met Ile
            165                 170                 175

Met Gly Ser Met Met Asn Ala Leu Ser Glu Gly Leu Cys Leu Ala Asp
        180                 185                 190

Lys Ser Gly Leu Ser Pro Gln Thr Leu Leu Asp Val Leu Asp Leu Gly
    195                 200                 205

Ala Ile Ala Asn Pro Met Phe Lys Leu Lys Gly Pro Thr Met Leu Gln
210                 215                 220

Gly Ser Tyr Asn Pro Ala Phe Pro Leu Lys His Gln Gln Lys Asp Met
225                 230                 235                 240

Arg Leu Ala Leu Ala Leu Gly Asp Glu Asn Ala Val Ala Met Pro Val
            245                 250                 255

Ser Ala Ala Ala Asn Glu Ala Phe Lys Lys Ala Arg Ser Leu Gly Leu
        260                 265                 270

Gly Asp Gln Asp Phe Ser Ala Val Tyr Glu Val Val Lys Gly Ala Gly
    275                 280                 285

Gly Ser Gly Ser Gly Gln Ala
        290                 295

<210> SEQ ID NO 17
<211> LENGTH: 876
<212> TYPE: DNA
```

<213> ORGANISM: Vitis vinifera
<220> FEATURE:
<221> NAME/KEY: CDS
<222> LOCATION: (1)..(876)

<400> SEQUENCE: 17

| | | | | | | | | | | | | | | | | |
|---|---|---|---|---|---|---|---|---|---|---|---|---|---|---|---|---|
| atg | gag | gtg | ggg | ttc | ttg | ggt | ctg | gga | ata | atg | gga | aag | gcc | atg | tcc | 48 |
| Met | Glu | Val | Gly | Phe | Leu | Gly | Leu | Gly | Ile | Met | Gly | Lys | Ala | Met | Ser | |
| 1 | | | | 5 | | | | | 10 | | | | | 15 | | |
| atc | aat | ctc | att | cgg | agt | ggc | ttc | aag | ctc | act | gtt | tgg | aac | aga | acc | 96 |
| Ile | Asn | Leu | Ile | Arg | Ser | Gly | Phe | Lys | Leu | Thr | Val | Trp | Asn | Arg | Thr | |
| | | | 20 | | | | | 25 | | | | | 30 | | | |
| ctc | tcc | aag | tgt | gat | gaa | ctt | gtg | gag | ctt | ggc | gct | tca | att | gga | gaa | 144 |
| Leu | Ser | Lys | Cys | Asp | Glu | Leu | Val | Glu | Leu | Gly | Ala | Ser | Ile | Gly | Glu | |
| | | 35 | | | | | 40 | | | | | 45 | | | | |
| act | cct | gca | gca | gta | gtt | aag | aag | tgc | aat | tat | acc | att | gca | atg | ctg | 192 |
| Thr | Pro | Ala | Ala | Val | Val | Lys | Lys | Cys | Asn | Tyr | Thr | Ile | Ala | Met | Leu | |
| | 50 | | | | | 55 | | | | | 60 | | | | | |
| tct | gat | cct | tct | gtt | gct | ctt | tcg | gtg | gtt | ttt | gac | aaa | gat | ggt | gtt | 240 |
| Ser | Asp | Pro | Ser | Val | Ala | Leu | Ser | Val | Val | Phe | Asp | Lys | Asp | Gly | Val | |
| 65 | | | | | 70 | | | | | 75 | | | | | 80 | |
| ctt | gaa | caa | att | tgc | cat | gga | aaa | ggt | tac | att | gac | atg | tca | act | gtt | 288 |
| Leu | Glu | Gln | Ile | Cys | His | Gly | Lys | Gly | Tyr | Ile | Asp | Met | Ser | Thr | Val | |
| | | | 85 | | | | | 90 | | | | | 95 | | | |
| ggt | gcc | gac | act | tct | tca | aaa | att | agt | gag | gca | att | aca | tca | aag | ggt | 336 |
| Gly | Ala | Asp | Thr | Ser | Ser | Lys | Ile | Ser | Glu | Ala | Ile | Thr | Ser | Lys | Gly | |
| | | | 100 | | | | | 105 | | | | | 110 | | | |
| ggt | tct | ttc | ctt | gaa | gct | cca | gtt | tct | gga | agt | aag | aaa | cct | gca | gaa | 384 |
| Gly | Ser | Phe | Leu | Glu | Ala | Pro | Val | Ser | Gly | Ser | Lys | Lys | Pro | Ala | Glu | |
| | | 115 | | | | | 120 | | | | | 125 | | | | |
| gat | ggt | caa | ctg | gta | att | ctt | gct | gct | ggg | gag | aag | gca | ttg | tac | gat | 432 |
| Asp | Gly | Gln | Leu | Val | Ile | Leu | Ala | Ala | Gly | Glu | Lys | Ala | Leu | Tyr | Asp | |
| | 130 | | | | | 135 | | | | | 140 | | | | | |
| gaa | gcg | att | cct | gct | ttt | gat | atc | atg | ggg | aag | aag | tct | ttt | ttc | ttg | 480 |
| Glu | Ala | Ile | Pro | Ala | Phe | Asp | Ile | Met | Gly | Lys | Lys | Ser | Phe | Phe | Leu | |
| 145 | | | | | 150 | | | | | 155 | | | | | 160 | |
| ggg | cag | gtt | gga | aat | gga | gct | aaa | atg | aaa | ctt | gtg | gtc | aac | atg | ata | 528 |
| Gly | Gln | Val | Gly | Asn | Gly | Ala | Lys | Met | Lys | Leu | Val | Val | Asn | Met | Ile | |
| | | | 165 | | | | | 170 | | | | | 175 | | | |
| atg | ggc | agt | atg | atg | aat | gca | ttt | tct | gaa | ggg | ctt | gta | ttg | gct | gac | 576 |
| Met | Gly | Ser | Met | Met | Asn | Ala | Phe | Ser | Glu | Gly | Leu | Val | Leu | Ala | Asp | |
| | | | 180 | | | | | 185 | | | | | 190 | | | |
| aga | agt | gga | ctg | aac | cct | cat | act | ctt | ctt | gat | gta | ttg | gac | ctg | ggt | 624 |
| Arg | Ser | Gly | Leu | Asn | Pro | His | Thr | Leu | Leu | Asp | Val | Leu | Asp | Leu | Gly | |
| | | 195 | | | | | 200 | | | | | 205 | | | | |
| gga | att | gct | aat | cca | atg | ttt | agg | ttg | aaa | gga | ccc | aca | atg | ata | caa | 672 |
| Gly | Ile | Ala | Asn | Pro | Met | Phe | Arg | Leu | Lys | Gly | Pro | Thr | Met | Ile | Gln | |
| | 210 | | | | | 215 | | | | | 220 | | | | | |
| aac | aat | tac | tcc | cct | gca | ttt | cct | ctg | aag | cat | cag | cag | aag | gat | atg | 720 |
| Asn | Asn | Tyr | Ser | Pro | Ala | Phe | Pro | Leu | Lys | His | Gln | Gln | Lys | Asp | Met | |
| 225 | | | | | 230 | | | | | 235 | | | | | 240 | |
| agg | ttg | gct | ctt | gct | ctt | ggg | gat | gaa | aat | gcg | gta | tcc | atg | cca | gta | 768 |
| Arg | Leu | Ala | Leu | Ala | Leu | Gly | Asp | Glu | Asn | Ala | Val | Ser | Met | Pro | Val | |
| | | | 245 | | | | | 250 | | | | | 255 | | | |
| gca | gct | gct | gcc | aat | gag | gct | ttc | aag | aaa | gct | agg | agc | ctg | gga | ttg | 816 |
| Ala | Ala | Ala | Ala | Asn | Glu | Ala | Phe | Lys | Lys | Ala | Arg | Ser | Leu | Gly | Leu | |
| | | | 260 | | | | | 265 | | | | | 270 | | | |
| ggg | gac | ctt | gac | ttt | tct | gct | gtg | tat | gag | acc | gtg | aag | acc | ctt | gaa | 864 |
| Gly | Asp | Leu | Asp | Phe | Ser | Ala | Val | Tyr | Glu | Thr | Val | Lys | Thr | Leu | Glu | |
| | | 275 | | | | | 280 | | | | | 285 | | | | |

```
cat tca tcc tga                                                           876
His Ser Ser
    290
```

<210> SEQ ID NO 18
<211> LENGTH: 291
<212> TYPE: PRT
<213> ORGANISM: Vitis vinifera

<400> SEQUENCE: 18

```
Met Glu Val Gly Phe Leu Gly Leu Gly Ile Met Gly Lys Ala Met Ser
1               5                   10                  15

Ile Asn Leu Ile Arg Ser Gly Phe Lys Leu Thr Val Trp Asn Arg Thr
            20                  25                  30

Leu Ser Lys Cys Asp Glu Leu Val Glu Leu Gly Ala Ser Ile Gly Glu
        35                  40                  45

Thr Pro Ala Ala Val Val Lys Lys Cys Asn Tyr Thr Ile Ala Met Leu
    50                  55                  60

Ser Asp Pro Ser Val Ala Leu Ser Val Val Phe Asp Lys Asp Gly Val
65                  70                  75                  80

Leu Glu Gln Ile Cys His Gly Lys Gly Tyr Ile Asp Met Ser Thr Val
                85                  90                  95

Gly Ala Asp Thr Ser Ser Lys Ile Ser Glu Ala Ile Thr Ser Lys Gly
            100                 105                 110

Gly Ser Phe Leu Glu Ala Pro Val Ser Gly Ser Lys Lys Pro Ala Glu
        115                 120                 125

Asp Gly Gln Leu Val Ile Leu Ala Ala Gly Glu Lys Ala Leu Tyr Asp
    130                 135                 140

Glu Ala Ile Pro Ala Phe Asp Ile Met Gly Lys Lys Ser Phe Phe Leu
145                 150                 155                 160

Gly Gln Val Gly Asn Gly Ala Lys Met Lys Leu Val Val Asn Met Ile
                165                 170                 175

Met Gly Ser Met Met Asn Ala Phe Ser Glu Gly Leu Val Leu Ala Asp
            180                 185                 190

Arg Ser Gly Leu Asn Pro His Thr Leu Leu Asp Val Leu Asp Leu Gly
        195                 200                 205

Gly Ile Ala Asn Pro Met Phe Arg Leu Lys Gly Pro Thr Met Ile Gln
    210                 215                 220

Asn Asn Tyr Ser Pro Ala Phe Pro Leu Lys His Gln Gln Lys Asp Met
225                 230                 235                 240

Arg Leu Ala Leu Ala Leu Gly Asp Glu Asn Ala Val Ser Met Pro Val
                245                 250                 255

Ala Ala Ala Ala Asn Glu Ala Phe Lys Lys Ala Arg Ser Leu Gly Leu
            260                 265                 270

Gly Asp Leu Asp Phe Ser Ala Val Tyr Glu Thr Val Lys Thr Leu Glu
        275                 280                 285

His Ser Ser
    290
```

<210> SEQ ID NO 19
<211> LENGTH: 234
<212> TYPE: DNA
<213> ORGANISM: Vitis vinifera
<220> FEATURE:
<221> NAME/KEY: CDS
<222> LOCATION: (1)..(234)

<400> SEQUENCE: 19

```
atg ata cca ata caa ata tgc tta cac tca caa tta aaa ata gtc atc       48
Met Ile Pro Ile Gln Ile Cys Leu His Ser Gln Leu Lys Ile Val Ile
1               5                   10                  15 ttc cgg tgg tct act cac agc tgc ata ctt cta tta cag gca att           96
Phe Arg Trp Ser Thr His Ser Cys Ile Leu Leu Leu Gln Ala Ile
            20                  25                  30 aca tca aag ggt ggt tct ttc ctt gaa gct cca gtt tct gga agt aag      144
Thr Ser Lys Gly Gly Ser Phe Leu Glu Ala Pro Val Ser Gly Ser Lys
        35                  40                  45 aaa cct gca gaa gat ggt caa ctg gta att ctt gct gct ggg gag aag      192
Lys Pro Ala Glu Asp Gly Gln Leu Val Ile Leu Ala Ala Gly Glu Lys
50                  55                  60 gta aac tta ttt gca atg ctg ctt act gtt ctt ttg tat tga              234
Val Asn Leu Phe Ala Met Leu Leu Thr Val Leu Leu Tyr
65                  70                  75

<210> SEQ ID NO 20
<211> LENGTH: 77
<212> TYPE: PRT
<213> ORGANISM: Vitis vinifera

<400> SEQUENCE: 20

Met Ile Pro Ile Gln Ile Cys Leu His Ser Gln Leu Lys Ile Val Ile
1               5                   10                  15

Phe Arg Trp Ser Thr His Ser Cys Ile Leu Leu Leu Gln Ala Ile
            20                  25                  30

Thr Ser Lys Gly Gly Ser Phe Leu Glu Ala Pro Val Ser Gly Ser Lys
        35                  40                  45

Lys Pro Ala Glu Asp Gly Gln Leu Val Ile Leu Ala Ala Gly Glu Lys
    50                  55                  60

Val Asn Leu Phe Ala Met Leu Leu Thr Val Leu Leu Tyr
65                  70                  75

<210> SEQ ID NO 21
<211> LENGTH: 888
<212> TYPE: DNA
<213> ORGANISM: Zea mays
<220> FEATURE:
<221> NAME/KEY: CDS
<222> LOCATION: (1)..(888)

<400> SEQUENCE: 21 atg gag gtg ggg ttc ttg ggt ctg ggc atc atg ggc aag gca atg gcg      48
Met Glu Val Gly Phe Leu Gly Leu Gly Ile Met Gly Lys Ala Met Ala
1               5                   10                  15 acc aac ctc ctc cgc cac ggc ttc cgc gtc acc gtc tgg aac agg acc      96
Thr Asn Leu Leu Arg His Gly Phe Arg Val Thr Val Trp Asn Arg Thr
            20                  25                  30 ctc gcc aag tgc caa gag ctc gcc gcg ctc ggc gcc acc gtc ggg gag     144
Leu Ala Lys Cys Gln Glu Leu Ala Ala Leu Gly Ala Thr Val Gly Glu
        35                  40                  45 acg cct gcc tcc gtc gtc tcc aag tgc aga tac acc atc gcc atg ctc     192
Thr Pro Ala Ser Val Val Ser Lys Cys Arg Tyr Thr Ile Ala Met Leu
    50                  55                  60 tcc gac ccc agc gcc gcc cta tca gtc gtc ttc gac aag gat ggc gtg     240
Ser Asp Pro Ser Ala Ala Leu Ser Val Val Phe Asp Lys Asp Gly Val
65                  70                  75                  80 ctc gag cag atc ggt agc ggg aag ggc tat gtg gac atg tcc act gtt     288
Leu Glu Gln Ile Gly Ser Gly Lys Gly Tyr Val Asp Met Ser Thr Val
                85                  90                  95
```

```
gac gct gca act tcg acc aag att agc gag gca gtt aaa caa aaa ggg    336
Asp Ala Ala Thr Ser Thr Lys Ile Ser Glu Ala Val Lys Gln Lys Gly
            100                 105                 110 gga gct ttc ctt gaa gct cca gtt tca ggg agc aag aag cca gct gaa    384
Gly Ala Phe Leu Glu Ala Pro Val Ser Gly Ser Lys Lys Pro Ala Glu
        115                 120                 125 gat ggc caa ttg gtc att ctt gct gca ggg gac aag cca ttg tat gat    432
Asp Gly Gln Leu Val Ile Leu Ala Ala Gly Asp Lys Pro Leu Tyr Asp
    130                 135                 140 ggt atg att cct gca ttt gat gta ctg ggg aag aag tca ttc ttt ctg    480
Gly Met Ile Pro Ala Phe Asp Val Leu Gly Lys Lys Ser Phe Phe Leu
145                 150                 155                 160 gga gag att gga aat ggg gca aag atg aag ctt gtg gtc aac atg gtc    528
Gly Glu Ile Gly Asn Gly Ala Lys Met Lys Leu Val Val Asn Met Val
                165                 170                 175 atg gga agt atg atg aat tct ttg tcc gag gga ctc tgt ttg gcc gac    576
Met Gly Ser Met Met Asn Ser Leu Ser Glu Gly Leu Cys Leu Ala Asp
            180                 185                 190 aaa agt ggg ctg agc ccc caa aca ctt ctt gat gta ctg gac ctt ggt    624
Lys Ser Gly Leu Ser Pro Gln Thr Leu Leu Asp Val Leu Asp Leu Gly
        195                 200                 205 gcc atc gca aac cca atg ttc aag ctg aag ggg cct aca atg ctg caa    672
Ala Ile Ala Asn Pro Met Phe Lys Leu Lys Gly Pro Thr Met Leu Gln
    210                 215                 220 ggc agc tac agc cct gcg ttt ccc ctg aag cat cag cag aag gac atg    720
Gly Ser Tyr Ser Pro Ala Phe Pro Leu Lys His Gln Gln Lys Asp Met
225                 230                 235                 240 agg tta gcg ctt gct ctg gga gat gag aac gcc gtc gcc atg ccc gtc    768
Arg Leu Ala Leu Ala Leu Gly Asp Glu Asn Ala Val Ala Met Pro Val
                245                 250                 255 tca gca gct gcc aat gag gcg ttc aag aag gcg agg agc ctg ggg ctg    816
Ser Ala Ala Ala Asn Glu Ala Phe Lys Lys Ala Arg Ser Leu Gly Leu
            260                 265                 270 gga gac cag gat ttt tcg gcg gtc tat gag gtt gtg aag ggc gcg ggt    864
Gly Asp Gln Asp Phe Ser Ala Val Tyr Glu Val Val Lys Gly Ala Gly
        275                 280                 285 ggt tct gga tct ggc cag ccg tga                                    888
Gly Ser Gly Ser Gly Gln Pro
    290                 295

<210> SEQ ID NO 22
<211> LENGTH: 295
<212> TYPE: PRT
<213> ORGANISM: Zea mays

<400> SEQUENCE: 22

Met Glu Val Gly Phe Leu Gly Leu Gly Ile Met Gly Lys Ala Met Ala
1               5                   10                  15

Thr Asn Leu Leu Arg His Gly Phe Arg Val Thr Val Trp Asn Arg Thr
            20                  25                  30

Leu Ala Lys Cys Gln Glu Leu Ala Ala Leu Gly Ala Thr Val Gly Glu
        35                  40                  45

Thr Pro Ala Ser Val Val Ser Lys Cys Arg Tyr Thr Ile Ala Met Leu
    50                  55                  60

Ser Asp Pro Ser Ala Ala Leu Ser Val Val Phe Asp Lys Asp Gly Val
65                  70                  75                  80

Leu Glu Gln Ile Gly Ser Gly Lys Gly Tyr Val Asp Met Ser Thr Val
                85                  90                  95

Asp Ala Ala Thr Ser Thr Lys Ile Ser Glu Ala Val Lys Gln Lys Gly
```

```
               100                 105                 110
Gly Ala Phe Leu Glu Ala Pro Val Ser Gly Lys Lys Pro Ala Glu
            115                 120                 125

Asp Gly Gln Leu Val Ile Leu Ala Ala Gly Asp Lys Pro Leu Tyr Asp
        130                 135                 140

Gly Met Ile Pro Ala Phe Asp Val Leu Gly Lys Lys Ser Phe Phe Leu
145                 150                 155                 160

Gly Glu Ile Gly Asn Gly Ala Lys Met Lys Leu Val Val Asn Met Val
                165                 170                 175

Met Gly Ser Met Met Asn Ser Leu Ser Glu Gly Leu Cys Leu Ala Asp
            180                 185                 190

Lys Ser Gly Leu Ser Pro Gln Thr Leu Leu Asp Val Leu Asp Leu Gly
        195                 200                 205

Ala Ile Ala Asn Pro Met Phe Lys Leu Lys Gly Pro Thr Met Leu Gln
    210                 215                 220

Gly Ser Tyr Ser Pro Ala Phe Pro Leu Lys His Gln Gln Lys Asp Met
225                 230                 235                 240

Arg Leu Ala Leu Ala Leu Gly Asp Glu Asn Ala Val Ala Met Pro Val
                245                 250                 255

Ser Ala Ala Ala Asn Glu Ala Phe Lys Lys Ala Arg Ser Leu Gly Leu
            260                 265                 270

Gly Asp Gln Asp Phe Ser Ala Val Tyr Glu Val Val Lys Gly Ala Gly
        275                 280                 285

Gly Ser Gly Ser Gly Gln Pro
    290                 295

<210> SEQ ID NO 23
<211> LENGTH: 174
<212> TYPE: DNA
<213> ORGANISM: Zea mays
<220> FEATURE:
<221> NAME/KEY: CDS
<222> LOCATION: (1)..(174)

<400> SEQUENCE: 23 atg ttc aag ctg aag ggg ccg aca atg ctg caa ggc agc tac agc cct      48
Met Phe Lys Leu Lys Gly Pro Thr Met Leu Gln Gly Ser Tyr Ser Pro
1               5                   10                  15 gcg ttc cct ctg aag cac cag cag aag gac atg agg cta gct ctt gcg      96
Ala Phe Pro Leu Lys His Gln Gln Lys Asp Met Arg Leu Ala Leu Ala
            20                  25                  30 ctg gga ctg gga gac gag aac gcc gta gcc atg cca aca ggg ggg acc     144
Leu Gly Leu Gly Asp Glu Asn Ala Val Ala Met Pro Thr Gly Gly Thr
        35                  40                  45 agg att tct cgg cgg tct acg agg ctg tga                              174
Arg Ile Ser Arg Arg Ser Thr Arg Leu
    50                  55

<210> SEQ ID NO 24
<211> LENGTH: 57
<212> TYPE: PRT
<213> ORGANISM: Zea mays

<400> SEQUENCE: 24

Met Phe Lys Leu Lys Gly Pro Thr Met Leu Gln Gly Ser Tyr Ser Pro
1               5                   10                  15

Ala Phe Pro Leu Lys His Gln Gln Lys Asp Met Arg Leu Ala Leu Ala
            20                  25                  30
```

Leu Gly Leu Gly Asp Glu Asn Ala Val Ala Met Pro Thr Gly Gly Thr
         35                  40                  45

Arg Ile Ser Arg Arg Ser Thr Arg Leu
 50                  55

<210> SEQ ID NO 25
<211> LENGTH: 1816
<212> TYPE: DNA
<213> ORGANISM: Arabidopsis thaliana

<400> SEQUENCE: 25

| | | | | |
|---|---|---|---|---|
| atgataatgg | ttctctgatt | agaaaaggct | ccggctttat | cattctcaga ccatcatcac | 60 |
| taagcagtaa | gtaagcacta | taatcgcaga | agatagataa | aatggaagta gggtttctgg | 120 |
| gtttgggaat | catgggaaaa | gccatgtcaa | tgaatctatt | gaagaatgga ttcaaagtca | 180 |
| ctgtatggaa | cagaacactc | tccaaggtaa | ttttttttt | ttttttgtct ttgattgtgt | 240 |
| tttggtatta | tggttttctg | atttagtttt | agttgttcag | atctgataaa gtcggaaact | 300 |
| ttttgagtaa | tttaatgcaa | ttttgggaat | ttttgatgat | tgtgacagtg tgatgagctt | 360 |
| gtggagcatg | gtgcatcagt | atgtgagagt | ccagctgaag | taatcaagaa atgcaaatac | 420 |
| actattgcta | tgctctctga | tccttgtgct | gctctttcgg | tatttgaaat ccttttttgc | 480 |
| ttcttttgtg | tgtgttttag | cattggtgat | gaatgatatg | aagtagttgt ttgattaggt | 540 |
| tgttttcgat | aaaggcggtg | ttttggagca | gatatgtgaa | ggaaaaggtt atatcgatat | 600 |
| gtcgactgtt | gatgcagaga | cttctttgaa | gatcaatgag | gttgaatctt ttgtactta | 660 |
| gatgctgatg | ataagattag | aagaaggttg | attagtttga | ttgagctgtg ttgcgcattg | 720 |
| gtaggcaatc | accgggaagg | gtggtcggtt | cgtagaaggt | ccggtttcag gtagcaaaaa | 780 |
| gccagctgaa | gatggccaac | tcattatcct | tgctgctggt | gacaaggtac aactcaaaac | 840 |
| tgtacttatg | gattgattga | tagatctcaa | gaactgtttt | agttggactt agtaggaagg | 900 |
| agctctcgat | gtgcggctat | aatccgtttg | tgttttaatc | cttttttgta aggcactctt | 960 |
| tgaggaatca | atcccagctt | tgatgtcttt | ggggaagaga | tcgttttact tgggacaagt | 1020 |
| tggaaacgga | gctaaaatga | agctaatagt | gaacatgata | atgggaaggt gaatgtcccg | 1080 |
| tctctttttac | aattactacc | attagtagta | ggaatggaac | atggcttcat gatcttattg | 1140 |
| tttttcgtct | gatacagcat | gatgaatgca | ttctctgagg | ggcttgtatt ggctgacaag | 1200 |
| agtggactta | gctctgacac | tctttttggat | attctggtga | ggtgatcaaa cttttgcaag | 1260 |
| ctctgaaata | atggtgttgg | tttgaatcgg | tttctgctat | gggcaggatc tgggagcaat | 1320 |
| gactaacccg | atgttcaagg | ggaaaggacc | ttcaatgaac | aagagtagtt acccaccagc | 1380 |
| atttccattg | aaacatcagc | agaaagacat | gaggctagct | cttgctcttg gcgatgaaaa | 1440 |
| cgcggtttcc | atgcctgtag | ccgcggctgc | aaacgaggtc | agttagttag ttagttactc | 1500 |
| agagacaata | acatattggc | tctccctcct | ctagattggt | ttcttagctt gaatcttaaa | 1560 |
| atatatgttt | cggttctcga | caggctttta | agaaggcgaa | aagcttggga ctaggagatc | 1620 |
| tcgacttctc | tgctgtgatt | gaagctgtga | aattctcccg | cgaatagcaa actgtttcaa | 1680 |
| aacatccact | catttggatt | ggctgagata | ctgaaatcat | tgttatcttc ccaaatagag | 1740 |
| atttactcat | ttggccaaac | acacatttta | ctccttcacc | aaataaaaag tcttaaccac | 1800 |
| atatccagaa | acgttc | | | | 1816 |

<210> SEQ ID NO 26
<211> LENGTH: 876

```
<212> TYPE: DNA
<213> ORGANISM: Hordeum vulgare
<220> FEATURE:
<221> NAME/KEY: CDS
<222> LOCATION: (1)..(876)

<400> SEQUENCE: 26
```

| | | | | | | | | | | | | | | | | |
|---|---|---|---|---|---|---|---|---|---|---|---|---|---|---|---|---|
| atg | gag | gtc | ggc | ttc | ttg | ggg | ctg | ggc | atc | atg | ggt | aag | gca | atg | gcg | 48 |
| Met | Glu | Val | Gly | Phe | Leu | Gly | Leu | Gly | Ile | Met | Gly | Lys | Ala | Met | Ala | |
| 1 | | | | 5 | | | | | 10 | | | | | 15 | | |
| gcc | aac | ctc | ctc | cgc | cac | ggc | ttc | cgc | gtc | acc | gtc | tgg | aac | cgg | acc | 96 |
| Ala | Asn | Leu | Leu | Arg | His | Gly | Phe | Arg | Val | Thr | Val | Trp | Asn | Arg | Thr | |
| | | | 20 | | | | | 25 | | | | | 30 | | | |
| ctc | tcc | aag | tgc | gac | gag | ctc | gtc | gcg | atg | ggc | gcc | gcc | gtc | ggg | gac | 144 |
| Leu | Ser | Lys | Cys | Asp | Glu | Leu | Val | Ala | Met | Gly | Ala | Ala | Val | Gly | Asp | |
| | | 35 | | | | | 40 | | | | | 45 | | | | |
| acg | ccg | gcg | tcc | gtc | gtg | gcc | aag | tgc | aag | tac | acc | atc | gcc | atg | ctc | 192 |
| Thr | Pro | Ala | Ser | Val | Val | Ala | Lys | Cys | Lys | Tyr | Thr | Ile | Ala | Met | Leu | |
| | 50 | | | | | 55 | | | | | 60 | | | | | |
| tcc | gat | ccc | agc | gcc | gcg | cta | tct | gtt | gtt | ttc | gac | aag | gat | ggt | gtg | 240 |
| Ser | Asp | Pro | Ser | Ala | Ala | Leu | Ser | Val | Val | Phe | Asp | Lys | Asp | Gly | Val | |
| 65 | | | | | 70 | | | | | 75 | | | | | 80 | |
| ctc | gag | caa | atc | ggg | gag | ggc | aag | ggc | tac | gtg | gac | atg | tcc | act | gtt | 288 |
| Leu | Glu | Gln | Ile | Gly | Glu | Gly | Lys | Gly | Tyr | Val | Asp | Met | Ser | Thr | Val | |
| | | | | 85 | | | | | 90 | | | | | 95 | | |
| gat | gct | gca | act | tct | tgc | aag | ata | agc | gag | gcg | gtt | aaa | caa | aag | ggc | 336 |
| Asp | Ala | Ala | Thr | Ser | Cys | Lys | Ile | Ser | Glu | Ala | Val | Lys | Gln | Lys | Gly | |
| | | | 100 | | | | | 105 | | | | | 110 | | | |
| gga | gct | ttt | gtt | gaa | gct | cca | gtt | tca | ggg | agc | aag | aag | cca | gct | gaa | 384 |
| Gly | Ala | Phe | Val | Glu | Ala | Pro | Val | Ser | Gly | Ser | Lys | Lys | Pro | Ala | Glu | |
| | | 115 | | | | | 120 | | | | | 125 | | | | |
| gat | ggc | caa | ttg | gtc | att | ctt | gct | gca | ggc | gac | aag | gca | cta | tat | gat | 432 |
| Asp | Gly | Gln | Leu | Val | Ile | Leu | Ala | Ala | Gly | Asp | Lys | Ala | Leu | Tyr | Asp | |
| | 130 | | | | | 135 | | | | | 140 | | | | | |
| gac | atg | gtc | cct | gca | ttt | gac | ata | ctt | ggg | aag | aag | tcg | ttc | ttt | ctg | 480 |
| Asp | Met | Val | Pro | Ala | Phe | Asp | Ile | Leu | Gly | Lys | Lys | Ser | Phe | Phe | Leu | |
| 145 | | | | | 150 | | | | | 155 | | | | | 160 | |
| ggg | gag | atg | gga | aat | gga | gca | aag | atg | aaa | ctg | gtg | gtc | aac | atg | atc | 528 |
| Gly | Glu | Met | Gly | Asn | Gly | Ala | Lys | Met | Lys | Leu | Val | Val | Asn | Met | Ile | |
| | | | | 165 | | | | | 170 | | | | | 175 | | |
| atg | gga | agt | atg | atg | aat | gct | ttc | tcc | gag | gga | ctc | tgt | ttg | gct | gac | 576 |
| Met | Gly | Ser | Met | Met | Asn | Ala | Phe | Ser | Glu | Gly | Leu | Cys | Leu | Ala | Asp | |
| | | | 180 | | | | | 185 | | | | | 190 | | | |
| aaa | agt | ggg | ttg | agc | ccc | cag | acg | ctt | ctt | gat | gtc | ctg | gat | ctc | ggt | 624 |
| Lys | Ser | Gly | Leu | Ser | Pro | Gln | Thr | Leu | Leu | Asp | Val | Leu | Asp | Leu | Gly | |
| | | 195 | | | | | 200 | | | | | 205 | | | | |
| gcc | atc | gca | aat | ccg | atg | ttc | aag | atg | aaa | ggg | cct | tcg | atg | cta | cag | 672 |
| Ala | Ile | Ala | Asn | Pro | Met | Phe | Lys | Met | Lys | Gly | Pro | Ser | Met | Leu | Gln | |
| | 210 | | | | | 215 | | | | | 220 | | | | | |
| ggc | agc | tac | aat | cca | gca | ttt | ccc | ctc | aaa | cat | cag | cag | aag | gat | atg | 720 |
| Gly | Ser | Tyr | Asn | Pro | Ala | Phe | Pro | Leu | Lys | His | Gln | Gln | Lys | Asp | Met | |
| 225 | | | | | 230 | | | | | 235 | | | | | 240 | |
| agg | ctg | gct | ctg | tca | ttg | gga | gat | gaa | aat | gcc | gtc | tcc | atg | cca | gtc | 768 |
| Arg | Leu | Ala | Leu | Ser | Leu | Gly | Asp | Glu | Asn | Ala | Val | Ser | Met | Pro | Val | |
| | | | | 245 | | | | | 250 | | | | | 255 | | |
| gca | gct | gct | gct | aat | gag | gca | ttc | aag | aaa | gca | aga | agc | ttg | gga | ctt | 816 |
| Ala | Ala | Ala | Ala | Asn | Glu | Ala | Phe | Lys | Lys | Ala | Arg | Ser | Leu | Gly | Leu | |
| | | | 260 | | | | | 265 | | | | | 270 | | | |
| ggc | gac | ctg | gat | ttt | tct | gcg | gtg | cac | gag | gtg | ctg | aaa | ggc | aca | ggt | 864 |
| Gly | Asp | Leu | Asp | Phe | Ser | Ala | Val | His | Glu | Val | Leu | Lys | Gly | Thr | Gly | |
| | | 275 | | | | | 280 | | | | | 285 | | | | |

```
ggt tca ggc taa                                                         876
Gly Ser Gly
    290

<210> SEQ ID NO 27
<211> LENGTH: 291
<212> TYPE: PRT
<213> ORGANISM: Hordeum vulgare

<400> SEQUENCE: 27

Met Glu Val Gly Phe Leu Gly Leu Gly Ile Met Gly Lys Ala Met Ala
1               5                   10                  15

Ala Asn Leu Leu Arg His Gly Phe Arg Val Thr Val Trp Asn Arg Thr
            20                  25                  30

Leu Ser Lys Cys Asp Glu Leu Val Ala Met Gly Ala Ala Val Gly Asp
        35                  40                  45

Thr Pro Ala Ser Val Val Ala Lys Cys Lys Tyr Thr Ile Ala Met Leu
    50                  55                  60

Ser Asp Pro Ser Ala Ala Leu Ser Val Val Phe Asp Lys Asp Gly Val
65                  70                  75                  80

Leu Glu Gln Ile Gly Glu Gly Lys Gly Tyr Val Asp Met Ser Thr Val
                85                  90                  95

Asp Ala Ala Thr Ser Cys Lys Ile Ser Glu Ala Val Lys Gln Lys Gly
            100                 105                 110

Gly Ala Phe Val Glu Ala Pro Val Ser Gly Ser Lys Lys Pro Ala Glu
        115                 120                 125

Asp Gly Gln Leu Val Ile Leu Ala Ala Gly Asp Lys Ala Leu Tyr Asp
    130                 135                 140

Asp Met Val Pro Ala Phe Asp Ile Leu Gly Lys Lys Ser Phe Phe Leu
145                 150                 155                 160

Gly Glu Met Gly Asn Gly Ala Lys Met Lys Leu Val Val Asn Met Ile
                165                 170                 175

Met Gly Ser Met Met Asn Ala Phe Ser Glu Gly Leu Cys Leu Ala Asp
            180                 185                 190

Lys Ser Gly Leu Ser Pro Gln Thr Leu Leu Asp Val Leu Asp Leu Gly
        195                 200                 205

Ala Ile Ala Asn Pro Met Phe Lys Met Lys Gly Pro Ser Met Leu Gln
    210                 215                 220

Gly Ser Tyr Asn Pro Ala Phe Pro Leu Lys His Gln Gln Lys Asp Met
225                 230                 235                 240

Arg Leu Ala Leu Ser Leu Gly Asp Glu Asn Ala Val Ser Met Pro Val
                245                 250                 255

Ala Ala Ala Ala Asn Glu Ala Phe Lys Lys Ala Arg Ser Leu Gly Leu
            260                 265                 270

Gly Asp Leu Asp Phe Ser Ala Val His Glu Val Leu Lys Gly Thr Gly
        275                 280                 285

Gly Ser Gly
    290

<210> SEQ ID NO 28
<211> LENGTH: 864
<212> TYPE: DNA
<213> ORGANISM: Solanum lycopersum
<220> FEATURE:
<221> NAME/KEY: CDS
<222> LOCATION: (1)..(864)
```

<400> SEQUENCE: 28

```
atg gag gaa ata ggg ttt cta ggg att ggt att atg gga aaa gca atg      48
Met Glu Glu Ile Gly Phe Leu Gly Ile Gly Ile Met Gly Lys Ala Met
1               5                   10                  15 gcg gtc aac ttg ctg cgc cat ggt ttc aag gtt act gtt tgg aat cgc      96
Ala Val Asn Leu Leu Arg His Gly Phe Lys Val Thr Val Trp Asn Arg
            20                  25                  30 acc ctc tcc agg tgt gat gag cta gtg caa cat gga gcc tct gtt gga     144
Thr Leu Ser Arg Cys Asp Glu Leu Val Gln His Gly Ala Ser Val Gly
        35                  40                  45 gaa act cct gca gaa gta atc aag aaa tgc aag tat aca att gca atg     192
Glu Thr Pro Ala Glu Val Ile Lys Lys Cys Lys Tyr Thr Ile Ala Met
    50                  55                  60 ttg tct gat cca gct gca gct ctt tca gtg gtt ttt gac aaa cac gga     240
Leu Ser Asp Pro Ala Ala Ala Leu Ser Val Val Phe Asp Lys His Gly
65                  70                  75                  80 gca ctt gag cac ata tgt gcc gga aag ggc tat ata gac atg tca acc     288
Ala Leu Glu His Ile Cys Ala Gly Lys Gly Tyr Ile Asp Met Ser Thr
                85                  90                  95 gtt gat gct gat act tct tca cag att agc cag gcc att aca tca aag     336
Val Asp Ala Asp Thr Ser Ser Gln Ile Ser Gln Ala Ile Thr Ser Lys
            100                 105                 110 ggt ggt tca ttc ctt gaa gct cca gtt tca ggg agc aaa aag cca gct     384
Gly Gly Ser Phe Leu Glu Ala Pro Val Ser Gly Ser Lys Lys Pro Ala
        115                 120                 125 gaa gat gga caa cta gta atc cta gca gct ggt gac aag gat ctg tac     432
Glu Asp Gly Gln Leu Val Ile Leu Ala Ala Gly Asp Lys Asp Leu Tyr
    130                 135                 140 gat caa gta gta cct gct ttt gat gtc ctg gga aag aaa tct ttt ttc     480
Asp Gln Val Val Pro Ala Phe Asp Val Leu Gly Lys Lys Ser Phe Phe
145                 150                 155                 160 ttg gga aag att ggg aat gga gca aaa atg aaa ctt gtt gtt aat atg     528
Leu Gly Lys Ile Gly Asn Gly Ala Lys Met Lys Leu Val Val Asn Met
                165                 170                 175 ata atg ggc agt atg atg aat gcg ttt tca gaa gga att gta ctg gct     576
Ile Met Gly Ser Met Met Asn Ala Phe Ser Glu Gly Ile Val Leu Ala
            180                 185                 190 gac aaa agt gga ttg gac cct cat acc ctt ctc gat gtg ttg gat ctt     624
Asp Lys Ser Gly Leu Asp Pro His Thr Leu Leu Asp Val Leu Asp Leu
        195                 200                 205 gga gcc ata gct aac cca atg ttc aaa atg aaa gga cct gcc atg ata     672
Gly Ala Ile Ala Asn Pro Met Phe Lys Met Lys Gly Pro Ala Met Ile
    210                 215                 220 aaa aat agc tac cca ccc gca ttt cct ctg aaa cat cag cag aag gac     720
Lys Asn Ser Tyr Pro Pro Ala Phe Pro Leu Lys His Gln Gln Lys Asp
225                 230                 235                 240 atg agg ctg gct ctt gca ctc gga gat gag aat gca gtg cca atg cca     768
Met Arg Leu Ala Leu Ala Leu Gly Asp Glu Asn Ala Val Pro Met Pro
                245                 250                 255 gtt gca gct gct gca aat gag gca ttc aag aag gca agg agc ttg ggc     816
Val Ala Ala Ala Ala Asn Glu Ala Phe Lys Lys Ala Arg Ser Leu Gly
            260                 265                 270 ttg gga gac ctt gac ttt tca gct gtg ttt gag act ctc agc aaa tga    864
Leu Gly Asp Leu Asp Phe Ser Ala Val Phe Glu Thr Leu Ser Lys
        275                 280                 285

<210> SEQ ID NO 29
<211> LENGTH: 287
<212> TYPE: PRT
<213> ORGANISM: Solanum lycopersum
```

```
<400> SEQUENCE: 29

Met Glu Glu Ile Gly Phe Leu Gly Ile Gly Met Gly Lys Ala Met
1               5                   10                  15

Ala Val Asn Leu Leu Arg His Gly Phe Lys Val Thr Val Trp Asn Arg
            20                  25                  30

Thr Leu Ser Arg Cys Asp Glu Leu Val Gln His Gly Ala Ser Val Gly
        35                  40                  45

Glu Thr Pro Ala Glu Val Ile Lys Lys Cys Lys Tyr Thr Ile Ala Met
    50                  55                  60

Leu Ser Asp Pro Ala Ala Ala Leu Ser Val Val Phe Asp Lys His Gly
65                  70                  75                  80

Ala Leu Glu His Ile Cys Ala Gly Lys Gly Tyr Ile Asp Met Ser Thr
                85                  90                  95

Val Asp Ala Asp Thr Ser Ser Gln Ile Ser Gln Ala Ile Thr Ser Lys
            100                 105                 110

Gly Gly Ser Phe Leu Glu Ala Pro Val Ser Gly Ser Lys Lys Pro Ala
        115                 120                 125

Glu Asp Gly Gln Leu Val Ile Leu Ala Ala Gly Asp Lys Asp Leu Tyr
    130                 135                 140

Asp Gln Val Val Pro Ala Phe Asp Val Leu Gly Lys Lys Ser Phe Phe
145                 150                 155                 160

Leu Gly Lys Ile Gly Asn Gly Ala Lys Met Lys Leu Val Asn Met
                165                 170                 175

Ile Met Gly Ser Met Met Asn Ala Phe Ser Glu Gly Ile Val Leu Ala
            180                 185                 190

Asp Lys Ser Gly Leu Asp Pro His Thr Leu Leu Asp Val Leu Asp Leu
        195                 200                 205

Gly Ala Ile Ala Asn Pro Met Phe Lys Met Lys Gly Pro Ala Met Ile
    210                 215                 220

Lys Asn Ser Tyr Pro Pro Ala Phe Pro Leu Lys His Gln Gln Lys Asp
225                 230                 235                 240

Met Arg Leu Ala Leu Ala Leu Gly Asp Glu Asn Ala Val Pro Met Pro
                245                 250                 255

Val Ala Ala Ala Ala Asn Glu Ala Phe Lys Lys Ala Arg Ser Leu Gly
            260                 265                 270

Leu Gly Asp Leu Asp Phe Ser Ala Val Phe Glu Thr Leu Ser Lys
        275                 280                 285

<210> SEQ ID NO 30
<211> LENGTH: 882
<212> TYPE: DNA
<213> ORGANISM: Brachypodium distachyon
<220> FEATURE:
<221> NAME/KEY: CDS
<222> LOCATION: (1)..(882)

<400> SEQUENCE: 30 atg gag gtg ggg ttc ctt ggg ctg ggc atc atg ggg aag gca atg gcg     48
Met Glu Val Gly Phe Leu Gly Leu Gly Ile Met Gly Lys Ala Met Ala
1               5                   10                  15 acc aac ctc ctc cgc cac ggc ttt cgc gtc acc gtc tgg aac cgg act     96
Thr Asn Leu Leu Arg His Gly Phe Arg Val Thr Val Trp Asn Arg Thr
            20                  25                  30 ctc tcc aag tgc caa gag ctc gtt gcg ttg ggg gct acc gtc ggg gag    144
Leu Ser Lys Cys Gln Glu Leu Val Ala Leu Gly Ala Thr Val Gly Glu
        35                  40                  45
```

| | | | | | | | | | | | | | | | |
|---|---|---|---|---|---|---|---|---|---|---|---|---|---|---|---|
| acg | ccg | gcg | gcc | gtc | gtc | gcc | aag | tgc | aag | ttt | acc | atc | gcc | atg | ctc | 192
| Thr | Pro | Ala | Ala | Val | Val | Ala | Lys | Cys | Lys | Phe | Thr | Ile | Ala | Met | Leu |
| | 50 | | | | 55 | | | | | 60 | | | | | |

| tcc | gat | ccc | aga | gcc | gcg | cta | tct | gtt | gtt | ttc | gac | aag | gat | ggt | gtg | 240
| Ser | Asp | Pro | Arg | Ala | Ala | Leu | Ser | Val | Val | Phe | Asp | Lys | Asp | Gly | Val |
| 65 | | | | 70 | | | | | 75 | | | | | 80 | |

| ctc | gag | caa | atc | gga | gag | ggg | aag | ggc | tat | gtg | gac | atg | tcc | act | gtt | 288
| Leu | Glu | Gln | Ile | Gly | Glu | Gly | Lys | Gly | Tyr | Val | Asp | Met | Ser | Thr | Val |
| | | | | 85 | | | | | 90 | | | | | 95 | |

| gat | gcc | gaa | acg | tct | tgc | aag | ata | agt | gag | gcg | atc | aaa | caa | aag | ggt | 336
| Asp | Ala | Glu | Thr | Ser | Cys | Lys | Ile | Ser | Glu | Ala | Ile | Lys | Gln | Lys | Gly |
| | | | 100 | | | | | 105 | | | | | 110 | | |

| gga | gct | ttt | gtt | gaa | gct | cct | gtt | tca | ggg | agc | aag | aaa | cca | gct | gaa | 384
| Gly | Ala | Phe | Val | Glu | Ala | Pro | Val | Ser | Gly | Ser | Lys | Lys | Pro | Ala | Glu |
| | | | 115 | | | | | 120 | | | | | 125 | | |

| gat | ggt | caa | ttg | gtc | gtt | ctt | gct | gca | ggg | gac | aag | gca | ctg | tat | gat | 432
| Asp | Gly | Gln | Leu | Val | Val | Leu | Ala | Ala | Gly | Asp | Lys | Ala | Leu | Tyr | Asp |
| | | 130 | | | | | 135 | | | | | 140 | | | |

| gat | atg | gtc | cct | gca | ttt | gat | gta | ctt | ggg | aaa | aag | tca | ttc | ttt | ttg | 480
| Asp | Met | Val | Pro | Ala | Phe | Asp | Val | Leu | Gly | Lys | Lys | Ser | Phe | Phe | Leu |
| 145 | | | | | 150 | | | | | 155 | | | | | 160 |

| ggg | gag | att | gga | aat | gga | gca | aag | atg | aag | ctg | gtg | gtt | aac | atg | atc | 528
| Gly | Glu | Ile | Gly | Asn | Gly | Ala | Lys | Met | Lys | Leu | Val | Val | Asn | Met | Ile |
| | | | | 165 | | | | | 170 | | | | | 175 | |

| atg | gga | agt | gtg | atg | aat | gct | ttt | tct | gag | gga | cta | tgt | tta | gct | gac | 576
| Met | Gly | Ser | Val | Met | Asn | Ala | Phe | Ser | Glu | Gly | Leu | Cys | Leu | Ala | Asp |
| | | | 180 | | | | | 185 | | | | | 190 | | |

| gaa | agt | ggg | ttg | agc | cca | cag | acg | ctt | ctt | gat | gtc | ctg | gac | ctt | gga | 624
| Glu | Ser | Gly | Leu | Ser | Pro | Gln | Thr | Leu | Leu | Asp | Val | Leu | Asp | Leu | Gly |
| | | 195 | | | | | 200 | | | | | 205 | | | |

| ggc | atc | gct | aat | ccg | atg | ttt | aag | atg | aaa | ggt | ccc | tca | atg | ctc | cag | 672
| Gly | Ile | Ala | Asn | Pro | Met | Phe | Lys | Met | Lys | Gly | Pro | Ser | Met | Leu | Gln |
| | | 210 | | | | | 215 | | | | | 220 | | | |

| ggc | agc | tac | aat | cct | gca | ttt | ccc | cta | aaa | cat | atg | cag | aag | gat | atg | 720
| Gly | Ser | Tyr | Asn | Pro | Ala | Phe | Pro | Leu | Lys | His | Met | Gln | Lys | Asp | Met |
| 225 | | | | | 230 | | | | | 235 | | | | | 240 |

| agg | ttg | gct | ctt | tcc | ttg | gga | gac | gag | aac | gct | gtc | gcc | atg | cca | gtc | 768
| Arg | Leu | Ala | Leu | Ser | Leu | Gly | Asp | Glu | Asn | Ala | Val | Ala | Met | Pro | Val |
| | | | | 245 | | | | | 250 | | | | | 255 | |

| gca | gct | gct | gcc | aat | gag | gca | ttc | aag | aaa | gca | aga | agc | ttg | gga | ctt | 816
| Ala | Ala | Ala | Ala | Asn | Glu | Ala | Phe | Lys | Lys | Ala | Arg | Ser | Leu | Gly | Leu |
| | | | 260 | | | | | 265 | | | | | 270 | | |

| ggg | gac | cag | gat | ttc | tca | gcg | gtg | cac | gag | gtt | ctg | aaa | gga | gca | ggt | 864
| Gly | Asp | Gln | Asp | Phe | Ser | Ala | Val | His | Glu | Val | Leu | Lys | Gly | Ala | Gly |
| | | 275 | | | | | 280 | | | | | 285 | | | |

| ggt | tca | ggc | caa | gca | tga | | | | | | | | | | | 882
| Gly | Ser | Gly | Gln | Ala | | | | | | | | | | | |
| | | 290 | | | | | | | | | | | | | |

<210> SEQ ID NO 31
<211> LENGTH: 293
<212> TYPE: PRT
<213> ORGANISM: Brachypodium distachyon

<400> SEQUENCE: 31

| | | | | | | | | | | | | | | |
|---|---|---|---|---|---|---|---|---|---|---|---|---|---|---|
| Met | Glu | Val | Gly | Phe | Leu | Gly | Leu | Gly | Ile | Met | Gly | Lys | Ala | Met | Ala |
| 1 | | | | 5 | | | | | 10 | | | | | 15 | |

| Thr | Asn | Leu | Leu | Arg | His | Gly | Phe | Arg | Val | Thr | Val | Trp | Asn | Arg | Thr |
| | | | 20 | | | | | 25 | | | | | 30 | | |

```
Leu Ser Lys Cys Gln Glu Leu Val Ala Leu Gly Ala Thr Val Gly Glu
         35                  40                  45
Thr Pro Ala Ala Val Val Ala Lys Cys Lys Phe Thr Ile Ala Met Leu
 50                  55                  60
Ser Asp Pro Arg Ala Ala Leu Ser Val Val Phe Asp Lys Asp Gly Val
 65                  70                  75                  80
Leu Glu Gln Ile Gly Glu Gly Lys Gly Tyr Val Asp Met Ser Thr Val
                 85                  90                  95
Asp Ala Glu Thr Ser Cys Lys Ile Ser Glu Ala Ile Lys Gln Lys Gly
             100                 105                 110
Gly Ala Phe Val Glu Ala Pro Val Ser Gly Ser Lys Lys Pro Ala Glu
         115                 120                 125
Asp Gly Gln Leu Val Val Leu Ala Ala Gly Asp Lys Ala Leu Tyr Asp
130                 135                 140
Asp Met Val Pro Ala Phe Asp Val Leu Gly Lys Lys Ser Phe Phe Leu
145                 150                 155                 160
Gly Glu Ile Gly Asn Gly Ala Lys Met Lys Leu Val Val Asn Met Ile
                165                 170                 175
Met Gly Ser Val Met Asn Ala Phe Ser Glu Gly Leu Cys Leu Ala Asp
            180                 185                 190
Glu Ser Gly Leu Ser Pro Gln Thr Leu Leu Asp Val Leu Asp Leu Gly
        195                 200                 205
Gly Ile Ala Asn Pro Met Phe Lys Met Lys Gly Pro Ser Met Leu Gln
210                 215                 220
Gly Ser Tyr Asn Pro Ala Phe Pro Leu Lys His Met Gln Lys Asp Met
225                 230                 235                 240
Arg Leu Ala Leu Ser Leu Gly Asp Glu Asn Ala Val Ala Met Pro Val
                245                 250                 255
Ala Ala Ala Ala Asn Glu Ala Phe Lys Lys Ala Arg Ser Leu Gly Leu
            260                 265                 270
Gly Asp Gln Asp Phe Ser Ala Val His Glu Val Leu Lys Gly Ala Gly
        275                 280                 285
Gly Ser Gly Gln Ala
        290

<210> SEQ ID NO 32
<211> LENGTH: 237
<212> TYPE: DNA
<213> ORGANISM: Brassica napus
<220> FEATURE:
<221> NAME/KEY: CDS
<222> LOCATION: (1)..(237)

<400> SEQUENCE: 32 atg gga atc atg ggt tct cct atg gca caa aac ctc ctc aaa gct ggg    48
Met Gly Ile Met Gly Ser Pro Met Ala Gln Asn Leu Leu Lys Ala Gly
 1               5                  10                  15 tgt gat gtg act gtg tgg aac cga act aag agc aaa tgt gat cct ctc    96
Cys Asp Val Thr Val Trp Asn Arg Thr Lys Ser Lys Cys Asp Pro Leu
                20                  25                  30 gtc gga tta gga gca aaa tac aag tct tct cct gaa gaa gtg act gca   144
Val Gly Leu Gly Ala Lys Tyr Lys Ser Ser Pro Glu Glu Val Thr Ala
             35                  40                  45 act tgt gat ctc aca ttt gca atg cta gca gat cct gag agt gca gtg   192
Thr Cys Asp Leu Thr Phe Ala Met Leu Ala Asp Pro Glu Ser Ala Val
 50                  55                  60 cat cga tgt tgc ctg tgg aaa gaa tgg agc cgt atc tgg aat tag       237
```

```
<210> SEQ ID NO 33
<211> LENGTH: 78
<212> TYPE: PRT
<213> ORGANISM: Brassica napus

<400> SEQUENCE: 33

Met Gly Ile Met Gly Ser Pro Met Ala Gln Asn Leu Leu Lys Ala Gly
1               5                   10                  15

Cys Asp Val Thr Val Trp Asn Arg Thr Lys Ser Lys Cys Asp Pro Leu
            20                  25                  30

Val Gly Leu Gly Ala Lys Tyr Lys Ser Ser Pro Glu Glu Val Thr Ala
        35                  40                  45

Thr Cys Asp Leu Thr Phe Ala Met Leu Ala Asp Pro Glu Ser Ala Val
    50                  55                  60

His Arg Cys Cys Leu Trp Lys Glu Trp Ser Arg Ile Trp Asn
65                  70                  75

<210> SEQ ID NO 34
<211> LENGTH: 705
<212> TYPE: DNA
<213> ORGANISM: Brassica napus
<220> FEATURE:
<221> NAME/KEY: CDS
<222> LOCATION: (1)..(705)

<400> SEQUENCE: 34
```

| | | | | | | | | | | | | | | | | |
|---|---|---|---|---|---|---|---|---|---|---|---|---|---|---|---|---|
| atg | caa | tac | aca | tct | tct | atg | ctc | tct | gac | cct | tgt | gct | gct | ctc | tcg | 48 |
| Met | Gln | Tyr | Thr | Ser | Ser | Met | Leu | Ser | Asp | Pro | Cys | Ala | Ala | Leu | Ser | |
| 1 | | | | 5 | | | | | 10 | | | | | 15 | | |
| gtt | gtt | ttc | gat | aaa | gat | ggt | gtt | tta | gag | caa | atc | tgt | gaa | gga | aaa | 96 |
| Val | Val | Phe | Asp | Lys | Asp | Gly | Val | Leu | Glu | Gln | Ile | Cys | Glu | Gly | Lys | |
| | | | 20 | | | | | 25 | | | | | 30 | | | |
| ggg | tat | atc | gat | atg | tca | aca | gtt | gat | gca | gag | act | tcc | tta | aag | atc | 144 |
| Gly | Tyr | Ile | Asp | Met | Ser | Thr | Val | Asp | Ala | Glu | Thr | Ser | Leu | Lys | Ile | |
| | | 35 | | | | | 40 | | | | | 45 | | | | |
| aac | aag | gca | atc | act | ggg | aaa | ggc | ggt | cgg | ttt | gta | gaa | ggt | cct | gtt | 192 |
| Asn | Lys | Ala | Ile | Thr | Gly | Lys | Gly | Gly | Arg | Phe | Val | Glu | Gly | Pro | Val | |
| 50 | | | | | 55 | | | | | 60 | | | | | | |
| tca | ggt | agc | aag | aag | ccg | gca | gaa | gat | ggc | cag | ctc | atc | ata | ctt | gct | 240 |
| Ser | Gly | Ser | Lys | Lys | Pro | Ala | Glu | Asp | Gly | Gln | Leu | Ile | Ile | Leu | Ala | |
| 65 | | | | | 70 | | | | | 75 | | | | | 80 | |
| gct | ggt | gac | aag | tcc | ctt | ttc | gat | gaa | acg | gtc | cca | gct | ttt | gac | gtc | 288 |
| Ala | Gly | Asp | Lys | Ser | Leu | Phe | Asp | Glu | Thr | Val | Pro | Ala | Phe | Asp | Val | |
| | | | | 85 | | | | | 90 | | | | | 95 | | |
| ttg | ggg | aag | aag | tct | ttt | tac | ttg | gga | caa | gtc | ggg | aac | gga | gct | aag | 336 |
| Leu | Gly | Lys | Lys | Ser | Phe | Tyr | Leu | Gly | Gln | Val | Gly | Asn | Gly | Ala | Lys | |
| | | | | 100 | | | | | 105 | | | | | 110 | | |
| atg | aaa | ctt | gta | gtc | aac | atg | gtc | atg | gga | agc | atg | atg | aac | gcg | ttt | 384 |
| Met | Lys | Leu | Val | Val | Asn | Met | Val | Met | Gly | Ser | Met | Met | Asn | Ala | Phe | |
| | | | 115 | | | | | 120 | | | | | 125 | | | |
| tct | gag | ggg | ctt | gta | tta | gct | gac | aag | agt | gga | ctt | agc | tct | gac | act | 432 |
| Ser | Glu | Gly | Leu | Val | Leu | Ala | Asp | Lys | Ser | Gly | Leu | Ser | Ser | Asp | Thr | |
| | | 130 | | | | | 135 | | | | | 140 | | | | |
| ctt | ctt | gat | att | ctg | gat | ctt | ggt | gca | atg | aca | aac | ccg | atg | ttc | aaa | 480 |
| Leu | Leu | Asp | Ile | Leu | Asp | Leu | Gly | Ala | Met | Thr | Asn | Pro | Met | Phe | Lys | |
| 145 | | | | | 150 | | | | | 155 | | | | | 160 | |
| ggg | aaa | gga | cct | tcg | atg | aat | aag | agt | agt | tac | cca | cca | gca | ttc | ccg | 528 |
| Gly | Lys | Gly | Pro | Ser | Met | Asn | Lys | Ser | Ser | Tyr | Pro | Pro | Ala | Phe | Pro | |

```
                            165                 170                 175
ttg aaa cat cag cag aag gac atg agg ctt gct ctt gct ctt ggt gat    576
Leu Lys His Gln Gln Lys Asp Met Arg Leu Ala Leu Ala Leu Gly Asp
            180                 185                 190 gaa aac gcc gtc tcc atg cct gta gct gcg gct gca aat gag gct ttt    624
Glu Asn Ala Val Ser Met Pro Val Ala Ala Ala Ala Asn Glu Ala Phe
        195                 200                 205 aag aag gcg aga agc atg gga ctt gga gat ctg gac ttc tct gct gtg    672
Lys Lys Ala Arg Ser Met Gly Leu Gly Asp Leu Asp Phe Ser Ala Val
    210                 215                 220 att gag gct gtg aaa ttc tcc agg gaa cag tag                        705
Ile Glu Ala Val Lys Phe Ser Arg Glu Gln
225                 230
```

<210> SEQ ID NO 35
<211> LENGTH: 234
<212> TYPE: PRT
<213> ORGANISM: Brassica napus

<400> SEQUENCE: 35

```
Met Gln Tyr Thr Ser Ser Met Leu Ser Asp Pro Cys Ala Ala Leu Ser
1               5                   10                  15

Val Val Phe Asp Lys Asp Gly Val Leu Glu Gln Ile Cys Glu Gly Lys
            20                  25                  30

Gly Tyr Ile Asp Met Ser Thr Val Asp Ala Glu Thr Ser Leu Lys Ile
        35                  40                  45

Asn Lys Ala Ile Thr Gly Lys Gly Arg Phe Val Glu Gly Pro Val
    50                  55                  60

Ser Gly Ser Lys Lys Pro Ala Glu Asp Gly Gln Leu Ile Ile Leu Ala
65                  70                  75                  80

Ala Gly Asp Lys Ser Leu Phe Asp Glu Thr Val Pro Ala Phe Asp Val
                85                  90                  95

Leu Gly Lys Lys Ser Phe Tyr Leu Gly Gln Val Gly Asn Gly Ala Lys
            100                 105                 110

Met Lys Leu Val Val Asn Met Val Met Gly Ser Met Met Asn Ala Phe
        115                 120                 125

Ser Glu Gly Leu Val Leu Ala Asp Lys Ser Gly Leu Ser Ser Asp Thr
    130                 135                 140

Leu Leu Asp Ile Leu Asp Leu Gly Ala Met Thr Asn Pro Met Phe Lys
145                 150                 155                 160

Gly Lys Gly Pro Ser Met Asn Lys Ser Ser Tyr Pro Pro Ala Phe Pro
                165                 170                 175

Leu Lys His Gln Gln Lys Asp Met Arg Leu Ala Leu Ala Leu Gly Asp
            180                 185                 190

Glu Asn Ala Val Ser Met Pro Val Ala Ala Ala Ala Asn Glu Ala Phe
        195                 200                 205

Lys Lys Ala Arg Ser Met Gly Leu Gly Asp Leu Asp Phe Ser Ala Val
    210                 215                 220

Ile Glu Ala Val Lys Phe Ser Arg Glu Gln
225                 230
```

<210> SEQ ID NO 36
<211> LENGTH: 594
<212> TYPE: DNA
<213> ORGANISM: Brassica napus
<220> FEATURE:
<221> NAME/KEY: CDS
<222> LOCATION: (1)..(594)

<400> SEQUENCE: 36

```
atg tca aca gtt gat gca gag act tcc tta aag atc aac cag gca atc       48
Met Ser Thr Val Asp Ala Glu Thr Ser Leu Lys Ile Asn Gln Ala Ile
1               5                   10                  15 act ggg aaa ggc ggt cgg ttt gta gaa ggt cct gtt tca ggt agc aag       96
Thr Gly Lys Gly Gly Arg Phe Val Glu Gly Pro Val Ser Gly Ser Lys
                20                  25                  30 aag ccg gca gaa gat ggc cag ctc atc ata ctt gct gct ggt gac aag      144
Lys Pro Ala Glu Asp Gly Gln Leu Ile Ile Leu Ala Ala Gly Asp Lys
            35                  40                  45 tcc ctt ttc gat gaa acg gtc cca gct ttt gac gta ttg ggg aag aag      192
Ser Leu Phe Asp Glu Thr Val Pro Ala Phe Asp Val Leu Gly Lys Lys
        50                  55                  60 tct ttt tac ttg gga caa gtc ggg aac gga gct aag atg aaa ctt gta      240
Ser Phe Tyr Leu Gly Gln Val Gly Asn Gly Ala Lys Met Lys Leu Val
65                  70                  75                  80 gtc aac atg gtc atg gga agc atg atg aac gcg ttt tct gag ggg ctt      288
Val Asn Met Val Met Gly Ser Met Met Asn Ala Phe Ser Glu Gly Leu
                85                  90                  95 gta tta gct gac aag agt gga ctt agc tct gac act ctt ctt gat att      336
Val Leu Ala Asp Lys Ser Gly Leu Ser Ser Asp Thr Leu Leu Asp Ile
            100                 105                 110 ctg gat ctt ggt gca atg aca aac ccg atg ttc aaa ggg aaa gga cct      384
Leu Asp Leu Gly Ala Met Thr Asn Pro Met Phe Lys Gly Lys Gly Pro
        115                 120                 125 tcg atg aat aag agt agt tac cca cct gcg ttc ccg ttg aaa cat cag      432
Ser Met Asn Lys Ser Ser Tyr Pro Pro Ala Phe Pro Leu Lys His Gln
130                 135                 140 cag aag gac atg agg cta gct ctt gct ctt ggc gat gaa aac gct gtc      480
Gln Lys Asp Met Arg Leu Ala Leu Ala Leu Gly Asp Glu Asn Ala Val
145                 150                 155                 160 tcc atg cct gta gct gca gct gca aat gag gct ttt aag aag gcg aga      528
Ser Met Pro Val Ala Ala Ala Ala Asn Glu Ala Phe Lys Lys Ala Arg
                165                 170                 175 agc atg gga ctt gga gat ctg gac ttc tct gct gtg att gag gct gtg      576
Ser Met Gly Leu Gly Asp Leu Asp Phe Ser Ala Val Ile Glu Ala Val
            180                 185                 190 aaa ttc tcc agg gaa tag                                              594
Lys Phe Ser Arg Glu
        195
```

<210> SEQ ID NO 37
<211> LENGTH: 197
<212> TYPE: PRT
<213> ORGANISM: Brassica napus

<400> SEQUENCE: 37

```
Met Ser Thr Val Asp Ala Glu Thr Ser Leu Lys Ile Asn Gln Ala Ile
1               5                   10                  15

Thr Gly Lys Gly Gly Arg Phe Val Glu Gly Pro Val Ser Gly Ser Lys
                20                  25                  30

Lys Pro Ala Glu Asp Gly Gln Leu Ile Ile Leu Ala Ala Gly Asp Lys
            35                  40                  45

Ser Leu Phe Asp Glu Thr Val Pro Ala Phe Asp Val Leu Gly Lys Lys
        50                  55                  60

Ser Phe Tyr Leu Gly Gln Val Gly Asn Gly Ala Lys Met Lys Leu Val
65                  70                  75                  80

Val Asn Met Val Met Gly Ser Met Met Asn Ala Phe Ser Glu Gly Leu
```

```
            85                  90                  95
Val Leu Ala Asp Lys Ser Gly Leu Ser Ser Asp Thr Leu Leu Asp Ile
            100                 105                 110

Leu Asp Leu Gly Ala Met Thr Asn Pro Met Phe Lys Gly Lys Gly Pro
        115                 120                 125

Ser Met Asn Lys Ser Ser Tyr Pro Pro Ala Phe Pro Leu Lys His Gln
    130                 135                 140

Gln Lys Asp Met Arg Leu Ala Leu Ala Leu Gly Asp Glu Asn Ala Val
145                 150                 155                 160

Ser Met Pro Val Ala Ala Ala Asn Glu Ala Phe Lys Lys Ala Arg
            165                 170                 175

Ser Met Gly Leu Gly Asp Leu Asp Phe Ser Ala Val Ile Glu Ala Val
            180                 185                 190

Lys Phe Ser Arg Glu
            195

<210> SEQ ID NO 38
<211> LENGTH: 735
<212> TYPE: DNA
<213> ORGANISM: Brassica rapa
<220> FEATURE:
<221> NAME/KEY: CDS
<222> LOCATION: (1)..(735)

<400> SEQUENCE: 38 atg ggt gag act cca gct caa gta atc aag aaa tgc aaa tac act atc        48
Met Gly Glu Thr Pro Ala Gln Val Ile Lys Lys Cys Lys Tyr Thr Ile
1               5                   10                  15 gct atg cta tct gac cct tgt gct gct ctc tcg gtt gtt ttc gat aaa        96
Ala Met Leu Ser Asp Pro Cys Ala Ala Leu Ser Val Val Phe Asp Lys
                20                  25                  30 gat ggt gtt tta gag caa atc tgt gaa gga aaa ggg tat atc gat atg       144
Asp Gly Val Leu Glu Gln Ile Cys Glu Gly Lys Gly Tyr Ile Asp Met
            35                  40                  45 tca aca gtt gat gca gag act tcc tta aag atc aac cag gca atc act       192
Ser Thr Val Asp Ala Glu Thr Ser Leu Lys Ile Asn Gln Ala Ile Thr
        50                  55                  60 ggg aaa ggc ggt cgg ttt gta gaa ggt cct gtt tca ggt agc aag aag       240
Gly Lys Gly Gly Arg Phe Val Glu Gly Pro Val Ser Gly Ser Lys Lys
65                  70                  75                  80 ccg gca gaa gat ggc cag ctc atc ata ctt gct gct ggt gac aag tcc       288
Pro Ala Glu Asp Gly Gln Leu Ile Ile Leu Ala Ala Gly Asp Lys Ser
                85                  90                  95 ctt ttc gat gaa acg gtc cca gct ttt gac gta ttg ggg aag aag tct       336
Leu Phe Asp Glu Thr Val Pro Ala Phe Asp Val Leu Gly Lys Lys Ser
            100                 105                 110 ttt tac ttg gga caa gtc ggg aac gga gct aag atg aaa ctt gta gtc       384
Phe Tyr Leu Gly Gln Val Gly Asn Gly Ala Lys Met Lys Leu Val Val
        115                 120                 125 aac atg gtc atg gga agc atg atg aac gcg ttt tct gag ggg ctt gta       432
Asn Met Val Met Gly Ser Met Met Asn Ala Phe Ser Glu Gly Leu Val
    130                 135                 140 tta gct gac aag agt gga ctt agc tct gac act ctt ctt gat att ctg       480
Leu Ala Asp Lys Ser Gly Leu Ser Ser Asp Thr Leu Leu Asp Ile Leu
145                 150                 155                 160 gat ctt ggt gca atg aca aac ccg atg ttc aaa ggg aaa gga cct tcg       528
Asp Leu Gly Ala Met Thr Asn Pro Met Phe Lys Gly Lys Gly Pro Ser
                165                 170                 175 atg aat aag agt agt tac cca cct gcg ttc ccg ttg aaa cat cag cag       576
Met Asn Lys Ser Ser Tyr Pro Pro Ala Phe Pro Leu Lys His Gln Gln
```

```
Met Asn Lys Ser Ser Tyr Pro Pro Ala Phe Pro Leu Lys His Gln Gln
                180                 185                 190 aag gac atg agg cta gct ctt gct ctt ggc gat gaa aac gct gtc tcc    624
Lys Asp Met Arg Leu Ala Leu Ala Leu Gly Asp Glu Asn Ala Val Ser
                195                 200                 205 atg cct gta gct gca gct gca aat gag gct ttt aag aag gcg aga agc    672
Met Pro Val Ala Ala Ala Ala Asn Glu Ala Phe Lys Lys Ala Arg Ser
    210                 215                 220 atg gga ctt gga gat ctg gac ttc tct gct gtg att gag gct gtg aaa    720
Met Gly Leu Gly Asp Leu Asp Phe Ser Ala Val Ile Glu Ala Val Lys
225                 230                 235                 240 ttc tcc agg gaa tag                                                 735
Phe Ser Arg Glu
```

<210> SEQ ID NO 39
<211> LENGTH: 244
<212> TYPE: PRT
<213> ORGANISM: Brassica rapa

<400> SEQUENCE: 39

```
Met Gly Glu Thr Pro Ala Gln Val Ile Lys Lys Cys Lys Tyr Thr Ile
1               5                   10                  15

Ala Met Leu Ser Asp Pro Cys Ala Ala Leu Ser Val Val Phe Asp Lys
                20                  25                  30

Asp Gly Val Leu Glu Gln Ile Cys Glu Gly Lys Gly Tyr Ile Asp Met
            35                  40                  45

Ser Thr Val Asp Ala Glu Thr Ser Leu Lys Ile Asn Gln Ala Ile Thr
        50                  55                  60

Gly Lys Gly Gly Arg Phe Val Glu Gly Pro Val Ser Gly Ser Lys Lys
65              70                  75                  80

Pro Ala Glu Asp Gly Gln Leu Ile Ile Leu Ala Ala Gly Asp Lys Ser
                85                  90                  95

Leu Phe Asp Glu Thr Val Pro Ala Phe Asp Val Leu Gly Lys Lys Ser
                100                 105                 110

Phe Tyr Leu Gly Gln Val Gly Asn Gly Ala Lys Met Lys Leu Val Val
            115                 120                 125

Asn Met Val Met Gly Ser Met Met Asn Ala Phe Ser Glu Gly Leu Val
        130                 135                 140

Leu Ala Asp Lys Ser Gly Leu Ser Ser Asp Thr Leu Leu Asp Ile Leu
145                 150                 155                 160

Asp Leu Gly Ala Met Thr Asn Pro Met Phe Lys Gly Lys Gly Pro Ser
                165                 170                 175

Met Asn Lys Ser Ser Tyr Pro Pro Ala Phe Pro Leu Lys His Gln Gln
                180                 185                 190

Lys Asp Met Arg Leu Ala Leu Ala Leu Gly Asp Glu Asn Ala Val Ser
                195                 200                 205

Met Pro Val Ala Ala Ala Ala Asn Glu Ala Phe Lys Lys Ala Arg Ser
    210                 215                 220

Met Gly Leu Gly Asp Leu Asp Phe Ser Ala Val Ile Glu Ala Val Lys
225                 230                 235                 240

Phe Ser Arg Glu
```

<210> SEQ ID NO 40
<211> LENGTH: 318
<212> TYPE: DNA
<213> ORGANISM: Brassica rapa
<220> FEATURE:

<221> NAME/KEY: CDS
<222> LOCATION: (1)..(318)

<400> SEQUENCE: 40

```
atg gag att ggt ttt ctg ggc ttg ggt atc atg gga aag gcc atg gca      48
Met Glu Ile Gly Phe Leu Gly Leu Gly Ile Met Gly Lys Ala Met Ala
1               5                   10                  15 atg aat ctg ttg aaa cat gga ttc aaa gtt acc gtc tgg aac agg aca      96
Met Asn Leu Leu Lys His Gly Phe Lys Val Thr Val Trp Asn Arg Thr
            20                  25                  30 ctc tcc aag tgt gat gaa ctt gtg gag cat gga gct tca atg ggt gag     144
Leu Ser Lys Cys Asp Glu Leu Val Glu His Gly Ala Ser Met Gly Glu
        35                  40                  45 act cca gct caa gta atc aag aaa tgc aaa tac act atc gct atg cta     192
Thr Pro Ala Gln Val Ile Lys Lys Cys Lys Tyr Thr Ile Ala Met Leu
    50                  55                  60 tct gac cct tgt gct gct ctc tcg gtt gtt ttc gat aaa gat ggt gtt     240
Ser Asp Pro Cys Ala Ala Leu Ser Val Val Phe Asp Lys Asp Gly Val
65                  70                  75                  80 tta gag caa atc tgt gaa gga aaa ggg tat atc gat atg tca aca gtt     288
Leu Glu Gln Ile Cys Glu Gly Lys Gly Tyr Ile Asp Met Ser Thr Val
                85                  90                  95 gat gca gag act tcc tta aag atc aac tag                             318
Asp Ala Glu Thr Ser Leu Lys Ile Asn
            100                 105
```

<210> SEQ ID NO 41
<211> LENGTH: 105
<212> TYPE: PRT
<213> ORGANISM: Brassica rapa

<400> SEQUENCE: 41

```
Met Glu Ile Gly Phe Leu Gly Leu Gly Ile Met Gly Lys Ala Met Ala
1               5                   10                  15

Met Asn Leu Leu Lys His Gly Phe Lys Val Thr Val Trp Asn Arg Thr
            20                  25                  30

Leu Ser Lys Cys Asp Glu Leu Val Glu His Gly Ala Ser Met Gly Glu
        35                  40                  45

Thr Pro Ala Gln Val Ile Lys Lys Cys Lys Tyr Thr Ile Ala Met Leu
    50                  55                  60

Ser Asp Pro Cys Ala Ala Leu Ser Val Val Phe Asp Lys Asp Gly Val
65                  70                  75                  80

Leu Glu Gln Ile Cys Glu Gly Lys Gly Tyr Ile Asp Met Ser Thr Val
                85                  90                  95

Asp Ala Glu Thr Ser Leu Lys Ile Asn
            100                 105
```

<210> SEQ ID NO 42
<211> LENGTH: 693
<212> TYPE: DNA
<213> ORGANISM: Brassica oleracea
<220> FEATURE:
<221> NAME/KEY: CDS
<222> LOCATION: (1)..(693)

<400> SEQUENCE: 42

```
atg gag att ggg ttt ctg ggc ttg ggt atc atg gga aag gcc atg gca      48
Met Glu Ile Gly Phe Leu Gly Leu Gly Ile Met Gly Lys Ala Met Ala
1               5                   10                  15 atg aat ctg ttg aaa cat gga ttc aaa gtt acc gtc tgg aac agg aca      96
Met Asn Leu Leu Lys His Gly Phe Lys Val Thr Val Trp Asn Arg Thr
            20                  25                  30
```

|  |  |
|---|---|
| ctc tcc aag tgt gat gaa ctt gtg gag cat gga gct tca atg ggt gag<br>Leu Ser Lys Cys Asp Glu Leu Val Glu His Gly Ala Ser Met Gly Glu<br>        35                     40                    45 | 144 |
| act cca gct caa gta atc aag aaa tgc aaa tac act atc gct atg ctc<br>Thr Pro Ala Gln Val Ile Lys Lys Cys Lys Tyr Thr Ile Ala Met Leu<br>50                     55                     60 | 192 |
| tct gac cct tgt gct gct ctc tcg gtt gtt ttc gat gat aaa gat ggt<br>Ser Asp Pro Cys Ala Ala Leu Ser Val Val Phe Asp Asp Lys Asp Gly<br>65                   70                   75                    80 | 240 |
| gtt tta gag caa atc tgt gaa gga aaa ggg tat atc gat atg tca aca<br>Val Leu Glu Gln Ile Cys Glu Gly Lys Gly Tyr Ile Asp Met Ser Thr<br>                    85                     90                    95 | 288 |
| gtt gat gca gag act tcc tta aag atc aac cag gca atc act ggg aaa<br>Val Asp Ala Glu Thr Ser Leu Lys Ile Asn Gln Ala Ile Thr Gly Lys<br>              100                    105                  110 | 336 |
| ggc ggt cgg ttt gta gaa ggt cct gtt tca ggt agc aag aag ccg gca<br>Gly Gly Arg Phe Val Glu Gly Pro Val Ser Gly Ser Lys Lys Pro Ala<br>              115                    120                  125 | 384 |
| gaa gat ggc cag ctc atc ata ctt gct gct ggt gac aag tcc ctt ttc<br>Glu Asp Gly Gln Leu Ile Ile Leu Ala Ala Gly Asp Lys Ser Leu Phe<br>130                    135                    140 | 432 |
| gat gaa acg gtc cca gct ttt gac gtc ttg ggg aag aag tct ttt tac<br>Asp Glu Thr Val Pro Ala Phe Asp Val Leu Gly Lys Lys Ser Phe Tyr<br>145                    150                    155                  160 | 480 |
| ttg gga caa gtc ggg aac gga gct aag atg aaa ctt gta gtc aac atg<br>Leu Gly Gln Val Gly Asn Gly Ala Lys Met Lys Leu Val Val Asn Met<br>              165                    170                  175 | 528 |
| gtc atg gga agc atg atg aac gcg ttt tct gag ggg ctt gta tta gct<br>Val Met Gly Ser Met Met Asn Ala Phe Ser Glu Gly Leu Val Leu Ala<br>              180                    185                  190 | 576 |
| gac aag agt gga ctt agc tct gac act ctt ctt gat att ctg gat ctt<br>Asp Lys Ser Gly Leu Ser Ser Asp Thr Leu Leu Asp Ile Leu Asp Leu<br>              195                    200                  205 | 624 |
| ggt gca atg aca aac ccg atg ttc aaa ggg aaa gga cct tcg atg aat<br>Gly Ala Met Thr Asn Pro Met Phe Lys Gly Lys Gly Pro Ser Met Asn<br>210                    215                    220 | 672 |
| aag agt agt tac cca cca gca<br>Lys Ser Ser Tyr Pro Pro Ala<br>225                  230 | 693 |

<210> SEQ ID NO 43
<211> LENGTH: 231
<212> TYPE: PRT
<213> ORGANISM: Brassica oleracea

<400> SEQUENCE: 43

Met Glu Ile Gly Phe Leu Gly Leu Gly Ile Met Gly Lys Ala Met Ala
1               5                   10                  15

Met Asn Leu Leu Lys His Gly Phe Lys Val Thr Val Trp Asn Arg Thr
            20                  25                  30

Leu Ser Lys Cys Asp Glu Leu Val Glu His Gly Ala Ser Met Gly Glu
        35                  40                  45

Thr Pro Ala Gln Val Ile Lys Lys Cys Lys Tyr Thr Ile Ala Met Leu
    50                  55                  60

Ser Asp Pro Cys Ala Ala Leu Ser Val Val Phe Asp Asp Lys Asp Gly
65                  70                  75                  80

Val Leu Glu Gln Ile Cys Glu Gly Lys Gly Tyr Ile Asp Met Ser Thr
                85                  90                  95

```
Val Asp Ala Glu Thr Ser Leu Lys Ile Asn Gln Ala Ile Thr Gly Lys
            100                 105                 110

Gly Gly Arg Phe Val Glu Gly Pro Val Ser Gly Ser Lys Lys Pro Ala
        115                 120                 125

Glu Asp Gly Gln Leu Ile Ile Leu Ala Ala Gly Asp Lys Ser Leu Phe
130                 135                 140

Asp Glu Thr Val Pro Ala Phe Asp Val Leu Gly Lys Lys Ser Phe Tyr
145                 150                 155                 160

Leu Gly Gln Val Gly Asn Gly Ala Lys Met Lys Leu Val Asn Met
                165                 170                 175

Val Met Gly Ser Met Met Asn Ala Phe Ser Glu Gly Leu Val Leu Ala
            180                 185                 190

Asp Lys Ser Gly Leu Ser Ser Asp Thr Leu Leu Asp Ile Leu Asp Leu
        195                 200                 205

Gly Ala Met Thr Asn Pro Met Phe Lys Gly Lys Gly Pro Ser Met Asn
    210                 215                 220

Lys Ser Ser Tyr Pro Pro Ala
225                 230

<210> SEQ ID NO 44
<211> LENGTH: 594
<212> TYPE: DNA
<213> ORGANISM: Brassica juncea
<220> FEATURE:
<221> NAME/KEY: CDS
<222> LOCATION: (1)..(594)
<220> FEATURE:
<221> NAME/KEY: misc_feature
<222> LOCATION: (13)..(13)
<223> OTHER INFORMATION: n is a, c, g, or t

<400> SEQUENCE: 44 atg tca aca gtg nat gct gag act tcc tta aag atc aac cag cca atc      48
Met Ser Thr Val Xaa Ala Glu Thr Ser Leu Lys Ile Asn Gln Pro Ile
1               5                   10                  15 acc ggg aaa ggt ggt cgg ttg cta gaa gct cct gtt tct ggt agc aag      96
Thr Gly Lys Gly Gly Arg Leu Leu Glu Ala Pro Val Ser Gly Ser Lys
            20                  25                  30 aaa cca gca gaa gat gga cag ctc atc att ctt gct gct gga gac aag     144
Lys Pro Ala Glu Asp Gly Gln Leu Ile Ile Leu Ala Ala Gly Asp Lys
        35                  40                  45 tcc ctt ttc gat gaa tca atc cca gct ttt gac gtc ttg ggg aag aag     192
Ser Leu Phe Asp Glu Ser Ile Pro Ala Phe Asp Val Leu Gly Lys Lys
    50                  55                  60 tct ttt tac ttg gga caa gtt ggg aac gga gct aag atg aaa ctt gta     240
Ser Phe Tyr Leu Gly Gln Val Gly Asn Gly Ala Lys Met Lys Leu Val
65                  70                  75                  80 gtc aac atg gtc atg gga agc atg atg aat gcg ttt tcc gag ggg ctt     288
Val Asn Met Val Met Gly Ser Met Met Asn Ala Phe Ser Glu Gly Leu
                85                  90                  95 gta tta gct gac aag agt gga ctt agc tct gac act ctt ctt gat att     336
Val Leu Ala Asp Lys Ser Gly Leu Ser Ser Asp Thr Leu Leu Asp Ile
            100                 105                 110 ctg gat ctt ggt gca atg aca aac ccg atg ttc aaa ggg aaa gga cct     384
Leu Asp Leu Gly Ala Met Thr Asn Pro Met Phe Lys Gly Lys Gly Pro
        115                 120                 125 gcg atg aac aag agt agt tac cca cca gcg ttc ccc ttg aaa cat cag     432
Ala Met Asn Lys Ser Ser Tyr Pro Pro Ala Phe Pro Leu Lys His Gln
    130                 135                 140
```

```
cag aag gac atg agg cta gct ctt gcc ctt ggc gat gaa aac gct gtc      480
Gln Lys Asp Met Arg Leu Ala Leu Ala Leu Gly Asp Glu Asn Ala Val
145                 150                 155                 160 tcc atg cct gtt gct gct gct gca aat gag gct ttt aag aag gcg aga      528
Ser Met Pro Val Ala Ala Ala Asn Glu Ala Phe Lys Lys Ala Arg
                165                 170                 175 agc atg gga ctt gga gat ctg gac ttc tct gct gtg att gag gct gtg      576
Ser Met Gly Leu Gly Asp Leu Asp Phe Ser Ala Val Ile Glu Ala Val
            180                 185                 190 aaa ttc tca aag gaa tag                                              594
Lys Phe Ser Lys Glu
        195
```

<210> SEQ ID NO 45
<211> LENGTH: 197
<212> TYPE: PRT
<213> ORGANISM: Brassica juncea
<220> FEATURE:
<221> NAME/KEY: misc_feature
<222> LOCATION: (5)..(5)
<223> OTHER INFORMATION: The 'Xaa' at location 5 stands for Asn, Asp, His, or Tyr.

<400> SEQUENCE: 45

```
Met Ser Thr Val Xaa Ala Glu Thr Ser Leu Lys Ile Asn Gln Pro Ile
1               5                   10                  15

Thr Gly Lys Gly Gly Arg Leu Leu Glu Ala Pro Val Ser Gly Ser Lys
            20                  25                  30

Lys Pro Ala Glu Asp Gly Gln Leu Ile Ile Leu Ala Ala Gly Asp Lys
        35                  40                  45

Ser Leu Phe Asp Glu Ser Ile Pro Ala Phe Asp Val Leu Gly Lys Lys
    50                  55                  60

Ser Phe Tyr Leu Gly Gln Val Gly Asn Gly Ala Lys Met Lys Leu Val
65                  70                  75                  80

Val Asn Met Val Met Gly Ser Met Met Asn Ala Phe Ser Glu Gly Leu
                85                  90                  95

Val Leu Ala Asp Lys Ser Gly Leu Ser Ser Asp Thr Leu Leu Asp Ile
            100                 105                 110

Leu Asp Leu Gly Ala Met Thr Asn Pro Met Phe Lys Gly Lys Gly Pro
        115                 120                 125

Ala Met Asn Lys Ser Ser Tyr Pro Pro Ala Phe Pro Leu Lys His Gln
    130                 135                 140

Gln Lys Asp Met Arg Leu Ala Leu Ala Leu Gly Asp Glu Asn Ala Val
145                 150                 155                 160

Ser Met Pro Val Ala Ala Ala Asn Glu Ala Phe Lys Lys Ala Arg
                165                 170                 175

Ser Met Gly Leu Gly Asp Leu Asp Phe Ser Ala Val Ile Glu Ala Val
            180                 185                 190

Lys Phe Ser Lys Glu
        195
```

<210> SEQ ID NO 46
<211> LENGTH: 645
<212> TYPE: DNA
<213> ORGANISM: Brassica juncea
<220> FEATURE:
<221> NAME/KEY: CDS
<222> LOCATION: (1)..(645)

<400> SEQUENCE: 46

-continued

| | |
|---|---|
| atg gag att ggg ttt ctg ggc ttg ggt atc atg gga aag gcc atg gca<br>Met Glu Ile Gly Phe Leu Gly Leu Gly Ile Met Gly Lys Ala Met Ala<br>1                   5                    10                  15 | 48 |
| atg aat cta ctg aaa cat gga ttc aaa gtt acc gtc tgg aac agg aca<br>Met Asn Leu Leu Lys His Gly Phe Lys Val Thr Val Trp Asn Arg Thr<br>          20                    25                  30 | 96 |
| ctc tcc aag tgt gat gaa ctt gtg gag cat gga gct tca gtg agt gag<br>Leu Ser Lys Cys Asp Glu Leu Val Glu His Gly Ala Ser Val Ser Glu<br>      35                    40                  45 | 144 |
| act cca gct caa gta atc aag aaa tgc aaa tac aca atc gct atg ctc<br>Thr Pro Ala Gln Val Ile Lys Lys Cys Lys Tyr Thr Ile Ala Met Leu<br>50                      55                  60 | 192 |
| tct gac cct tct gct gct ctt tcg gtt gtt ttc gat aaa gat ggt gtc<br>Ser Asp Pro Ser Ala Ala Leu Ser Val Val Phe Asp Lys Asp Gly Val<br>65                    70                  75                  80 | 240 |
| ttg gag caa atc tgt gaa ggg aaa ggc tat atc gat atg tca aca gtt<br>Leu Glu Gln Ile Cys Glu Gly Lys Gly Tyr Ile Asp Met Ser Thr Val<br>                    85                    90                  95 | 288 |
| gat gct gag act tcc tta aag atc aac cag gca atc acc ggg aaa ggt<br>Asp Ala Glu Thr Ser Leu Lys Ile Asn Gln Ala Ile Thr Gly Lys Gly<br>                100                  105                110 | 336 |
| ggt cgg ttt gta gaa ggt cct gtt tct ggt agc aag aaa cca gca gaa<br>Gly Arg Phe Val Glu Gly Pro Val Ser Gly Ser Lys Lys Pro Ala Glu<br>              115                  120                125 | 384 |
| gat gga cag ctc atc att ctt gct gct gga gac aag tcc ctt ttc gat<br>Asp Gly Gln Leu Ile Ile Leu Ala Ala Gly Asp Lys Ser Leu Phe Asp<br>      130                  135                140 | 432 |
| gaa tca atc cca gct ttt gac gtc ttg ggg aag aag tct ttt tac ttg<br>Glu Ser Ile Pro Ala Phe Asp Val Leu Gly Lys Lys Ser Phe Tyr Leu<br>145                    150                  155                160 | 480 |
| gga caa gtt ggg aac gga gct aag atg aaa ctt gta gtc aac atg gtc<br>Gly Gln Val Gly Asn Gly Ala Lys Met Lys Leu Val Val Asn Met Val<br>                165                  170                175 | 528 |
| atg gga agc atg atg aat gcg ttt tcc gag ggg ctt gta tta gct gac<br>Met Gly Ser Met Met Asn Ala Phe Ser Glu Gly Leu Val Leu Ala Asp<br>      180                  185                190 | 576 |
| aag agt gga ctt agc tct gac act ctt ctt gat att ctg gat ctt ggt<br>Lys Ser Gly Leu Ser Ser Asp Thr Leu Leu Asp Ile Leu Asp Leu Gly<br>          195                  200                205 | 624 |
| gca atg aca aac ccg atg ttc<br>Ala Met Thr Asn Pro Met Phe<br>210                    215 | 645 |

<210> SEQ ID NO 47
<211> LENGTH: 215
<212> TYPE: PRT
<213> ORGANISM: Brassica juncea

<400> SEQUENCE: 47

Met Glu Ile Gly Phe Leu Gly Leu Gly Ile Met Gly Lys Ala Met Ala
1               5                   10                  15

Met Asn Leu Leu Lys His Gly Phe Lys Val Thr Val Trp Asn Arg Thr
            20                  25                  30

Leu Ser Lys Cys Asp Glu Leu Val Glu His Gly Ala Ser Val Ser Glu
        35                  40                  45

Thr Pro Ala Gln Val Ile Lys Lys Cys Lys Tyr Thr Ile Ala Met Leu
    50                  55                  60

Ser Asp Pro Ser Ala Ala Leu Ser Val Val Phe Asp Lys Asp Gly Val
65                  70                  75                  80

```
Leu Glu Gln Ile Cys Glu Gly Lys Gly Tyr Ile Asp Met Ser Thr Val
                85                  90                  95

Asp Ala Glu Thr Ser Leu Lys Ile Asn Gln Ala Ile Thr Gly Lys Gly
            100                 105                 110

Gly Arg Phe Val Glu Gly Pro Val Ser Gly Ser Lys Lys Pro Ala Glu
        115                 120                 125

Asp Gly Gln Leu Ile Ile Leu Ala Ala Gly Asp Lys Ser Leu Phe Asp
    130                 135                 140

Glu Ser Ile Pro Ala Phe Asp Val Leu Gly Lys Lys Ser Phe Tyr Leu
145                 150                 155                 160

Gly Gln Val Gly Asn Gly Ala Lys Met Lys Leu Val Val Asn Met Val
                165                 170                 175

Met Gly Ser Met Met Asn Ala Phe Ser Glu Gly Leu Val Leu Ala Asp
            180                 185                 190

Lys Ser Gly Leu Ser Ser Asp Thr Leu Leu Asp Ile Leu Asp Leu Gly
        195                 200                 205

Ala Met Thr Asn Pro Met Phe
    210                 215

<210> SEQ ID NO 48
<211> LENGTH: 993
<212> TYPE: DNA
<213> ORGANISM: Gossypium hirsutum
<220> FEATURE:
<221> NAME/KEY: CDS
<222> LOCATION: (1)..(993)

<400> SEQUENCE: 48
```

| | | | | | | | | | | | | | | | | |
|---|---|---|---|---|---|---|---|---|---|---|---|---|---|---|---|---|
| atg | gag | gtt | ggg | ttt | tta | gga | ttg | gga | ata | atg | ggc | aaa | gcc | atg | tca | 48 |
| Met | Glu | Val | Gly | Phe | Leu | Gly | Leu | Gly | Ile | Met | Gly | Lys | Ala | Met | Ser | |
| 1 | | | | 5 | | | | | 10 | | | | | 15 | | |
| atg | aat | ttg | ctg | aag | aat | gga | ttt | aaa | gtc | act | gtt | tgg | aat | aga | acc | 96 |
| Met | Asn | Leu | Leu | Lys | Asn | Gly | Phe | Lys | Val | Thr | Val | Trp | Asn | Arg | Thr | |
| | | | 20 | | | | | 25 | | | | | 30 | | | |
| ctt | tct | aag | tgt | aat | gaa | tta | gtg | gct | cat | ggt | gca | tca | att | gga | aaa | 144 |
| Leu | Ser | Lys | Cys | Asn | Glu | Leu | Val | Ala | His | Gly | Ala | Ser | Ile | Gly | Lys | |
| | | 35 | | | | | 40 | | | | | 45 | | | | |
| acc | cca | gct | gaa | gtg | att | aac | aag | tgt | acg | atc | acc | att | gct | atg | cta | 192 |
| Thr | Pro | Ala | Glu | Val | Ile | Asn | Lys | Cys | Thr | Ile | Thr | Ile | Ala | Met | Leu | |
| | 50 | | | | | 55 | | | | | 60 | | | | | |
| tct | gat | cct | gct | gct | gct | ctt | tcg | gtt | gtt | ctc | gac | aaa | gac | ggt | gtt | 240 |
| Ser | Asp | Pro | Ala | Ala | Ala | Leu | Ser | Val | Val | Leu | Asp | Lys | Asp | Gly | Val | |
| 65 | | | | | 70 | | | | | 75 | | | | | 80 | |
| ctt | gaa | caa | att | tgc | ggc | ggt | aaa | ggt | tac | atc | gac | atg | tcg | acc | gtc | 288 |
| Leu | Glu | Gln | Ile | Cys | Gly | Gly | Lys | Gly | Tyr | Ile | Asp | Met | Ser | Thr | Val | |
| | | | | 85 | | | | | 90 | | | | | 95 | | |
| gat | ccc | gaa | act | tct | tgc | aag | atc | aat | gag | gcg | att | aca | tcg | aaa | ggt | 336 |
| Asp | Pro | Glu | Thr | Ser | Cys | Lys | Ile | Asn | Glu | Ala | Ile | Thr | Ser | Lys | Gly | |
| | | | 100 | | | | | 105 | | | | | 110 | | | |
| gga | cga | ttc | ctt | gag | gcc | cct | gtt | tcc | ggt | agt | aaa | cag | cct | gca | gaa | 384 |
| Gly | Arg | Phe | Leu | Glu | Ala | Pro | Val | Ser | Gly | Ser | Lys | Gln | Pro | Ala | Glu | |
| | | | 115 | | | | | 120 | | | | | 125 | | | |
| acc | ggt | caa | ctg | gtg | att | ctt | gct | gct | gga | gac | aag | gca | ttg | tat | gaa | 432 |
| Thr | Gly | Gln | Leu | Val | Ile | Leu | Ala | Ala | Gly | Asp | Lys | Ala | Leu | Tyr | Glu | |
| | | 130 | | | | | 135 | | | | | 140 | | | | |
| gca | gca | att | ccg | gct | ttc | gat | atc | ttg | ggg | aag | aag | tct | ttc | ttc | ttg | 480 |
| Ala | Ala | Ile | Pro | Ala | Phe | Asp | Ile | Leu | Gly | Lys | Lys | Ser | Phe | Phe | Leu | |
| 145 | | | | | 150 | | | | | 155 | | | | | 160 | |
| gga | caa | gtc | gga | aat | gga | gct | aaa | atg | aaa | ctt | gtt | gtc | aac | atg | att | 528 |

```
                                                                     -continued Gly Gln Val Gly Asn Gly Ala Lys Met Lys Leu Val Val Asn Met Ile
            165                 170                 175 atg ggc agt atg atg aat gca ttt tca gag gga ctc aca cta gct gat      576
Met Gly Ser Met Met Asn Ala Phe Ser Glu Gly Leu Thr Leu Ala Asp
            180                 185                 190 cga agt gga ctg aac cca cat gac ctt ctt gat gtg ctg gac ttg ggt      624
Arg Ser Gly Leu Asn Pro His Asp Leu Leu Asp Val Leu Asp Leu Gly
            195                 200                 205 gcc att gct aat ccg atg ttc aaa ggg aaa gga cca gcg atg ctc caa      672
Ala Ile Ala Asn Pro Met Phe Lys Gly Lys Gly Pro Ala Met Leu Gln
    210                 215                 220 aac aac tat tcc cct gca ttt cct tta aaa cat caa caa aaa gac atg      720
Asn Asn Tyr Ser Pro Ala Phe Pro Leu Lys His Gln Gln Lys Asp Met
225                 230                 235                 240 agg ttg gct ctt gcc ctg ggg gat gaa aat tca gta ccg atg cca gta      768
Arg Leu Ala Leu Ala Leu Gly Asp Glu Asn Ser Val Pro Met Pro Val
                245                 250                 255 gct gct gct tcc aat gag ctt tta aga agg cta gaa aca tgg gat tgg      816
Ala Ala Ala Ser Asn Glu Leu Leu Arg Arg Leu Glu Thr Trp Asp Trp
            260                 265                 270 gag aca tgg att ttt tca cca gtg ttt gat acc ttg aaa ggt ctt aaa      864
Glu Thr Trp Ile Phe Ser Pro Val Phe Asp Thr Leu Lys Gly Leu Lys
            275                 280                 285 ctt tct ctt aaa tat ccc atg gat ttt aaa tgg cat gaa aac ccg aac      912
Leu Ser Leu Lys Tyr Pro Met Asp Phe Lys Trp His Glu Asn Pro Asn
    290                 295                 300 caa ggt agg gga aaa ttt act gat tta ggg ttt ttg atc ttc ttt ttg      960
Gln Gly Arg Gly Lys Phe Thr Asp Leu Gly Phe Leu Ile Phe Phe Leu
305                 310                 315                 320 aaa aac ctt tct gaa tgg gac ctg gat ttt tag                          993
Lys Asn Leu Ser Glu Trp Asp Leu Asp Phe
                325                 330

<210> SEQ ID NO 49
<211> LENGTH: 330
<212> TYPE: PRT
<213> ORGANISM: Gossypium hirsutum

<400> SEQUENCE: 49

Met Glu Val Gly Phe Leu Gly Leu Gly Ile Met Gly Lys Ala Met Ser
1               5                   10                  15

Met Asn Leu Leu Lys Asn Gly Phe Lys Val Thr Val Trp Asn Arg Thr
            20                  25                  30

Leu Ser Lys Cys Asn Glu Leu Val Ala His Gly Ala Ser Ile Gly Lys
        35                  40                  45

Thr Pro Ala Glu Val Ile Asn Lys Cys Thr Ile Thr Ile Ala Met Leu
    50                  55                  60

Ser Asp Pro Ala Ala Leu Ser Val Val Leu Asp Lys Asp Gly Val
65                  70                  75                  80

Leu Glu Gln Ile Cys Gly Gly Lys Gly Tyr Ile Asp Met Ser Thr Val
                85                  90                  95

Asp Pro Glu Thr Ser Cys Lys Ile Asn Glu Ala Ile Thr Ser Lys Gly
            100                 105                 110

Gly Arg Phe Leu Glu Ala Pro Val Ser Gly Ser Lys Gln Pro Ala Glu
        115                 120                 125

Thr Gly Gln Leu Val Ile Leu Ala Ala Gly Asp Lys Ala Leu Tyr Glu
    130                 135                 140

Ala Ala Ile Pro Ala Phe Asp Ile Leu Gly Lys Lys Ser Phe Phe Leu
```

```
                145                 150                 155                 160
            Gly Gln Val Gly Asn Gly Ala Lys Met Lys Leu Val Val Asn Met Ile
                            165                 170                 175

Met Gly Ser Met Met Asn Ala Phe Ser Glu Gly Leu Thr Leu Ala Asp
                        180                 185                 190

Arg Ser Gly Leu Asn Pro His Asp Leu Leu Asp Val Leu Asp Leu Gly
                    195                 200                 205

Ala Ile Ala Asn Pro Met Phe Lys Gly Lys Gly Pro Ala Met Leu Gln
                210                 215                 220

Asn Asn Tyr Ser Pro Ala Phe Pro Leu Lys His Gln Gln Lys Asp Met
            225                 230                 235                 240

Arg Leu Ala Leu Ala Leu Gly Asp Glu Asn Ser Val Pro Met Pro Val
                            245                 250                 255

Ala Ala Ala Ser Asn Glu Leu Leu Arg Arg Leu Glu Thr Trp Asp Trp
                        260                 265                 270

Glu Thr Trp Ile Phe Ser Pro Val Phe Asp Thr Leu Lys Gly Leu Lys
                    275                 280                 285

Leu Ser Leu Lys Tyr Pro Met Asp Phe Lys Trp His Glu Asn Pro Asn
                290                 295                 300

Gln Gly Arg Gly Lys Phe Thr Asp Leu Gly Phe Leu Ile Phe Phe Leu
            305                 310                 315                 320

Lys Asn Leu Ser Glu Trp Asp Leu Asp Phe
                            325                 330

<210> SEQ ID NO 50
<211> LENGTH: 747
<212> TYPE: DNA
<213> ORGANISM: Gossypium hirsutum
<220> FEATURE:
<221> NAME/KEY: CDS
<222> LOCATION: (1)..(747)
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t

<400> SEQUENCE: 50 atg gag gtt ggg ttt tta gga ttg gga ata atg ggc aaa gcc atg tca         48
Met Glu Val Gly Phe Leu Gly Leu Gly Ile Met Gly Lys Ala Met Ser
1               5                   10                  15 atg aat ttg ctg atg aat gga ttt aaa gtc act gtt tgg aac aga acc         96
Met Asn Leu Leu Met Asn Gly Phe Lys Val Thr Val Trp Asn Arg Thr
                20                  25                  30 ctt tct aag tgt aat gaa cta gtg gct cat ggt gct tca att gga aaa        144
Leu Ser Lys Cys Asn Glu Leu Val Ala His Gly Ala Ser Ile Gly Lys
            35                  40                  45 acc cca gct gaa gtg att aac aag tgt aag atc acc att gct atg cta        192
```

```
                Thr Pro Ala Glu Val Ile Asn Lys Cys Lys Ile Thr Ile Ala Met Leu
                    50                  55                  60 tct gat cct gct gct gct ctt tcg gtt gtt ctc gac aaa gat ggt gtt      240
Ser Asp Pro Ala Ala Ala Leu Ser Val Val Leu Asp Lys Asp Gly Val
 65                  70                  75                  80 ctc gaa caa att tgt ggc ggt aaa ggt tac atc gac atg tcg acc gtc      288
Leu Glu Gln Ile Cys Gly Gly Lys Gly Tyr Ile Asp Met Ser Thr Val
                     85                  90                  95 gat ccc gaa act tct tgc agg atc aat gag gcg att aca tca aaa ggt      336
Asp Pro Glu Thr Ser Cys Arg Ile Asn Glu Ala Ile Thr Ser Lys Gly
                100                 105                 110 gga caa ttc ctc gag gcc cct gtt tcc ggt agt aaa cag cct gca gaa      384
Gly Gln Phe Leu Glu Ala Pro Val Ser Gly Ser Lys Gln Pro Ala Glu
            115                 120                 125 acc ggt caa ctg gtg att ctt gcc gct gga gat aag gca ttg tat gaa      432
Thr Gly Gln Leu Val Ile Leu Ala Ala Gly Asp Lys Ala Leu Tyr Glu
        130                 135                 140 gca gca atg cca gct ttc gat atc ttg ggg aag aag tct ttc ttc ttg      480
Ala Ala Met Pro Ala Phe Asp Ile Leu Gly Lys Lys Ser Phe Phe Leu
145                 150                 155                 160 gga caa gtc gga aat gga gct aaa atg aaa ctt gtt gtc aac atg atc      528
Gly Gln Val Gly Asn Gly Ala Lys Met Lys Leu Val Val Asn Met Ile
                165                 170                 175 atg ggc agt atg atg aat gca ttt tcg gag gga ctc aca cta gct gat      576
Met Gly Ser Met Met Asn Ala Phe Ser Glu Gly Leu Thr Leu Ala Asp
                180                 185                 190 cga agc gga ctg aac cca cgt gac ctt ctt gat gtg ctg gac ttg ggt      624
Arg Ser Gly Leu Asn Pro Arg Asp Leu Leu Asp Val Leu Asp Leu Gly
            195                 200                 205 gcc att gct aat ccg atg tnt caa ggg aaa gga ccc agc atg ctc caa      672
Ala Ile Ala Asn Pro Met Xaa Gln Gly Lys Gly Pro Ser Met Leu Gln
        210                 215                 220 aac aat tat tcc cct gca ttt cct tta ana cat cna cag aaa gac atg      720
Asn Asn Tyr Ser Pro Ala Phe Pro Leu Xaa His Xaa Gln Lys Asp Met
225                 230                 235                 240 ang ttg gct att gcc ctg ngg gga tga                                   747
Xaa Leu Ala Ile Ala Leu Xaa Gly
                245

<210> SEQ ID NO 51
<211> LENGTH: 248
<212> TYPE: PRT
<213> ORGANISM: Gossypium hirsutum
<220> FEATURE:
<221> NAME/KEY: misc_feature
<222> LOCATION: (215)..(215)
<223> OTHER INFORMATION: The 'Xaa' at location 215 stands for Tyr, Cys,
      Ser, or Phe.
<220> FEATURE:
<221> NAME/KEY: misc_feature
<222> LOCATION: (234)..(234)
<223> OTHER INFORMATION: The 'Xaa' at location 234 stands for Lys, Arg,
      Thr, or Ile.
<220> FEATURE:
<221> NAME/KEY: misc_feature
<222> LOCATION: (236)..(236)
<223> OTHER INFORMATION: The 'Xaa' at location 236 stands for Gln, Arg,
      Pro, or Leu.
<220> FEATURE:
<221> NAME/KEY: misc_feature
<222> LOCATION: (241)..(241)
<223> OTHER INFORMATION: The 'Xaa' at location 241 stands for Lys, Arg,
      Thr, or Met.
<220> FEATURE:
<221> NAME/KEY: misc_feature
<222> LOCATION: (247)..(247)
```

<223> OTHER INFORMATION: The 'Xaa' at location 247 stands for Arg, Gly, or Trp.

<400> SEQUENCE: 51

```
Met Glu Val Gly Phe Leu Gly Leu Gly Ile Met Gly Lys Ala Met Ser
1               5                   10                  15
Met Asn Leu Leu Met Asn Gly Phe Lys Val Thr Val Trp Asn Arg Thr
            20                  25                  30
Leu Ser Lys Cys Asn Glu Leu Val Ala His Gly Ala Ser Ile Gly Lys
        35                  40                  45
Thr Pro Ala Glu Val Ile Asn Lys Cys Lys Ile Thr Ile Ala Met Leu
    50                  55                  60
Ser Asp Pro Ala Ala Leu Ser Val Val Leu Asp Lys Asp Gly Val
65                  70                  75                  80
Leu Glu Gln Ile Cys Gly Gly Lys Gly Tyr Ile Asp Met Ser Thr Val
                85                  90                  95
Asp Pro Glu Thr Ser Cys Arg Ile Asn Glu Ala Ile Thr Ser Lys Gly
            100                 105                 110
Gly Gln Phe Leu Glu Ala Pro Val Ser Gly Ser Lys Gln Pro Ala Glu
        115                 120                 125
Thr Gly Gln Leu Val Ile Leu Ala Ala Gly Asp Lys Ala Leu Tyr Glu
    130                 135                 140
Ala Ala Met Pro Ala Phe Asp Ile Leu Gly Lys Lys Ser Phe Phe Leu
145                 150                 155                 160
Gly Gln Val Gly Asn Gly Ala Lys Met Lys Leu Val Val Asn Met Ile
                165                 170                 175
Met Gly Ser Met Met Asn Ala Phe Ser Glu Gly Leu Thr Leu Ala Asp
            180                 185                 190
Arg Ser Gly Leu Asn Pro Arg Asp Leu Leu Asp Val Leu Asp Leu Gly
        195                 200                 205
Ala Ile Ala Asn Pro Met Xaa Gln Gly Lys Gly Pro Ser Met Leu Gln
    210                 215                 220
Asn Asn Tyr Ser Pro Ala Phe Pro Leu Xaa His Xaa Gln Lys Asp Met
225                 230                 235                 240
Xaa Leu Ala Ile Ala Leu Xaa Gly
                245
```

<210> SEQ ID NO 52
<211> LENGTH: 669
<212> TYPE: DNA
<213> ORGANISM: Gossypium arboreum
<220> FEATURE:
<221> NAME/KEY: CDS
<222> LOCATION: (1)..(669)

<400> SEQUENCE: 52

```
atg ggc aaa gcc atg tca atg aat ttg ctg atg aat gga ttt aaa gtc    48
Met Gly Lys Ala Met Ser Met Asn Leu Leu Met Asn Gly Phe Lys Val
1               5                   10                  15 act gtt tgg aac aga acc ctt tct aag tgt aat gaa cta gtg gct cat    96
Thr Val Trp Asn Arg Thr Leu Ser Lys Cys Asn Glu Leu Val Ala His
            20                  25                  30 ggt gct tca att gga aaa acc cca gct gaa gtg att aac aag tgt aag   144
Gly Ala Ser Ile Gly Lys Thr Pro Ala Glu Val Ile Asn Lys Cys Lys
        35                  40                  45 atc acc att gct atg cta tct gat cct gct gct gct ctt tcg gtt gtt   192
Ile Thr Ile Ala Met Leu Ser Asp Pro Ala Ala Ala Leu Ser Val Val
    50                  55                  60
```

```
ctc aac aaa gat ggt gtt ctc gaa caa att tgt ggc ggt aaa ggt tac      240
Leu Asn Lys Asp Gly Val Leu Glu Gln Ile Cys Gly Gly Lys Gly Tyr
 65                  70                  75                  80 atc gac atg tcg acc gtc gat ccc gaa act tct tgc agg atc aat gag      288
Ile Asp Met Ser Thr Val Asp Pro Glu Thr Ser Cys Arg Ile Asn Glu
                 85                  90                  95 gcg att aca tca aaa ggt gga caa ttc ctc gag gcc cct gtt tcc ggt      336
Ala Ile Thr Ser Lys Gly Gly Gln Phe Leu Glu Ala Pro Val Ser Gly
            100                 105                 110 agt aaa cag cct gca gaa acc ggt caa ctg gtg att ctt gcc gct gga      384
Ser Lys Gln Pro Ala Glu Thr Gly Gln Leu Val Ile Leu Ala Ala Gly
        115                 120                 125 gat aag gca ttg tat gaa gca gca atg cca gct ttc gat atc ttg ggg      432
Asp Lys Ala Leu Tyr Glu Ala Ala Met Pro Ala Phe Asp Ile Leu Gly
130                 135                 140 aag aag tct ttc ttc ttg gga caa gtc gga aat gga gct aaa atg aaa      480
Lys Lys Ser Phe Phe Leu Gly Gln Val Gly Asn Gly Ala Lys Met Lys
145                 150                 155                 160 ctt gtt gtc aac atg atc atg ggc agt atg atg aat gca ttt tcg gag      528
Leu Val Val Asn Met Ile Met Gly Ser Met Met Asn Ala Phe Ser Glu
                165                 170                 175 gga ctc aca cta gct gat cga agc gga ctg aac cca cgt gac ctt ctt      576
Gly Leu Thr Leu Ala Asp Arg Ser Gly Leu Asn Pro Arg Asp Leu Leu
            180                 185                 190 gat gtg ctg gac ttg ggt gcc att gct aat ccg atg ttc aaa ggg aaa      624
Asp Val Leu Asp Leu Gly Ala Ile Ala Asn Pro Met Phe Lys Gly Lys
        195                 200                 205 gga cca gca atg ctc caa aac aac tat tcc cct gca ttt cct taa          669
Gly Pro Ala Met Leu Gln Asn Asn Tyr Ser Pro Ala Phe Pro
210                 215                 220
```

<210> SEQ ID NO 53
<211> LENGTH: 222
<212> TYPE: PRT
<213> ORGANISM: Gossypium arboreum

<400> SEQUENCE: 53

```
Met Gly Lys Ala Met Ser Met Asn Leu Leu Met Asn Gly Phe Lys Val
 1               5                  10                  15

Thr Val Trp Asn Arg Thr Leu Ser Lys Cys Asn Glu Leu Val Ala His
             20                  25                  30

Gly Ala Ser Ile Gly Lys Thr Pro Ala Glu Val Ile Asn Lys Cys Lys
         35                  40                  45

Ile Thr Ile Ala Met Leu Ser Asp Pro Ala Ala Leu Ser Val Val
 50                  55                  60

Leu Asn Lys Asp Gly Val Leu Glu Gln Ile Cys Gly Gly Lys Gly Tyr
 65                  70                  75                  80

Ile Asp Met Ser Thr Val Asp Pro Glu Thr Ser Cys Arg Ile Asn Glu
                 85                  90                  95

Ala Ile Thr Ser Lys Gly Gly Gln Phe Leu Glu Ala Pro Val Ser Gly
            100                 105                 110

Ser Lys Gln Pro Ala Glu Thr Gly Gln Leu Val Ile Leu Ala Ala Gly
        115                 120                 125

Asp Lys Ala Leu Tyr Glu Ala Ala Met Pro Ala Phe Asp Ile Leu Gly
130                 135                 140

Lys Lys Ser Phe Phe Leu Gly Gln Val Gly Asn Gly Ala Lys Met Lys
145                 150                 155                 160
```

```
Leu Val Val Asn Met Ile Met Gly Ser Met Met Asn Ala Phe Ser Glu
                165                 170                 175

Gly Leu Thr Leu Ala Asp Arg Ser Gly Leu Asn Pro Arg Asp Leu Leu
        180                 185                 190

Asp Val Leu Asp Leu Gly Ala Ile Ala Asn Pro Met Phe Lys Gly Lys
            195                 200                 205

Gly Pro Ala Met Leu Gln Asn Asn Tyr Ser Pro Ala Phe Pro
210                 215                 220
```

<210> SEQ ID NO 54
<211> LENGTH: 876
<212> TYPE: DNA
<213> ORGANISM: Triticum aestivum
<220> FEATURE:
<221> NAME/KEY: CDS
<222> LOCATION: (1)..(876)

<400> SEQUENCE: 54

```
atg gag gtg ggc ttc ctg ggg ctg ggc atc atg ggc aag gca atg gcg      48
Met Glu Val Gly Phe Leu Gly Leu Gly Ile Met Gly Lys Ala Met Ala
1               5                   10                  15 gcc aac ctc ctc cgc cac ggc ttc cgc gtc acc gtc tgg aac cgg acc      96
Ala Asn Leu Leu Arg His Gly Phe Arg Val Thr Val Trp Asn Arg Thr
                20                  25                  30 ctc tcc aag tgc gac gag ctc gtc gcg atg ggt gcc gcc gtc ggg gac     144
Leu Ser Lys Cys Asp Glu Leu Val Ala Met Gly Ala Ala Val Gly Asp
            35                  40                  45 acg ccg gcg tcc gtc gtc gcc aag tgc aag tac acc atc gcc atg ctc     192
Thr Pro Ala Ser Val Val Ala Lys Cys Lys Tyr Thr Ile Ala Met Leu
        50                  55                  60 tcc gat ccc agc gcc gcg cta tct gtt gtt ttc gac aag gat ggt gtg     240
Ser Asp Pro Ser Ala Ala Leu Ser Val Val Phe Asp Lys Asp Gly Val
65                  70                  75                  80 ctc gag caa atc gga gag ggc aag ggc tac gtg gac atg tcc act gtc     288
Leu Glu Gln Ile Gly Glu Gly Lys Gly Tyr Val Asp Met Ser Thr Val
                85                  90                  95 gat gct gca act tct tgc aag ata agc gag gcg gtt aaa caa aag ggc     336
Asp Ala Ala Thr Ser Cys Lys Ile Ser Glu Ala Val Lys Gln Lys Gly
                100                 105                 110 gga gct ttt gtt gaa gct cca gtt tca ggg agc aag aag cca gct gaa     384
Gly Ala Phe Val Glu Ala Pro Val Ser Gly Ser Lys Lys Pro Ala Glu
        115                 120                 125 gat ggc caa ttg gtc att ctt gct gca ggc gac aag gca cta tat gat     432
Asp Gly Gln Leu Val Ile Leu Ala Ala Gly Asp Lys Ala Leu Tyr Asp
    130                 135                 140 gat atg gtc cct gca ttt gat gta ctt ggg aag aag tcg ttc ttt ctg     480
Asp Met Val Pro Ala Phe Asp Val Leu Gly Lys Lys Ser Phe Phe Leu
145                 150                 155                 160 ggg gag atg gga aat gga gca aag atg aaa ctg gtg gtc aac atg atc     528
Gly Glu Met Gly Asn Gly Ala Lys Met Lys Leu Val Val Asn Met Ile
                165                 170                 175 atg gga agt atg atg aat gct ttt tct gag gga ctc tgt ttg gct gac     576
Met Gly Ser Met Met Asn Ala Phe Ser Glu Gly Leu Cys Leu Ala Asp
            180                 185                 190 aaa agt ggg ttg agc ccc cag acg ctt ctt gat gtc ctg gat ctc ggt     624
Lys Ser Gly Leu Ser Pro Gln Thr Leu Leu Asp Val Leu Asp Leu Gly
        195                 200                 205 gca atc gca aat ccg atg ttc aag atg aaa ggg cct tca atg ctg cag     672
Ala Ile Ala Asn Pro Met Phe Lys Met Lys Gly Pro Ser Met Leu Gln
    210                 215                 220
```

```
ggc agc tac aat cca gcg ttt ccc ctc aaa cat cag cag aag gat atg    720
Gly Ser Tyr Asn Pro Ala Phe Pro Leu Lys His Gln Gln Lys Asp Met
225                 230                 235                 240 agg ttg gct ctg tcg ttg gga gat gaa aat gcc gtg tcc atg cca gtg    768
Arg Leu Ala Leu Ser Leu Gly Asp Glu Asn Ala Val Ser Met Pro Val
            245                 250                 255 gca gct gct tcc aat gag gca ttc aag aaa gca aga agc ttg gga ctt    816
Ala Ala Ala Ser Asn Glu Ala Phe Lys Lys Ala Arg Ser Leu Gly Leu
        260                 265                 270 ggc gac ctg gat ttt tct gca gtg cac gag gtg ctg aaa ggc aca ggt    864
Gly Asp Leu Asp Phe Ser Ala Val His Glu Val Leu Lys Gly Thr Gly
    275                 280                 285 ggt tca ggc taa                                                     876
Gly Ser Gly
    290

<210> SEQ ID NO 55
<211> LENGTH: 291
<212> TYPE: PRT
<213> ORGANISM: Triticum aestivum

<400> SEQUENCE: 55

Met Glu Val Gly Phe Leu Gly Leu Gly Ile Met Gly Lys Ala Met Ala
1               5                   10                  15

Ala Asn Leu Leu Arg His Gly Phe Arg Val Thr Val Trp Asn Arg Thr
            20                  25                  30

Leu Ser Lys Cys Asp Glu Leu Ala Met Gly Ala Ala Val Gly Asp
        35                  40                  45

Thr Pro Ala Ser Val Val Ala Lys Cys Lys Tyr Thr Ile Ala Met Leu
    50                  55                  60

Ser Asp Pro Ser Ala Ala Leu Ser Val Val Phe Asp Lys Asp Gly Val
65                  70                  75                  80

Leu Glu Gln Ile Gly Glu Gly Lys Gly Tyr Val Asp Met Ser Thr Val
                85                  90                  95

Asp Ala Ala Thr Ser Cys Lys Ile Ser Glu Ala Val Lys Gln Lys Gly
            100                 105                 110

Gly Ala Phe Val Glu Ala Pro Val Ser Gly Ser Lys Lys Pro Ala Glu
        115                 120                 125

Asp Gly Gln Leu Val Ile Leu Ala Ala Gly Asp Lys Ala Leu Tyr Asp
    130                 135                 140

Asp Met Val Pro Ala Phe Asp Val Leu Gly Lys Lys Ser Phe Phe Leu
145                 150                 155                 160

Gly Glu Met Gly Asn Gly Ala Lys Met Lys Leu Val Val Asn Met Ile
                165                 170                 175

Met Gly Ser Met Met Asn Ala Phe Ser Glu Gly Leu Cys Leu Ala Asp
            180                 185                 190

Lys Ser Gly Leu Ser Pro Gln Thr Leu Leu Asp Val Leu Asp Leu Gly
        195                 200                 205

Ala Ile Ala Asn Pro Met Phe Lys Met Lys Gly Pro Ser Met Leu Gln
    210                 215                 220

Gly Ser Tyr Asn Pro Ala Phe Pro Leu Lys His Gln Gln Lys Asp Met
225                 230                 235                 240

Arg Leu Ala Leu Ser Leu Gly Asp Glu Asn Ala Val Ser Met Pro Val
                245                 250                 255

Ala Ala Ala Ser Asn Glu Ala Phe Lys Lys Ala Arg Ser Leu Gly Leu
            260                 265                 270
```

Gly Asp Leu Asp Phe Ser Ala Val His Glu Val Leu Lys Gly Thr Gly
        275                 280                 285

Gly Ser Gly
    290

<210> SEQ ID NO 56
<211> LENGTH: 609
<212> TYPE: DNA
<213> ORGANISM: Triticum aestivum
<220> FEATURE:
<221> NAME/KEY: CDS
<222> LOCATION: (1)..(609)

<400> SEQUENCE: 56

```
atg gag gtg ggc ttc ctg gga ctg ggc atc atg ggc aag gca atg gcg      48
Met Glu Val Gly Phe Leu Gly Leu Gly Ile Met Gly Lys Ala Met Ala
1               5                   10                  15 gcc aac ctc ctc cgc cac ggc ttc cgc gtc acc gtg tgg aac cgg acc      96
Ala Asn Leu Leu Arg His Gly Phe Arg Val Thr Val Trp Asn Arg Thr
            20                  25                  30 ctg tcc aag tgc gac gag ctc gtc gcg atg ggt gcc gcc gtc ggg gac     144
Leu Ser Lys Cys Asp Glu Leu Val Ala Met Gly Ala Ala Val Gly Asp
        35                  40                  45 acg ccg gcg tcc gtc gtc gct aag tgc aag tac acc atc gcc atg ctc     192
Thr Pro Ala Ser Val Val Ala Lys Cys Lys Tyr Thr Ile Ala Met Leu
    50                  55                  60 tcc gat ccc agc gcc gcg cta tcc gtt gtt ttc gac aag gat ggc gtg     240
Ser Asp Pro Ser Ala Ala Leu Ser Val Val Phe Asp Lys Asp Gly Val
65                  70                  75                  80 ctc gag caa atc gga gag ggc aag ggc tac gtg gat atg tcc act gtt     288
Leu Glu Gln Ile Gly Glu Gly Lys Gly Tyr Val Asp Met Ser Thr Val
                85                  90                  95 gat gct gca act tct tgc aag ata agc gag gcg gtt aaa caa aag ggc     336
Asp Ala Ala Thr Ser Cys Lys Ile Ser Glu Ala Val Lys Gln Lys Gly
            100                 105                 110 gga gct ttt gtt gaa gct cca gtt tca ggg agc aag aag cca gct gaa     384
Gly Ala Phe Val Glu Ala Pro Val Ser Gly Ser Lys Lys Pro Ala Glu
        115                 120                 125 gat ggc caa ttg gtc att ctt gct gca ggc gac aag gca cta tat gat     432
Asp Gly Gln Leu Val Ile Leu Ala Ala Gly Asp Lys Ala Leu Tyr Asp
    130                 135                 140 gat atg gtc cct gca ttt gat gta ctt ggg aag aag tca ttc ttt ctg     480
Asp Met Val Pro Ala Phe Asp Val Leu Gly Lys Lys Ser Phe Phe Leu
145                 150                 155                 160 ggg gag atg gga aat gga gca aag atg aaa ctg gtg gtc aac atg atc     528
Gly Glu Met Gly Asn Gly Ala Lys Met Lys Leu Val Val Asn Met Ile
                165                 170                 175 atg gga agt atg atg aat gct ttt tct gag gga ctc tgt ttg gct gac     576
Met Gly Ser Met Met Asn Ala Phe Ser Glu Gly Leu Cys Leu Ala Asp
            180                 185                 190 aaa agt ggg ttt gag ccc cca gac gct tct tga                         609
Lys Ser Gly Phe Glu Pro Pro Asp Ala Ser
        195                 200
```

<210> SEQ ID NO 57
<211> LENGTH: 202
<212> TYPE: PRT
<213> ORGANISM: Triticum aestivum

<400> SEQUENCE: 57

Met Glu Val Gly Phe Leu Gly Leu Gly Ile Met Gly Lys Ala Met Ala
1               5                   10                  15

```
Ala Asn Leu Leu Arg His Gly Phe Arg Val Thr Val Trp Asn Arg Thr
         20                  25                  30

Leu Ser Lys Cys Asp Glu Leu Val Ala Met Gly Ala Ala Val Gly Asp
             35                  40                  45

Thr Pro Ala Ser Val Val Ala Lys Cys Lys Tyr Thr Ile Ala Met Leu
 50                  55                  60

Ser Asp Pro Ser Ala Ala Leu Ser Val Val Phe Asp Lys Asp Gly Val
 65                  70                  75                  80

Leu Glu Gln Ile Gly Glu Gly Lys Gly Tyr Val Asp Met Ser Thr Val
                 85                  90                  95

Asp Ala Ala Thr Ser Cys Lys Ile Ser Glu Ala Val Lys Gln Lys Gly
                100                 105                 110

Gly Ala Phe Val Glu Ala Pro Val Ser Gly Ser Lys Lys Pro Ala Glu
            115                 120                 125

Asp Gly Gln Leu Val Ile Leu Ala Ala Gly Asp Lys Ala Leu Tyr Asp
130                 135                 140

Asp Met Val Pro Ala Phe Asp Val Leu Gly Lys Lys Ser Phe Phe Leu
145                 150                 155                 160

Gly Glu Met Gly Asn Gly Ala Lys Met Lys Leu Val Val Asn Met Ile
                165                 170                 175

Met Gly Ser Met Met Asn Ala Phe Ser Glu Gly Leu Cys Leu Ala Asp
            180                 185                 190

Lys Ser Gly Phe Glu Pro Pro Asp Ala Ser
            195                 200
```

<210> SEQ ID NO 58
<211> LENGTH: 600
<212> TYPE: DNA
<213> ORGANISM: Triticum aestivum
<220> FEATURE:
<221> NAME/KEY: CDS
<222> LOCATION: (1)..(600)

<400> SEQUENCE: 58

```
atg tcc act gtc gat gct gca act tct tgc aag ata agc gag gcg gtt      48
Met Ser Thr Val Asp Ala Ala Thr Ser Cys Lys Ile Ser Glu Ala Val
 1               5                  10                  15 aaa caa aag ggc gga gct ttt gtt gaa gct cca gtt tca ggg agc aag      96
Lys Gln Lys Gly Gly Ala Phe Val Glu Ala Pro Val Ser Gly Ser Lys
             20                  25                  30 aag cca gct gaa gat ggc caa ttg gtc att ctt gct gca ggc gac aag     144
Lys Pro Ala Glu Asp Gly Gln Leu Val Ile Leu Ala Ala Gly Asp Lys
         35                  40                  45 gca cta tat gat gat atg gtc cct gca ttt gat gta ctt ggg aag aag     192
Ala Leu Tyr Asp Asp Met Val Pro Ala Phe Asp Val Leu Gly Lys Lys
 50                  55                  60 tcg ttc ttt ctg ggg gag atg gga aat gga gca aag atg aaa ctg gtg     240
Ser Phe Phe Leu Gly Glu Met Gly Asn Gly Ala Lys Met Lys Leu Val
 65                  70                  75                  80 gtc aac atg atc atg gga agt atg atg aat gct ttt tct gag gga ctc     288
Val Asn Met Ile Met Gly Ser Met Met Asn Ala Phe Ser Glu Gly Leu
                 85                  90                  95 tgt ttg gct gac aaa agt ggg ttg agc ccc cag acg ctt ctt gat gtc     336
Cys Leu Ala Asp Lys Ser Gly Leu Ser Pro Gln Thr Leu Leu Asp Val
            100                 105                 110 ctg gat ctc ggt gca atc gca aat ccg atg ttc aag atg aaa ggg cct     384
Leu Asp Leu Gly Ala Ile Ala Asn Pro Met Phe Lys Met Lys Gly Pro
        115                 120                 125
```

```
tca atg ctg cag ggc agc tac aat cca gcg ttt ccc ctc aaa cat cag      432
Ser Met Leu Gln Gly Ser Tyr Asn Pro Ala Phe Pro Leu Lys His Gln
    130                 135                 140 cag aag gat atg agg ttg gct ctg tcg ttg gga gat gaa aat gcc gtg      480
Gln Lys Asp Met Arg Leu Ala Leu Ser Leu Gly Asp Glu Asn Ala Val
145                 150                 155                 160 tcc atg cca gtg gca gct gct tcc aat gag gca ttc aag aaa gca aga      528
Ser Met Pro Val Ala Ala Ala Ser Asn Glu Ala Phe Lys Lys Ala Arg
                165                 170                 175 agc ttg gga ctt ggc gac ctg gat ttt tct gtg gtg cac gag gtg ctg      576
Ser Leu Gly Leu Gly Asp Leu Asp Phe Ser Val Val His Glu Val Leu
            180                 185                 190 aaa ggc aca ggt ggt tca ggc taa                                      600
Lys Gly Thr Gly Gly Ser Gly
        195
```

<210> SEQ ID NO 59
<211> LENGTH: 199
<212> TYPE: PRT
<213> ORGANISM: Triticum aestivum

<400> SEQUENCE: 59

```
Met Ser Thr Val Asp Ala Ala Thr Ser Cys Lys Ile Ser Glu Ala Val
1               5                   10                  15

Lys Gln Lys Gly Gly Ala Phe Val Glu Ala Pro Val Ser Gly Ser Lys
            20                  25                  30

Lys Pro Ala Glu Asp Gly Gln Leu Val Ile Leu Ala Ala Gly Asp Lys
        35                  40                  45

Ala Leu Tyr Asp Asp Met Val Pro Ala Phe Asp Val Leu Gly Lys Lys
    50                  55                  60

Ser Phe Phe Leu Gly Glu Met Gly Asn Gly Ala Lys Met Lys Leu Val
65                  70                  75                  80

Val Asn Met Ile Met Gly Ser Met Met Asn Ala Phe Ser Glu Gly Leu
                85                  90                  95

Cys Leu Ala Asp Lys Ser Gly Leu Ser Pro Gln Thr Leu Leu Asp Val
            100                 105                 110

Leu Asp Leu Gly Ala Ile Ala Asn Pro Met Phe Lys Met Lys Gly Pro
        115                 120                 125

Ser Met Leu Gln Gly Ser Tyr Asn Pro Ala Phe Pro Leu Lys His Gln
    130                 135                 140

Gln Lys Asp Met Arg Leu Ala Leu Ser Leu Gly Asp Glu Asn Ala Val
145                 150                 155                 160

Ser Met Pro Val Ala Ala Ala Ser Asn Glu Ala Phe Lys Lys Ala Arg
                165                 170                 175

Ser Leu Gly Leu Gly Asp Leu Asp Phe Ser Val Val His Glu Val Leu
            180                 185                 190

Lys Gly Thr Gly Gly Ser Gly
        195
```

<210> SEQ ID NO 60
<211> LENGTH: 1077
<212> TYPE: DNA
<213> ORGANISM: Arabidopsis thaliana
<220> FEATURE:
<221> NAME/KEY: CDS
<222> LOCATION: (1)..(1077)

<400> SEQUENCE: 60

```
atg cct ttg gtt tca tta tct ttt gct tca tct tct tca aaa gcc atg      48
Met Pro Leu Val Ser Leu Ser Phe Ala Ser Ser Ser Ser Lys Ala Met
1               5                   10                  15 gct ttg tgc tct atc tgt cct cgc atc cct ctt cga ttc agg cca aaa      96
Ala Leu Cys Ser Ile Cys Pro Arg Ile Pro Leu Arg Phe Arg Pro Lys
                20                  25                  30 ccc att tcc cct ttt ctc tca aaa cct caa att tgt ctc gct tac agg     144
Pro Ile Ser Pro Phe Leu Ser Lys Pro Gln Ile Cys Leu Ala Tyr Arg
            35                  40                  45 gtt tac tct tcc ctg caa tct act act ccc tct acc aga gat gaa ctt     192
Val Tyr Ser Ser Leu Gln Ser Thr Thr Pro Ser Thr Arg Asp Glu Leu
        50                  55                  60 gga act gtt agc att ggg ttt ctg ggt atg gga atc atg ggt tct cca     240
Gly Thr Val Ser Ile Gly Phe Leu Gly Met Gly Ile Met Gly Ser Pro
65              70                  75                  80 atg gca cag aac ctc atc aaa gct ggg tgt gat gtg act gta tgg aat     288
Met Ala Gln Asn Leu Ile Lys Ala Gly Cys Asp Val Thr Val Trp Asn
                85                  90                  95 cga act aag agc aaa tgt gat cct ctc gtt gga tta gga gca aag tac     336
Arg Thr Lys Ser Lys Cys Asp Pro Leu Val Gly Leu Gly Ala Lys Tyr
            100                 105                 110 aag tct tct cct gaa gaa gtg act gca act tgt gat ctc aca ttt gca     384
Lys Ser Ser Pro Glu Glu Val Thr Ala Thr Cys Asp Leu Thr Phe Ala
        115                 120                 125 atg ctt gct gat cct gaa agt gca att gat gtt gca tgt gga aag aat     432
Met Leu Ala Asp Pro Glu Ser Ala Ile Asp Val Ala Cys Gly Lys Asn
130                 135                 140 gga gcc ata ttt ggg att agt tca gga aaa ggg tat gtt gat gtc tca     480
Gly Ala Ile Phe Gly Ile Ser Ser Gly Lys Gly Tyr Val Asp Val Ser
145                 150                 155                 160 acc gtt gat gtg gcc tca tca ata cta atc agc aag caa ata aag gat     528
Thr Val Asp Val Ala Ser Ser Ile Leu Ile Ser Lys Gln Ile Lys Asp
                165                 170                 175 acc gga gcc ttg ttc ttg gag gca cca gtt tca ggt tcc aaa aag cct     576
Thr Gly Ala Leu Phe Leu Glu Ala Pro Val Ser Gly Ser Lys Lys Pro
            180                 185                 190 gcc gaa gat ggg cag tta ata ttt ctc act gca ggt gac aag ccg cta     624
Ala Glu Asp Gly Gln Leu Ile Phe Leu Thr Ala Gly Asp Lys Pro Leu
        195                 200                 205 tac gaa aaa gct gct cct ttc tta gac atc atg gga aag tca aaa ttc     672
Tyr Glu Lys Ala Ala Pro Phe Leu Asp Ile Met Gly Lys Ser Lys Phe
210                 215                 220 tat ttg ggt gaa gtt ggt aat gga gca gca atg aaa ctt gtc gtc aac     720
Tyr Leu Gly Glu Val Gly Asn Gly Ala Ala Met Lys Leu Val Val Asn
225                 230                 235                 240 atg atc atg gga agt atg atg gca tca ttc gcg gag gga ata ctt cta     768
Met Ile Met Gly Ser Met Met Ala Ser Phe Ala Glu Gly Ile Leu Leu
                245                 250                 255 agc cag aaa gtt gga ctc gat cca aat gta ctt gtc gag gtt gtc tca     816
Ser Gln Lys Val Gly Leu Asp Pro Asn Val Leu Val Glu Val Val Ser
            260                 265                 270 cag gga gct atc aat gcg cca atg tac tca cta aag ggt cct tca atg     864
Gln Gly Ala Ile Asn Ala Pro Met Tyr Ser Leu Lys Gly Pro Ser Met
        275                 280                 285 atc aag tca gtg tac ccg acg gct ttt cca tta aag cat cag cag aag     912
Ile Lys Ser Val Tyr Pro Thr Ala Phe Pro Leu Lys His Gln Gln Lys
290                 295                 300 gat atg aga ctc gca ctt gga cta gcg gaa tcc gta tcg caa tct act     960
Asp Met Arg Leu Ala Leu Gly Leu Ala Glu Ser Val Ser Gln Ser Thr
305                 310                 315                 320
```

```
ccg att gca gcc gct gcg aac gag ctt tac aag gtt gca aaa tct tat    1008
Pro Ile Ala Ala Ala Ala Asn Glu Leu Tyr Lys Val Ala Lys Ser Tyr
            325                 330                 335 ggg ttg agc gat gaa gat ttc tct gca gta att gaa gca cta aaa gct    1056
Gly Leu Ser Asp Glu Asp Phe Ser Ala Val Ile Glu Ala Leu Lys Ala
            340                 345                 350 gca aaa tcc cga gaa gct tag                                        1077
Ala Lys Ser Arg Glu Ala
        355
```

<210> SEQ ID NO 61
<211> LENGTH: 358
<212> TYPE: PRT
<213> ORGANISM: Arabidopsis thaliana

<400> SEQUENCE: 61

Met Pro Leu Val Ser Leu Ser Phe Ala Ser Ser Ser Lys Ala Met
1               5                   10                  15

Ala Leu Cys Ser Ile Cys Pro Arg Ile Pro Leu Arg Phe Arg Pro Lys
            20                  25                  30

Pro Ile Ser Pro Phe Leu Ser Lys Pro Gln Ile Cys Leu Ala Tyr Arg
        35                  40                  45

Val Tyr Ser Ser Leu Gln Ser Thr Thr Pro Ser Thr Arg Asp Glu Leu
    50                  55                  60

Gly Thr Val Ser Ile Gly Phe Leu Gly Met Gly Ile Met Gly Ser Pro
65                  70                  75                  80

Met Ala Gln Asn Leu Ile Lys Ala Gly Cys Asp Val Thr Val Trp Asn
                85                  90                  95

Arg Thr Lys Ser Lys Cys Asp Pro Leu Val Gly Leu Gly Ala Lys Tyr
            100                 105                 110

Lys Ser Ser Pro Glu Glu Val Thr Ala Thr Cys Asp Leu Thr Phe Ala
        115                 120                 125

Met Leu Ala Asp Pro Glu Ser Ala Ile Asp Val Ala Cys Gly Lys Asn
    130                 135                 140

Gly Ala Ile Phe Gly Ile Ser Ser Gly Lys Gly Tyr Val Asp Val Ser
145                 150                 155                 160

Thr Val Asp Val Ala Ser Ser Ile Leu Ile Ser Lys Gln Ile Lys Asp
                165                 170                 175

Thr Gly Ala Leu Phe Leu Glu Ala Pro Val Ser Gly Ser Lys Lys Pro
            180                 185                 190

Ala Glu Asp Gly Gln Leu Ile Phe Leu Thr Ala Gly Asp Lys Pro Leu
        195                 200                 205

Tyr Glu Lys Ala Ala Pro Phe Leu Asp Ile Met Gly Lys Ser Lys Phe
    210                 215                 220

Tyr Leu Gly Glu Val Gly Asn Gly Ala Ala Met Lys Leu Val Val Asn
225                 230                 235                 240

Met Ile Met Gly Ser Met Met Ala Ser Phe Ala Glu Gly Ile Leu Leu
                245                 250                 255

Ser Gln Lys Val Gly Leu Asp Pro Asn Val Leu Val Glu Val Val Ser
            260                 265                 270

Gln Gly Ala Ile Asn Ala Pro Met Tyr Ser Leu Lys Gly Pro Ser Met
        275                 280                 285

Ile Lys Ser Val Tyr Pro Thr Ala Phe Pro Leu Lys His Gln Gln Lys
    290                 295                 300

Asp Met Arg Leu Ala Leu Gly Leu Ala Glu Ser Val Ser Gln Ser Thr

```
                305                 310                 315                 320
Pro Ile Ala Ala Ala Asn Glu Leu Tyr Lys Val Ala Lys Ser Tyr
            325                 330                 335
Gly Leu Ser Asp Glu Asp Phe Ser Ala Val Ile Glu Ala Leu Lys Ala
            340                 345                 350
Ala Lys Ser Arg Glu Ala
        355

<210> SEQ ID NO 62
<211> LENGTH: 864
<212> TYPE: DNA
<213> ORGANISM: Glycine max
<220> FEATURE:
<221> NAME/KEY: CDS
<222> LOCATION: (1)..(864)

<400> SEQUENCE: 62 atg gag gtg ggg ttc ttg ggt ctg gga ata atg gga aag gcc atg tcc      48
Met Glu Val Gly Phe Leu Gly Leu Gly Ile Met Gly Lys Ala Met Ser
1               5                   10                  15 atc aat ctc att cgg agt ggc ttc aag ctc act gtt tgg aac aga acc      96
Ile Asn Leu Ile Arg Ser Gly Phe Lys Leu Thr Val Trp Asn Arg Thr
                20                  25                  30 ctc tcc aag tgt gat gaa ctt gtg gag ctt ggc gct tca att gga gaa     144
Leu Ser Lys Cys Asp Glu Leu Val Glu Leu Gly Ala Ser Ile Gly Glu
            35                  40                  45 act cct gca gca gta gtt aag aag tgc aat tat acc att gca atg ctg     192
Thr Pro Ala Ala Val Val Lys Lys Cys Asn Tyr Thr Ile Ala Met Leu
        50                  55                  60 tct gat cct tct gtt gct ctt tcg gtt aat ggt gtt ctt gaa caa att     240
Ser Asp Pro Ser Val Ala Leu Ser Val Asn Gly Val Leu Glu Gln Ile
65                  70                  75                  80 tgc cat gga aaa ggt tac att gac atg tca act gtt ggt gcc gac act     288
Cys His Gly Lys Gly Tyr Ile Asp Met Ser Thr Val Gly Ala Asp Thr
                85                  90                  95 tct tca aaa att agt gag gca att aca tca aag ggt ggt tct ttc ctt     336
Ser Ser Lys Ile Ser Glu Ala Ile Thr Ser Lys Gly Gly Ser Phe Leu
            100                 105                 110 gaa gct cca gtt tct gga agt aag aaa cct gca gaa gat ggt caa ctg     384
Glu Ala Pro Val Ser Gly Ser Lys Lys Pro Ala Glu Asp Gly Gln Leu
        115                 120                 125 gta att ctt gct gct ggg gag aag gca ttg tac gat gaa gcg att cct     432
Val Ile Leu Ala Ala Gly Glu Lys Ala Leu Tyr Asp Glu Ala Ile Pro
    130                 135                 140 gct ttt gat atc atg ggg aag aag tct ttt ttc ttg ggg cag gtt gga     480
Ala Phe Asp Ile Met Gly Lys Lys Ser Phe Phe Leu Gly Gln Val Gly
145                 150                 155                 160 aat gga gct aaa atg aaa ctt gtg gtc aac atg ata atg ggc agt atg     528
Asn Gly Ala Lys Met Lys Leu Val Val Asn Met Ile Met Gly Ser Met
                165                 170                 175 atg aat gca ttt tct gaa ggg ctt gta ttg gct gac aga agt gga ctg     576
Met Asn Ala Phe Ser Glu Gly Leu Val Leu Ala Asp Arg Ser Gly Leu
            180                 185                 190 aac cct cat act ctt ctt gat gta ttg gac ctg ggt gga att gct aat     624
Asn Pro His Thr Leu Leu Asp Val Leu Asp Leu Gly Gly Ile Ala Asn
        195                 200                 205 cca atg ttt agg ttg aaa gga ccc aca atg ata caa aac aat tac tcc     672
Pro Met Phe Arg Leu Lys Gly Pro Thr Met Ile Gln Asn Asn Tyr Ser
    210                 215                 220 cct gca ttt cct ctg aag cat cag cag aag gat atg agg ttg gct ctt     720
```

```
Pro Ala Phe Pro Leu Lys His Gln Gln Lys Asp Met Arg Leu Ala Leu
225                 230                 235                 240 gct ctt ggg gat gaa aat gcg gta tcc atg cca gta gca gct gct gcc         768
Ala Leu Gly Asp Glu Asn Ala Val Ser Met Pro Val Ala Ala Ala Ala
                245                 250                 255 aat gag gct ttc aag aaa gct agg agc ctg gga ttg ggg gac ctt gac         816
Asn Glu Ala Phe Lys Lys Ala Arg Ser Leu Gly Leu Gly Asp Leu Asp
                260                 265                 270 ttt tct gct gtg tat gag acc gtg aag acc ctt gaa cat tca tcc tga         864
Phe Ser Ala Val Tyr Glu Thr Val Lys Thr Leu Glu His Ser Ser
                275                 280                 285
```

<210> SEQ ID NO 63
<211> LENGTH: 287
<212> TYPE: PRT
<213> ORGANISM: Glycine max

<400> SEQUENCE: 63

```
Met Glu Val Gly Phe Leu Gly Leu Gly Ile Met Gly Lys Ala Met Ser
1               5                   10                  15

Ile Asn Leu Ile Arg Ser Gly Phe Lys Leu Thr Val Trp Asn Arg Thr
                20                  25                  30

Leu Ser Lys Cys Asp Glu Leu Val Glu Leu Gly Ala Ser Ile Gly Glu
            35                  40                  45

Thr Pro Ala Ala Val Val Lys Lys Cys Asn Tyr Thr Ile Ala Met Leu
50                  55                  60

Ser Asp Pro Ser Val Ala Leu Ser Val Asn Gly Val Leu Glu Gln Ile
65                  70                  75                  80

Cys His Gly Lys Gly Tyr Ile Asp Met Ser Thr Val Gly Ala Asp Thr
                85                  90                  95

Ser Ser Lys Ile Ser Glu Ala Ile Thr Ser Lys Gly Gly Ser Phe Leu
            100                 105                 110

Glu Ala Pro Val Ser Gly Ser Lys Lys Pro Ala Glu Asp Gly Gln Leu
        115                 120                 125

Val Ile Leu Ala Ala Gly Glu Lys Ala Leu Tyr Asp Glu Ala Ile Pro
130                 135                 140

Ala Phe Asp Ile Met Gly Lys Lys Ser Phe Phe Leu Gly Gln Val Gly
145                 150                 155                 160

Asn Gly Ala Lys Met Lys Leu Val Val Asn Met Ile Met Gly Ser Met
                165                 170                 175

Met Asn Ala Phe Ser Glu Gly Leu Val Leu Ala Asp Arg Ser Gly Leu
            180                 185                 190

Asn Pro His Thr Leu Leu Asp Val Leu Asp Leu Gly Ile Ala Asn
        195                 200                 205

Pro Met Phe Arg Leu Lys Gly Pro Thr Met Ile Gln Asn Asn Tyr Ser
210                 215                 220

Pro Ala Phe Pro Leu Lys His Gln Gln Lys Asp Met Arg Leu Ala Leu
225                 230                 235                 240

Ala Leu Gly Asp Glu Asn Ala Val Ser Met Pro Val Ala Ala Ala Ala
                245                 250                 255

Asn Glu Ala Phe Lys Lys Ala Arg Ser Leu Gly Leu Gly Asp Leu Asp
            260                 265                 270

Phe Ser Ala Val Tyr Glu Thr Val Lys Thr Leu Glu His Ser Ser
        275                 280                 285
```

<210> SEQ ID NO 64

```
<211> LENGTH: 1002
<212> TYPE: DNA
<213> ORGANISM: Glycine max
<220> FEATURE:
<221> NAME/KEY: CDS
<222> LOCATION: (1)..(1002)

<400> SEQUENCE: 64 atg cgt tcc acg ttt tgc tgt cac ttg aac ctt tca ccc gtc atg att      48
Met Arg Ser Thr Phe Cys Cys His Leu Asn Leu Ser Pro Val Met Ile
 1               5                  10                  15 atg aag ggc ttc tct gct ccc att tca tca tat gtt tcg cct cga gct      96
Met Lys Gly Phe Ser Ala Pro Ile Ser Ser Tyr Val Ser Pro Arg Ala
             20                  25                  30 caa gcc gtc act gag cca ccg gcg cgg att ggc ttt ttg ggc ctc gga     144
Gln Ala Val Thr Glu Pro Pro Ala Arg Ile Gly Phe Leu Gly Leu Gly
         35                  40                  45 atc atg ggc tcc cca atg gcc cac aat ctc ctt aaa gct ggt gtt gat     192
Ile Met Gly Ser Pro Met Ala His Asn Leu Leu Lys Ala Gly Val Asp
 50                  55                  60 ctc act gtt tgg aat agg acc aag agc aag tgt gac cct cta atc agc     240
Leu Thr Val Trp Asn Arg Thr Lys Ser Lys Cys Asp Pro Leu Ile Ser
 65                  70                  75                  80 ctc gga gca aaa tat aaa cca tct cct gag gaa gta gca gca tct tgt     288
Leu Gly Ala Lys Tyr Lys Pro Ser Pro Glu Glu Val Ala Ala Ser Cys
                 85                  90                  95 gat gtc acc ttt gcc atg ctc gct gat cct caa agt gca gtg gat gtc     336
Asp Val Thr Phe Ala Met Leu Ala Asp Pro Gln Ser Ala Val Asp Val
            100                 105                 110 gct tgc ggg aag cat ggg gct gca aat gga atg ggt cca ggg aaa gga     384
Ala Cys Gly Lys His Gly Ala Ala Asn Gly Met Gly Pro Gly Lys Gly
        115                 120                 125 tat gtg gat gtt tca act gtt gat ggg gac act tct aaa ttg att aat     432
Tyr Val Asp Val Ser Thr Val Asp Gly Asp Thr Ser Lys Leu Ile Asn
    130                 135                 140 ggg cac atg aaa tcc act gga gcc tta ttt ttg gag gct cca gtt tcc     480
Gly His Met Lys Ser Thr Gly Ala Leu Phe Leu Glu Ala Pro Val Ser
145                 150                 155                 160 gga tca aaa aag cca gca gaa gat gga caa ttg ata ttt ctt aca gca     528
Gly Ser Lys Lys Pro Ala Glu Asp Gly Gln Leu Ile Phe Leu Thr Ala
                165                 170                 175 ggg gac aaa aat ctt tat gaa gca gtt ggt tct ctc ttg gac atc atg     576
Gly Asp Lys Asn Leu Tyr Glu Ala Val Gly Ser Leu Leu Asp Ile Met
            180                 185                 190 ggg aaa tct aaa ttt tat ctt ggt gat gtt gga aat gga gct gca atg     624
Gly Lys Ser Lys Phe Tyr Leu Gly Asp Val Gly Asn Gly Ala Ala Met
        195                 200                 205 aaa ctt gtt gtc aat atg atc atg ggc agt atg atg gca tcc ttt tct     672
Lys Leu Val Val Asn Met Ile Met Gly Ser Met Met Ala Ser Phe Ser
    210                 215                 220 gaa ggc tta ctt ctc agc gag aaa gtt ggg ctt gat cca gat gtg cta     720
Glu Gly Leu Leu Leu Ser Glu Lys Val Gly Leu Asp Pro Asp Val Leu
225                 230                 235                 240 gtg cag gta gtt tca cag ggt gcc att agt gct cca atg tac tca acc     768
Val Gln Val Val Ser Gln Gly Ala Ile Ser Ala Pro Met Tyr Ser Thr
                245                 250                 255 aaa ggt cct tcc atg ata cag tcg ctt tat cca act gcg ttc cct cta     816
Lys Gly Pro Ser Met Ile Gln Ser Leu Tyr Pro Thr Ala Phe Pro Leu
            260                 265                 270 aag cat cag cag aag gat cta aga cta gcc ttg ggg tta gca gag tct     864
Lys His Gln Gln Lys Asp Leu Arg Leu Ala Leu Gly Leu Ala Glu Ser
```

```
            275                 280                 285
gtt tcc caa cct act ccg att gca tca gct gct aat gag tta tat aaa      912
Val Ser Gln Pro Thr Pro Ile Ala Ser Ala Ala Asn Glu Leu Tyr Lys
290                 295                 300 gtt gca aaa tcc aat ggc ctt agt gat cag gat ttt tca gct gtc att      960
Val Ala Lys Ser Asn Gly Leu Ser Asp Gln Asp Phe Ser Ala Val Ile
305                 310                 315                 320 gaa gca tta aaa tcc aaa ttt cag cac tcg gaa acc aag tga             1002
Glu Ala Leu Lys Ser Lys Phe Gln His Ser Glu Thr Lys
                325                 330
```

<210> SEQ ID NO 65
<211> LENGTH: 333
<212> TYPE: PRT
<213> ORGANISM: Glycine max

<400> SEQUENCE: 65

```
Met Arg Ser Thr Phe Cys Cys His Leu Asn Leu Ser Pro Val Met Ile
1               5                   10                  15

Met Lys Gly Phe Ser Ala Pro Ile Ser Ser Tyr Val Ser Pro Arg Ala
                20                  25                  30

Gln Ala Val Thr Glu Pro Pro Ala Arg Ile Gly Phe Leu Gly Leu Gly
            35                  40                  45

Ile Met Gly Ser Pro Met Ala His Asn Leu Leu Lys Ala Gly Val Asp
        50                  55                  60

Leu Thr Val Trp Asn Arg Thr Lys Ser Lys Cys Asp Pro Leu Ile Ser
65                  70                  75                  80

Leu Gly Ala Lys Tyr Lys Pro Ser Pro Glu Glu Val Ala Ala Ser Cys
                85                  90                  95

Asp Val Thr Phe Ala Met Leu Ala Asp Pro Gln Ser Ala Val Asp Val
            100                 105                 110

Ala Cys Gly Lys His Gly Ala Ala Asn Gly Met Gly Pro Gly Lys Gly
        115                 120                 125

Tyr Val Asp Val Ser Thr Val Asp Gly Asp Thr Ser Lys Leu Ile Asn
    130                 135                 140

Gly His Met Lys Ser Thr Gly Ala Leu Phe Leu Glu Ala Pro Val Ser
145                 150                 155                 160

Gly Ser Lys Lys Pro Ala Glu Asp Gly Gln Leu Ile Phe Leu Thr Ala
                165                 170                 175

Gly Asp Lys Asn Leu Tyr Glu Ala Val Gly Ser Leu Leu Asp Ile Met
            180                 185                 190

Gly Lys Ser Lys Phe Tyr Leu Gly Asp Val Gly Asn Gly Ala Ala Met
        195                 200                 205

Lys Leu Val Val Asn Met Ile Met Gly Ser Met Met Ala Ser Phe Ser
    210                 215                 220

Glu Gly Leu Leu Leu Ser Glu Lys Val Gly Leu Asp Pro Asp Val Leu
225                 230                 235                 240

Val Gln Val Val Ser Gln Gly Ala Ile Ser Ala Pro Met Tyr Ser Thr
                245                 250                 255

Lys Gly Pro Ser Met Ile Gln Ser Leu Tyr Pro Thr Ala Phe Pro Leu
            260                 265                 270

Lys His Gln Gln Lys Asp Leu Arg Leu Ala Leu Gly Leu Ala Glu Ser
        275                 280                 285

Val Ser Gln Pro Thr Pro Ile Ala Ser Ala Ala Asn Glu Leu Tyr Lys
    290                 295                 300
```

| | | | | | | | | | | | | | | | | |
|---|---|---|---|---|---|---|---|---|---|---|---|---|---|---|---|---|
| Val | Ala | Lys | Ser | Asn | Gly | Leu | Ser | Asp | Gln | Asp | Phe | Ser | Ala | Val | Ile | |
| 305 | | | | 310 | | | | 315 | | | | 320 | | | | |
| Glu | Ala | Leu | Lys | Ser | Lys | Phe | Gln | His | Ser | Glu | Thr | Lys | | | | |
| | | | | 325 | | | | | 330 | | | | | | | |

```
<210> SEQ ID NO 66
<211> LENGTH: 1020
<212> TYPE: DNA
<213> ORGANISM: Medicago truncatula
<220> FEATURE:
<221> NAME/KEY: CDS
<222> LOCATION: (1)..(1020)

<400> SEQUENCE: 66
```

| atg | aac | tgc | agt | cag | ttt | gcg | act | aca | atg | cgc | tct | gcc | ttt | tcc | ctt | | 48 |
|---|---|---|---|---|---|---|---|---|---|---|---|---|---|---|---|---|---|
| Met | Asn | Cys | Ser | Gln | Phe | Ala | Thr | Thr | Met | Arg | Ser | Ala | Phe | Ser | Leu | | |
| 1 | | | | 5 | | | | | 10 | | | | | 15 | | | |
| cat | cac | ttc | aac | tct | ccg | cgc | ttg | tct | cgc | cac | gta | tcc | aat | gtc | tct | | 96 |
| His | His | Phe | Asn | Ser | Pro | Arg | Leu | Ser | Arg | His | Val | Ser | Asn | Val | Ser | | |
| | | | 20 | | | | | 25 | | | | | 30 | | | | |
| gct | tct | cta | cag | ccc | caa | gga | caa | ggg | act | gac | act | cct | cca | cgg | att | | 144 |
| Ala | Ser | Leu | Gln | Pro | Gln | Gly | Gln | Gly | Thr | Asp | Thr | Pro | Pro | Arg | Ile | | |
| | | 35 | | | | | 40 | | | | | 45 | | | | | |
| ggc | ttt | ttg | ggc | ctt | gga | atc | atg | ggc | acc | cca | atg | gct | cta | aat | ctc | | 192 |
| Gly | Phe | Leu | Gly | Leu | Gly | Ile | Met | Gly | Thr | Pro | Met | Ala | Leu | Asn | Leu | | |
| 50 | | | | | 55 | | | | | 60 | | | | | | | |
| atc | aaa | gct | gga | gtt | gat | ctc | aca | gtt | tgg | aat | agg | act | aag | agc | aag | | 240 |
| Ile | Lys | Ala | Gly | Val | Asp | Leu | Thr | Val | Trp | Asn | Arg | Thr | Lys | Ser | Lys | | |
| 65 | | | | 70 | | | | | 75 | | | | | 80 | | | |
| tgt | gat | cct | cta | atc | agc | ttg | gga | gcc | aaa | tat | aaa | cca | tct | cct | gag | | 288 |
| Cys | Asp | Pro | Leu | Ile | Ser | Leu | Gly | Ala | Lys | Tyr | Lys | Pro | Ser | Pro | Glu | | |
| | | | | 85 | | | | | 90 | | | | | 95 | | | |
| gaa | gta | gcg | gca | tct | tgt | gat | ctc | aca | ttt | gcc | atg | ctt | gct | gat | cct | | 336 |
| Glu | Val | Ala | Ala | Ser | Cys | Asp | Leu | Thr | Phe | Ala | Met | Leu | Ala | Asp | Pro | | |
| | | | 100 | | | | | 105 | | | | | 110 | | | | |
| caa | agt | gcg | gtg | gat | gtt | gct | tgt | gga | aag | cat | gga | gtt | gct | aat | gga | | 384 |
| Gln | Ser | Ala | Val | Asp | Val | Ala | Cys | Gly | Lys | His | Gly | Val | Ala | Asn | Gly | | |
| | | 115 | | | | | 120 | | | | | 125 | | | | | |
| ata | ggt | cca | gga | aaa | gga | tac | gtg | gat | gta | tca | act | gtt | gat | gtg | gac | | 432 |
| Ile | Gly | Pro | Gly | Lys | Gly | Tyr | Val | Asp | Val | Ser | Thr | Val | Asp | Val | Asp | | |
| 130 | | | | | 135 | | | | | 140 | | | | | | | |
| act | tct | aaa | ttg | att | aat | gga | cac | ata | aaa | tcc | act | gga | gca | tta | ttt | | 480 |
| Thr | Ser | Lys | Leu | Ile | Asn | Gly | His | Ile | Lys | Ser | Thr | Gly | Ala | Leu | Phe | | |
| 145 | | | | | 150 | | | | | 155 | | | | | 160 | | |
| ttg | gag | gct | cca | gtt | tca | ggt | tcc | aaa | aag | cca | gca | gaa | gat | gga | caa | | 528 |
| Leu | Glu | Ala | Pro | Val | Ser | Gly | Ser | Lys | Lys | Pro | Ala | Glu | Asp | Gly | Gln | | |
| | | | | 165 | | | | | 170 | | | | | 175 | | | |
| ttg | ata | ttt | ctt | aca | gca | ggg | gac | aga | aat | ctt | tat | gaa | acg | gtt | gct | | 576 |
| Leu | Ile | Phe | Leu | Thr | Ala | Gly | Asp | Arg | Asn | Leu | Tyr | Glu | Thr | Val | Ala | | |
| | | | 180 | | | | | 185 | | | | | 190 | | | | |
| cct | ttc | ttg | gac | atc | atg | ggg | aag | tct | aaa | ttt | tac | ctt | ggt | gat | gtt | | 624 |
| Pro | Phe | Leu | Asp | Ile | Met | Gly | Lys | Ser | Lys | Phe | Tyr | Leu | Gly | Asp | Val | | |
| | | 195 | | | | | 200 | | | | | 205 | | | | | |
| gga | aat | ggt | gct | gcg | atg | aaa | ctt | gtt | gtc | aat | atg | atc | atg | ggc | agt | | 672 |
| Gly | Asn | Gly | Ala | Ala | Met | Lys | Leu | Val | Val | Asn | Met | Ile | Met | Gly | Ser | | |
| | 210 | | | | | 215 | | | | | 220 | | | | | | |
| atg | atg | gca | tcc | ttt | tcg | gaa | ggt | tta | ctt | ttg | agt | gaa | aaa | gtt | ggg | | 720 |
| Met | Met | Ala | Ser | Phe | Ser | Glu | Gly | Leu | Leu | Leu | Ser | Glu | Lys | Val | Gly | | |
| 225 | | | | | 230 | | | | | 235 | | | | | 240 | | |
| cta | gat | cca | aaa | gta | cta | gtg | gag | gta | att | tca | caa | ggt | gcc | att | aat | | 768 |
| Leu | Asp | Pro | Lys | Val | Leu | Val | Glu | Val | Ile | Ser | Gln | Gly | Ala | Ile | Asn | | |

```
                    245                 250                 255
gct cca atg tac tcg atg aaa ggc cca tcc atg ata cag tca aat tat      816
Ala Pro Met Tyr Ser Met Lys Gly Pro Ser Met Ile Gln Ser Asn Tyr
        260                 265                 270 cca act gca ttt ccc cta aaa cat cag cag aag gat cta aga ctt gcc      864
Pro Thr Ala Phe Pro Leu Lys His Gln Gln Lys Asp Leu Arg Leu Ala
        275                 280                 285 ctg ggg tta gca gag tct gtt tcc caa cct att ccg att gca gcc gct      912
Leu Gly Leu Ala Glu Ser Val Ser Gln Pro Ile Pro Ile Ala Ala Ala
    290                 295                 300 gct aac gaa tta tat aaa gtt gca aaa tca cac ggc tat agt gat gag      960
Ala Asn Glu Leu Tyr Lys Val Ala Lys Ser His Gly Tyr Ser Asp Glu
305                 310                 315                 320 gac ttt tca gct gtc att gaa gca tta aaa tcc aaa ttt cag cac tca     1008
Asp Phe Ser Ala Val Ile Glu Ala Leu Lys Ser Lys Phe Gln His Ser
            325                 330                 335 gaa aac cag tga                                                     1020
Glu Asn Gln
```

<210> SEQ ID NO 67
<211> LENGTH: 339
<212> TYPE: PRT
<213> ORGANISM: Medicago truncatula

<400> SEQUENCE: 67

Met Asn Cys Ser Gln Phe Ala Thr Thr Met Arg Ser Ala Phe Ser Leu
1               5                   10                  15

His His Phe Asn Ser Pro Arg Leu Ser Arg His Val Ser Asn Val Ser
            20                  25                  30

Ala Ser Leu Gln Pro Gln Gly Gln Gly Thr Asp Thr Pro Pro Arg Ile
        35                  40                  45

Gly Phe Leu Gly Leu Gly Ile Met Gly Thr Pro Met Ala Leu Asn Leu
    50                  55                  60

Ile Lys Ala Gly Val Asp Leu Thr Val Trp Asn Arg Thr Lys Ser Lys
65                  70                  75                  80

Cys Asp Pro Leu Ile Ser Leu Gly Ala Lys Tyr Lys Pro Ser Pro Glu
                85                  90                  95

Glu Val Ala Ala Ser Cys Asp Leu Thr Phe Ala Met Leu Ala Asp Pro
            100                 105                 110

Gln Ser Ala Val Asp Val Ala Cys Gly Lys His Gly Val Ala Asn Gly
        115                 120                 125

Ile Gly Pro Gly Lys Gly Tyr Val Asp Val Ser Thr Val Asp Val Asp
    130                 135                 140

Thr Ser Lys Leu Ile Asn Gly His Ile Lys Ser Thr Gly Ala Leu Phe
145                 150                 155                 160

Leu Glu Ala Pro Val Ser Gly Ser Lys Lys Pro Ala Glu Asp Gly Gln
                165                 170                 175

Leu Ile Phe Leu Thr Ala Gly Asp Arg Asn Leu Tyr Glu Thr Val Ala
            180                 185                 190

Pro Phe Leu Asp Ile Met Gly Lys Ser Lys Phe Tyr Leu Gly Asp Val
        195                 200                 205

Gly Asn Gly Ala Ala Met Lys Leu Val Val Asn Met Ile Met Gly Ser
    210                 215                 220

Met Met Ala Ser Phe Ser Glu Gly Leu Leu Leu Ser Glu Lys Val Gly
225                 230                 235                 240

Leu Asp Pro Lys Val Leu Val Glu Val Ile Ser Gln Gly Ala Ile Asn

```
                         245                 250                 255
Ala Pro Met Tyr Ser Met Lys Gly Pro Ser Met Ile Gln Ser Asn Tyr
                260                 265                 270

Pro Thr Ala Phe Pro Leu Lys His Gln Gln Lys Asp Leu Arg Leu Ala
            275                 280                 285

Leu Gly Leu Ala Glu Ser Val Ser Gln Pro Ile Pro Ile Ala Ala Ala
        290                 295                 300

Ala Asn Glu Leu Tyr Lys Val Ala Lys Ser His Gly Tyr Ser Asp Glu
305                 310                 315                 320

Asp Phe Ser Ala Val Ile Glu Ala Leu Lys Ser Lys Phe Gln His Ser
                325                 330                 335

Glu Asn Gln

<210> SEQ ID NO 68
<211> LENGTH: 1026
<212> TYPE: DNA
<213> ORGANISM: Oryza sativa japonica
<220> FEATURE:
<221> NAME/KEY: CDS
<222> LOCATION: (1)..(1026)

<400> SEQUENCE: 68 atg gcg gcg atg gcg gcg gcc tcc ctc ctg tgc gcg agg gcg gcg gcg    48
Met Ala Ala Met Ala Ala Ala Ser Leu Leu Cys Ala Arg Ala Ala Ala
1               5                   10                  15 gcg gcg ccc acg ctg cgc cta cgc ggc gga ggc agg gga gca cgc ctc    96
Ala Ala Pro Thr Leu Arg Leu Arg Gly Gly Gly Arg Gly Ala Arg Leu
            20                  25                  30 gtc ttc tcc tgc tcc gcc tcc tcg tcg ccg tcc ggg gaa gga ggg       144
Val Phe Ser Cys Ser Ala Ser Ser Ser Pro Ser Gly Glu Gly Gly
        35                  40                  45 ttc agt ggg aag gtg ggg ttc ctc ggc ctc ggg atc atg ggc gca ccc    192
Phe Ser Gly Lys Val Gly Phe Leu Gly Leu Gly Ile Met Gly Ala Pro
    50                  55                  60 atg gcc tcc aac ctc atc aac gcc ggg tgc gat gtc acg gtg tgg aac    240
Met Ala Ser Asn Leu Ile Asn Ala Gly Cys Asp Val Thr Val Trp Asn
65                  70                  75                  80 agg acc agg agc aag tgc gac ccg ctc ctc agc ctc ggc gcc aag tac    288
Arg Thr Arg Ser Lys Cys Asp Pro Leu Leu Ser Leu Gly Ala Lys Tyr
                85                  90                  95 gag cct tca ccg gcc gat gtt gct tcg tct tgc gat gtg acc ttc gcg    336
Glu Pro Ser Pro Ala Asp Val Ala Ser Ser Cys Asp Val Thr Phe Ala
            100                 105                 110 atg ctt gct gat ccg gag agc gcg gtt gag gtt gca tgc ggg gcc aat    384
Met Leu Ala Asp Pro Glu Ser Ala Val Glu Val Ala Cys Gly Ala Asn
        115                 120                 125 gga gct gca cag ggg atg gcc cca ggg aaa ggg tat gtg gat gtg tcg    432
Gly Ala Ala Gln Gly Met Ala Pro Gly Lys Gly Tyr Val Asp Val Ser
    130                 135                 140 acg gtt gac gct gct aca tcc aag ctg att ggc aag cac att aca agt    480
Thr Val Asp Ala Ala Thr Ser Lys Leu Ile Gly Lys His Ile Thr Ser
145                 150                 155                 160 act ggg gca tct ttc ctt gag gct cca gtt tca ggc tca aaa aag cca    528
Thr Gly Ala Ser Phe Leu Glu Ala Pro Val Ser Gly Ser Lys Lys Pro
                165                 170                 175 gca gaa gat ggg ctg ctc atc ttt ctt acc gca ggt gat gag tcc ttg    576
Ala Glu Asp Gly Leu Leu Ile Phe Leu Thr Ala Gly Asp Glu Ser Leu
            180                 185                 190 tac aat aga gtg gca tcc ctc ctt gat gtt atg ggc aag tca aga ttt    624
Tyr Asn Arg Val Ala Ser Leu Leu Asp Val Met Gly Lys Ser Arg Phe
```

```
Tyr Asn Arg Val Ala Ser Leu Leu Asp Val Met Gly Lys Ser Arg Phe
            195                 200                 205 ttc ctc ggt gac gtt ggc aaa ggt gca gac atg aag ctc gtt gtt aat       672
Phe Leu Gly Asp Val Gly Lys Gly Ala Asp Met Lys Leu Val Val Asn
    210                 215                 220 atg gtc atg ggg agc atg atg gtt tcg ttt tca gaa gga ctc ctc ctg       720
Met Val Met Gly Ser Met Met Val Ser Phe Ser Glu Gly Leu Leu Leu
225                 230                 235                 240 agc gaa aaa gtt ggc cta gac ccc aat act ctt gtc gag gtt att tca       768
Ser Glu Lys Val Gly Leu Asp Pro Asn Thr Leu Val Glu Val Ile Ser
                245                 250                 255 caa ggt gct atc agt gct ccc atg ttc tcc ctc aag ggc cct tcc atg       816
Gln Gly Ala Ile Ser Ala Pro Met Phe Ser Leu Lys Gly Pro Ser Met
            260                 265                 270 gtt aaa gct gca tac cct act gct ttt cct ctg aag cat cag cag aag       864
Val Lys Ala Ala Tyr Pro Thr Ala Phe Pro Leu Lys His Gln Gln Lys
        275                 280                 285 gat ttg agg ctc gca ttg gcc ctg gca gaa tcg gtg tcc cag tct att       912
Asp Leu Arg Leu Ala Leu Ala Leu Ala Glu Ser Val Ser Gln Ser Ile
    290                 295                 300 cct aca gtc gca gct gca aac gag ctg tac aag gtc gcg aaa tcg ctt       960
Pro Thr Val Ala Ala Ala Asn Glu Leu Tyr Lys Val Ala Lys Ser Leu
305                 310                 315                 320 ggg ctt gca gac cag gac ttc tct gct gta atc gag gcg ctg aag gca      1008
Gly Leu Ala Asp Gln Asp Phe Ser Ala Val Ile Glu Ala Leu Lys Ala
                325                 330                 335 aag gag cag agc aag tga                                              1026
Lys Glu Gln Ser Lys
            340

<210> SEQ ID NO 69
<211> LENGTH: 341
<212> TYPE: PRT
<213> ORGANISM: Oryza sativa japonica

<400> SEQUENCE: 69

Met Ala Ala Met Ala Ala Ala Ser Leu Leu Cys Ala Arg Ala Ala Ala
1               5                   10                  15

Ala Ala Pro Thr Leu Arg Leu Arg Gly Gly Arg Gly Ala Arg Leu
            20                  25                  30

Val Phe Ser Cys Ser Ala Ser Ser Ser Pro Ser Glu Gly Gly
        35                  40                  45

Phe Ser Gly Lys Val Gly Phe Leu Gly Leu Gly Ile Met Gly Ala Pro
    50                  55                  60

Met Ala Ser Asn Leu Ile Asn Ala Gly Cys Asp Val Thr Val Trp Asn
65                  70                  75                  80

Arg Thr Arg Ser Lys Cys Asp Pro Leu Leu Ser Leu Gly Ala Lys Tyr
                85                  90                  95

Glu Pro Ser Pro Ala Asp Val Ala Ser Ser Cys Asp Val Thr Phe Ala
            100                 105                 110

Met Leu Ala Asp Pro Glu Ser Ala Val Glu Val Ala Cys Gly Ala Asn
        115                 120                 125

Gly Ala Ala Gln Gly Met Ala Pro Gly Lys Gly Tyr Val Asp Val Ser
    130                 135                 140

Thr Val Asp Ala Ala Thr Ser Lys Leu Ile Gly Lys His Ile Thr Ser
145                 150                 155                 160

Thr Gly Ala Ser Phe Leu Glu Ala Pro Val Ser Gly Ser Lys Lys Pro
                165                 170                 175
```

```
Ala Glu Asp Gly Leu Leu Ile Phe Leu Thr Ala Gly Asp Glu Ser Leu
            180                 185                 190

Tyr Asn Arg Val Ala Ser Leu Leu Asp Val Met Gly Lys Ser Arg Phe
        195                 200                 205

Phe Leu Gly Asp Val Gly Lys Gly Ala Asp Met Lys Leu Val Val Asn
    210                 215                 220

Met Val Met Gly Ser Met Met Val Ser Phe Ser Glu Gly Leu Leu Leu
225                 230                 235                 240

Ser Glu Lys Val Gly Leu Asp Pro Asn Thr Leu Val Glu Val Ile Ser
                245                 250                 255

Gln Gly Ala Ile Ser Ala Pro Met Phe Ser Leu Lys Gly Pro Ser Met
            260                 265                 270

Val Lys Ala Ala Tyr Pro Thr Ala Phe Pro Leu Lys His Gln Gln Lys
        275                 280                 285

Asp Leu Arg Leu Ala Leu Ala Leu Ala Glu Ser Val Ser Gln Ser Ile
    290                 295                 300

Pro Thr Val Ala Ala Ala Asn Glu Leu Tyr Lys Val Ala Lys Ser Leu
305                 310                 315                 320

Gly Leu Ala Asp Gln Asp Phe Ser Ala Val Ile Glu Ala Leu Lys Ala
                325                 330                 335

Lys Glu Gln Ser Lys
            340

<210> SEQ ID NO 70
<211> LENGTH: 864
<212> TYPE: DNA
<213> ORGANISM: Oryza sativa indica
<220> FEATURE:
<221> NAME/KEY: CDS
<222> LOCATION: (1)..(864)

<400> SEQUENCE: 70 atg gag gtg ggg ttc ttg ggt ctg gga ata atg gga aag gcc atg tcc     48
Met Glu Val Gly Phe Leu Gly Leu Gly Ile Met Gly Lys Ala Met Ser
1               5                   10                  15 atc aat ctc att cgg agt ggc ttc aag ctc act gtt tgg aac aga acc     96
Ile Asn Leu Ile Arg Ser Gly Phe Lys Leu Thr Val Trp Asn Arg Thr
            20                  25                  30 ctc tcc aag tgt gat gaa ctt gtg gag ctt ggc gct tca att gga gaa    144
Leu Ser Lys Cys Asp Glu Leu Val Glu Leu Gly Ala Ser Ile Gly Glu
        35                  40                  45 act cct gca gca gta gtt aag aag tgc aat tat acc att gca atg ctg    192
Thr Pro Ala Ala Val Val Lys Lys Cys Asn Tyr Thr Ile Ala Met Leu
    50                  55                  60 tct gat cct tct gtt gct ctt tcg gtt aat ggt gtt ctt gaa caa att    240
Ser Asp Pro Ser Val Ala Leu Ser Val Asn Gly Val Leu Glu Gln Ile
65                  70                  75                  80 tgc cat gga aaa ggt tac att gac atg tca act gtt ggt gcc gac act    288
Cys His Gly Lys Gly Tyr Ile Asp Met Ser Thr Val Gly Ala Asp Thr
                85                  90                  95 tct tca aaa att agt gag gca att aca tca aag ggt ggt tct ttc ctt    336
Ser Ser Lys Ile Ser Glu Ala Ile Thr Ser Lys Gly Gly Ser Phe Leu
            100                 105                 110 gaa gct cca gtt tct gga agt aag aaa cct gca gaa gat ggt caa ctg    384
Glu Ala Pro Val Ser Gly Ser Lys Lys Pro Ala Glu Asp Gly Gln Leu
        115                 120                 125 gta att ctt gct gct ggg gag aag gca ttg tac gat gaa gcg att cct    432
Val Ile Leu Ala Ala Gly Glu Lys Ala Leu Tyr Asp Glu Ala Ile Pro
```

```
gct ttt gat atc atg ggg aag aag tct ttc ttg ggg cag gtt gga      480
Ala Phe Asp Ile Met Gly Lys Lys Ser Phe Phe Leu Gly Gln Val Gly
145                 150                 155                 160 aat gga gct aaa atg aaa ctt gtg gtc aac atg ata atg ggc agt atg  528
Asn Gly Ala Lys Met Lys Leu Val Val Asn Met Ile Met Gly Ser Met
                165                 170                 175 atg aat gca ttt tct gaa ggg ctt gta ttg gct gac aga agt gga ctg  576
Met Asn Ala Phe Ser Glu Gly Leu Val Leu Ala Asp Arg Ser Gly Leu
            180                 185                 190 aac cct cat act ctt ctt gat gta ttg gac ctg ggt gga att gct aat  624
Asn Pro His Thr Leu Leu Asp Val Leu Asp Leu Gly Gly Ile Ala Asn
        195                 200                 205 cca atg ttt agg ttg aaa gga ccc aca atg ata caa aac aat tac tcc  672
Pro Met Phe Arg Leu Lys Gly Pro Thr Met Ile Gln Asn Asn Tyr Ser
210                 215                 220 cct gca ttt cct ctg aag cat cag cag aag gat atg agg ttg gct ctt  720
Pro Ala Phe Pro Leu Lys His Gln Gln Lys Asp Met Arg Leu Ala Leu
225                 230                 235                 240 gct ctt ggg gat gaa aat gcg gta tcc atg cca gta gca gct gct gcc  768
Ala Leu Gly Asp Glu Asn Ala Val Ser Met Pro Val Ala Ala Ala Ala
                245                 250                 255 aat gag gct ttc aag aaa gct agg agc ctg gga ttg ggg gac ctt gac  816
Asn Glu Ala Phe Lys Lys Ala Arg Ser Leu Gly Leu Gly Asp Leu Asp
            260                 265                 270 ttt tct gct gtg tat gag acc gtg aag acc ctt gaa cat tca tcc tga  864
Phe Ser Ala Val Tyr Glu Thr Val Lys Thr Leu Glu His Ser Ser
        275                 280                 285
```

<210> SEQ ID NO 71
<211> LENGTH: 287
<212> TYPE: PRT
<213> ORGANISM: Oryza sativa indica

<400> SEQUENCE: 71

```
Met Glu Val Gly Phe Leu Gly Leu Gly Ile Met Gly Lys Ala Met Ser
1               5                   10                  15

Ile Asn Leu Ile Arg Ser Gly Phe Lys Leu Thr Val Trp Asn Arg Thr
            20                  25                  30

Leu Ser Lys Cys Asp Glu Leu Val Glu Leu Gly Ala Ser Ile Gly Glu
        35                  40                  45

Thr Pro Ala Ala Val Val Lys Lys Cys Asn Tyr Thr Ile Ala Met Leu
    50                  55                  60

Ser Asp Pro Ser Val Ala Leu Ser Val Asn Gly Val Leu Glu Gln Ile
65                  70                  75                  80

Cys His Gly Lys Gly Tyr Ile Asp Met Ser Thr Val Gly Ala Asp Thr
                85                  90                  95

Ser Ser Lys Ile Ser Glu Ala Ile Thr Ser Lys Gly Gly Ser Phe Leu
            100                 105                 110

Glu Ala Pro Val Ser Gly Ser Lys Lys Pro Ala Glu Asp Gly Gln Leu
        115                 120                 125

Val Ile Leu Ala Ala Gly Glu Lys Ala Leu Tyr Asp Glu Ala Ile Pro
    130                 135                 140

Ala Phe Asp Ile Met Gly Lys Lys Ser Phe Phe Leu Gly Gln Val Gly
145                 150                 155                 160

Asn Gly Ala Lys Met Lys Leu Val Val Asn Met Ile Met Gly Ser Met
                165                 170                 175
```

-continued

```
Met Asn Ala Phe Ser Glu Gly Leu Val Leu Ala Asp Arg Ser Gly Leu
            180                 185                 190

Asn Pro His Thr Leu Leu Asp Val Leu Asp Leu Gly Gly Ile Ala Asn
        195                 200                 205

Pro Met Phe Arg Leu Lys Gly Pro Thr Met Ile Gln Asn Asn Tyr Ser
    210                 215                 220

Pro Ala Phe Pro Leu Lys His Gln Gln Lys Asp Met Arg Leu Ala Leu
225                 230                 235                 240

Ala Leu Gly Asp Glu Asn Ala Val Ser Met Pro Val Ala Ala Ala Ala
                245                 250                 255

Asn Glu Ala Phe Lys Lys Ala Arg Ser Leu Gly Leu Gly Asp Leu Asp
            260                 265                 270

Phe Ser Ala Val Tyr Glu Thr Val Lys Thr Leu Glu His Ser Ser
        275                 280                 285

<210> SEQ ID NO 72
<211> LENGTH: 843
<212> TYPE: DNA
<213> ORGANISM: Populus balsamifera subsp. trichocarpa
<220> FEATURE:
<221> NAME/KEY: CDS
<222> LOCATION: (1)..(843)

<400> SEQUENCE: 72 atg ggt tct cca atg gct cag aat ctt ata aaa tcc ggg tgt gat gtg      48
Met Gly Ser Pro Met Ala Gln Asn Leu Ile Lys Ser Gly Cys Asp Val
1               5                   10                  15 act gtt tgg aac agg acc aag agc aaa tgt gat cct ctc atc agc ttg      96
Thr Val Trp Asn Arg Thr Lys Ser Lys Cys Asp Pro Leu Ile Ser Leu
            20                  25                  30 gga gca aaa tat aag cct tct ccc gag gaa gta act gca gcc tgt gat     144
Gly Ala Lys Tyr Lys Pro Ser Pro Glu Glu Val Thr Ala Ala Cys Asp
        35                  40                  45 gtc aca ttt gca atg ctt gct gat cca gaa tgt gca gtg gag gtt gca     192
Val Thr Phe Ala Met Leu Ala Asp Pro Glu Cys Ala Val Glu Val Ala
    50                  55                  60 tgt gga aag cat gga gct gca agt ggt atg ggt cca gga aaa ggg tat     240
Cys Gly Lys His Gly Ala Ala Ser Gly Met Gly Pro Gly Lys Gly Tyr
65                  70                  75                  80 gtg gat gtt tca act gtt gat ggt ggg act tct aaa ttg att tgt gga     288
Val Asp Val Ser Thr Val Asp Gly Gly Thr Ser Lys Leu Ile Cys Gly
                85                  90                  95 cat atc aaa gct tcc ggg gca tca ttt ttg gaa gct cct gtt tct ggc     336
His Ile Lys Ala Ser Gly Ala Ser Phe Leu Glu Ala Pro Val Ser Gly
            100                 105                 110 tca aag aaa cca gca gaa gat ggg caa ctt ata ttt ctt act gca ggt     384
Ser Lys Lys Pro Ala Glu Asp Gly Gln Leu Ile Phe Leu Thr Ala Gly
        115                 120                 125 gac aaa tct ctg tat gaa aca gtc gct ccg ttc tta gat atc atg ggg     432
Asp Lys Ser Leu Tyr Glu Thr Val Ala Pro Phe Leu Asp Ile Met Gly
    130                 135                 140 aag tca aga ttt tac ctt ggg gaa gtc gga aat ggg gct gca atg aaa     480
Lys Ser Arg Phe Tyr Leu Gly Glu Val Gly Asn Gly Ala Ala Met Lys
145                 150                 155                 160 ctt att gtc aac atg atc atg ggc agt atg atg gca acc ttt tct gaa     528
Leu Ile Val Asn Met Ile Met Gly Ser Met Met Ala Thr Phe Ser Glu
                165                 170                 175 gga ttg ctt ctc agc gag aaa gta gga ctg gac cca aat gta ctg gtt     576
Gly Leu Leu Leu Ser Glu Lys Val Gly Leu Asp Pro Asn Val Leu Val
            180                 185                 190
```

```
gag gta gtg tct gag ggt gcc att agt gca ccg atg tat tcg ctg aaa    624
Glu Val Val Ser Glu Gly Ala Ile Ser Ala Pro Met Tyr Ser Leu Lys
        195                 200                 205 ggt cca tca atg gtc aaa tct cta tac ccc act gct ttt ccc tta aag    672
Gly Pro Ser Met Val Lys Ser Leu Tyr Pro Thr Ala Phe Pro Leu Lys
    210                 215                 220 cat cag cag aag gac atg aga ctt gcc ctg gga tta gca gaa tct gtt    720
His Gln Gln Lys Asp Met Arg Leu Ala Leu Gly Leu Ala Glu Ser Val
225                 230                 235                 240 tcc caa ccc act cca att gca gca gct gca aat gaa cta tac aag gta    768
Ser Gln Pro Thr Pro Ile Ala Ala Ala Ala Asn Glu Leu Tyr Lys Val
                245                 250                 255 gca aaa agt cac ggg ctt agc gat agt gat ttt tca gca gtg att gaa    816
Ala Lys Ser His Gly Leu Ser Asp Ser Asp Phe Ser Ala Val Ile Glu
            260                 265                 270 gca ctg aaa gga aaa gtg caa tcc tga                                843
Ala Leu Lys Gly Lys Val Gln Ser
        275                 280

<210> SEQ ID NO 73
<211> LENGTH: 280
<212> TYPE: PRT
<213> ORGANISM: Populus balsamifera subsp. trichocarpa

<400> SEQUENCE: 73

Met Gly Ser Pro Met Ala Gln Asn Leu Ile Lys Ser Gly Cys Asp Val
1               5                   10                  15

Thr Val Trp Asn Arg Thr Lys Ser Lys Cys Asp Pro Leu Ile Ser Leu
            20                  25                  30

Gly Ala Lys Tyr Lys Pro Ser Pro Glu Glu Val Thr Ala Ala Cys Asp
        35                  40                  45

Val Thr Phe Ala Met Leu Ala Asp Pro Glu Cys Ala Val Glu Val Ala
    50                  55                  60

Cys Gly Lys His Gly Ala Ala Ser Gly Met Gly Pro Gly Lys Gly Tyr
65                  70                  75                  80

Val Asp Val Ser Thr Val Asp Gly Gly Thr Ser Lys Leu Ile Cys Gly
            85                  90                  95

His Ile Lys Ala Ser Gly Ala Ser Phe Leu Glu Ala Pro Val Ser Gly
        100                 105                 110

Ser Lys Lys Pro Ala Glu Asp Gly Gln Leu Ile Phe Leu Thr Ala Gly
    115                 120                 125

Asp Lys Ser Leu Tyr Glu Thr Val Ala Pro Phe Leu Asp Ile Met Gly
130                 135                 140

Lys Ser Arg Phe Tyr Leu Gly Glu Val Gly Asn Gly Ala Ala Met Lys
145                 150                 155                 160

Leu Ile Val Asn Met Ile Met Gly Ser Met Met Ala Thr Phe Ser Glu
            165                 170                 175

Gly Leu Leu Leu Ser Glu Lys Val Gly Leu Asp Pro Asn Val Leu Val
        180                 185                 190

Glu Val Val Ser Glu Gly Ala Ile Ser Ala Pro Met Tyr Ser Leu Lys
    195                 200                 205

Gly Pro Ser Met Val Lys Ser Leu Tyr Pro Thr Ala Phe Pro Leu Lys
210                 215                 220

His Gln Gln Lys Asp Met Arg Leu Ala Leu Gly Leu Ala Glu Ser Val
225                 230                 235                 240

Ser Gln Pro Thr Pro Ile Ala Ala Ala Ala Asn Glu Leu Tyr Lys Val
```

```
                245                 250                 255
Ala Lys Ser His Gly Leu Ser Asp Ser Asp Phe Ser Ala Val Ile Glu
        260                 265                 270

Ala Leu Lys Gly Lys Val Gln Ser
        275                 280

<210> SEQ ID NO 74
<211> LENGTH: 1227
<212> TYPE: DNA
<213> ORGANISM: Sorghum bicolor
<220> FEATURE:
<221> NAME/KEY: CDS
<222> LOCATION: (1)..(1227)

<400> SEQUENCE: 74 atg gcg gcc cag aga gga aaa gcc gac ctg ccc tgc cct gcc ctg ccc      48
Met Ala Ala Gln Arg Gly Lys Ala Asp Leu Pro Cys Pro Ala Leu Pro
1               5                   10                  15 tgc tcc gtc tgc cgg cgg gcc cag atc ggc cca ccc cgc gca agc ccc      96
Cys Ser Val Cys Arg Arg Ala Gln Ile Gly Pro Pro Arg Ala Ser Pro
                20                  25                  30 gag gcc acc cgc cca acg cca aaa agt gga aag ggg cca tcc aag cga     144
Glu Ala Thr Arg Pro Thr Pro Lys Ser Gly Lys Gly Pro Ser Lys Arg
            35                  40                  45 cag gcg cac gtg acg tgg ctt atc ccc ctc tcg ctc tcg ccc cgc atc     192
Gln Ala His Val Thr Trp Leu Ile Pro Leu Ser Leu Ser Pro Arg Ile
        50                  55                  60 cac cct cca agc agc aag cag cag cag cca tcg gcc atg gcc gcg gcg     240
His Pro Pro Ser Ser Lys Gln Gln Gln Pro Ser Ala Met Ala Ala Ala
65                  70                  75                  80 gcc ttc ctc tcc gcc agg gcg gcg ccc gcg ctg ctc tct ccc ttg cgc     288
Ala Phe Leu Ser Ala Arg Ala Ala Pro Ala Leu Leu Ser Pro Leu Arg
                85                  90                  95 tcg cgc agg ctg tac cgc cgc ctc gtc gca tcc tcg tcc tcc gcc ggg     336
Ser Arg Arg Leu Tyr Arg Arg Leu Val Ala Ser Ser Ser Ser Ala Gly
            100                 105                 110 ggt caa ggt ggt ggc ggg gga gtg gag ttc cag ggg aag gtg ggc ttc     384
Gly Gln Gly Gly Gly Gly Gly Val Glu Phe Gln Gly Lys Val Gly Phe
        115                 120                 125 ctg ggg ctc ggg atc atg ggc gcg ccc atg gca tcc aac ctc atc agc     432
Leu Gly Leu Gly Ile Met Gly Ala Pro Met Ala Ser Asn Leu Ile Ser
130                 135                 140 gca ggc tgc gac gtt acg gtg tgg aac agg acc aag agc aag tgc gat     480
Ala Gly Cys Asp Val Thr Val Trp Asn Arg Thr Lys Ser Lys Cys Asp
145                 150                 155                 160 ccc ctc ctc agc ctc ggt gcc aag tac gag cct tca ccg gcc caa gtc     528
Pro Leu Leu Ser Leu Gly Ala Lys Tyr Glu Pro Ser Pro Ala Gln Val
                165                 170                 175 gct tca tct tgt gac gtg aca ttc gcg atg ctc gct gat cca caa agc     576
Ala Ser Ser Cys Asp Val Thr Phe Ala Met Leu Ala Asp Pro Gln Ser
            180                 185                 190 gcg gct gag gtt gca tgc ggg tcc agt gga gct gct gaa ggg ctg gcc     624
Ala Ala Glu Val Ala Cys Gly Ser Ser Gly Ala Ala Glu Gly Leu Ala
        195                 200                 205 cct ggg aaa ggc tat gtc gat gtg tcg acg gtt gat ggt gct aca tcc     672
Pro Gly Lys Gly Tyr Val Asp Val Ser Thr Val Asp Gly Ala Thr Ser
    210                 215                 220 aag ctg atc gct gaa cgc att aca agt acc ggg gca tct ttt ctt gag     720
Lys Leu Ile Ala Glu Arg Ile Thr Ser Thr Gly Ala Ser Phe Leu Glu
225                 230                 235                 240
```

```
gct cca gtt tca ggc tcg aaa aag cca gca gaa gat ggg ctg ctc atc      768
Ala Pro Val Ser Gly Ser Lys Lys Pro Ala Glu Asp Gly Leu Leu Ile
            245                 250                 255 ttt ctc acc gca ggt gat gaa tcc ttg tac aag aga gtg gcg ccc ctc      816
Phe Leu Thr Ala Gly Asp Glu Ser Leu Tyr Lys Arg Val Ala Pro Leu
        260                 265                 270 ctt gat gtc atg ggg aag tca aga ttt tat ctt ggc gat gta ggc aat      864
Leu Asp Val Met Gly Lys Ser Arg Phe Tyr Leu Gly Asp Val Gly Asn
                275                 280                 285 ggt gcg gca atg aag atc gtg gtt aac atg gtc atg ggg agc atg atg      912
Gly Ala Ala Met Lys Ile Val Val Asn Met Val Met Gly Ser Met Met
        290                 295                 300 gtt tcc ttc tca gaa ggg ttg ctc ctg agt gaa aaa gtt ggc tta gac      960
Val Ser Phe Ser Glu Gly Leu Leu Leu Ser Glu Lys Val Gly Leu Asp
305                 310                 315                 320 cct aat act ctt gtt gag gtt att tcc cag ggt gct atc agt gcc ccc     1008
Pro Asn Thr Leu Val Glu Val Ile Ser Gln Gly Ala Ile Ser Ala Pro
                325                 330                 335 atg ttc tcc ctt aag ggc cca tcc atg gtt aaa gct gca tat cct act     1056
Met Phe Ser Leu Lys Gly Pro Ser Met Val Lys Ala Ala Tyr Pro Thr
            340                 345                 350 gcc ttt cct ctg aag cat caa cag aag gac atg agg ctc gca ttg gcc     1104
Ala Phe Pro Leu Lys His Gln Gln Lys Asp Met Arg Leu Ala Leu Ala
        355                 360                 365 ctg gcg gaa tca gtg tcc cag tcc att cct aca gtt gca gct gcg aac     1152
Leu Ala Glu Ser Val Ser Gln Ser Ile Pro Thr Val Ala Ala Ala Asn
    370                 375                 380 gag ctg tac aag gct gca aaa tcg ctt ggc ctt agt gac cac gac ttc     1200
Glu Leu Tyr Lys Ala Ala Lys Ser Leu Gly Leu Ser Asp His Asp Phe
385                 390                 395                 400 tcg gcg gtt att gaa gca ctt aaa taa                                 1227
Ser Ala Val Ile Glu Ala Leu Lys
                405

<210> SEQ ID NO 75
<211> LENGTH: 408
<212> TYPE: PRT
<213> ORGANISM: Sorghum bicolor

<400> SEQUENCE: 75

Met Ala Ala Gln Arg Gly Lys Ala Asp Leu Pro Cys Pro Ala Leu Pro
1               5                   10                  15

Cys Ser Val Cys Arg Arg Ala Gln Ile Gly Pro Pro Arg Ala Ser Pro
            20                  25                  30

Glu Ala Thr Arg Pro Thr Pro Lys Ser Gly Lys Gly Pro Ser Lys Arg
        35                  40                  45

Gln Ala His Val Thr Trp Leu Ile Pro Leu Ser Leu Ser Pro Arg Ile
    50                  55                  60

His Pro Pro Ser Ser Lys Gln Gln Pro Ser Ala Met Ala Ala Ala
65                  70                  75                  80

Ala Phe Leu Ser Ala Arg Ala Ala Pro Ala Leu Leu Ser Pro Leu Arg
                85                  90                  95

Ser Arg Arg Leu Tyr Arg Arg Leu Val Ala Ser Ser Ser Ser Ala Gly
            100                 105                 110

Gly Gln Gly Gly Gly Gly Gly Val Glu Phe Gln Gly Lys Val Gly Phe
        115                 120                 125

Leu Gly Leu Gly Ile Met Gly Ala Pro Met Ala Ser Asn Leu Ile Ser
    130                 135                 140
```

```
Ala Gly Cys Asp Val Thr Val Trp Asn Arg Thr Lys Ser Lys Cys Asp
145                 150                 155                 160

Pro Leu Leu Ser Leu Gly Ala Lys Tyr Glu Pro Ser Pro Ala Gln Val
                165                 170                 175

Ala Ser Ser Cys Asp Val Thr Phe Ala Met Leu Ala Asp Pro Gln Ser
            180                 185                 190

Ala Ala Glu Val Ala Cys Gly Ser Gly Ala Ala Glu Gly Leu Ala
        195                 200                 205

Pro Gly Lys Gly Tyr Val Asp Val Ser Thr Val Asp Gly Ala Thr Ser
    210                 215                 220

Lys Leu Ile Ala Glu Arg Ile Thr Ser Thr Gly Ala Ser Phe Leu Glu
225                 230                 235                 240

Ala Pro Val Ser Gly Ser Lys Lys Pro Ala Glu Asp Gly Leu Leu Ile
                245                 250                 255

Phe Leu Thr Ala Gly Asp Glu Ser Leu Tyr Lys Arg Val Ala Pro Leu
            260                 265                 270

Leu Asp Val Met Gly Lys Ser Arg Phe Tyr Leu Gly Asp Val Gly Asn
        275                 280                 285

Gly Ala Ala Met Lys Ile Val Val Asn Met Val Met Gly Ser Met Met
    290                 295                 300

Val Ser Phe Ser Glu Gly Leu Leu Leu Ser Glu Lys Val Gly Leu Asp
305                 310                 315                 320

Pro Asn Thr Leu Val Glu Val Ile Ser Gln Gly Ala Ile Ser Ala Pro
                325                 330                 335

Met Phe Ser Leu Lys Gly Pro Ser Met Val Lys Ala Ala Tyr Pro Thr
            340                 345                 350

Ala Phe Pro Leu Lys His Gln Gln Lys Asp Met Arg Leu Ala Leu Ala
        355                 360                 365

Leu Ala Glu Ser Val Ser Gln Ser Ile Pro Thr Val Ala Ala Ala Asn
    370                 375                 380

Glu Leu Tyr Lys Ala Ala Lys Ser Leu Gly Leu Ser Asp His Asp Phe
385                 390                 395                 400

Ser Ala Val Ile Glu Ala Leu Lys
                405

<210> SEQ ID NO 76
<211> LENGTH: 1098
<212> TYPE: DNA
<213> ORGANISM: Vitis vinifera
<220> FEATURE:
<221> NAME/KEY: CDS
<222> LOCATION: (1)..(1098)

<400> SEQUENCE: 76 atg tcc ttg gtc aag agt cat tgc tgt tac aat ctc ctc aat cca tcc      48
Met Ser Leu Val Lys Ser His Cys Cys Tyr Asn Leu Leu Asn Pro Ser
1               5                   10                  15 aac act gct tca ctg gcc atg gct atg tgc tca agc ttc tgt cct cct      96
Asn Thr Ala Ser Leu Ala Met Ala Met Cys Ser Ser Phe Cys Pro Pro
            20                  25                  30 cag gtt ccc aac cac ttc aga gga aca aca ccc att cct tct ttc ctc     144
Gln Val Pro Asn His Phe Arg Gly Thr Thr Pro Ile Pro Ser Phe Leu
        35                  40                  45 ccc aaa cca cct tct ttc aag gcc ttc tct tct caa aca gcc act gct     192
Pro Lys Pro Pro Ser Phe Lys Ala Phe Ser Ser Gln Thr Ala Thr Ala
50                  55                  60 tcc acc aaa gat gaa ttt ccg gca cgt gtt ggc ttt ctg ggt ctt ggt     240
Ser Thr Lys Asp Glu Phe Pro Ala Arg Val Gly Phe Leu Gly Leu Gly
```

| | | | | | | | | | | | | | | | |
|---|---|---|---|---|---|---|---|---|---|---|---|---|---|---|---|
| Ser | Thr | Lys | Asp | Glu | Phe | Pro | Ala | Arg | Val | Gly | Phe | Leu | Gly | Leu | Gly |
| 65 | | | | 70 | | | | | 75 | | | | | 80 | |

```
atc atg ggt tct cca atg gca caa aat ctt att aaa tcg gga tgt gat      288
Ile Met Gly Ser Pro Met Ala Gln Asn Leu Ile Lys Ser Gly Cys Asp
             85                  90                  95 gtg act gtc tgg aat agg acc aag agc aaa tgt gat ccc ctc atc agc      336
Val Thr Val Trp Asn Arg Thr Lys Ser Lys Cys Asp Pro Leu Ile Ser
            100                 105                 110 ttg ggt gcc aaa tac aaa tcc tct cca gaa gaa gta gct gca tct tgt      384
Leu Gly Ala Lys Tyr Lys Ser Ser Pro Glu Glu Val Ala Ala Ser Cys
        115                 120                 125 gat gtc aca ttc gct atg ctt gca gac cct gaa agt gca gtg gat gtt      432
Asp Val Thr Phe Ala Met Leu Ala Asp Pro Glu Ser Ala Val Asp Val
    130                 135                 140 gct tgc ggg aag cat ggt gct gca agt gga att ggt cca gga aaa ggg      480
Ala Cys Gly Lys His Gly Ala Ala Ser Gly Ile Gly Pro Gly Lys Gly
145                 150                 155                 160 tac gta gat gtt tca aca gtt gat ggt gcc act tct aaa ttg att ggt      528
Tyr Val Asp Val Ser Thr Val Asp Gly Ala Thr Ser Lys Leu Ile Gly
                165                 170                 175 gaa cat att aaa gct act ggg gca ttg ttt ttg gag gct cca gtt tca      576
Glu His Ile Lys Ala Thr Gly Ala Leu Phe Leu Glu Ala Pro Val Ser
            180                 185                 190 ggc tcc aaa aag cca gca gaa gat gga caa cta ata ttt ctt aca ggc      624
Gly Ser Lys Lys Pro Ala Glu Asp Gly Gln Leu Ile Phe Leu Thr Gly
        195                 200                 205 ggt gac aaa tct cta tat gaa act gtt gct cca ctc tta gac atc atg      672
Gly Asp Lys Ser Leu Tyr Glu Thr Val Ala Pro Leu Leu Asp Ile Met
    210                 215                 220 gga aag tca aga ttt ttc ctt ggg agt gtt gga aat gga gct gca atg      720
Gly Lys Ser Arg Phe Phe Leu Gly Ser Val Gly Asn Gly Ala Ala Met
225                 230                 235                 240 aaa ctt gtt gtc aac atg gtg atg gga agt atg atg gcc tct ttt tct      768
Lys Leu Val Val Asn Met Val Met Gly Ser Met Met Ala Ser Phe Ser
                245                 250                 255 gaa ggg ttg ctt ctc ggt gag aaa gtg ggg ttg gat cca gat gtt att      816
Glu Gly Leu Leu Leu Gly Glu Lys Val Gly Leu Asp Pro Asp Val Ile
            260                 265                 270 gtc gag gta ata tca cag gga gcc ata agt gca cca atg ttc tcc atg      864
Val Glu Val Ile Ser Gln Gly Ala Ile Ser Ala Pro Met Phe Ser Met
        275                 280                 285 aaa ggt cct tca atg gtg aaa tcc gtc tac cca act gca ttt ccc tta      912
Lys Gly Pro Ser Met Val Lys Ser Val Tyr Pro Thr Ala Phe Pro Leu
    290                 295                 300 aag cat caa caa aag gat ctc agg ctt gcc ctt gga tta gca gaa tct      960
Lys His Gln Gln Lys Asp Leu Arg Leu Ala Leu Gly Leu Ala Glu Ser
305                 310                 315                 320 gtt tcc cag cct act cca atc gca gca gct gcc aat gaa cta tac aaa     1008
Val Ser Gln Pro Thr Pro Ile Ala Ala Ala Ala Asn Glu Leu Tyr Lys
                325                 330                 335 gta gcc aaa tct cat ggc ctc agc gac cat gac ttc tca gca gtc att     1056
Val Ala Lys Ser His Gly Leu Ser Asp His Asp Phe Ser Ala Val Ile
            340                 345                 350 gaa gca ctg aaa gtg aag atg cag gac ccc cca gaa tac taa             1098
Glu Ala Leu Lys Val Lys Met Gln Asp Pro Pro Glu Tyr
        355                 360                 365

<210> SEQ ID NO 77
<211> LENGTH: 365
<212> TYPE: PRT
```

<213> ORGANISM: Vitis vinifera

<400> SEQUENCE: 77

Met Ser Leu Val Lys Ser His Cys Cys Tyr Asn Leu Leu Asn Pro Ser
1               5                   10                  15

Asn Thr Ala Ser Leu Ala Met Ala Met Cys Ser Ser Phe Cys Pro Pro
            20                  25                  30

Gln Val Pro Asn His Phe Arg Gly Thr Thr Pro Ile Pro Ser Phe Leu
        35                  40                  45

Pro Lys Pro Pro Ser Phe Lys Ala Phe Ser Ser Gln Thr Ala Thr Ala
    50                  55                  60

Ser Thr Lys Asp Glu Phe Pro Ala Arg Val Gly Phe Leu Gly Leu Gly
65                  70                  75                  80

Ile Met Gly Ser Pro Met Ala Gln Asn Leu Ile Lys Ser Gly Cys Asp
                85                  90                  95

Val Thr Val Trp Asn Arg Thr Lys Ser Lys Cys Asp Pro Leu Ile Ser
            100                 105                 110

Leu Gly Ala Lys Tyr Lys Ser Pro Glu Glu Val Ala Ala Ser Cys
        115                 120                 125

Asp Val Thr Phe Ala Met Leu Ala Asp Pro Glu Ser Ala Val Asp Val
    130                 135                 140

Ala Cys Gly Lys His Gly Ala Ala Ser Gly Ile Gly Pro Gly Lys Gly
145                 150                 155                 160

Tyr Val Asp Val Ser Thr Val Asp Gly Ala Thr Ser Lys Leu Ile Gly
                165                 170                 175

Glu His Ile Lys Ala Thr Gly Ala Leu Phe Leu Glu Ala Pro Val Ser
            180                 185                 190

Gly Ser Lys Lys Pro Ala Glu Asp Gly Gln Leu Ile Phe Leu Thr Gly
        195                 200                 205

Gly Asp Lys Ser Leu Tyr Glu Thr Val Ala Pro Leu Leu Asp Ile Met
    210                 215                 220

Gly Lys Ser Arg Phe Phe Leu Gly Ser Val Gly Asn Gly Ala Ala Met
225                 230                 235                 240

Lys Leu Val Val Asn Met Val Met Gly Ser Met Met Ala Ser Phe Ser
                245                 250                 255

Glu Gly Leu Leu Leu Gly Glu Lys Val Gly Leu Asp Pro Asp Val Ile
            260                 265                 270

Val Glu Val Ile Ser Gln Gly Ala Ile Ser Ala Pro Met Phe Ser Met
        275                 280                 285

Lys Gly Pro Ser Met Val Lys Ser Val Tyr Pro Thr Ala Phe Pro Leu
    290                 295                 300

Lys His Gln Gln Lys Asp Leu Arg Leu Ala Leu Gly Leu Ala Glu Ser
305                 310                 315                 320

Val Ser Gln Pro Thr Pro Ile Ala Ala Ala Asn Glu Leu Tyr Lys
                325                 330                 335

Val Ala Lys Ser His Gly Leu Ser Asp His Asp Phe Ser Ala Val Ile
            340                 345                 350

Glu Ala Leu Lys Val Lys Met Gln Asp Pro Pro Glu Tyr
        355                 360                 365

<210> SEQ ID NO 78
<211> LENGTH: 888
<212> TYPE: DNA
<213> ORGANISM: Zea mays
<220> FEATURE:

```
<221> NAME/KEY: CDS
<222> LOCATION: (1)..(888)

<400> SEQUENCE: 78 atg gag gtg ggg ttc ttg ggt ctg ggc atc atg ggc aag gca atg gcg      48
Met Glu Val Gly Phe Leu Gly Leu Gly Ile Met Gly Lys Ala Met Ala
1               5                   10                  15 acc aac ctc ctc cgc cac ggc ttc cgc gtc acc gtc tgg aac agg acc      96
Thr Asn Leu Leu Arg His Gly Phe Arg Val Thr Val Trp Asn Arg Thr
            20                  25                  30 ctc gcc aag tgc caa gag ctc gcc gcg ctc ggc gcc acc gtc ggg gag      144
Leu Ala Lys Cys Gln Glu Leu Ala Ala Leu Gly Ala Thr Val Gly Glu
        35                  40                  45 acg cct gcc tcc gtc gtc tcc aag tgc aga tac acc atc gcc atg ctc      192
Thr Pro Ala Ser Val Val Ser Lys Cys Arg Tyr Thr Ile Ala Met Leu
    50                  55                  60 tcc gac ccc agc gcc gcc cta tca gtc gtc ttc gac aag gat ggc gtg      240
Ser Asp Pro Ser Ala Ala Leu Ser Val Val Phe Asp Lys Asp Gly Val
65                  70                  75                  80 ctc gag cag atc ggt agc ggg aag ggc tat gtg gac atg tcc act gtt      288
Leu Glu Gln Ile Gly Ser Gly Lys Gly Tyr Val Asp Met Ser Thr Val
                85                  90                  95 gac gct gca act tcg acc aag att agc gag gca gtt aaa caa aaa ggg      336
Asp Ala Ala Thr Ser Thr Lys Ile Ser Glu Ala Val Lys Gln Lys Gly
            100                 105                 110 gga gct ttc ctt gaa gct cca gtt tca ggg agc aag aag cca gct gaa      384
Gly Ala Phe Leu Glu Ala Pro Val Ser Gly Ser Lys Lys Pro Ala Glu
        115                 120                 125 gat ggc caa ttg gtc att ctt gct gca ggg aac aag cca ttg tat gat      432
Asp Gly Gln Leu Val Ile Leu Ala Ala Gly Asn Lys Pro Leu Tyr Asp
    130                 135                 140 ggt atg att cct gca ttt gat gta ctg ggg aag aag tca ttc ttt ctg      480
Gly Met Ile Pro Ala Phe Asp Val Leu Gly Lys Lys Ser Phe Phe Leu
145                 150                 155                 160 gga gag att gga aat ggg gca aag atg aag ctt gtg gtc aac atg gtc      528
Gly Glu Ile Gly Asn Gly Ala Lys Met Lys Leu Val Val Asn Met Val
                165                 170                 175 atg gga agt atg atg aat tct ttg tcc gag gga ctc tgt ttg gcc gac      576
Met Gly Ser Met Met Asn Ser Leu Ser Glu Gly Leu Cys Leu Ala Asp
            180                 185                 190 aaa agt ggg ctg agc ccc caa aca ctt ctt gat gta ctg gac ctt ggc      624
Lys Ser Gly Leu Ser Pro Gln Thr Leu Leu Asp Val Leu Asp Leu Gly
        195                 200                 205 gcc atc gca aac cca atg ttc aag ctg aag ggg cct aca atg ctg caa      672
Ala Ile Ala Asn Pro Met Phe Lys Leu Lys Gly Pro Thr Met Leu Gln
    210                 215                 220 ggc agc tac agc cct gcg ttt ccc ctg aag cat cag cag aag gac atg      720
Gly Ser Tyr Ser Pro Ala Phe Pro Leu Lys His Gln Gln Lys Asp Met
225                 230                 235                 240 agg tta gcg ctt gct ctg gga gat gag aac gcc gtc gcc atg ccc gtc      768
Arg Leu Ala Leu Ala Leu Gly Asp Glu Asn Ala Val Ala Met Pro Val
                245                 250                 255 tca gca gct gcc aat gag gcg ttc aag aag gcg agg agc ctg ggg ctg      816
Ser Ala Ala Ala Asn Glu Ala Phe Lys Lys Ala Arg Ser Leu Gly Leu
            260                 265                 270 gga gac cag gat ttt tcg gcg gtc tat gag gtt gtg aag ggc gcg ggt      864
Gly Asp Gln Asp Phe Ser Ala Val Tyr Glu Val Val Lys Gly Ala Gly
        275                 280                 285 ggt tct gga tct ggc cag ccg tga                                       888
Gly Ser Gly Ser Gly Gln Pro
```

<210> SEQ ID NO 79
<211> LENGTH: 295
<212> TYPE: PRT
<213> ORGANISM: Zea mays

<400> SEQUENCE: 79

Met Glu Val Gly Phe Leu Gly Leu Gly Ile Met Gly Lys Ala Met Ala
1               5                   10                  15

Thr Asn Leu Leu Arg His Gly Phe Arg Val Thr Val Trp Asn Arg Thr
            20                  25                  30

Leu Ala Lys Cys Gln Glu Leu Ala Ala Leu Gly Ala Thr Val Gly Glu
        35                  40                  45

Thr Pro Ala Ser Val Val Ser Lys Cys Arg Tyr Thr Ile Ala Met Leu
    50                  55                  60

Ser Asp Pro Ser Ala Ala Leu Ser Val Val Phe Asp Lys Asp Gly Val
65                  70                  75                  80

Leu Glu Gln Ile Gly Ser Gly Lys Gly Tyr Val Asp Met Ser Thr Val
                85                  90                  95

Asp Ala Ala Thr Ser Thr Lys Ile Ser Glu Ala Val Lys Gln Lys Gly
            100                 105                 110

Gly Ala Phe Leu Glu Ala Pro Val Ser Gly Ser Lys Lys Pro Ala Glu
        115                 120                 125

Asp Gly Gln Leu Val Ile Leu Ala Ala Gly Asn Lys Pro Leu Tyr Asp
    130                 135                 140

Gly Met Ile Pro Ala Phe Asp Val Leu Gly Lys Lys Ser Phe Phe Leu
145                 150                 155                 160

Gly Glu Ile Gly Asn Gly Ala Lys Met Lys Leu Val Val Asn Met Val
                165                 170                 175

Met Gly Ser Met Met Asn Ser Leu Ser Glu Gly Leu Cys Leu Ala Asp
            180                 185                 190

Lys Ser Gly Leu Ser Pro Gln Thr Leu Leu Asp Val Leu Asp Leu Gly
        195                 200                 205

Ala Ile Ala Asn Pro Met Phe Lys Leu Lys Gly Pro Thr Met Leu Gln
    210                 215                 220

Gly Ser Tyr Ser Pro Ala Phe Pro Leu Lys His Gln Gln Lys Asp Met
225                 230                 235                 240

Arg Leu Ala Leu Ala Leu Gly Asp Glu Asn Ala Val Ala Met Pro Val
                245                 250                 255

Ser Ala Ala Ala Asn Glu Ala Phe Lys Lys Ala Arg Ser Leu Gly Leu
            260                 265                 270

Gly Asp Gln Asp Phe Ser Ala Val Tyr Glu Val Val Lys Gly Ala Gly
        275                 280                 285

Gly Ser Gly Ser Gly Gln Pro
    290                 295

<210> SEQ ID NO 80
<211> LENGTH: 1014
<212> TYPE: DNA
<213> ORGANISM: Hordeum vulgare
<220> FEATURE:
<221> NAME/KEY: CDS
<222> LOCATION: (1)..(1014)

<400> SEQUENCE: 80 atg gcc gcg gcc agc ttc ctc ctc agc ccc agg gtg acg ctg ccc ctg      48

```
Met Ala Ala Ala Ser Phe Leu Leu Ser Pro Arg Val Thr Leu Pro Leu
1               5                   10                  15 cgc cga gga tcc cgc ctc ctc gtg tcc tgc tcc gcc tct tcg tcg tcc         96
Arg Arg Gly Ser Arg Leu Leu Val Ser Cys Ser Ala Ser Ser Ser Ser
                20                  25                  30 tcc tcg tca gat gct gct gga ggg atg gga ttc cag gga agg gtg ggg         144
Ser Ser Ser Asp Ala Ala Gly Gly Met Gly Phe Gln Gly Arg Val Gly
            35                  40                  45 ttc ttg ggc ctc ggg atc atg ggc gcc ccc atg gca tca aac ctc atc         192
Phe Leu Gly Leu Gly Ile Met Gly Ala Pro Met Ala Ser Asn Leu Ile
50                  55                  60 aag gct ggt tgt gat att aca gtt tgg aac aga acc aag agc aag tgc         240
Lys Ala Gly Cys Asp Ile Thr Val Trp Asn Arg Thr Lys Ser Lys Cys
65                  70                  75                  80 gat cct ctt ctc agc ctc ggt gcc aag ttc gaa tct tcg ccc gcc aga         288
Asp Pro Leu Leu Ser Leu Gly Ala Lys Phe Glu Ser Ser Pro Ala Arg
                85                  90                  95 gtt tca tca tcc tgt gat gtc acc ttt gca atg ctt gct gac cca gaa         336
Val Ser Ser Ser Cys Asp Val Thr Phe Ala Met Leu Ala Asp Pro Glu
            100                 105                 110 agc gcg ttt gag gtt gca tgt ggg gct aat gga gcc gca gaa ggg atg         384
Ser Ala Phe Glu Val Ala Cys Gly Ala Asn Gly Ala Ala Glu Gly Met
        115                 120                 125 gcc cca ggg aaa ggg tat gtc gat gtg tca aca gtc gat gat gca aca         432
Ala Pro Gly Lys Gly Tyr Val Asp Val Ser Thr Val Asp Asp Ala Thr
130                 135                 140 tct aag cta att ggc aaa cgt att aca agt act ggg gca tct ttt ctc         480
Ser Lys Leu Ile Gly Lys Arg Ile Thr Ser Thr Gly Ala Ser Phe Leu
145                 150                 155                 160 gag gct cca gtt tca ggc tca aaa aag cca gca gaa gat gga ctg cta         528
Glu Ala Pro Val Ser Gly Ser Lys Lys Pro Ala Glu Asp Gly Leu Leu
                165                 170                 175 atc ttt ctt act gca ggt gat gaa tct ttg tac aag aga gtg gcg ccc         576
Ile Phe Leu Thr Ala Gly Asp Glu Ser Leu Tyr Lys Arg Val Ala Pro
            180                 185                 190 cta ctt gat gtg atg ggc aag tcc aga ttt tat ctt ggg gat gtc gga         624
Leu Leu Asp Val Met Gly Lys Ser Arg Phe Tyr Leu Gly Asp Val Gly
        195                 200                 205 aac ggc gca gta atg aag ctc gtg gtt aac atg gtg atg ggg agc atg         672
Asn Gly Ala Val Met Lys Leu Val Val Asn Met Val Met Gly Ser Met
210                 215                 220 atg gtc tca ttt gca gaa ggg cta ctc ttg agt gaa aaa gtt ggg tta         720
Met Val Ser Phe Ala Glu Gly Leu Leu Leu Ser Glu Lys Val Gly Leu
225                 230                 235                 240 gac ccg aat act gtc gtc gag gtt att tca caa ggt gct atc aat gct         768
Asp Pro Asn Thr Val Val Glu Val Ile Ser Gln Gly Ala Ile Asn Ala
                245                 250                 255 ccc atg ttc tcc ctc aag ggc cct tcc atg gtt aag gct gca tac cct         816
Pro Met Phe Ser Leu Lys Gly Pro Ser Met Val Lys Ala Ala Tyr Pro
            260                 265                 270 act gcc ttt ccc ctg aaa cat cag cag aag gat cta agg ctg gcg ctg         864
Thr Ala Phe Pro Leu Lys His Gln Gln Lys Asp Leu Arg Leu Ala Leu
        275                 280                 285 gcc ctg gca gaa tcg gtg tcc cag ccc att cct aca gct gca gct gca         912
Ala Leu Ala Glu Ser Val Ser Gln Pro Ile Pro Thr Ala Ala Ala Ala
290                 295                 300 aac gag ctg tac aag gtt gcc aaa tcg ttg ggc ctc gcc gac cag gac         960
Asn Glu Leu Tyr Lys Val Ala Lys Ser Leu Gly Leu Ala Asp Gln Asp
305                 310                 315                 320
```

```
ttc tcc gcg gtc att gag gcg ctc aag gcc aaa gtg cag agc tcg cag      1008
Phe Ser Ala Val Ile Glu Ala Leu Lys Ala Lys Val Gln Ser Ser Gln
                325                 330                 335 cac tag                                                              1014
His
```

<210> SEQ ID NO 81
<211> LENGTH: 337
<212> TYPE: PRT
<213> ORGANISM: Hordeum vulgare

<400> SEQUENCE: 81

```
Met Ala Ala Ala Ser Phe Leu Leu Ser Pro Arg Val Thr Leu Pro Leu
1               5                   10                  15

Arg Arg Gly Ser Arg Leu Leu Val Ser Cys Ser Ala Ser Ser Ser Ser
            20                  25                  30

Ser Ser Ser Asp Ala Ala Gly Gly Met Gly Phe Gln Gly Arg Val Gly
        35                  40                  45

Phe Leu Gly Leu Gly Ile Met Gly Ala Pro Met Ala Ser Asn Leu Ile
    50                  55                  60

Lys Ala Gly Cys Asp Ile Thr Val Trp Asn Arg Thr Lys Ser Lys Cys
65                  70                  75                  80

Asp Pro Leu Leu Ser Leu Gly Ala Lys Phe Glu Ser Ser Pro Ala Arg
                85                  90                  95

Val Ser Ser Cys Asp Val Thr Phe Ala Met Leu Ala Asp Pro Glu
            100                 105                 110

Ser Ala Phe Glu Val Ala Cys Gly Ala Asn Gly Ala Ala Glu Gly Met
        115                 120                 125

Ala Pro Gly Lys Gly Tyr Val Asp Val Ser Thr Val Asp Asp Ala Thr
    130                 135                 140

Ser Lys Leu Ile Gly Lys Arg Ile Thr Ser Thr Gly Ala Ser Phe Leu
145                 150                 155                 160

Glu Ala Pro Val Ser Gly Ser Lys Lys Pro Ala Glu Asp Gly Leu Leu
                165                 170                 175

Ile Phe Leu Thr Ala Gly Asp Glu Ser Leu Tyr Lys Arg Val Ala Pro
            180                 185                 190

Leu Leu Asp Val Met Gly Lys Ser Arg Phe Tyr Leu Gly Asp Val Gly
        195                 200                 205

Asn Gly Ala Val Met Lys Leu Val Val Asn Met Val Met Gly Ser Met
    210                 215                 220

Met Val Ser Phe Ala Glu Gly Leu Leu Leu Ser Glu Lys Val Gly Leu
225                 230                 235                 240

Asp Pro Asn Thr Val Val Glu Val Ile Ser Gln Gly Ala Ile Asn Ala
                245                 250                 255

Pro Met Phe Ser Leu Lys Gly Pro Ser Met Val Lys Ala Ala Tyr Pro
            260                 265                 270

Thr Ala Phe Pro Leu Lys His Gln Gln Lys Asp Leu Arg Leu Ala Leu
        275                 280                 285

Ala Leu Ala Glu Ser Val Ser Gln Pro Ile Pro Thr Ala Ala Ala Ala
    290                 295                 300

Asn Glu Leu Tyr Lys Val Ala Lys Ser Leu Gly Leu Ala Asp Gln Asp
305                 310                 315                 320

Phe Ser Ala Val Ile Glu Ala Leu Lys Ala Lys Val Gln Ser Ser Gln
                325                 330                 335

His
```

<210> SEQ ID NO 82
<211> LENGTH: 1092
<212> TYPE: DNA
<213> ORGANISM: Solanum lycopersum
<220> FEATURE:
<221> NAME/KEY: CDS
<222> LOCATION: (1)..(1092)

<400> SEQUENCE: 82

```
atg gca atg tgc tca aca ttt tgt ccc cgg tta tcc ttt cac ctg aat     48
Met Ala Met Cys Ser Thr Phe Cys Pro Arg Leu Ser Phe His Leu Asn
1               5                   10                  15 tgc aaa aaa tcc tta tca ctt ttc cca gtt aag cat cgc ttc ttt gtt     96
Cys Lys Lys Ser Leu Ser Leu Phe Pro Val Lys His Arg Phe Phe Val
            20                  25                  30 aca atc aag gcc ttc tct tct caa act tct gct ccc aaa gct gat gat    144
Thr Ile Lys Ala Phe Ser Ser Gln Thr Ser Ala Pro Lys Ala Asp Asp
        35                  40                  45 ctt cca gca agt att ggc ttt tta ggt ctt gga att atg ggc aac cca    192
Leu Pro Ala Ser Ile Gly Phe Leu Gly Leu Gly Ile Met Gly Asn Pro
    50                  55                  60 atg gct caa aat ctc ata aaa gca gga tgt gat gtg aca gtt tgg aat    240
Met Ala Gln Asn Leu Ile Lys Ala Gly Cys Asp Val Thr Val Trp Asn
65                  70                  75                  80 agg acc aag agc aaa tgt gaa ccc ctt atc tcc ttg ggt gca aaa tac    288
Arg Thr Lys Ser Lys Cys Glu Pro Leu Ile Ser Leu Gly Ala Lys Tyr
                85                  90                  95 aag tcc tct cct gag gag gtt gca gca tct tgt gat gtc aca ttt gcc    336
Lys Ser Ser Pro Glu Glu Val Ala Ala Ser Cys Asp Val Thr Phe Ala
            100                 105                 110 atg ctt gcg gac cct gag agt gca gcg gat gtt gct tgt gga aaa tat    384
Met Leu Ala Asp Pro Glu Ser Ala Ala Asp Val Ala Cys Gly Lys Tyr
        115                 120                 125 gga gct gct aaa gga atg ggt cca gga aaa ggt tat gta gat gcc tca    432
Gly Ala Ala Lys Gly Met Gly Pro Gly Lys Gly Tyr Val Asp Ala Ser
    130                 135                 140 aca gtt gat ggg gaa aca tct aaa ctg atc tgt gaa cat att aga gct    480
Thr Val Asp Gly Glu Thr Ser Lys Leu Ile Cys Glu His Ile Arg Ala
145                 150                 155                 160 act gga gct cat ttt ttg gag gct cca gta tca ggg tcc aag aag cca    528
Thr Gly Ala His Phe Leu Glu Ala Pro Val Ser Gly Ser Lys Lys Pro
                165                 170                 175 gca gaa gat gga cag cta ata ttt ctc act gca ggt gac agc gtg ctg    576
Ala Glu Asp Gly Gln Leu Ile Phe Leu Thr Ala Gly Asp Ser Val Leu
            180                 185                 190 tat gat aaa gct gct cct cta ttg gat atc atg ggg aag tca aga ttt    624
Tyr Asp Lys Ala Ala Pro Leu Leu Asp Ile Met Gly Lys Ser Arg Phe
        195                 200                 205 tac ctt ggt gaa gtt ggt aat gga gct gca atg aaa ctt gtc gtc aat    672
Tyr Leu Gly Glu Val Gly Asn Gly Ala Ala Met Lys Leu Val Val Asn
    210                 215                 220 atg gtt atg gga agt atg atg gcc tca ttt gct gaa gga tta gtt ctc    720
Met Val Met Gly Ser Met Met Ala Ser Phe Ala Glu Gly Leu Val Leu
225                 230                 235                 240 agt gag aaa gtc ggg ctt gat cca agt gta tta gtg gag gtg atc tca    768
Ser Glu Lys Val Gly Leu Asp Pro Ser Val Leu Val Glu Val Ile Ser
                245                 250                 255 cag ggt gct att agt gct cca atg tat gcc gtt aaa ggt cct tca atg    816
Gln Gly Ala Ile Ser Ala Pro Met Tyr Ala Val Lys Gly Pro Ser Met
            260                 265                 270
```

```
gtt aaa tct tcg tat cca aca gcg ttt cct ctg aag cat cag caa aag    864
Val Lys Ser Ser Tyr Pro Thr Ala Phe Pro Leu Lys His Gln Gln Lys
        275                 280                 285 gac ctt cgt cta gct ctg ggt tta gcg gaa tct gtt tca caa cct att    912
Asp Leu Arg Leu Ala Leu Gly Leu Ala Glu Ser Val Ser Gln Pro Ile
    290                 295                 300 cca att gct gca gca act aat gaa ctc tac aag gtt gcg aaa tct cat    960
Pro Ile Ala Ala Ala Thr Asn Glu Leu Tyr Lys Val Ala Lys Ser His
305                 310                 315                 320 gga ctt agt gac cag gac ttc tct gca gta att gaa gca ttg aaa gtg   1008
Gly Leu Ser Asp Gln Asp Phe Ser Ala Val Ile Glu Ala Leu Lys Val
            325                 330                 335 aaa ttt gca aca gtt aaa cac aaa agc agt ctt tgc ctg gta agc ttg   1056
Lys Phe Ala Thr Val Lys His Lys Ser Ser Leu Cys Leu Val Ser Leu
                340                 345                 350 tgt gca tta tgc tat ata tcc acc gtg ata tgt taa                   1092
Cys Ala Leu Cys Tyr Ile Ser Thr Val Ile Cys
            355                 360
```

<210> SEQ ID NO 83
<211> LENGTH: 363
<212> TYPE: PRT
<213> ORGANISM: Solanum lycopersum

<400> SEQUENCE: 83

```
Met Ala Met Cys Ser Thr Phe Cys Pro Arg Leu Ser Phe His Leu Asn
1               5                   10                  15

Cys Lys Lys Ser Leu Ser Leu Phe Pro Val Lys His Arg Phe Phe Val
            20                  25                  30

Thr Ile Lys Ala Phe Ser Ser Gln Thr Ser Ala Pro Lys Ala Asp Asp
        35                  40                  45

Leu Pro Ala Ser Ile Gly Phe Leu Gly Leu Gly Ile Met Gly Asn Pro
    50                  55                  60

Met Ala Gln Asn Leu Ile Lys Ala Gly Cys Asp Val Thr Val Trp Asn
65                  70                  75                  80

Arg Thr Lys Ser Lys Cys Glu Pro Leu Ile Ser Leu Gly Ala Lys Tyr
                85                  90                  95

Lys Ser Ser Pro Glu Glu Val Ala Ala Ser Cys Asp Val Thr Phe Ala
            100                 105                 110

Met Leu Ala Asp Pro Glu Ser Ala Ala Asp Val Ala Cys Gly Lys Tyr
        115                 120                 125

Gly Ala Ala Lys Gly Met Gly Pro Gly Lys Gly Tyr Val Asp Ala Ser
    130                 135                 140

Thr Val Asp Gly Glu Thr Ser Lys Leu Ile Cys Glu His Ile Arg Ala
145                 150                 155                 160

Thr Gly Ala His Phe Leu Glu Ala Pro Val Ser Gly Ser Lys Lys Pro
                165                 170                 175

Ala Glu Asp Gly Gln Leu Ile Phe Leu Thr Ala Gly Asp Ser Val Leu
            180                 185                 190

Tyr Asp Lys Ala Ala Pro Leu Leu Asp Ile Met Gly Lys Ser Arg Phe
        195                 200                 205

Tyr Leu Gly Glu Val Gly Asn Gly Ala Ala Met Lys Leu Val Val Asn
    210                 215                 220

Met Val Met Gly Ser Met Met Ala Ser Phe Ala Glu Gly Leu Val Leu
225                 230                 235                 240

Ser Glu Lys Val Gly Leu Asp Pro Ser Val Leu Val Glu Val Ile Ser
```

```
                        245                 250                 255
Gln Gly Ala Ile Ser Ala Pro Met Tyr Ala Val Lys Gly Pro Ser Met
            260                 265                 270

Val Lys Ser Ser Tyr Pro Thr Ala Phe Pro Leu Lys His Gln Gln Lys
        275                 280                 285

Asp Leu Arg Leu Ala Leu Gly Leu Ala Glu Ser Val Ser Gln Pro Ile
    290                 295                 300

Pro Ile Ala Ala Ala Thr Asn Glu Leu Tyr Lys Val Ala Lys Ser His
305                 310                 315                 320

Gly Leu Ser Asp Gln Asp Phe Ser Ala Val Ile Glu Ala Leu Lys Val
                325                 330                 335

Lys Phe Ala Thr Val Lys His Lys Ser Ser Leu Cys Leu Val Ser Leu
            340                 345                 350

Cys Ala Leu Cys Tyr Ile Ser Thr Val Ile Cys
            355                 360

<210> SEQ ID NO 84
<211> LENGTH: 999
<212> TYPE: DNA
<213> ORGANISM: Brachypodium distachyon
<220> FEATURE:
<221> NAME/KEY: CDS
<222> LOCATION: (1)..(999)

<400> SEQUENCE: 84
```

| | | | | | | | | | | | | | | | | |
|---|---|---|---|---|---|---|---|---|---|---|---|---|---|---|---|---|
| atg | gcc | gct | gcc | ttc | cta | ctc | tgc | ccc | agg | gtg | gca | ctg | cct | ctg | cgc | 48 |
| Met | Ala | Ala | Ala | Phe | Leu | Leu | Cys | Pro | Arg | Val | Ala | Leu | Pro | Leu | Arg | |
| 1 | | | | 5 | | | | | 10 | | | | | 15 | | |
| agg | gga | tgc | cgc | ctc | gtc | gtg | tcc | tgc | tcc | gcc | tcc | tcg | tca | gat | gct | 96 |
| Arg | Gly | Cys | Arg | Leu | Val | Val | Ser | Cys | Ser | Ala | Ser | Ser | Ser | Asp | Ala | |
| | | | 20 | | | | | 25 | | | | | 30 | | | |
| cca | gga | ggg | gtg | gaa | ttc | cag | gga | agg | gtg | ggg | ttt | ttg | ggc | ctc | ggg | 144 |
| Pro | Gly | Gly | Val | Glu | Phe | Gln | Gly | Arg | Val | Gly | Phe | Leu | Gly | Leu | Gly | |
| | | | | 35 | | | | | 40 | | | | | 45 | | |
| atc | atg | ggc | gcc | ccc | atg | gca | tcc | aat | ctc | atc | aag | gcc | ggt | tgt | gat | 192 |
| Ile | Met | Gly | Ala | Pro | Met | Ala | Ser | Asn | Leu | Ile | Lys | Ala | Gly | Cys | Asp | |
| | | 50 | | | | | 55 | | | | | 60 | | | | |
| gtg | aca | gtg | tgg | aac | agg | acc | aag | agc | aag | tgc | gat | cct | ctc | ctc | agc | 240 |
| Val | Thr | Val | Trp | Asn | Arg | Thr | Lys | Ser | Lys | Cys | Asp | Pro | Leu | Leu | Ser | |
| 65 | | | | | 70 | | | | | 75 | | | | | 80 | |
| ctt | ggg | gcc | aaa | ttt | gag | gct | tca | ccg | gcc | aga | gtt | gca | tca | tct | tgc | 288 |
| Leu | Gly | Ala | Lys | Phe | Glu | Ala | Ser | Pro | Ala | Arg | Val | Ala | Ser | Ser | Cys | |
| | | | | 85 | | | | | 90 | | | | | 95 | | |
| gat | gtg | acc | ttt | gca | atg | ctt | gct | gat | cca | gaa | agc | gcg | gct | gag | gtt | 336 |
| Asp | Val | Thr | Phe | Ala | Met | Leu | Ala | Asp | Pro | Glu | Ser | Ala | Ala | Glu | Val | |
| | | | 100 | | | | | 105 | | | | | 110 | | | |
| gca | tgt | gga | aca | aat | gga | gct | gca | gaa | ggg | atg | gcc | cca | ggg | aaa | ggg | 384 |
| Ala | Cys | Gly | Thr | Asn | Gly | Ala | Ala | Glu | Gly | Met | Ala | Pro | Gly | Lys | Gly | |
| | | | 115 | | | | | 120 | | | | | 125 | | | |
| tat | gtt | gat | gtg | tcg | acg | gtc | gat | gat | gta | aca | tct | aag | ttg | atc | ggc | 432 |
| Tyr | Val | Asp | Val | Ser | Thr | Val | Asp | Asp | Val | Thr | Ser | Lys | Leu | Ile | Gly | |
| | | 130 | | | | | 135 | | | | | 140 | | | | |
| gaa | cgt | att | aca | agt | act | ggg | gca | tct | ttt | ctt | gag | gct | cca | gtt | tca | 480 |
| Glu | Arg | Ile | Thr | Ser | Thr | Gly | Ala | Ser | Phe | Leu | Glu | Ala | Pro | Val | Ser | |
| 145 | | | | | 150 | | | | | 155 | | | | | 160 | |
| ggc | tcg | aaa | aag | cca | gca | gaa | gat | gga | ctg | ctg | atc | ttt | ctt | act | gca | 528 |
| Gly | Ser | Lys | Lys | Pro | Ala | Glu | Asp | Gly | Leu | Leu | Ile | Phe | Leu | Thr | Ala | |
| | | | | 165 | | | | | 170 | | | | | 175 | | |
| ggc | gat | gaa | tcc | ctg | tac | aag | aga | gtg | aca | ccc | cta | ctt | gac | gtc | atg | 576 |

```
Gly Asp Glu Ser Leu Tyr Lys Arg Val Thr Pro Leu Leu Asp Val Met
            180                 185                 190 ggc aag tca aga ttt ttt ctc ggg gat gtt gga aat ggt gcg gcg atg     624
Gly Lys Ser Arg Phe Phe Leu Gly Asp Val Gly Asn Gly Ala Ala Met
        195                 200                 205 aag ctc gta gtt aat atg atc atg ggg agc atg atg gtc tcc ttt gca     672
Lys Leu Val Val Asn Met Ile Met Gly Ser Met Met Val Ser Phe Ala
    210                 215                 220 gaa ggg ttg ctc ctg agt gaa aaa gtc ggg tta gac cgg aat act gta     720
Glu Gly Leu Leu Leu Ser Glu Lys Val Gly Leu Asp Arg Asn Thr Val
225                 230                 235                 240 atc gag gct att tca caa ggt gca atc aat gct ccc atg ttc tcc ctc     768
Ile Glu Ala Ile Ser Gln Gly Ala Ile Asn Ala Pro Met Phe Ser Leu
                245                 250                 255 aaa ggc cct tcc atg gtt aaa gct tca tac cct acc gcc ttt ccc ctg     816
Lys Gly Pro Ser Met Val Lys Ala Ser Tyr Pro Thr Ala Phe Pro Leu
            260                 265                 270 aaa cat cag cag aag gat ctg agg ctg gct ttg gcc ctt gca gaa tca     864
Lys His Gln Gln Lys Asp Leu Arg Leu Ala Leu Ala Leu Ala Glu Ser
        275                 280                 285 gtg tcc cag ccc att cct act gcc gcg gct gct aat gag ctg tac aag     912
Val Ser Gln Pro Ile Pro Thr Ala Ala Ala Ala Asn Glu Leu Tyr Lys
    290                 295                 300 gct gcg aaa tcg ctc ggc ctc gcc aat cag gac ttc tcc gca gtc att     960
Ala Ala Lys Ser Leu Gly Leu Ala Asn Gln Asp Phe Ser Ala Val Ile
305                 310                 315                 320 gag gcg ctc aag gca aaa gtg cag agt tcg cag cag tag                 999
Glu Ala Leu Lys Ala Lys Val Gln Ser Ser Gln Gln
                325                 330

<210> SEQ ID NO 85
<211> LENGTH: 332
<212> TYPE: PRT
<213> ORGANISM: Brachypodium distachyon

<400> SEQUENCE: 85

Met Ala Ala Ala Phe Leu Leu Cys Pro Arg Val Ala Leu Pro Leu Arg
1               5                   10                  15

Arg Gly Cys Arg Leu Val Val Ser Cys Ser Ala Ser Ser Ser Asp Ala
            20                  25                  30

Pro Gly Gly Val Glu Phe Gln Gly Arg Val Gly Phe Leu Gly Leu Gly
        35                  40                  45

Ile Met Gly Ala Pro Met Ala Ser Asn Leu Ile Lys Ala Gly Cys Asp
    50                  55                  60

Val Thr Val Trp Asn Arg Thr Lys Ser Lys Cys Asp Pro Leu Leu Ser
65                  70                  75                  80

Leu Gly Ala Lys Phe Glu Ala Ser Pro Ala Arg Val Ala Ser Ser Cys
                85                  90                  95

Asp Val Thr Phe Ala Met Leu Ala Asp Pro Glu Ser Ala Ala Glu Val
            100                 105                 110

Ala Cys Gly Thr Asn Gly Ala Ala Glu Gly Met Ala Pro Gly Lys Gly
        115                 120                 125

Tyr Val Asp Val Ser Thr Val Asp Val Thr Ser Lys Leu Ile Gly
    130                 135                 140

Glu Arg Ile Thr Ser Thr Gly Ala Ser Phe Leu Glu Ala Pro Val Ser
145                 150                 155                 160

Gly Ser Lys Lys Pro Ala Glu Asp Gly Leu Leu Ile Phe Leu Thr Ala
                165                 170                 175
```

```
Gly Asp Glu Ser Leu Tyr Lys Arg Val Thr Pro Leu Leu Asp Val Met
            180                 185                 190

Gly Lys Ser Arg Phe Phe Leu Gly Asp Val Gly Asn Gly Ala Ala Met
        195                 200                 205

Lys Leu Val Val Asn Met Ile Met Gly Ser Met Met Val Ser Phe Ala
    210                 215                 220

Glu Gly Leu Leu Leu Ser Glu Lys Val Gly Leu Asp Arg Asn Thr Val
225                 230                 235                 240

Ile Glu Ala Ile Ser Gln Gly Ala Ile Asn Ala Pro Met Phe Ser Leu
                245                 250                 255

Lys Gly Pro Ser Met Val Lys Ala Ser Tyr Pro Thr Ala Phe Pro Leu
            260                 265                 270

Lys His Gln Gln Lys Asp Leu Arg Leu Ala Leu Ala Leu Ala Glu Ser
        275                 280                 285

Val Ser Gln Pro Ile Pro Thr Ala Ala Ala Asn Glu Leu Tyr Lys
    290                 295                 300

Ala Ala Lys Ser Leu Gly Leu Ala Asn Gln Asp Phe Ser Ala Val Ile
305                 310                 315                 320

Glu Ala Leu Lys Ala Lys Val Gln Ser Ser Gln Gln
                325                 330

<210> SEQ ID NO 86
<211> LENGTH: 813
<212> TYPE: DNA
<213> ORGANISM: Brassica napus
<220> FEATURE:
<221> NAME/KEY: CDS
<222> LOCATION: (1)..(813)

<400> SEQUENCE: 86 atg ata ccc agc tcg tat ata gac cat act aaa ggg aac aca agc tgg     48
Met Ile Pro Ser Ser Tyr Ile Asp His Thr Lys Gly Asn Thr Ser Trp
1               5                   10                  15 agc tcc acc gcg gtg gcg gcc gct cta gaa cta gtg gat ccc ccg ggc     96
Ser Ser Thr Ala Val Ala Ala Ala Leu Glu Leu Val Asp Pro Pro Gly
                20                  25                  30 tgc aag ctc tct tat agg gtt tac tct tcc ctg caa cct act ccc tct    144
Cys Lys Leu Ser Tyr Arg Val Tyr Ser Ser Leu Gln Pro Thr Pro Ser
            35                  40                  45 acc aaa gat gaa ctt gga agt gta agc att ggg ttt ctg ggt atg gga    192
Thr Lys Asp Glu Leu Gly Ser Val Ser Ile Gly Phe Leu Gly Met Gly
        50                  55                  60 atc atg ggt tct cct atg gca caa aac ctc ctc aaa gct ggg tgt gat    240
Ile Met Gly Ser Pro Met Ala Gln Asn Leu Leu Lys Ala Gly Cys Asp
65                  70                  75                  80 gtg act gtg tgg aac cga act aag agc aaa tgt gat cct ctc gtc gga    288
Val Thr Val Trp Asn Arg Thr Lys Ser Lys Cys Asp Pro Leu Val Gly
                85                  90                  95 tta gga gca aaa tac aag tct tct cct gaa gaa gtg act gca act tgt    336
Leu Gly Ala Lys Tyr Lys Ser Ser Pro Glu Glu Val Thr Ala Thr Cys
            100                 105                 110 gat ctc aca ttt gca atg cta gca gat cct gag agt gca atc gat gtt    384
Asp Leu Thr Phe Ala Met Leu Ala Asp Pro Glu Ser Ala Ile Asp Val
        115                 120                 125 gcc tgt gga aag aat gga gcc gta tct gga att agc tca gga aaa ggg    432
Ala Cys Gly Lys Asn Gly Ala Val Ser Gly Ile Ser Ser Gly Lys Gly
    130                 135                 140 tat gtt gat gtc tca acc gtt gat gct gcc tca tcc atc tta atc agc    480
```

```
Tyr Val Asp Val Ser Thr Val Asp Ala Ala Ser Ser Ile Leu Ile Ser
145                 150                 155                 160 aag caa ata aag gat act gga gca ttg ttt tta gag gca cca gtt tct       528
Lys Gln Ile Lys Asp Thr Gly Ala Leu Phe Leu Glu Ala Pro Val Ser
                165                 170                 175 ggt tcc aaa aag cct gca gaa gat ggt cag ctg ata ttc ctc act gca       576
Gly Ser Lys Lys Pro Ala Glu Asp Gly Gln Leu Ile Phe Leu Thr Ala
            180                 185                 190 ggt gac aag cta cta tac gaa aaa gct gct cct ttc tta gac atc atg       624
Gly Asp Lys Leu Leu Tyr Glu Lys Ala Ala Pro Phe Leu Asp Ile Met
        195                 200                 205 gga aag tca aga ttc tat ttg ggt gat gtt ggt aat gga gca gca atg       672
Gly Lys Ser Arg Phe Tyr Leu Gly Asp Val Gly Asn Gly Ala Ala Met
    210                 215                 220 aaa ctt gtc gtc aac atg atc atg gga agt atg atg gca tca ttc gcc       720
Lys Leu Val Val Asn Met Ile Met Gly Ser Met Met Ala Ser Phe Ala
225                 230                 235                 240 gag gga ata ctt ctc agc cag aag gta gga ctt gat cca gat gta cta       768
Glu Gly Ile Leu Leu Ser Gln Lys Val Gly Leu Asp Pro Asp Val Leu
                245                 250                 255 gtc gag gtt ggt tca caa gga gct aat aat ggg ccc atg tac taa           813
Val Glu Val Gly Ser Gln Gly Ala Asn Asn Gly Pro Met Tyr
            260                 265                 270
```

<210> SEQ ID NO 87
<211> LENGTH: 270
<212> TYPE: PRT
<213> ORGANISM: Brassica napus

<400> SEQUENCE: 87

```
Met Ile Pro Ser Ser Tyr Ile Asp His Thr Lys Gly Asn Thr Ser Trp
1               5                   10                  15

Ser Ser Thr Ala Val Ala Ala Leu Glu Leu Val Asp Pro Pro Gly
                20                  25                  30

Cys Lys Leu Ser Tyr Arg Val Tyr Ser Ser Leu Gln Pro Thr Pro Ser
                35                  40                  45

Thr Lys Asp Glu Leu Gly Ser Val Ser Ile Gly Phe Leu Gly Met Gly
50                  55                  60

Ile Met Gly Ser Pro Met Ala Gln Asn Leu Leu Lys Ala Gly Cys Asp
65                  70                  75                  80

Val Thr Val Trp Asn Arg Thr Lys Ser Lys Cys Asp Pro Leu Val Gly
                85                  90                  95

Leu Gly Ala Lys Tyr Lys Ser Ser Pro Glu Glu Val Thr Ala Thr Cys
                100                 105                 110

Asp Leu Thr Phe Ala Met Leu Ala Asp Pro Glu Ser Ala Ile Asp Val
            115                 120                 125

Ala Cys Gly Lys Asn Gly Ala Val Ser Gly Ile Ser Ser Gly Lys Gly
        130                 135                 140

Tyr Val Asp Val Ser Thr Val Asp Ala Ala Ser Ser Ile Leu Ile Ser
145                 150                 155                 160

Lys Gln Ile Lys Asp Thr Gly Ala Leu Phe Leu Glu Ala Pro Val Ser
                165                 170                 175

Gly Ser Lys Lys Pro Ala Glu Asp Gly Gln Leu Ile Phe Leu Thr Ala
            180                 185                 190

Gly Asp Lys Leu Leu Tyr Glu Lys Ala Ala Pro Phe Leu Asp Ile Met
        195                 200                 205

Gly Lys Ser Arg Phe Tyr Leu Gly Asp Val Gly Asn Gly Ala Ala Met
```

```
                     210                 215                 220
Lys Leu Val Val Asn Met Ile Met Gly Ser Met Met Ala Ser Phe Ala
225                 230                 235                 240

Glu Gly Ile Leu Leu Ser Gln Lys Val Gly Leu Asp Pro Asp Val Leu
                245                 250                 255

Val Glu Val Gly Ser Gln Gly Ala Asn Asn Gly Pro Met Tyr
            260                 265                 270

<210> SEQ ID NO 88
<211> LENGTH: 237
<212> TYPE: DNA
<213> ORGANISM: Brassica napus
<220> FEATURE:
<221> NAME/KEY: CDS
<222> LOCATION: (1)..(237)

<400> SEQUENCE: 88 atg gga atc atg ggt tct cct atg gca caa aac ctc ctc aaa gct ggg     48
Met Gly Ile Met Gly Ser Pro Met Ala Gln Asn Leu Leu Lys Ala Gly
1               5                   10                  15 tgt gat gtg act gtg tgg aat cga act aag agc aaa tgt gat cct ctc     96
Cys Asp Val Thr Val Trp Asn Arg Thr Lys Ser Lys Cys Asp Pro Leu
            20                  25                  30 gtc ggt tta gga gca aaa tac aag tct tct cct gaa gaa gtg act gca    144
Val Gly Leu Gly Ala Lys Tyr Lys Ser Ser Pro Glu Glu Val Thr Ala
        35                  40                  45 act tgc gat ctc aca ttt gca atg cta gca gat cct gaa agt gca gtg    192
Thr Cys Asp Leu Thr Phe Ala Met Leu Ala Asp Pro Glu Ser Ala Val
    50                  55                  60 cat cga tgt tgc ctg tgg aaa gaa tgg agc cgt atc tgg aat tag        237
His Arg Cys Cys Leu Trp Lys Glu Trp Ser Arg Ile Trp Asn
65                  70                  75

<210> SEQ ID NO 89
<211> LENGTH: 78
<212> TYPE: PRT
<213> ORGANISM: Brassica napus

<400> SEQUENCE: 89

Met Gly Ile Met Gly Ser Pro Met Ala Gln Asn Leu Leu Lys Ala Gly
1               5                   10                  15

Cys Asp Val Thr Val Trp Asn Arg Thr Lys Ser Lys Cys Asp Pro Leu
            20                  25                  30

Val Gly Leu Gly Ala Lys Tyr Lys Ser Ser Pro Glu Glu Val Thr Ala
        35                  40                  45

Thr Cys Asp Leu Thr Phe Ala Met Leu Ala Asp Pro Glu Ser Ala Val
    50                  55                  60

His Arg Cys Cys Leu Trp Lys Glu Trp Ser Arg Ile Trp Asn
65                  70                  75

<210> SEQ ID NO 90
<211> LENGTH: 891
<212> TYPE: DNA
<213> ORGANISM: Brassica rapa
<220> FEATURE:
<221> NAME/KEY: CDS
<222> LOCATION: (1)..(891)
<220> FEATURE:
<221> NAME/KEY: misc_feature
<222> LOCATION: (888)..(888)
<223> OTHER INFORMATION: n is a, c, g, or t

<400> SEQUENCE: 90
```

```
atg gct ttg tgc tcc atc ttc tgc cct cgc atc cct gtt cga ttc aga    48
Met Ala Leu Cys Ser Ile Phe Cys Pro Arg Ile Pro Val Arg Phe Arg
1               5                   10                  15 ccc aaa ccc att tct cct ttc ctc tca aaa cct ttg ttt ccc ctc tct    96
Pro Lys Pro Ile Ser Pro Phe Leu Ser Lys Pro Leu Phe Pro Leu Ser
            20                  25                  30 tat agg gtt tac tct tcc ctg caa cct act ccc tct acc aaa gat gaa   144
Tyr Arg Val Tyr Ser Ser Leu Gln Pro Thr Pro Ser Thr Lys Asp Glu
        35                  40                  45 ctt gga agt gta agc att ggg ttt ctg ggt atg gga atc atg ggt tct   192
Leu Gly Ser Val Ser Ile Gly Phe Leu Gly Met Gly Ile Met Gly Ser
    50                  55                  60 cct atg gca caa aac ctc ctc aaa gct ggg tgt gat gtg act gtg tgg   240
Pro Met Ala Gln Asn Leu Leu Lys Ala Gly Cys Asp Val Thr Val Trp
65                  70                  75                  80 aac cga act aag agc aaa tgt gat cct ctc gtc gga tta gga gca aaa   288
Asn Arg Thr Lys Ser Lys Cys Asp Pro Leu Val Gly Leu Gly Ala Lys
                85                  90                  95 tac aag tct tct cct gaa gaa gtg act gca act tgt gat ctc aca ttt   336
Tyr Lys Ser Ser Pro Glu Glu Val Thr Ala Thr Cys Asp Leu Thr Phe
            100                 105                 110 gca atg cta gca gat cct gag agt gca atc gat gtt gcc tgt gga aag   384
Ala Met Leu Ala Asp Pro Glu Ser Ala Ile Asp Val Ala Cys Gly Lys
        115                 120                 125 aat gga gcc gta tct gga att agc tca gga aaa ggg tat gtt gat gtc   432
Asn Gly Ala Val Ser Gly Ile Ser Ser Gly Lys Gly Tyr Val Asp Val
    130                 135                 140 tca acc gtt gat gct gcc tca tcc atc tta atc agc aag caa ata aag   480
Ser Thr Val Asp Ala Ala Ser Ser Ile Leu Ile Ser Lys Gln Ile Lys
145                 150                 155                 160 gat act gga gca ttg ttt tta gtg gca cca gtt tct ggt tcc aaa aag   528
Asp Thr Gly Ala Leu Phe Leu Val Ala Pro Val Ser Gly Ser Lys Lys
                165                 170                 175 cct gca gaa gat ggt cag ctg ata ttc ctc act gca ggt gac aag cta   576
Pro Ala Glu Asp Gly Gln Leu Ile Phe Leu Thr Ala Gly Asp Lys Leu
            180                 185                 190 cta tac gaa aaa gct gct cct ttc tta gac atc atg gga aag tca aga   624
Leu Tyr Glu Lys Ala Ala Pro Phe Leu Asp Ile Met Gly Lys Ser Arg
        195                 200                 205 ttc tat ttg ggt gat gtt ggt aat gga gca gca atg aaa ctt gtc gtc   672
Phe Tyr Leu Gly Asp Val Gly Asn Gly Ala Ala Met Lys Leu Val Val
    210                 215                 220 aac atg atc atg gga agt atg atg gca tca ttc gcc gag gga ata ctt   720
Asn Met Ile Met Gly Ser Met Met Ala Ser Phe Ala Glu Gly Ile Leu
225                 230                 235                 240 ctc agc cag aaa gta gga ctt gat cca tat gta cta gtc gag gtt gtt   768
Leu Ser Gln Lys Val Gly Leu Asp Pro Tyr Val Leu Val Glu Val Val
                245                 250                 255 tca caa gga gct atc aat gcg cca atg tac tca ctt aag ggt cct tcc   816
Ser Gln Gly Ala Ile Asn Ala Pro Met Tyr Ser Leu Lys Gly Pro Ser
            260                 265                 270 atg atc aag tca gtg tac cct aca gct ttc cca ttg aag cac cag cag   864
Met Ile Lys Ser Val Tyr Pro Thr Ala Phe Pro Leu Lys His Gln Gln
        275                 280                 285 aag gat atg aga ctg gca ctg gan tag                                891
Lys Asp Met Arg Leu Ala Leu Xaa
    290                 295
```

<210> SEQ ID NO 91

-continued

```
<211> LENGTH: 296
<212> TYPE: PRT
<213> ORGANISM: Brassica rapa
<220> FEATURE:
<221> NAME/KEY: misc_feature
<222> LOCATION: (296)..(296)
<223> OTHER INFORMATION: The 'Xaa' at location 296 stands for Glu, or
      Asp.

<400> SEQUENCE: 91
```

| Met<br>1 | Ala | Leu | Cys | Ser<br>5 | Ile | Phe | Cys | Pro | Arg<br>10 | Ile | Pro | Val | Arg | Phe<br>15 | Arg |
|---|---|---|---|---|---|---|---|---|---|---|---|---|---|---|---|
| Pro | Lys | Pro | Ile<br>20 | Ser | Pro | Phe | Leu | Ser<br>25 | Lys | Pro | Leu | Phe | Pro<br>30 | Leu | Ser |
| Tyr | Arg | Val<br>35 | Tyr | Ser | Ser | Leu | Gln<br>40 | Pro | Thr | Pro | Ser | Thr<br>45 | Lys | Asp | Glu |
| Leu | Gly<br>50 | Ser | Val | Ser | Ile<br>55 | Gly | Phe | Leu | Gly | Met<br>60 | Gly | Ile | Met | Gly | Ser |
| Pro<br>65 | Met | Ala | Gln | Asn | Leu<br>70 | Leu | Lys | Ala | Gly | Cys<br>75 | Asp | Val | Thr | Val | Trp<br>80 |
| Asn | Arg | Thr | Lys | Ser<br>85 | Lys | Cys | Asp | Pro | Leu<br>90 | Val | Gly | Leu | Gly | Ala<br>95 | Lys |
| Tyr | Lys | Ser | Ser<br>100 | Pro | Glu | Glu | Val | Thr<br>105 | Ala | Thr | Cys | Asp | Leu<br>110 | Thr | Phe |
| Ala | Met | Leu<br>115 | Ala | Asp | Pro | Glu | Ser<br>120 | Ala | Ile | Asp | Val | Ala<br>125 | Cys | Gly | Lys |
| Asn | Gly<br>130 | Ala | Val | Ser | Gly<br>135 | Ile | Ser | Ser | Gly | Lys<br>140 | Gly | Tyr | Val | Asp | Val |
| Ser<br>145 | Thr | Val | Asp | Ala | Ala<br>150 | Ser | Ser | Ile | Leu | Ile<br>155 | Ser | Lys | Gln | Ile | Lys<br>160 |
| Asp | Thr | Gly | Ala | Leu<br>165 | Phe | Leu | Val | Ala | Pro<br>170 | Val | Ser | Gly | Ser | Lys<br>175 | Lys |
| Pro | Ala | Glu | Asp<br>180 | Gly | Gln | Leu | Ile | Phe<br>185 | Leu | Thr | Ala | Gly | Asp<br>190 | Lys | Leu |
| Leu | Tyr | Glu<br>195 | Lys | Ala | Ala | Pro | Phe<br>200 | Leu | Asp | Ile | Met | Gly<br>205 | Lys | Ser | Arg |
| Phe | Tyr<br>210 | Leu | Gly | Asp | Val | Gly<br>215 | Asn | Gly | Ala | Ala | Met<br>220 | Lys | Leu | Val | Val |
| Asn<br>225 | Met | Ile | Met | Gly | Ser<br>230 | Met | Met | Ala | Ser | Phe<br>235 | Ala | Glu | Gly | Ile | Leu<br>240 |
| Leu | Ser | Gln | Lys | Val<br>245 | Gly | Leu | Asp | Pro | Tyr<br>250 | Val | Leu | Val | Glu | Val<br>255 | Val |
| Ser | Gln | Gly | Ala<br>260 | Ile | Asn | Ala | Pro | Met<br>265 | Tyr | Ser | Leu | Lys | Gly<br>270 | Pro | Ser |
| Met | Ile | Lys<br>275 | Ser | Val | Tyr | Pro | Thr<br>280 | Ala | Phe | Pro | Leu | Lys<br>285 | His | Gln | Gln |
| Lys | Asp<br>290 | Met | Arg | Leu | Ala | Leu<br>295 | Xaa | | | | | | | | |

```
<210> SEQ ID NO 92
<211> LENGTH: 633
<212> TYPE: DNA
<213> ORGANISM: Brassica rapa
<220> FEATURE:
<221> NAME/KEY: CDS
<222> LOCATION: (1)..(633)

<400> SEQUENCE: 92
```

```
atg gga atc atg ggt tct cct atg gca caa aac ctc ctc aaa gct ggg    48
Met Gly Ile Met Gly Ser Pro Met Ala Gln Asn Leu Leu Lys Ala Gly
1               5                   10                  15 tgt gat gtg act gtg tgg aac cga act aag agc aaa tgt gat cct ctc    96
Cys Asp Val Thr Val Trp Asn Arg Thr Lys Ser Lys Cys Asp Pro Leu
                20                  25                  30 gtc gga tta gga gca aaa tac aag tct tct cct gaa gaa gtg act gca   144
Val Gly Leu Gly Ala Lys Tyr Lys Ser Ser Pro Glu Glu Val Thr Ala
            35                  40                  45 act tgt gat ctc aca ttt gca atg cta gca gat cct gag agt gca atc   192
Thr Cys Asp Leu Thr Phe Ala Met Leu Ala Asp Pro Glu Ser Ala Ile
50                  55                  60 gat gtt gcc tgt gga aag aat gga gcc gta tct gga att agc tca gga   240
Asp Val Ala Cys Gly Lys Asn Gly Ala Val Ser Gly Ile Ser Ser Gly
65                  70                  75                  80 aaa ggg tat gtt gat gtc tca acc gtt gat gct gcc tca tcc atc tta   288
Lys Gly Tyr Val Asp Val Ser Thr Val Asp Ala Ala Ser Ser Ile Leu
                85                  90                  95 atc agc aag caa ata aag gat act gga gca ttg ttt tta gag gca cca   336
Ile Ser Lys Gln Ile Lys Asp Thr Gly Ala Leu Phe Leu Glu Ala Pro
            100                 105                 110 gtt tct ggt tcc aaa aag cct gca gaa gat ggt cag ctg ata ttc ctc   384
Val Ser Gly Ser Lys Lys Pro Ala Glu Asp Gly Gln Leu Ile Phe Leu
        115                 120                 125 act gca ggt gac aag cta cta tac gaa aaa gct gct cct ttc tta gac   432
Thr Ala Gly Asp Lys Leu Leu Tyr Glu Lys Ala Ala Pro Phe Leu Asp
130                 135                 140 atc atg gga aag tca aga ttc tat ttg ggt gat gtt ggt aat gga gca   480
Ile Met Gly Lys Ser Arg Phe Tyr Leu Gly Asp Val Gly Asn Gly Ala
145                 150                 155                 160 gca atg aaa ctt gtc gtc aac atg atc atg gga agt atg atg gca tca   528
Ala Met Lys Leu Val Val Asn Met Ile Met Gly Ser Met Met Ala Ser
                165                 170                 175 ttc gcc gag gga ata ctt ctc agc cag aaa gta gga ctt gat cca tat   576
Phe Ala Glu Gly Ile Leu Leu Ser Gln Lys Val Gly Leu Asp Pro Tyr
            180                 185                 190 gta cta agt cga ggt tgt ttc aca agg agc tat caa tgc gcc aat gta   624
Val Leu Ser Arg Gly Cys Phe Thr Arg Ser Tyr Gln Cys Ala Asn Val
        195                 200                 205 ctc act taa                                                       633
Leu Thr
    210
```

<210> SEQ ID NO 93
<211> LENGTH: 210
<212> TYPE: PRT
<213> ORGANISM: Brassica rapa

<400> SEQUENCE: 93

```
Met Gly Ile Met Gly Ser Pro Met Ala Gln Asn Leu Leu Lys Ala Gly
1               5                   10                  15

Cys Asp Val Thr Val Trp Asn Arg Thr Lys Ser Lys Cys Asp Pro Leu
                20                  25                  30

Val Gly Leu Gly Ala Lys Tyr Lys Ser Ser Pro Glu Glu Val Thr Ala
            35                  40                  45

Thr Cys Asp Leu Thr Phe Ala Met Leu Ala Asp Pro Glu Ser Ala Ile
        50                  55                  60

Asp Val Ala Cys Gly Lys Asn Gly Ala Val Ser Gly Ile Ser Ser Gly
65                  70                  75                  80
```

```
        Lys Gly Tyr Val Asp Val Ser Thr Val Asp Ala Ala Ser Ser Ile Leu
                    85                  90                  95

Ile Ser Lys Gln Ile Lys Asp Thr Gly Ala Leu Phe Leu Glu Ala Pro
                100                 105                 110

Val Ser Gly Ser Lys Lys Pro Ala Glu Asp Gly Gln Leu Ile Phe Leu
                    115                 120                 125

Thr Ala Gly Asp Lys Leu Leu Tyr Glu Lys Ala Ala Pro Phe Leu Asp
                130                 135                 140

Ile Met Gly Lys Ser Arg Phe Tyr Leu Gly Asp Val Gly Asn Gly Ala
        145                 150                 155                 160

Ala Met Lys Leu Val Val Asn Met Ile Met Gly Ser Met Met Ala Ser
                        165                 170                 175

Phe Ala Glu Gly Ile Leu Leu Ser Gln Lys Val Gly Leu Asp Pro Tyr
                    180                 185                 190

Val Leu Ser Arg Gly Cys Phe Thr Arg Ser Tyr Gln Cys Ala Asn Val
                    195                 200                 205

Leu Thr
            210

<210> SEQ ID NO 94
<211> LENGTH: 693
<212> TYPE: DNA
<213> ORGANISM: Brassica oleracea
<220> FEATURE:
<221> NAME/KEY: CDS
<222> LOCATION: (1)..(693)

<400> SEQUENCE: 94 atg gct ttt ttc tcg atc ttc tgc cct cgt atc cct gtt cga ttc aga        48
Met Ala Phe Phe Ser Ile Phe Cys Pro Arg Ile Pro Val Arg Phe Arg
1               5                   10                  15 ccc aaa ccc att tct cct ttc ctc tca aag cct ttg ttt ccc ctc tct        96
Pro Lys Pro Ile Ser Pro Phe Leu Ser Lys Pro Leu Phe Pro Leu Ser
            20                  25                  30 tat aga gtt tac tct tcc ctg caa cct act ccc tct acc aaa gat gaa       144
Tyr Arg Val Tyr Ser Ser Leu Gln Pro Thr Pro Ser Thr Lys Asp Glu
        35                  40                  45 ctt gga agt gta agc att ggg ttt ctg ggt atg gga atc atg ggt tct       192
Leu Gly Ser Val Ser Ile Gly Phe Leu Gly Met Gly Ile Met Gly Ser
    50                  55                  60 cct atg gca caa aac ctc ctc aaa gct ggg tgt gat gtg act gtg tgg       240
Pro Met Ala Gln Asn Leu Leu Lys Ala Gly Cys Asp Val Thr Val Trp
65                  70                  75                  80 aat cga act aag agc aaa tgt gat cct ctc gtc ggt tta gga gca aaa       288
Asn Arg Thr Lys Ser Lys Cys Asp Pro Leu Val Gly Leu Gly Ala Lys
                85                  90                  95 tac aag tct tct cct gaa gaa gtg act gca act tgc gat ctc aca ttt       336
Tyr Lys Ser Ser Pro Glu Glu Val Thr Ala Thr Cys Asp Leu Thr Phe
            100                 105                 110 gca atg cta gca gat cct gaa agt gca atc gat gtt gcc tgt gga aag       384
Ala Met Leu Ala Asp Pro Glu Ser Ala Ile Asp Val Ala Cys Gly Lys
        115                 120                 125 aat gga gcc gta tct gga att agc tca gga aaa ggg tat gtt gat gtc       432
Asn Gly Ala Val Ser Gly Ile Ser Ser Gly Lys Gly Tyr Val Asp Val
    130                 135                 140 tca acc gtt gat gct gcc tca tcc atc tta atc agc aag caa ata aag       480
Ser Thr Val Asp Ala Ala Ser Ser Ile Leu Ile Ser Lys Gln Ile Lys
145                 150                 155                 160 gac acc gga gca ttg ttt ttg gag gca cca gct tct ggt tcc aaa aag       528
```

```
                Asp Thr Gly Ala Leu Phe Leu Glu Ala Pro Ala Ser Gly Ser Lys Lys
                                165                 170                 175 cct gca gaa gat ggt cag ctg ata ttc ctc act gca ggt gac aaa cta        576
Pro Ala Glu Asp Gly Gln Leu Ile Phe Leu Thr Ala Gly Asp Lys Leu
            180                 185                 190 ctc tac gaa aaa gct gca cct ttc tta gac atc atg gga aag tca aga        624
Leu Tyr Glu Lys Ala Ala Pro Phe Leu Asp Ile Met Gly Lys Ser Arg
        195                 200                 205 ttc tat ttg gga gat gtt ggt aat gga gca gca atg aaa ctt gtc gtc        672
Phe Tyr Leu Gly Asp Val Gly Asn Gly Ala Ala Met Lys Leu Val Val
    210                 215                 220 aac atg atc atg gaa gta tga                                             693
Asn Met Ile Met Glu Val
225                 230

<210> SEQ ID NO 95
<211> LENGTH: 230
<212> TYPE: PRT
<213> ORGANISM: Brassica oleracea

<400> SEQUENCE: 95

Met Ala Phe Phe Ser Ile Phe Cys Pro Arg Ile Pro Val Arg Phe Arg
1               5                   10                  15

Pro Lys Pro Ile Ser Pro Phe Leu Ser Lys Pro Leu Phe Pro Leu Ser
            20                  25                  30

Tyr Arg Val Tyr Ser Ser Leu Gln Pro Thr Pro Ser Thr Lys Asp Glu
        35                  40                  45

Leu Gly Ser Val Ser Ile Gly Phe Leu Gly Met Gly Ile Met Gly Ser
    50                  55                  60

Pro Met Ala Gln Asn Leu Leu Lys Ala Gly Cys Asp Val Thr Val Trp
65                  70                  75                  80

Asn Arg Thr Lys Ser Lys Cys Asp Pro Leu Val Gly Leu Gly Ala Lys
                85                  90                  95

Tyr Lys Ser Ser Pro Glu Glu Val Thr Ala Thr Cys Asp Leu Thr Phe
            100                 105                 110

Ala Met Leu Ala Asp Pro Glu Ser Ala Ile Asp Val Ala Cys Gly Lys
        115                 120                 125

Asn Gly Ala Val Ser Gly Ile Ser Ser Gly Lys Gly Tyr Val Asp Val
    130                 135                 140

Ser Thr Val Asp Ala Ala Ser Ser Ile Leu Ile Ser Lys Gln Ile Lys
145                 150                 155                 160

Asp Thr Gly Ala Leu Phe Leu Glu Ala Pro Ala Ser Gly Ser Lys Lys
                165                 170                 175

Pro Ala Glu Asp Gly Gln Leu Ile Phe Leu Thr Ala Gly Asp Lys Leu
            180                 185                 190

Leu Tyr Glu Lys Ala Ala Pro Phe Leu Asp Ile Met Gly Lys Ser Arg
        195                 200                 205

Phe Tyr Leu Gly Asp Val Gly Asn Gly Ala Ala Met Lys Leu Val Val
    210                 215                 220

Asn Met Ile Met Glu Val
225                 230

<210> SEQ ID NO 96
<211> LENGTH: 423
<212> TYPE: DNA
<213> ORGANISM: Brassica oleracea
<220> FEATURE:
<221> NAME/KEY: CDS
```

<222> LOCATION: (1)..(423)

<400> SEQUENCE: 96

```
atg gga aag tca aga ttc tat ttg gga gat gtt ggt aat gga gca gca      48
Met Gly Lys Ser Arg Phe Tyr Leu Gly Asp Val Gly Asn Gly Ala Ala
1               5                   10                  15 atg aaa ctt gtc gtc aac atg atc atg gga agt atg atg gca tca ttt      96
Met Lys Leu Val Val Asn Met Ile Met Gly Ser Met Met Ala Ser Phe
                20                  25                  30 gcc gag gga ata ctt cta agc cag aaa gta gga ctt gat cca aat gta     144
Ala Glu Gly Ile Leu Leu Ser Gln Lys Val Gly Leu Asp Pro Asn Val
            35                  40                  45 cta gtc gag gtt gtt tca cag gga gct atc aat gcg cca atg tac tcg     192
Leu Val Glu Val Val Ser Gln Gly Ala Ile Asn Ala Pro Met Tyr Ser
        50                  55                  60 ctt aaa ggt cct tca atg atc aag tca gtg tac cct acg gct ttt cca     240
Leu Lys Gly Pro Ser Met Ile Lys Ser Val Tyr Pro Thr Ala Phe Pro
65                  70                  75                  80 ttg aag cac cag cag aag gat atg aga ctc gca ctg gga cta gct gag     288
Leu Lys His Gln Gln Lys Asp Met Arg Leu Ala Leu Gly Leu Ala Glu
                85                  90                  95 tcc gtg tct cag tct act cca att gca gca gca aac gag ctt tac         336
Ser Val Ser Gln Ser Thr Pro Ile Ala Ala Ala Ala Asn Glu Leu Tyr
            100                 105                 110 aaa gtt gcc aag tct tac ggt ttg agc gat gaa gac ttc tct gcg gtt     384
Lys Val Ala Lys Ser Tyr Gly Leu Ser Asp Glu Asp Phe Ser Ala Val
        115                 120                 125 att gaa gca ctg aaa gct gca aga tct caa caa agc taa                 423
Ile Glu Ala Leu Lys Ala Ala Arg Ser Gln Gln Ser
130                 135                 140
```

<210> SEQ ID NO 97
<211> LENGTH: 140
<212> TYPE: PRT
<213> ORGANISM: Brassica oleracea

<400> SEQUENCE: 97

```
Met Gly Lys Ser Arg Phe Tyr Leu Gly Asp Val Gly Asn Gly Ala Ala
1               5                   10                  15

Met Lys Leu Val Val Asn Met Ile Met Gly Ser Met Met Ala Ser Phe
                20                  25                  30

Ala Glu Gly Ile Leu Leu Ser Gln Lys Val Gly Leu Asp Pro Asn Val
            35                  40                  45

Leu Val Glu Val Val Ser Gln Gly Ala Ile Asn Ala Pro Met Tyr Ser
        50                  55                  60

Leu Lys Gly Pro Ser Met Ile Lys Ser Val Tyr Pro Thr Ala Phe Pro
65                  70                  75                  80

Leu Lys His Gln Gln Lys Asp Met Arg Leu Ala Leu Gly Leu Ala Glu
                85                  90                  95

Ser Val Ser Gln Ser Thr Pro Ile Ala Ala Ala Ala Asn Glu Leu Tyr
            100                 105                 110

Lys Val Ala Lys Ser Tyr Gly Leu Ser Asp Glu Asp Phe Ser Ala Val
        115                 120                 125

Ile Glu Ala Leu Lys Ala Ala Arg Ser Gln Gln Ser
130                 135                 140
```

<210> SEQ ID NO 98
<211> LENGTH: 756
<212> TYPE: DNA

<213> ORGANISM: Gossypium hirsutum
<220> FEATURE:
<221> NAME/KEY: CDS
<222> LOCATION: (1)..(756)

<400> SEQUENCE: 98

```
atg gga tcg cca atg gca ctg aat ctc ata aaa gct gga tgt gat gtg      48
Met Gly Ser Pro Met Ala Leu Asn Leu Ile Lys Ala Gly Cys Asp Val
1               5                   10                  15 ata gta tgg aat aga acg aaa agc aaa tgt gat cct ctc atc agc ctt      96
Ile Val Trp Asn Arg Thr Lys Ser Lys Cys Asp Pro Leu Ile Ser Leu
            20                  25                  30 ggt gca aag tat agt tcc tct cct gag gaa gta gct gca aac tgt gat     144
Gly Ala Lys Tyr Ser Ser Ser Pro Glu Glu Val Ala Ala Asn Cys Asp
        35                  40                  45 gtc act ttt gcc atg ctt gcc gat cct gaa agt gca att gat gtc gcc     192
Val Thr Phe Ala Met Leu Ala Asp Pro Glu Ser Ala Ile Asp Val Ala
    50                  55                  60 tgt gga aag aat gga gct gtg agc gga atg ggt cca gga aaa ggc tat     240
Cys Gly Lys Asn Gly Ala Val Ser Gly Met Gly Pro Gly Lys Gly Tyr
65                  70                  75                  80 gta gac gtt tca acg gtt gat gtt gcc act tct aaa tta atc aat gaa     288
Val Asp Val Ser Thr Val Asp Val Ala Thr Ser Lys Leu Ile Asn Glu
                85                  90                  95 cat atc aaa gca agg ggg gca tta ttt ctg gag gct cca gtt tca ggt     336
His Ile Lys Ala Arg Gly Ala Leu Phe Leu Glu Ala Pro Val Ser Gly
            100                 105                 110 tca aaa aag cca gcg gaa gat gga caa ctg ata ttc ctt act gca ggt     384
Ser Lys Lys Pro Ala Glu Asp Gly Gln Leu Ile Phe Leu Thr Ala Gly
        115                 120                 125 gac aga tca tta tat gag tta gtt tct cca ctg ttg gat ata ttg ggc     432
Asp Arg Ser Leu Tyr Glu Leu Val Ser Pro Leu Leu Asp Ile Leu Gly
    130                 135                 140 aag tca aga ttt tac ctt ggg aag gtc gga aat gga gct gct atg aaa     480
Lys Ser Arg Phe Tyr Leu Gly Lys Val Gly Asn Gly Ala Ala Met Lys
145                 150                 155                 160 ctt gtt gtt aac atg atc atg gga agt atg atg gca tcg ttt tct gaa     528
Leu Val Val Asn Met Ile Met Gly Ser Met Met Ala Ser Phe Ser Glu
                165                 170                 175 gga ata ctt ctt agc aag aaa gta gga ctc gac cca agt gtt cta gtt     576
Gly Ile Leu Leu Ser Lys Lys Val Gly Leu Asp Pro Ser Val Leu Val
            180                 185                 190 gag gtg gtt tcg cag ggt gca att agt gca cca atg tac ttg ctt aaa     624
Glu Val Val Ser Gln Gly Ala Ile Ser Ala Pro Met Tyr Leu Leu Lys
        195                 200                 205 ggt cca tca atg gtt aaa tcc caa tat ccc aca gcc ttt ccc tta aag     672
Gly Pro Ser Met Val Lys Ser Gln Tyr Pro Thr Ala Phe Pro Leu Lys
    210                 215                 220 cat caa cag aag gac ctt aga ctt gca ttg ggg att ggc aga atc tgt     720
His Gln Gln Lys Asp Leu Arg Leu Ala Leu Gly Ile Gly Arg Ile Cys
225                 230                 235                 240 ttc tca gtc cac ttc aat tgc agc tgc tgc caa tga                     756
Phe Ser Val His Phe Asn Cys Ser Cys Cys Gln
                245                 250
```

<210> SEQ ID NO 99
<211> LENGTH: 251
<212> TYPE: PRT
<213> ORGANISM: Gossypium hirsutum

<400> SEQUENCE: 99

```
Met Gly Ser Pro Met Ala Leu Asn Leu Ile Lys Ala Gly Cys Asp Val
1               5                   10                  15

Ile Val Trp Asn Arg Thr Lys Ser Lys Cys Asp Pro Leu Ile Ser Leu
            20                  25                  30

Gly Ala Lys Tyr Ser Ser Pro Glu Glu Val Ala Ala Asn Cys Asp
                35                  40                  45

Val Thr Phe Ala Met Leu Ala Asp Pro Glu Ser Ala Ile Asp Val Ala
50                  55                  60

Cys Gly Lys Asn Gly Ala Val Ser Gly Met Gly Pro Lys Gly Tyr
65                  70                  75                  80

Val Asp Val Ser Thr Val Asp Val Ala Thr Ser Lys Leu Ile Asn Glu
                85                  90                  95

His Ile Lys Ala Arg Gly Ala Leu Phe Leu Glu Ala Pro Val Ser Gly
                100                 105                 110

Ser Lys Lys Pro Ala Glu Asp Gly Gln Leu Ile Phe Leu Thr Ala Gly
            115                 120                 125

Asp Arg Ser Leu Tyr Glu Leu Val Ser Pro Leu Leu Asp Ile Leu Gly
            130                 135                 140

Lys Ser Arg Phe Tyr Leu Gly Lys Val Gly Asn Gly Ala Ala Met Lys
145                 150                 155                 160

Leu Val Val Asn Met Ile Met Gly Ser Met Met Ala Ser Phe Ser Glu
                165                 170                 175

Gly Ile Leu Leu Ser Lys Lys Val Gly Leu Asp Pro Ser Val Leu Val
                180                 185                 190

Glu Val Val Ser Gln Gly Ala Ile Ser Ala Pro Met Tyr Leu Leu Lys
            195                 200                 205

Gly Pro Ser Met Val Lys Ser Gln Tyr Pro Thr Ala Phe Pro Leu Lys
            210                 215                 220

His Gln Gln Lys Asp Leu Arg Leu Ala Leu Gly Ile Gly Arg Ile Cys
225                 230                 235                 240

Phe Ser Val His Phe Asn Cys Ser Cys Cys Gln
                245                 250

<210> SEQ ID NO 100
<211> LENGTH: 1014
<212> TYPE: DNA
<213> ORGANISM: Triticum aestivum
<220> FEATURE:
<221> NAME/KEY: CDS
<222> LOCATION: (1)..(1014)

<400> SEQUENCE: 100 atg gct gcg gcc agc ttc ctc cta agc ccc agg gtg acg ctg ccc ctg    48
Met Ala Ala Ala Ser Phe Leu Leu Ser Pro Arg Val Thr Leu Pro Leu
1               5                   10                  15 cgc cga gga tcc cgc ctc ctc gtg tcc tgc tcc gcc act tcg tca tcc    96
Arg Arg Gly Ser Arg Leu Leu Val Ser Cys Ser Ala Thr Ser Ser Ser
            20                  25                  30 tcc tcg tca gat gct gct gga ggg gtg gga ttc cag gga agg gtg ggg   144
Ser Ser Ser Asp Ala Ala Gly Gly Val Gly Phe Gln Gly Arg Val Gly
        35                  40                  45 ttc ttg ggc ctc ggg atc atg ggc gcc ccc atg gca tca aac ctc ata   192
Phe Leu Gly Leu Gly Ile Met Gly Ala Pro Met Ala Ser Asn Leu Ile
50                  55                  60 aag gct ggt tgt gat att aca gtt tgg aac aga acc aag agc aag tgt   240
Lys Ala Gly Cys Asp Ile Thr Val Trp Asn Arg Thr Lys Ser Lys Cys
65                  70                  75                  80
```

```
gat cct ctt ctc agc ctc ggt gcc aag ttc gaa tct tca ccc gcc aga    288
Asp Pro Leu Leu Ser Leu Gly Ala Lys Phe Glu Ser Ser Pro Ala Arg
            85                  90                  95 gtt gca tca tct tgt gat gtc acc ttt gca atg ctt gct gac cca gaa    336
Val Ala Ser Ser Cys Asp Val Thr Phe Ala Met Leu Ala Asp Pro Glu
        100                 105                 110 agc gcg ttt gag gtt gca tgc ggc gct aat gga gcc gca gaa ggg atg    384
Ser Ala Phe Glu Val Ala Cys Gly Ala Asn Gly Ala Ala Glu Gly Met
    115                 120                 125 gcc gca ggg aaa ggg tat gtc gat gtg tcg aca gtc gat gat gca aca    432
Ala Ala Gly Lys Gly Tyr Val Asp Val Ser Thr Val Asp Asp Ala Thr
130                 135                 140 tct aag cta atc ggc aaa cgt att aca agt act ggg gca tct ttt ctc    480
Ser Lys Leu Ile Gly Lys Arg Ile Thr Ser Thr Gly Ala Ser Phe Leu
145                 150                 155                 160 gag gct cca gtt tca ggc tca aaa aag cca gca gaa gat gga ctg ctg    528
Glu Ala Pro Val Ser Gly Ser Lys Lys Pro Ala Glu Asp Gly Leu Leu
            165                 170                 175 atc ttt ctt act gca ggt gat gaa tcc ttg tac aag aga gtg gcg ccc    576
Ile Phe Leu Thr Ala Gly Asp Glu Ser Leu Tyr Lys Arg Val Ala Pro
        180                 185                 190 cta ctt gat gtc atg ggc aag tca aga ttt tat ctt ggg gat gtc ggg    624
Leu Leu Asp Val Met Gly Lys Ser Arg Phe Tyr Leu Gly Asp Val Gly
    195                 200                 205 aat ggc gca gca atg aag ctc gtg gtt aat atg gtg atg ggg agc atg    672
Asn Gly Ala Ala Met Lys Leu Val Val Asn Met Val Met Gly Ser Met
210                 215                 220 atg gtc tcc ttt gca gaa ggg cta ctc ctg agt gaa aaa gtg ggg tta    720
Met Val Ser Phe Ala Glu Gly Leu Leu Leu Ser Glu Lys Val Gly Leu
225                 230                 235                 240 gac ccg aat act gtc gtc gag gtt att tca caa ggt gct atc aat gct    768
Asp Pro Asn Thr Val Val Glu Val Ile Ser Gln Gly Ala Ile Asn Ala
            245                 250                 255 ccc atg ttc tcc ctc aag ggc cct tcc atg gtt aaa gct gca tac cct    816
Pro Met Phe Ser Leu Lys Gly Pro Ser Met Val Lys Ala Ala Tyr Pro
        260                 265                 270 act gcc ttt ccc ctg aaa cat cag cag aag gat cta agg ctg gcg ctg    864
Thr Ala Phe Pro Leu Lys His Gln Gln Lys Asp Leu Arg Leu Ala Leu
    275                 280                 285 gcc ctg gca gaa tcg gtg tcc cag ccc att cct aca gct gca gct gca    912
Ala Leu Ala Glu Ser Val Ser Gln Pro Ile Pro Thr Ala Ala Ala Ala
290                 295                 300 aac gag ctg tac aag gta gcc aaa tcg ctg ggc ctc gcc gac cac gac    960
Asn Glu Leu Tyr Lys Val Ala Lys Ser Leu Gly Leu Ala Asp His Asp
305                 310                 315                 320 ttc tcc gca gtc atc gag gcg ctc aag gcc aaa gtg cag agc tcg cag   1008
Phe Ser Ala Val Ile Glu Ala Leu Lys Ala Lys Val Gln Ser Ser Gln
            325                 330                 335 cac tag                                                           1014
His
```

<210> SEQ ID NO 101
<211> LENGTH: 337
<212> TYPE: PRT
<213> ORGANISM: Triticum aestivum

<400> SEQUENCE: 101

Met Ala Ala Ala Ser Phe Leu Leu Ser Pro Arg Val Thr Leu Pro Leu
1               5                   10                  15

Arg Arg Gly Ser Arg Leu Leu Val Ser Cys Ser Ala Thr Ser Ser Ser

```
                20                  25                  30
    Ser Ser Ser Asp Ala Gly Gly Val Gly Phe Gln Gly Arg Val Gly
                35                  40                  45
    Phe Leu Gly Leu Gly Ile Met Gly Ala Pro Met Ala Ser Asn Leu Ile
    50                  55                  60
    Lys Ala Gly Cys Asp Ile Thr Val Trp Asn Arg Thr Lys Ser Lys Cys
    65                  70                  75                  80
    Asp Pro Leu Leu Ser Leu Gly Ala Lys Phe Glu Ser Pro Ala Arg
                85                  90                  95
    Val Ala Ser Ser Cys Asp Val Thr Phe Ala Met Leu Ala Asp Pro Glu
                100                 105                 110
    Ser Ala Phe Glu Val Ala Cys Gly Ala Asn Gly Ala Ala Glu Gly Met
                115                 120                 125
    Ala Ala Gly Lys Gly Tyr Val Asp Val Ser Thr Val Asp Asp Ala Thr
                130                 135                 140
    Ser Lys Leu Ile Gly Lys Arg Ile Thr Ser Thr Gly Ala Ser Phe Leu
    145                 150                 155                 160
    Glu Ala Pro Val Ser Gly Ser Lys Lys Pro Ala Glu Asp Gly Leu Leu
                165                 170                 175
    Ile Phe Leu Thr Ala Gly Asp Glu Ser Leu Tyr Lys Arg Val Ala Pro
                180                 185                 190
    Leu Leu Asp Val Met Gly Lys Ser Arg Phe Tyr Leu Gly Asp Val Gly
                195                 200                 205
    Asn Gly Ala Ala Met Lys Leu Val Val Asn Met Val Met Gly Ser Met
                210                 215                 220
    Met Val Ser Phe Ala Glu Gly Leu Leu Leu Ser Glu Lys Val Gly Leu
    225                 230                 235                 240
    Asp Pro Asn Thr Val Val Glu Val Ile Ser Gln Gly Ala Ile Asn Ala
                245                 250                 255
    Pro Met Phe Ser Leu Lys Gly Pro Ser Met Val Lys Ala Ala Tyr Pro
                260                 265                 270
    Thr Ala Phe Pro Leu Lys His Gln Gln Lys Asp Leu Arg Leu Ala Leu
                275                 280                 285
    Ala Leu Ala Glu Ser Val Ser Gln Pro Ile Pro Thr Ala Ala Ala Ala
                290                 295                 300
    Asn Glu Leu Tyr Lys Val Ala Lys Ser Leu Gly Leu Ala Asp His Asp
    305                 310                 315                 320
    Phe Ser Ala Val Ile Glu Ala Leu Lys Ala Lys Val Gln Ser Ser Gln
                325                 330                 335
    His

<210> SEQ ID NO 102
<211> LENGTH: 1014
<212> TYPE: DNA
<213> ORGANISM: Triticum aestivum
<220> FEATURE:
<221> NAME/KEY: CDS
<222> LOCATION: (1)..(1014)

<400> SEQUENCE: 102 atg gct gcg gcc agc ttc ctc cta agc ccc agg gtg acg ctg ccc ctg    48
Met Ala Ala Ala Ser Phe Leu Leu Ser Pro Arg Val Thr Leu Pro Leu
1               5                   10                  15 cgc cga gga tcc cgc ctc ctc gtg tcc tgc tcc gcc act tcg tca tcc    96
Arg Arg Gly Ser Arg Leu Leu Val Ser Cys Ser Ala Thr Ser Ser Ser
            20                  25                  30
```

| | | |
|---|---|---|
| tcc tcg tca gat gct gct gga ggg gtg gga ttc cag gga agg gtg ggg<br>Ser Ser Ser Asp Ala Ala Gly Gly Val Gly Phe Gln Gly Arg Val Gly<br>            35                    40                    45 | | 144 |
| ttc ttg ggc ctc ggg atc atg ggc gcc ccc atg gca tca aac ctc ata<br>Phe Leu Gly Leu Gly Ile Met Gly Ala Pro Met Ala Ser Asn Leu Ile<br>50                      55                    60 | | 192 |
| aag gct ggt tgt gat att aca gtt tgg aac aga acc aag agc aag tgt<br>Lys Ala Gly Cys Asp Ile Thr Val Trp Asn Arg Thr Lys Ser Lys Cys<br>65                      70                    75                    80 | | 240 |
| gat cct ctt ctc agc ctc ggt gcc aag ttc gaa tct tca ccc gcc aga<br>Asp Pro Leu Leu Ser Leu Gly Ala Lys Phe Glu Ser Ser Pro Ala Arg<br>                  85                    90                    95 | | 288 |
| gtt gca tca tct tgt gat gtc acc ttt gca atg ctt gct gac cca gaa<br>Val Ala Ser Ser Cys Asp Val Thr Phe Ala Met Leu Ala Asp Pro Glu<br>                  100                  105               110 | | 336 |
| agc gcg ttt gag gtt gca tgc ggc gct aat gga gcc gca gaa ggg atg<br>Ser Ala Phe Glu Val Ala Cys Gly Ala Asn Gly Ala Ala Glu Gly Met<br>            115                    120                  125 | | 384 |
| gcc gca ggg aaa ggg tat gtc gat gtg tcg aca gtc gat gat gca aca<br>Ala Ala Gly Lys Gly Tyr Val Asp Val Ser Thr Val Asp Asp Ala Thr<br>130                     135                    140 | | 432 |
| tct aag cta atc ggc aaa cgt att aca agt act ggg gca tct ttt ctc<br>Ser Lys Leu Ile Gly Lys Arg Ile Thr Ser Thr Gly Ala Ser Phe Leu<br>145                     150                    155                    160 | | 480 |
| gag gct cca gtt tca ggc tca aaa aag cca gca gaa gat gga ctg ctg<br>Glu Ala Pro Val Ser Gly Ser Lys Lys Pro Ala Glu Asp Gly Leu Leu<br>                  165                    170                  175 | | 528 |
| atc ttt ctt act gca ggt gat gaa tcc ttg tac aag aga gtg gcg ccc<br>Ile Phe Leu Thr Ala Gly Asp Glu Ser Leu Tyr Lys Arg Val Ala Pro<br>                  180                    185                  190 | | 576 |
| cta ctt gat gtc atg ggc aag tca aga ttt tat ctt ggg gat gtc ggg<br>Leu Leu Asp Val Met Gly Lys Ser Arg Phe Tyr Leu Gly Asp Val Gly<br>            195                    200                  205 | | 624 |
| aat ggc gca gca atg aag ctc gtg gtt aat atg gtg atg ggg agc atg<br>Asn Gly Ala Ala Met Lys Leu Val Val Asn Met Val Met Gly Ser Met<br>210                     215                    220 | | 672 |
| atg gtc tcc ttt gca gaa ggg cta ctc ctg agt gaa aaa gtg ggg tta<br>Met Val Ser Phe Ala Glu Gly Leu Leu Leu Ser Glu Lys Val Gly Leu<br>225                     230                    235                    240 | | 720 |
| gac ccg aat act gtc gtc gag gtt att tca caa ggt gct atc aat gct<br>Asp Pro Asn Thr Val Val Glu Val Ile Ser Gln Gly Ala Ile Asn Ala<br>                  245                    250                  255 | | 768 |
| ccc atg ttc tcc ctc aag ggc cct tcc atg gtt aaa gct gca tac cct<br>Pro Met Phe Ser Leu Lys Gly Pro Ser Met Val Lys Ala Ala Tyr Pro<br>            260                    265                  270 | | 816 |
| act gcc ttt ccc ctg aaa cat cag cag aag gat cta agg ctg gcg ctg<br>Thr Ala Phe Pro Leu Lys His Gln Gln Lys Asp Leu Arg Leu Ala Leu<br>            275                    280                  285 | | 864 |
| gcc ctg gca gaa tcg gtg tcc cag ccc att cct aca gct gca gct gca<br>Ala Leu Ala Glu Ser Val Ser Gln Pro Ile Pro Thr Ala Ala Ala Ala<br>290                     295                    300 | | 912 |
| aac gag ctg tac aag gta gcc aaa tcg ctg ggc ctc gcc gac cag gac<br>Asn Glu Leu Tyr Lys Val Ala Lys Ser Leu Gly Leu Ala Asp Gln Asp<br>305                     310                    315                    320 | | 960 |
| ttc tcc gcg gtc att gag gcg ctc aag gct gaa atg cag agc tcg cag<br>Phe Ser Ala Val Ile Glu Ala Leu Lys Ala Glu Met Gln Ser Ser Gln<br>                  325                    330                  335 | | 1008 |
| cac tag<br>His | | 1014 |

<210> SEQ ID NO 103
<211> LENGTH: 337
<212> TYPE: PRT
<213> ORGANISM: Triticum aestivum

<400> SEQUENCE: 103

Met Ala Ala Ala Ser Phe Leu Leu Ser Pro Arg Val Thr Leu Pro Leu
1               5                   10                  15

Arg Arg Gly Ser Arg Leu Leu Val Ser Cys Ser Ala Thr Ser Ser Ser
            20                  25                  30

Ser Ser Ser Asp Ala Ala Gly Gly Val Gly Phe Gln Gly Arg Val Gly
        35                  40                  45

Phe Leu Gly Leu Gly Ile Met Gly Ala Pro Met Ala Ser Asn Leu Ile
    50                  55                  60

Lys Ala Gly Cys Asp Ile Thr Val Trp Asn Arg Thr Lys Ser Lys Cys
65                  70                  75                  80

Asp Pro Leu Leu Ser Leu Gly Ala Lys Phe Glu Ser Ser Pro Ala Arg
                85                  90                  95

Val Ala Ser Ser Cys Asp Val Thr Phe Ala Met Leu Ala Asp Pro Glu
            100                 105                 110

Ser Ala Phe Glu Val Ala Cys Gly Ala Asn Gly Ala Ala Glu Gly Met
        115                 120                 125

Ala Ala Gly Lys Gly Tyr Val Asp Val Ser Thr Val Asp Asp Ala Thr
    130                 135                 140

Ser Lys Leu Ile Gly Lys Arg Ile Thr Ser Thr Gly Ala Ser Phe Leu
145                 150                 155                 160

Glu Ala Pro Val Ser Gly Ser Lys Lys Pro Ala Glu Asp Gly Leu Leu
                165                 170                 175

Ile Phe Leu Thr Ala Gly Asp Glu Ser Leu Tyr Lys Arg Val Ala Pro
            180                 185                 190

Leu Leu Asp Val Met Gly Lys Ser Arg Phe Tyr Leu Gly Asp Val Gly
        195                 200                 205

Asn Gly Ala Ala Met Lys Leu Val Val Asn Met Val Met Gly Ser Met
    210                 215                 220

Met Val Ser Phe Ala Glu Gly Leu Leu Leu Ser Glu Lys Val Gly Leu
225                 230                 235                 240

Asp Pro Asn Thr Val Val Glu Val Ile Ser Gln Gly Ala Ile Asn Ala
                245                 250                 255

Pro Met Phe Ser Leu Lys Gly Pro Ser Met Val Lys Ala Ala Tyr Pro
            260                 265                 270

Thr Ala Phe Pro Leu Lys His Gln Gln Lys Asp Leu Arg Leu Ala Leu
        275                 280                 285

Ala Leu Ala Glu Ser Val Ser Gln Pro Ile Pro Thr Ala Ala Ala Ala
    290                 295                 300

Asn Glu Leu Tyr Lys Val Ala Lys Ser Leu Gly Leu Ala Asp Gln Asp
305                 310                 315                 320

Phe Ser Ala Val Ile Glu Ala Leu Lys Ala Glu Met Gln Ser Ser Gln
                325                 330                 335

His

<210> SEQ ID NO 104
<211> LENGTH: 406
<212> TYPE: DNA
<213> ORGANISM: Artificial Sequence

```
<220> FEATURE:
<223> OTHER INFORMATION: miRNA precursor
<220> FEATURE:
<221> NAME/KEY: misc_feature
<222> LOCATION: (88)..(108)
<223> OTHER INFORMATION: miRNA*
<220> FEATURE:
<221> NAME/KEY: misc_feature
<222> LOCATION: (239)..(259)
<223> OTHER INFORMATION: miRNA

<400> SEQUENCE: 104
caaacacacg ctcggacgca tattacacat gttcatacac ttaatactcg ctgttttgaa      60
ttgatgtttt aggaatatat atgtagagta caattctccc ccgaatattc acaggtcgtg     120
atatgattca attagcttcc gactcattca tccaaatacc gagtcgccaa aattcaaact     180
agactcgtta aatgaatgaa tgatgcggta gacaaattgg atcattgatt ctctttgatt     240
attcgcggga gaattgcact ctctcttttg tattccaatt ttcttgatta atctttcctg     300
cacaaaaaca tgcttgatcc actaagtgac atatatgctg ccttcgtata tatagttctg     360
gtaaaattaa cattttgggt ttatctttat ttaaggcatc gccatg                    406

<210> SEQ ID NO 105
<211> LENGTH: 404
<212> TYPE: DNA
<213> ORGANISM: Artificial Sequence
<220> FEATURE:
<223> OTHER INFORMATION: miRNA precursor
<220> FEATURE:
<221> NAME/KEY: misc_feature
<222> LOCATION: (88)..(107)
<223> OTHER INFORMATION: miRNA*
<220> FEATURE:
<221> NAME/KEY: misc_feature
<222> LOCATION: (238)..(257)
<223> OTHER INFORMATION: miRNA

<400> SEQUENCE: 105
caaacacacg ctcggacgca tattacacat gttcatacac ttaatactcg ctgttttgaa      60
ttgatgtttt aggaatatat atgtagagag agcttccttg agtccattca caggtcgtga     120
tatgattcaa ttagcttccg actcattcat ccaaataccg agtcgccaaa attcaaacta     180
gactcgttaa atgaatgaat gatgcggtag acaaattgga tcattgattc tctttgattg     240
gactgaaggg agctccctct ctcttttgta ttccaattt cttgattaat ctttcctgca      300
caaaaacatg cttgatccac taagtgacat atatgctgcc ttcgtatata tagttctggt     360
aaaattaaca ttttgggttt atctttattt aaggcatcgc catg                      404
```